US006852753B2

(12) United States Patent
Koeller et al.

(10) Patent No.: US 6,852,753 B2
(45) Date of Patent: Feb. 8, 2005

(54) ALKYL/ARYL HYDROXY OR KETO THIEPINE COMPOUNDS AS INHIBITORS OF APICAL SODIUM CO-DEPENDENT BILE ACID TRANSPORT (ASBT) AND TAUROCHOLATE UPTAKE

(75) Inventors: Kevin J. Koeller, Richmond Heights, MO (US); Samuel J. Tremont, St. Louis, MO (US)

(73) Assignee: Pharmacia Corporation, St. Louis, MO (US)

( * ) Notice: Subject to any disclaimer, the term of this patent is extended or adjusted under 35 U.S.C. 154(b) by 24 days.

(21) Appl. No.: 10/342,201

(22) Filed: Jan. 15, 2003

(65) Prior Publication Data

US 2003/0195218 A1 Oct. 16, 2003

Related U.S. Application Data

(60) Provisional application No. 60/348,605, filed on Jan. 17, 2002.

(51) Int. Cl.[7] .................. A61K 31/38; A61K 31/44; C07D 471/02; C07D 337/00; C07D 409/00
(52) U.S. Cl. .................. 514/431; 514/336; 514/300; 549/9; 546/279.7; 546/122
(58) Field of Search .................. 514/431, 336, 514/300; 549/9; 546/279.7, 122

(56) References Cited

U.S. PATENT DOCUMENTS

| | | |
|---|---|---|
| 3,262,850 A | 7/1966 | Glynne |
| 3,287,370 A | 11/1966 | Mohrbacher |
| 3,389,144 A | 6/1968 | Mohrbacher |
| 3,520,891 A | 7/1970 | Mohrbacher |
| 3,674,836 A | 7/1972 | Creger |
| 3,692,895 A | 9/1972 | Nelson |
| 3,694,446 A | 9/1972 | Houlhan et al. |
| 3,714,190 A | 1/1973 | Boissier |
| 3,781,328 A | 12/1973 | Witte |
| 3,948,973 A | 4/1976 | Phillips |
| 3,962,261 A | 6/1976 | Zinnes |
| 3,972,878 A | 8/1976 | Schirmann |
| 3,983,140 A | 9/1976 | Endo |
| 4,002,750 A | 1/1977 | Ambrogi |
| 4,058,552 A | 11/1977 | Mieville |
| 4,185,109 A | 1/1980 | Rosen |
| 4,231,938 A | 11/1980 | Monaghan |
| 4,251,526 A | 2/1981 | McCall |
| 4,346,227 A | 8/1982 | Terahara et al. |
| 4,410,629 A | 10/1983 | Terahara et al. |
| 4,444,784 A | 4/1984 | Hoffman |
| 4,448,979 A | 5/1984 | Terahara et al. |
| 4,559,332 A | 12/1985 | Grob et al. |
| 5,075,293 A | 12/1991 | Reifschneider |
| 5,153,184 A | 10/1992 | Reifschneider |
| 5,158,943 A | 10/1992 | Sohda et al. |
| 5,244,887 A | 9/1993 | Straub |
| 5,260,316 A | 11/1993 | Van Duzer |
| 5,334,600 A | 8/1994 | Van Duzer |
| 5,350,761 A | 9/1994 | Van Duzer |
| 5,354,772 A | 10/1994 | Kathawala |
| 5,430,116 A | 7/1995 | Kramer |
| 5,502,045 A | 3/1996 | Miettinen |
| 5,512,558 A | 4/1996 | Enhsen |
| 5,519,001 A | 5/1996 | Rampratap |
| 5,602,152 A | 2/1997 | Berthelon |
| 5,610,151 A | 3/1997 | Glombik |
| 5,663,165 A | 9/1997 | Brieaddy |
| 5,703,188 A | 12/1997 | Mandeville |
| 5,705,524 A | 1/1998 | McGee |
| 5,723,458 A | 3/1998 | Brieaddy |
| 5,767,115 A | 6/1998 | Rosenblum |
| 5,811,450 A * | 9/1998 | Bischofberger et al. ..... 514/431 |
| 5,929,062 A | 7/1999 | Haines |
| 5,994,391 A | 11/1999 | Lee et al. |
| 6,020,330 A | 2/2000 | Enhsen et al. |
| 6,034,118 A | 3/2000 | Bischofberger et al. |

FOREIGN PATENT DOCUMENTS

| | | |
|---|---|---|
| AU | A-30209/92 | 12/1992 |
| AU | A-61946/94 | 6/1994 |
| AU | A-61948/94 | 6/1994 |
| AU | A-61949/94 | 6/1994 |
| CA | 2025294 | 3/1991 |
| CA | 2078588 | 3/1993 |
| CA | 2085782 | 6/1993 |
| CA | 2085830 | 6/1993 |
| DE | 1211258 | 2/1968 |
| DE | 3 122 499 A1 | 5/1990 |
| DE | 196 27 430 A1 | 8/1996 |
| EP | 0 022 487 A1 | 1/1981 |
| EP | 0 244 364 A2 | 4/1981 |
| EP | 0 067 086 | 10/1982 |
| EP | 0 129 748 | 2/1985 |
| EP | 0 033 538 B1 | 11/1985 |
| EP | 0 250 265 | 6/1987 |
| EP | 0 338 331 | 6/1989 |
| EP | 0 379 161 | 1/1990 |
| EP | 0 409 281 A1 | 1/1991 |
| EP | 0 531 901 A2 | 2/1992 |
| EP | 0 508 425 A1 | 9/1992 |
| EP | 0 549 967 A1 | 12/1992 |
| EP | 0 526 402 A1 | 2/1993 |
| EP | 0 559 064 A2 | 2/1993 |
| EP | 0 563 731 A1 | 3/1993 |
| EP | 0 568 898 A1 | 4/1993 |

(List continued on next page.)

OTHER PUBLICATIONS

Angelin, B., "Regulation of Hepatic Cholesterol Metabolism in Man," Ann. Med. 23, pp. 10–27 (1991).

(List continued on next page.)

*Primary Examiner*—Deborah C. Lambkin
(74) *Attorney, Agent, or Firm*—Harness, Dickey & Pierce, P.L.C.

(57) ABSTRACT

Thiepine apical sodium co-dependent bile acid transport (ASBT) inhibitors are disclosed together with methods of making the same, methods of using the same to treat hyperlipidemic conditions as well as pharmaceutical compositions containing the same compounds.

150 Claims, No Drawings

FOREIGN PATENT DOCUMENTS

| | | |
|---|---|---|
| EP | 0 818 197 A1 | 6/1997 |
| EP | 0 818 448 A1 | 6/1997 |
| EP | 0 796 846 A1 | 7/1997 |
| EP | 0 801 060 A1 | 10/1997 |
| FR | 2 661 676 A1 | 2/1990 |
| GB | 1 211 258 | 11/1970 |
| GB | 2 077 264 A | 12/1981 |
| GB | 2 305 665 | 4/1997 |
| GB | 2 329 334 | 3/1999 |
| JP | 10-287662 | 10/1998 |
| WO | 89/01477 | 2/1989 |
| WO | 91/08205 | 6/1991 |
| WO | 92/17467 | 10/1992 |
| WO | 92/18115 | 10/1992 |
| WO | 92/18462 | 10/1992 |
| WO | 93/16055 | 8/1993 |
| WO | 93/21146 | 10/1993 |
| WO | 94/18183 | 8/1994 |
| WO | 94/18184 | 8/1994 |
| WO | 94/24087 | 10/1994 |
| WO | 95/21843 | 8/1995 |
| WO | 96/05188 | 2/1996 |
| WO | 96/08484 | 3/1996 |
| WO | 96/16051 | 5/1996 |
| WO | 96/40255 | 12/1996 |
| WO | 97/03953 | 2/1997 |
| WO | 97/33882 | 9/1997 |
| WO | 97/49387 | 12/1997 |
| WO | 97/49736 | 12/1997 |
| WO | 98/02432 | 1/1998 |
| WO | 98/06405 | 2/1998 |
| WO | 98/23593 | 6/1998 |
| WO | 98/35937 | 8/1998 |
| WO | WO 98/38182 | 9/1998 |
| WO | 98/38182 | 9/1998 |
| WO | 98/39299 | 9/1998 |
| WO | 98/40375 | 9/1998 |
| WO | WO 98/40375 | 9/1998 |
| WO | 98/56757 | 12/1998 |
| WO | 99/11259 | 3/1999 |
| WO | 99/11260 | 3/1999 |
| WO | 99/11263 | 3/1999 |
| WO | 99/14174 | 3/1999 |
| WO | 99/14204 | 3/1999 |
| WO | 99/14215 | 3/1999 |
| WO | 99/32478 | 7/1999 |
| WO | 99/35135 | 7/1999 |
| WO | 99/64409 | 12/1999 |
| WO | 00/35889 | 6/2000 |

OTHER PUBLICATIONS

Blum, C. B., "Comparison of Properties of Four Inhibitors of 3–Hydroxy–3–Methylglutaryl–Coenzyme A Reductase," Am. J. Cardiol., 73(14), 3D–11D, (1994).

Cayen, M.N., "Dispositi9n, Metabolism and Pharmacokinetics of Anthyperlipidemic Agents in Laboratory Animals and Man," Pharmac. & Ther., 29, pp. 157–204 (1985).

Da Col, et al., "Tolerability and Efficacy of Combination Therapy with Simvastatin Plus Gemfibroail in Type II Refractory Familial Combined Hyperlipidemia," Curr. Therap. Research, vol. 53, No. 5, pp. 473–483 (1993).

Davignon, et al. "HMG CoA Reductase Inhibitors: A look back and a look ahead," Can. J. Cardiol., 8(8), pp. 843–864 (1992).

Endo, A. "Chemistry, biochemistry and pharmacology of HMG–Co–A reductase inhibitors," Klin. Wochenschr. 66, pp. 421–427 (1988).

Kramer et al., "Bile acid derived HMG–CoA reductase inhibitors," Biochimica dt Biophysica Acta, 1227 pp. 137–154 (1994).

Marcus, A., "Role of the HMG–CoA Reductase Inhibitiors in the Treatment of Dyslipidemia: An Evolutionary Review," CVR&R, pp. 13–27 (Jan. 1996).

International Search Report PCT/US03/00025, Issued Sep. 5, 2003.

A. Barrett et al., "Total Synthesis and Stereochemical Assignment of the Quinquecyclopropane–Containing Cholesteryl Ester Transfer Protein Inhibitor U–106305", J. Am Chem. Soc., 1996, 118, pp. 7863–7864.

P. Barter et al. "High Density Lipoproteins and Coronary Heart Disease", Atherosclerosis, 121 1996, pp. 1–12.

A. Beckwith et al., "Iododediazoniation of Arenediazonium Salts Accompanied by Aryl Radical Ring Closure" J. Org. Chem. 1987, vol. 52, pp. 1922–1930.

D. Bilheimer et al., "Mevinolin and Colestipol Stimulate Receptor–Mediated Clearance of Low Density Lipoprotein From Plasma In Familial Hypercholesterolemia Heterzygotes", Proc. Natl. Acad. Sci. USA, vol. 80, Jul. 1983, pp. 4124–4128.

C. Bisgaier et al., Cholesteryl Ester Transfer Protein Inhibition By PD 140195, Lipids, vol. 29, No. 12, 1994, pp. 811–818.

D. Blankenhorn et al., "Beneficial Effects of Combined Colestipol–Niacin Therapy On Coronary Atherosclerosis and Coronary Venous Bypass Grafts", JAMA, Jun. 19, 1987, vol. 257, No. 23, pp. 3233–3240.

D. Blankenhorn et al., "Beneficial Effects of Colestipol–Niacin Therapy on the Common Carotid Artery" Circulation vol. 88, Jul. 1, 1993, pp. 20–28.

P. Bonin et al., "A Peptide Inhibitor Of Cholesteryl Ester Transfer Protein Identified By Screening a Bacteriophage Display Library", Journal of Peptide Research, 51, 1998, pp. 216–225.

G. Brown, et al., "Regression of Coronary Artery Disease As A Result of Intensive Lipid–Lowering Therapy in Men With High Levels Of Apolipoprotein B", The New England Journal of Medicine, vol. 323, Nov. 8, 1990, No. 19, pp. 1289–1339.

M. Brown et al., Induction of 3–hydroxy–3Methylglutaryl Coenzyme A Reductase Activity in Human Fibroblasts Incubated with Compactin (ML–236B), A Competitive Inhibitor of the Reductase, The Journal of Biological Chemistry, vol. 253, No. 4, Feb. 22, 1978, pp. 1121–1128.

S. Busch et al., "Cholesteryl Ester Analogs Inhibit Cholesteryl Ester But Not Triglyceride Transfer Catalyzed By The Plasma Cholesteryl Ester–Triglyceride Transfer Protein", Lipids, vol. 25, No. 4 (1990), pp. 216–220.

C. Camoutsis et al., "N–Substituted 4, 5–Dihydro–1, 2–Benzothiazepin–3–One 1, 1–Dioxide", J. Heterocyclic Chem. 17, pp. 1135–1136 (1980).

L. Cashin–Hemphill et al., "Beneficial Effects of Colestipol–Niacin in Coronary Atherosclerosis A 4–Year Follow–up", JAMA, Dec. 19, 1990, vol. 264, No. 23, pp. 3013–3017.

P. Catsoulacos et al., "Synthesis of Some N–Substituted 4,5–Dihydro–7,8–dimethoxybenzothiazepin–3–one 1,1–Dioxides", J. Heterocyclic Chem., vol. 13 (1976), pp. 1309–1314.

P. Catsoulacos et al., "Thiazo Compounds. Derivatives of 4,5–Dihydro–7, 8–Dimethoxybenzothiazepin–3 one 1,1–Dioxides", Journal of Chemical and Engineering Data, vol. 22, No. 3, 1977, pp. 353–354.

K. Cho et al, "A Peptide From Hog Plasma that Inhibits Human Cholesteryl Ester Transfer Protein", Biochimica et Biophysica Acta, 1391, 1998, pp. 133–144.

D. Connolly et al., "Inactivation of Cholesteryl Ester Transfer Protein by Cysteine Modification", Biochemical and Biophysical Research Communications 223, pp. 42–47, 1996.

S. Coval et al., "Wiedendiol–A and–B, Cholesteryl Ester Transfer Protein Inhibitors From The Marine Sponge Xestosponga Wiedenmayeri", Bioorganic & Medicinal Chemistry Letter, vol. 5, No. 6, pp. 605–610, 1995.

J. Davignon et al., "Apolipoprotiein E and Atherosclerosis: Quest for an APO E Receptor Defect Leads to the Discovery of Pseudo Type III Dyslipoproteinemia in a Family", Atherosclerosis IX, pp. 199–203.

J. Davignon et al., "Comparative Efficacy and Safety of Pravastatin, Nicotinic Acid and The Two Combined in Patients with Hypercholesterolemia", The American Journal of Cardiology, Feb. 15, 1994, pp. 339–345.

C. East et al., "Combination Drug Therapy for Familial Combined Hyperlipidemia", Annals of Internal Medicine, Jul. 1, 1988, pp. 25–32.

J. Emmerich et al., "Efficacy and Safety of Simvastatin (Alone or in Association with Cholestramine) A 1 yr. Study in 66 Patients with Type II Hyperlipoproteinaemia", European Heart Journal (1990), 11, pgs. 149–155.

D. Erkelens, "Combination Drug Therapy with HMG Co A Reductase Inhibitors and Bile Acid Sequestrants for Hypercholesterolmia", Cardiology, 1990, 77, (suppl 4). pp. 33–38.

H. Ginsberg, "Update on the Treatment of Hypercholesterolemia, with a Focus on HMG–CoA Reductase Inhibitors and Combination Regimens", Clinical Cardiology 18, pp. 307–315, (1995).

C. Glueck et al., "Gemfibrozil–Lovastatin Therapy for Primary Hyperlipoproteinemias" The American Journal of Cardiology, Jul. 1, 1992, vol. 70, No. 1, pp. 1–9.

S. Grundy et al., "Influence of Combined Therapy with Mevinolin and Interruption of Bile–Acid Reabsorption on Low Density Lipoproteins in Heterozygous Familial Hypercholesterolemia", Annals of Internal Medicine, 1985, 103: pp. 339–343.

H. Gylling et al., "Effects Of Inhibiting Cholesterol Absorption And Synthesis On Cholesterol And Lipoprotein Metabolism In Hypercholesterolemic Non–Insulin–Dependent Diabetic Men", Journal of Lipid Research, vol. 37, 1996, pp. 1776–1785.

E. Haber, "Molecular Cardiovascular Medicine" Scientific American pp. 35–40.

V. Hegde et al., "A Depsipeptide Fungal Metabolite Inhibitor Of Cholesteryl Ester Transfer Protein", Bioorganic & Medicinal Chemistry Letters 8, 1998, pp. 1277–1280.

L.Hellberg et al., "5a–Hydroxy–3a–Cholestanecarboxylic" The New Journal for Organic Synthesis, vol. 15, No. 1–2, Feb.–Apr. 1983, pp. 154–156.

J. Heubi et al., "Primary Bile Acid Malabsorption: Defective In Vitro Ileal Active Bile Acid Transport", Gastroenterology 1982, 83: pp. 804–811.

N. Hoogerbrugge et al.,"The Additional Effects of Acipimox To Simvastatin In The Treatment of Combined Hyperlipidaemia", Journal of Internal Medicine, 1997, 241: pp. 151–155.

N. Hoogerbrugge et al., "The Effacy and Safety of Pravastatin, Compared To And In Combination With Bile Acid Binding Resins, In Familial Hypercholesterolaemia", Journal of Internal Medicine 1990, 228; pp. 261–266.

A. Hutchesson et al., "Dual Bezafibrate–Simvastatin Therapy For Combined Hyperlipidaemia", Journal of Clinical Pharmacy and Therapeutics 1994, 19, pp. 387–389.

T. Ichihashi, "Mechanism of Hypocholesterolemic Action of S–8921 in Rats: S–8921 Inhibits Ileal Bile Acid Absorption", The Journal Of Pharmacology And Experimental Therapeutics, vol. 284, No. 1, pp. 43–50.

D. Illingworth, et al., "Influence of Lovstatin plus Gemfibrozil on Plasma Lipids and Lipoproteins in Patients With Heterozygous Familial Hypercholesterolemia", Circulation vol. 79, No. 3, Mar. 1989, 590–596.

D. Illingworth, "Mevinolin Plus Colestipol in Therapy for Severe Heterozygous Familial Hypercholesterolemia", Annalos of Internal Medicine, 1984; 101, pp. 598–604.

International Search Report mailed May 23, 2000 based on PCT/US 99/27942.

International Search Report mailed May 23, 2000 based on PCT/US 99/27943.

International Search Report mailed May 23, 2000 based on PCT/US 99/27944.

International Search Report mailed May 23, 2000 based on PCT/US 99/27945.

International Search Report mailed May 18, 2000 based on PCT/US 99/27947.

International Search Report mailed May 15, 2000 based on PCT/US 99/27948.

International Search Report mailed May 17, 2000 based on PCT/US 99/27949.

J. Kane, et al., "Regression of Coronary Atherosclerosis During Treatment of Familial Hypercholesterolemia With Combined Drug Regimens", JAMA, Dec. 19, 1990, Chapter 26, vol. 264, No. 23, pp. 3007–3012.

A. Katritzky et al., "Preparation Of 6–7– And 8–Membered Sultams By Friedel–Crafts Cyclization Of w–Phenylalkanesulfamoyl Chlorides", Organic Preparations and Procedures Int., 24 (4), pp. 463–467 (1992).

T. Kazumi et al., "Effects of Niceritrol On Elevated Serum Lipoprotein LP (A) Levels in Diabetic Patients With Or Without Overt Proteinuria", Current Therapeutic Research, vol. 55, No. 5, May 1994, pp. 546–551.

W. Kramer, et al., "Intestinal Bile Acid Absorption", The Journal of Biological Chemistry. vol. 268, No. 24 Issue of Aug. 25, pp. 18035–18046, 1993.

Kuo, M.S. et al., "Discovery, Isolation, Structure Elucidation, and Biosynthesis of U–106305, a Choresteryl Ester Transfer Protein Inhibitor from UC 11136", J. Am. Chem. Soc. 117, pp. 10629–10634 (1995).

Kvis, K. et al. , "Benzocycloheptenes and Heterocyclic Analogues as Potential Drugs. VII, 4–Phenyl–,3,4,5–Tetrahydro–1–Benzothiepins and Some Related Compounds", Chem. Commun./Vo.37/(1973) pp. 3808–3816.

Lee, J.C. et al., "A Cholesteryl Ester Transfer Protein Inhibitor from an Insect–associated Fungus", The Journal of Antibiotics 49(7), pp. 693–696.

A.M. Lees et al., "Therapy of Hypercholesterolemia With Mevinolin And Other Lipid–Lowering Drugs", Arteriosclerosis 6, 1986, p. 544a.

T. Leren et al., "Effects of Lovastatin Alone and In Combination with Cholestyramine on Serum Lipids and Apolipoproteins in Heterozygotes for Familial Hypercholesterolemia", International Journal for Research and Investigation on Atherosclerosis and Related Diseases, 73, (1988), pp. 135–141.

M. Lewis, et al., Effects Of 2164U90 on Ileal Bile Acid Absorption and Serum Cholesterol in Rats and Mice, Journal of Lipid Research, vol. 36, 1995,pp. 1098–1105.

R. Lewis, Hawley's Condensed Chemical Dictionary, p. 1238.

W. Ling et al., "Minireview Dietary Phytosterols A Review of Metabolism, Benefits and Side Effects", Life Sciences, vol. 57, No. 3, 1995, pp. 195–206.

H. Mabuchi et al., "Reduction of Serum Cholesterol In Heterozygous Patients with Familial Hypercholesterolemia", The New England Journal of Medicine, vol. 308, Mar. 17, 1983,pp. 609–613.

M. Malloy et al., "Complementarity of Colestipol, Niacin, and Lovastatin in Treatment of Severe Familial Hypercholesterolemia", Annals of Internal Medicine 1987; 107: pp. 616–623.

W. Mandeville et al., Bile Acid Sequestrants: Their Use In Combination With Other Lipid–Lowering Agents, Idrugs 1999 vol. 2., No. 3, pp. 237–242.

G. Marais et al., "Rhabdomyolysis and Acute Renal Failure Induced by Combination Lovastatin and Gemfibrozil Therapy", Annals of Internal Medicine, Feb. 1, 1990, vol. 112, No. 3, pp. 228–230.

P. McCarthy, "New Approaches to Atherosclerosis: An Overview", Medicinal Research Reviews, vol. 13, No. 2, 1993, pp. 139–159.

R. Morton, Regulation of Lipid Transfer Between Lipoproteins By An Endogenous Plasma Protein: Selective Inhibition Among Lipoprotein Classes, Journal of Lipid Research, vol. 35, 1994, pp. 836–847.

F. Nerdel et al., "Quartermay Salts of B–Amino Aldehydes and B–Iodoaldehydes", Chemische Berichte (Ed. H. Zahn), vol. 98 (1965), pp. 728–734.

M. Newman et al., "The Conversion of Phenols to Thiophenols via Dialkylthiocarbamates", The Journal Of Organic Chemistry, vol. 31, Sep.–Dec. 1966, pp. 3980–3984.

A. Orahovats et al., "A Ring Enlargement from Seven–to Ten–Membered–Ring Sulfonamide Derivatives", Helvetica Chimica Acta, vol. 79, (1996), pp. 1121–1128.

H. Pan et al., "Pharmacokinetics and Pharmacodynamics of Pravastatin Alone and With Cholestyramine in Hypercholesterolemia", Clin. Pharmacol Ther. (1980) 9, 313, pp. 201–207.

N. Panagiotopoulos et al., "N(P–Bromophenyl)–4,5–Dihydro–7,8–Dimethoxy Benzothiazepine–ONE 1, 1–Dioxide C17 H16 brNO5S", Cryst. Struct. Comm. (1980) 9, pp. 313–319.

R. Pasternak et al., "Effect of Combination Therapy with Lipid–Reducing Drugs in Patients with Coronary Heart Disease and "Normal" Cholesterol Levels", Annals of Internal Medicine, Oct. 1, 1996, vol. 125, No. 7, pp. 529–538.

R. Patra et al., "Conformational and Steric Requirements Of The Side Chain For Sulphur Participation In Benzthiepin Derivatives", Tetrahedron Letters, vol. 30, No. 32, pp. 4279–4282, 1989.

R. Pierce et al., Myopathy and Rhabdomyolysis Associated With Lovastatin–Gemfibrozil Combination Therapy, JAMA, Jul. 4, 1990, vol. 264, No. 1, pp. 71–75.

W. Pirkle et al., "Trichlorosilane–Induced Cleavage. A Mild Method for Retrieving Carbinols From Carbamates", Jouranal Organic Chemistry, vol. 42, No. 15, 1977, pp. 2781–2782.

W. Pirkle et al., "Dynamic NMR Studies of Disatereomeric Carbamates: Implications toward the Determination of Relative Configuration by NMR" Journal of Organic Chemistry, vol. 44, No. 26, 1979, pp. 4891–4896.

W. Pirkle et al., "An Example of Automated Liquid Chromatography Synthesis of a Broad–Spectrum Resolving Agent and Resolution of 1–(Naphthyl) 2, 2, 2–Trifluroethanol", The Journal of Organic Chemistry vol. 39, No. 26, 1974, pp. 3904–3906.

T. Pietzonka et al., "Phosphonate–Containing Analogs Of Cholesteryl Ester As Novel Inhibitors Of Cholesteryl Ester Transfer Protein", Bioorganic & Medicinal Chemistry Letters, vol. 6, No. 16, pp. 1951–1954.

Pravastatin Multicenter Study Group II, "Comparative Efficacy and Safety of Pravastatin and Cholestyramine Alone And Combined in Patients With Hypercholesterolemia", Archives of Internal Medicine, vol. 153, Jun. 14, 1993, pp. 1321–1328.

E. Reihner et al., Regulation of Hepatic Cholesterol Metabolism In Humans: Stimulatory Effects of Cholestyramine on HMG–CoA Reductase Activity and Low Density Lipoprotein Receptor Expression In Gallstone Patients, Journal of Lipid Research, vol. 31, 1990, pp. 2219–2226.

R. Remick et al., "Comparison of Fluoxetine and Desipramine In Depressed Outpatients", Therapeutic Research, vol. 53, No. 5, May 1993, pp. 457–483.

S. Rosenblum et al., Discovery of 1–(4–Fluorophenyl)–(3R)–[3–(4–fluorophenyl)–(3S)–hydroxypropyl]–(4S)–(4–hydroxyphenyl)–2–azetidinone (SCH 58235): A Designed, Potent, Orally Active Inhibitor of Cholesterol Absorption, Journal of Medicinal Chemistry, 1998, vol. 41, No. 6, pp. 973–980.

G. Salem et al., "Benzothiazine and Benzothizepine Derivatives: Structures of N–p–Bromophenyl–6, 7–Dimethoxy–1, 2–Benzothiazin–3(4H)–One 1, 1–Dioxide (BBTZ) and 4, 5–Dihydro–8,9–Dimethoxy–N–(5–Methyl–2–Pyridyl)–1, 2–Benzothiazepin–3–One 1, 1–Dioxide (MPTE)", Acta Cryst. (1986) C42, pp. 1581–1584.

J. Sasaki et al., "Effects of Fluvastatin, A New Inhibitor of HMG–CoA Reductase, and Niceritol on Serum Lipids, Lipoproteins and Cholesterol Ester Transfer Activity In Primary Hypercholesterolemic Patients", International Journal of Clinical Pharmacology and Therapeutics, vol. 33, No. 7, 1995, pp. 420–426.

K. Sindelar et al., Neurotropic and Psychotropic Compounds. XXIX. Derivatives Of 2,3,4,5–Tetrahydro–1–Benzothiepin, Chemical Commun., vol. 33, 1968, pp. 4315–4327.

K. Sindelar et al., Benzocycloheptenes and Hetelrocyclic Analogues As Potential Drugs. III. Further Synthetic Experiments In The Series Of 1–Benzothiepin Derivatives, vol. 37, 1972, 1195–1206.

C. Sirtori, "New Targets For Lipid Lowering And Atherosclerosis Prevention", Pharmac. Ther. vol. 67, No. 3., pp. 433–447, 1995.

Y. Son, "Purification and Characterization of Human Plasma Proteins That Inhibit Liquid Transfer Activities", Biochimica et Biophysica Acta, 795, 1984, pp. 473–480.

D. Sprecher et al., "Low–Dose Combined Therapy with Fluvastin and Cholestyramine in Hyperlipidemic Patients", Ann Intern Med. 1994; 120: pp. 537–543.

C.I. Stassinopoulou, et al., "C NMR Spectra of Benzothiazepinone, Benzothiazinone and Benzosulphonamide N–Substituted Derivatives" Department of Biology, Nuclear Research Center.

E. Stedronsky et al., "Interaction of Bile Acids and Cholesterol with Non–Systemic Agents Having Hypocholesterolemic Properties", Biochimica et Biophysica Acta., 1210, 1994, pp. 255–287.

I. Stein, et al., "Effects of Simvastatin and Cholestryamine in Familial and Nonfamilial Hypercholesterolemia", Arch Intern Med. vol. 150, Feb. 1990, pp. 341–345.

E. Stein, et al., "Lovastatin Alone And In Combination For Treatment Of Primary Hypercholesterolema", Alan R. Liss, Inc. 1988, pp. 281–293.

K. Suckling, et al., Cholesterol Lowering and Bile Acid Excretion in the Hamster with Cholestyramine Treatment, Atherosclerosis, 89, (1991) pp. 183–190.

T. Swenson, "Mechanism of Cholesteryl Ester Transfer Protein Inhibition by a Neutralizing Monoclonal Antibody and Mapping of the Monoclonal Antibody Epitope", The Journal of Biological Chemistry, vol. 264, No. 24, Aug. 25, pp. 14318–14326, 1989.

A. Tall, "Plasma Cholesteryl Ester Transfer Protein", Journal of Lipid Research, Vol. 34, 1993, pp. 1255–1274.

Y. Tamura et al., Novel Conversions of Benzo [b] thiophen–3 (2–H)–ones into 1, 2–Benzisothiazole and Tetrahydro–1, 2–Benzothiazepin–5–One Systems via Sulphimide Intermediates, J.C.S. Perkin I, pp. 2830–2834.

K. Thurmond et al., "Water–Soluble Knedel–like Structures: The Preparation of Shell–Cross–Linked Small Particles", Journal American Chemistry Soc. vol., 118, No. 30, 1996, pp. 7239–7240.

P. Tyle, "Iontophoretic Devices for Drug Delivery", Pharmaceutical Research, vol. 3. No. 6 1986, pp. 318–325.

M. Une et al., Metabolism of 3a, 7a–Dihydroxy–7b–Methyl–5b–Cholanoic Acid and 3a, 7B–Dihydroxy–7a–Methyl–5B–Cholanoic Acid Hamsters, Biochimica et Biophysica Acta, 833 (1985), pp. 196–202.

J. Vacek et al., Comparison of Lavastatin (20 mg) and Nicotinic Acid (1.2g) With Either Drug Alone for Type II Hyperlipoproteinemia, The American Journal of Cardiology, vol. 76, Jul. 15, 1995, pp. 182–184.

M. Van Heek et al., "In Vivo Metabolism–Based Discovery of a Potent Cholesterol Absorption Inhibitor, SCH58235, in the Rat and Rhesus Monkey Through the Identification of the Active Metabolites of SCH48461", The Journal of Pharmacology and Experimental Therapeutics, vol. 283, No. 1, pp. 157–754.

G. Vega et al., "Treatment of Primary Moderate Hypercholesterolemia With Lovastatin (Mevinolin) and Colestipol", JAMA, Jan. 2, 1987, vol. 257, No. 1, pp. 33–37.

G. Wess et al., "Synthesis and Biological Activity of Bile Acid–Derived HMG–CoA Reductase Inhibitors. The Role of 21–Methyl in Recognition of HMG–CoA Reductase and the Ileal Bile Acid Transport System", Journal Of Medicinal Chemistry 1994, 37, pp. 3240–3246.

J. Wetterau et al., "An MTP Inhibitor that Normalizes Atherogenic Lipoprotein Levels In WHHL Rabbits", Science vol. 282, Oct. 23, 1998, pp. 751–754.

O. Wiklund et al., "Pravastatin and Gemfibrozil Alone and in Combination for the Treatment of Hypercholesterolemia", The American Journal of Medicine vol. 94, Jan. 1993, pp. 13–19.

S. Wirebaugh et al., "A Retrospective Review of the Use of Lipid–Lowering Agents in Combination, Specifically, Gemfibrozil and Lovastatin", Pharmacotherapy vol. 12, No. 6, 1992, pp. 445–450.

J. Witztum, "Drugs Used In The Treatment of Hyperlipoproteinemias", The Pharmacological Basis of Therapeutics, 9th Edition, pp. 875–894.

Yan Xia et al., "Substituted 1,3,5–Triazines As Cholesteral Ester Transfer Protein Inhibitors", Bioorganic & Medicinal Chemistry Letters, vol. 6, No. 7, 1996, pp. 919–922.

A. Yamamoto et al., "Effects of Probucol on Xanthomata Regression in Familial Hypercholesterolemia", Am Journal Cardiology, 1986, 57: pp. 29H–35H.

K. Ytre–Arne et al., "Simvastatin and Cholestyramine In The Long–Term Treatment of Hypercholesterolaemia", Journal of Internal Medicine (1989): 226, pp. 285–290.

* cited by examiner

ALKYL/ARYL HYDROXY OR KETO THIEPINE COMPOUNDS AS INHIBITORS OF APICAL SODIUM CO-DEPENDENT BILE ACID TRANSPORT (ASBT) AND TAUROCHOLATE UPTAKE

This is a non-provisional of provisional application Ser. No. 60/348,605, filed Jan. 17, 2002.

FIELD OF THE INVENTION

The present invention relates to compounds, pharmaceutical compositions, and methods for treating high blood cholesterol levels in a subject. More particularly, the present invention relates to novel alkyl/aryl hydroxy or keto thiepine compounds that are useful as apical sodium co-dependent bile acid transport (ASBT) inhibitors, pharmaceutical compositions containing the same, methods for making the same and methods for treating hyperlipidemic conditions.

DESCRIPTION OF THE RELATED ART

The major metabolic fate of cholesterol in the human body is in the hepatic synthesis of bile acids. Bile acids are both passively and actively reabsorbed from the small intestine and recycled via the enterohepatic circulation to conserve the total pool of bile acids. Dietschy, "Mechanisms for the intestinal absorption of bile acids", *J. Lipid Res.*, 9:297–309 (1968). Bile acids undergo passive absorption in the proximal small intestine and active transport in the terminal ileum. Love et al., "New insights into bile acid transport", *Curr. Opin. Lipidol.*, 9(3):225–229 (1998). Ileal active transport accounts for the majority of intestinal bile acid uptake and is the exclusive route for taurine-conjugated bile acids. Id. Ileal active transport is mediated by the apical sodium co-dependent bile acid transporter ("ASBT", also known as the ileal bile acid transporter or "IBAT") localized to the distal one-third of the ileum. Craddock et al., "Expression and transport properties of the human ileal and renal sodium-dependent bile acid transporter", *Am. J. Physiol.*, 274 (Gastrointest. Liver Physiol. 37):G157–G169 (1998).

An equilibrium generally exists between hepatic cholesterol and the bile acid pool. Interruption of the enterohepatic recirculation of bile acids (e.g., the binding of intestinal bile acids to a sequestering resin such as cholestyramine; the surgical removal of the ileum to physically eliminate ileal ASBT; or the specific inhibition of ileal ASBT) results in a decrease in the liver bile acid pool and stimulates increased hepatic synthesis of bile acids from cholesterol (i.e., an upregulation of cholesterol-7α-hydroxylase activity), eventually depleting the liver's pool of esterified cholesterol. In order to maintain liver cholesterol levels necessary to support bile acid synthesis, the de novo synthesis of cholesterol increases in the hepatocytes (i.e., an upregulation of 3-hydroxy-3-methylglutaryl coenzyme-A reductase activity) and also increases the uptake of serum cholesterol by upregulating the number of cell surface low density lipoprotein cholesterol receptors ("LDL receptors"). The number of hepatic LDL receptors directly impacts serum low density lipoprotein ("LDL") cholesterol levels, with an increase in the number of LDL receptors resulting in a decrease in serum cholesterol. The net result, therefore, is that serum LDL cholesterol levels decrease when intestinal bile acid reabsorption is reduced.

A class of antihyperlipidemic agents that operates by inhibiting bile acid reabsorption in the ileum recently has been identified. Examples of this class of agents include the substituted benzothiepines disclosed in U.S. Pat. No. 5,994, 391. PCT Patent Application No. WO99/35135 discloses additional substituted benzothiazepine compounds for use as ASBT inhibitors. By way of further example, PCT Patent Application No. WO94/24087 discloses a group of substituted naphthalene compounds for use as ABST inhibitors. The United States Food and Drug Administration, however, has not approved any ASBT inhibitor for use as an antihyperlipidemic agent at this time.

Numerous antihyperlipidemic agents having other modes of action also have been disclosed in the literature as useful for the treatment of hyperlipidemic conditions and disorders. These agents include, for example, commercially available drugs such as nicotinic acid, bile acid sequestrants including cholestryramine and colestipol, 3-hydroxy-3-methylglutaryl coenzyme-A reductase inhibitors ("HMG Co-A reductase inhibitors"), probucol, and fibric acid derivatives including gemfibrozil and clofibrate.

The class of antihyperlipidemic agents known as HMG Co-A reductase inhibitors operates by inhibiting the hepatic enzyme 3-hydroxy-3-methylglutaryl coenzyme-A reductase ("HMG Co-A reductase"). Direct inhibition of HMG Co-A reductase by the monotherapeutic administration of HMG Co-A reductase inhibitors such as pravastatin has been shown to be a clinically effective method of lowering serum LDL cholesterol. Sacks et al., "The Effect of Pravastatin on Coronary Events after Myocardial Infarction in Patients with Average Cholesterol Levels", *New England Journal of Medicine*, 335(14):1001–9 (1996). Monotherapeutic treatment with pravastatin may lead to upregulation of cell surface LDL receptors as a mechanism to provide cholesterol to the liver in support of bile acid synthesis. Fujioka et al., "The Mechanism of Comparable Serum Cholesterol Lowering Effects of Pravastatin Sodium, a 3-Hydroxy-3-Methylglutaryl Coenzyme A Inhibitor, between Once- and Twice-Daily Treatment Regimens in Beagle Dogs and Rabbits", *Jpn. J. Pharmacol.*, Vol. 70, pp. 329–335 (1996).

The administration of an ASBT inhibitor in combination with an HMG Co-A reductase inhibitor is generally disclosed in PCT Application WO98/40375.

The treatment of hypercholesterolemia with an HMG Co-A reductase inhibitor in combination with a bile acid sequestering resin also has been reported in the literature. The administration of the HMG Co-A reductase inhibitor lovastatin in combination with the bile acid sequestering resin colestipol is disclosed in Vega et al., "Treatment of Primary Moderate Hypercholesterolemia With Lovastatin (Mevinolin) and Colestipol", *JAMA*, Vol. 257(1), pp. 33–38 (1987). The administration of the HMG Co-A reductase inhibitor pravastatin in combination with the bile acid sequestering resin cholestyramine is disclosed in Pan et al., "Pharmacokinetics and pharmacodynamics of pravastatin alone and with cholestyramine in hypercholesterolemia", *Clin. Pharmacol. Ther.*, Vol. 48, No. 2, pp. 201–207 (August 1990).

The treatment of hypercholesterolemia with other selected combination regimens also has been reported in the literature. Ginsberg, "Update on the Treatment of Hypercholesterolemia, with a Focus on HMG Co-A Reductase Inhibitors and Combination Regimens", *Clin. Cardiol.*, Vol. 18(6), pp. 307–315 (June 1995), reports that, for resistant cases of hypercholesterolemia, therapy combining an HMG Co-A reductase inhibitor with either a bile acid sequestering resin, niacin or a fibric acid derivative generally is effective and well tolerated. Pasternak et al., "Effect of Combination Therapy with Lipid-Reducing Drugs in Patients with Coronary Heart Disease and 'Normal' Cholesterol Levels", *Annals of Internal Medicine*, Vol. 125, No. 7, pp. 529–540 (Oct. 1, 1996) reports that treatment with either a combination of the HMG Co-A reductase inhibitor pravastatin and nicotinic acid or a combination of pravastatin and the fibric acid derivative gemfibrazol can be effective in lowering LDL cholesterol levels.

It is desirable to provide novel ASBT inhibitors that exhibit improved efficacy, improved potency, and/or reduced dosing requirements for the active compounds relative to the specific combination regimens previously disclosed in the published literature.

SUMMARY OF THE INVENTION

According to one embodiment, the invention comprises novel alkyl/aryl hydroxy or keto thiepine compounds corresponding to Formulas I-1 to I-24 (see the Detailed Description, infra) that are effective agents for the treatment of one or more hyperlipidemic condition(s).

According to another embodiment, the invention comprises pharmaceutical compositions comprising one or more of the novel alkyl/aryl hydroxy or keto thiepine compounds corresponding to Formulas I-1 to I-24 that are suitable for use in treating one or more hyperlipidemic condition(s).

According to yet another embodiment, the invention comprises a method for treating one or more hyperlipidemic condition(s) comprising administering to a subject a therapeutically effective amount of one or more of the novel alkyl/aryl hydroxy or keto thiepine compounds corresponding to Formulas I-1 to I-24.

According to still another embodiment, the invention comprises methods for making the novel alkyl/aryl hydroxy or keto thiepine compounds corresponding to Formulas I-1 to I-24. Other aspects of the invention will be apparent to those of ordinary skill in view of the present description provided below.

DETAILED DESCRIPTION OF THE PREFERRED EMBODIMENTS

According to one embodiment, the invention comprises novel alkyl/aryl hydroxy or keto thiepine compounds defined by Formulas I-1 to I-8:

I-1

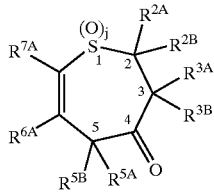

I-1a

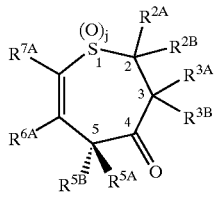

I-1b

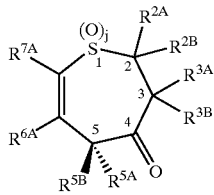

I-2

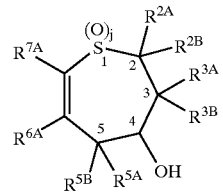

I-3

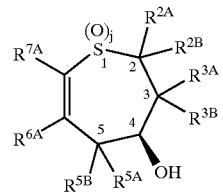

I-4

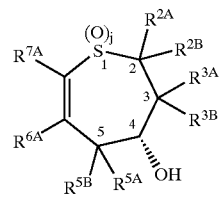

I-5

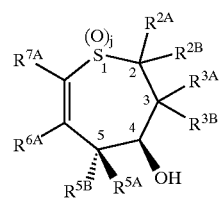

I-6

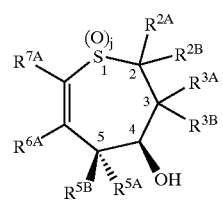

I-7

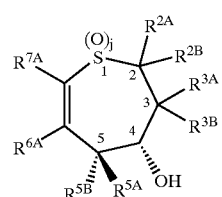

I-8 or a pharmaceutically acceptable salt, solvate, or prodrug thereof wherein j is 0, 1 or 2;

wherein $R^{2A}$ and $R^{2B}$ are independently selected from the group consisting of hydrogen and hydrocarbyl;

wherein $R^{3A}$, $R^{3B}$, $R^{5A}$, and $R^{5B}$ are independently selected from the group consisting of hydrogen, alkyl; cycloalkyl; alkenyl; alkynyl; aryl; heterocyclyl; quaternary heterocyclyl, oxo; aryl-$R^5$; —$OR^9$; —$NR^9R^{10}$; —$SR^9$; —$S(O)R^9$; —$SO_2R^9$; and —$SO_3R^9$;

wherein $R^9$ and $R^{10}$ are independently selected from the group consisting of hydrogen; hydrocarbyl; amino; and hydrocarbylamino;

wherein $R^5$ is selected from the group consisting of hydrogen; alkyl; cycloalkyl; alkenyl; alkynyl; aryl; heterocyclyl; quaternary heterocyclyl; —$OR^9$; —$SR^9$; —$S(O)R^9$; —$SO_2R^9$; and —$SO_3R^9$;

wherein when $R^5$ is said cycloalkyl, aryl or heterocyclyl, said cycloalkyl, aryl or heterocyclyl are optionally substituted with —NH—X—R or —O—X—R;

wherein X is selected from the group consisting of —(C=O)$_s$-alkyl-; —(C=O)$_s$-alkyl-NH—; —(C=O)$_s$-alkyl-O—; —(C=O)$_s$-alkyl-(C=O)$_t$; and a covalent bond, wherein s and t are independently 0 or 1;

wherein R is selected from the group consisting of monosaccharides, disaccharides, and polysaccharides, wherein said monosaccharides, disaccharides, and polysaccharides are optionally protected with one or more sugar protecting groups;

wherein $R^9$ and $R^{10}$ are as previously defined;

wherein, when $R^5 \neq H$, $R^5$ is optionally substituted with one or more radicals independently selected from the group consisting of halogen; —$NO_2$; —CN; oxo; hydrocarbyl; —$OR^{13}$; —$NR^{13}R^{14}$; —$SR^{13}$; —$S(O)R^{13}$; —$SO_2R^{13}$; —$SO_3R^{13}$; —$NR^{13}OR^{14}$; —$NR^{13}NR^{14}R^{15}$; —$CO_2R^{13}$; —OM; —$SO_2OM$; —$SO_2NR^{13}R^{14}$; —$C(O)NR^{13}R^{14}$; —C(O)OM; —$COR^{13}$; —$NR^{13}C(O)R^{14}$; —$NR^{13}C(O)NR^{14}R^{15}$; —$NR^{13}CO_2R^{14}$; —$OC(O)R^{13}$; —$OC(O)NR^{13}R^{14}$; —$NR^{13}SOR^{14}$; —$NR^{13}SO_2R^{14}$; —$NR^{13}SONR^{14}R^{15}$; —$NR^{13}SO_2NR^{14}R^{15}$; —$PR^{13}R^{14}$; —$P(O)R^{13}R^{14}$; —$P^+R^{13}R^{14}R^{15}A^-$; —$P(OR^{13})OR^{14}$; —$S^+R^{13}R^{14}A^-$; and —$N^+R^{13}R^{14}R^{15}A^-$;

wherein $R^{13}$, $R^{14}$, and $R^{15}$ are independently selected from the group consisting of hydrogen and hydrocarbyl;

wherein $A^-$ is a pharmaceutically acceptable anion;

wherein M is a pharmaceutically acceptable cation;

wherein one or more $R^6$ radicals are independently selected from the group consisting of hydrogen; alkyl; cycloalkyl; alkenyl; alkynyl; aryl; heterocyclyl; quaternary heterocyclyl; aryl-$R^5$; $OR^9$; —$NR^9R^{10}$; —$SR^9$; —$S(O)R^9$; and —$SO_3R^9$; halogen; —CN; —$NO_2$; hydrocarbyl; —$R^5$; —$OR^{13}$; —$NR^{13}R^{14}$; —$SR^{13}$; —$S(O)R^{13}$; —$S(O)_2R^{13}$; —$SO_3R^{13}$; —$S^+R^{13}R^{14}A^-$; —$NR^{13}OR^{14}$; —$NR^{13}NR^{14}R^{15}$; —OM; —$SO_2OM$; —$SO_2NR^{13}R^{14}$;—$NR^{14}C(O)R^{13}$;—C(O)OM;—$S(O)NR^{13}R^{14}$; —$N^+R^{13}R^{14}R^{15}A^-$; —$PR^{13}R^{14}$; —$P(O)R^{13}R^{14}$; —$P^-R^{13}R^{14}R^{15}A^-$; amino acid residue; peptide residue; polypeptide residue; and carbohydrate residue;

wherein $R^{13}$, $R^{14}$, $R^{15}$, $A^-$, and M are as defined above; and wherein, in each instance, said hydrocarbyl may be optionally substituted with one or more groups comprising one or more heteroatoms, and wherein, in each instance, said hydrocarbyl optionally may have one or more carbon atoms replaced by one or more heteroatoms independently selected from the group consisting of oxygen, nitrogen, sulfur, phosphorus and combinations thereof.

In one embodiment, aryl-$R^5$ is phenyl substituted with —N(H)—X—$R^{33}$ or —O—X—$R^{33}$ wherein X is selected from the group consisting of:
—(C=O)s-alkyl-; —(C=O)s-alkyl-NH—; —(C=O)s-alkyl-O—; —(C=O)s-alkyl-C=O)t; and a covalent bond; wherein $R^{33}$ is selected from selected from the group consisting of monosaccharides, disaccharides, and polysaccharides; and s and t are independently 0 or 1.

In another embodiment, aryl-$R^5$ is phenyl substituted at the para-position (or ortho-position) with —N(H)—X—$R^{33}$ or —O—X—$R^{33}$ wherein X is selected from the group consisting of:
—(C=O)s-alkyl-; —(C=O)s-alkyl-NH—; —(C=O)s-alkyl-O—; —(C=O)s-alkyl-C=O)t; and a covalent bond; and wherein $R^{33}$ is selected from selected from the group consisting of monosaccharides, disaccharides, and polysaccharides; and s and t are independently 0 or 1.

In another embodiment, aryl-$R^5$ is phenyl substituted at the meta-position with —N(H)—X—$R^{33}$ or —O—X—$R^{33}$ wherein X is selected from the group consisting of:
—(C=O)s-alkyl-; —(C=O)s-alkyl-NH—; —(C=O)s-alkyl-O—; —(C=O)s-alkyl-C=O)t; and a covalent bond; and $R^{33}$ is selected from selected from the group consisting of monosaccharides, disaccharides, and polysaccharides; and s and t are independently 0 or 1.

In another embodiment, aryl-$R^5$ is phenyl substituted with a radical selected from the group consisting of members (1)–(24), (25)–(48), or (49)–(70), of Table 1 below.

Furthermore, the term "hydrocarbyl" includes, but is not limited to moieties such as alkyl, cycloalkyl, alkenyl, cycloalkenyl, alkynyl and moieties optionally substituted with aliphatic or cyclic hydrocarbon groups such as alkaryl, alkenaryl and alkynaryl. Typically, the "hydrocarbyl" moieties comprise 1–20 carbon atoms, 1–18 carbon atoms, 1–12 carbon atoms, 3–12 carbon atoms, 1–6 carbon atoms, or 3–6 carbon atoms.

Also, $R^{5A}$, $R^{5B}$, $R^{6A}$ and $R^{7A}$ may be independently selected from the group consisting of hydrogen, aryl, heterocycle, quaternary heterocycle and quaternary heteroaryl wherein said aryl, heteroaryl, quaternary heterocycle, and quaternary heteroaryl can be substituted with one or more substituent groups independently selected from the group consisting of alkyl, alkenyl, alkynyl, polyalkyl, polyether, aryl, haloalkyl, cycloalkyl, heterocycle, arylalkyl, halogen, oxo, $OR^{13}NR^{13}R^{14}$, $SR^{13}$, $S(O)R^{13}$, $SO_2R^{13}$, $SO_3R^{13}$, $NR^{13}OR^{14}$, $NR^{13}NR^{14}R^{15}$, $NO_2$, $CO_2R^{13}$, CN, OM, $SO_2OM$, $SO_2NR^{13}R^{14}$, C(O)$NR^{13}R^{14}$, C(O)OM, $COR^{13}$, $P(O)R^{13}R^{14}$, $P^+R^{13}R^{14}R^{15}A^-$, $P(OR^{13})OR^{14}$, $S^+R^{13}R^{14}A^-$, and $N^+R^9R^{11}R^{12}A^-$;

wherein said alkyl, alkenyl, alkynyl, polyalkyl, polyether, aryl, haloalkyl, cycloalkyl, and heterocycle can optionally have one or more carbons replaced by O, $NR^7$, $N^+R^7R^8A^-$, S, SO, $SO_2$, $S^+R^7A^-$, $PR^7$, $P(O)R^7$, $P^+P^7R^8A^-$, or phenylene;

wherein said alkyl, alkenyl, alkynyl, polyalkyl, polyether, aryl, haloalkyl, cycloalkyl, and heterocycle can be further substituted with one or more substituent groups selected from the group consisting of $OR^7$, $NR^7R^8$, SR, $S(O)R^7$, $SO_2R^7$, $SO_3R^7$, $CO_2R^7$, CN, oxo, $CONR^7R^8$, $N^+R^7R^8R^9A^-$; alkyl alkenyl, alkynyl, aryl, cycloalkyl, heterocycle, arylalkyl, quaternary heterocycle, quaternary heteroaryl, $P(O)R^7R^8$, $P^+R^7R^8A^-$, and $P(O)(OR^7)OR^8$ wherein $R^7$ and $R^8$ are independently selected from hydrogen and alkyl.

Even further, $R^{5A}$, $R^{5B}$, $R^{6A}$ and $R^{7A}$ may independently have the formula (I):

wherein t is an integer selected from 0, 1, 2, 3, 4 and 5;
wherein Ar is selected from the group consisting of phenyl, thiophenyl, pyridyl, piperazinyl, piperonyl, pyrrolyl, naphthyl, furanyl, anthracenyl, quinolinyl, isoquinolinyl, quinoxalinyl, imidazolyl, pyrazolyl, oxazolyl, isoxazolyl, pyrimidinyl, thiazolyl, triazolyl, isothiazolyl, indolyl, benzoimidazolyl, benzoxazolyl, benzothiazolyl, and benzoisothiazolyl;

wherein one or more $R^5$ are independently selected from the group consisting of alkyl, alkenyl, alkynyl, polyalkyl, polyether, aryl, haloalkyl, cycloalkyl, heterocycle, arylalkyl, halogen, oxo, $OR^{13}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}R^{15}$, $NO_2$, $CO_2R^{13}$, $CN$, $OM$, $SO_2OM$, $SO_2NR^{13}R^{14}$, $C(O)NR^{13}R^{14}$, $C(O)OM$, $CR^{13}$, $P(O)R^{13}R^{14}$, $P^+R^{13}R^{14}R^{15}A^-$, $P(OR^{13})OR^{14}$, $S^+R^{13}R^{14}A^-$, and $N^+R^9R^{11}R^{12}A^-$;

wherein said alkyl, alkenyl, alkynyl, polyalkyl, polyether, aryl, haloalkyl, cycloalkyl, and heterocycle can be further substituted with one or more substituent groups selected from the group consisting of $OR^7$, $NR^7R^8$, $SR^7$, $S(O)R^7$, $SO_2R^7$, $SO_3R^7$, $CO_2R^7$, $CN$, oxo, $CONR^7R^8$, $N^+R^7R^8R^9R^-$; alkyl, alkenyl, alkynyl, aryl, cycloalkyl, heterocycle, arylalkyl, quaternary heterocycle, quaternary heteroaryl, $P(O)R^7R^8$, $P^+R^7R^8A^-$, and $P(O)(OR^7)OR^8$;

wherein said alkyl, alkenyl, alkynyl, polyalkyl, polyether, aryl, haloalkyl, cycloalkyl, and heterocycle can optionally have one or more carbons replaced by O, $NR^7$, $N^+R^7R^8A^-$, S, SO, $SO_2$, $S^+R^7A^-$, $PR^7$, $P(O)R^7$, $P^+R^7R^1A^-$; or phenylene; and wherein t and $R^5$ are as previously described.

Yet, even further, $R^{5A}$, $R^{5B}$, $R^{6A}$ and $R^{7A}$ may independently have the formula (II):

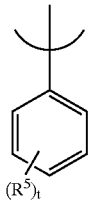

(II)

wherein t and $R^5$ are as previously described.

Furthermore, $R^{6A}$ and $R^{7A}$ are independently selected from the group consisting of:

(a) alkyl, aryl, cycloalkyl, heterocycle, polyalkyl, acyloxy, polyether, halogen, $OR^{13}$, $NR^{13}R^{14}$, $NR^{13}NR^{14}R^{15}$, $N^+R^{11}R^{12}A^-$, $SR^{13}S^+R^{13}R^{14}$, $CO_2R^{13}$, $NR^{14}C(O)R^{13}$, and $NR^{14}C(O)R^{13}$, wherein alkyl, aryl, cycloalkyl, heterocycle, polyalkyl, acyloxy, and polyether, can be further substituted with $OR^9$, $NR^9R^{10}$, $N^+R^9R^{10}R^{12}A^-$, $SR^9$, $S(O)R^9$, $SO_2R^9$, $SO_3R^9$, oxo, $CO_2R^9$, CN, halogen, $CONR^9R^{10}SO_2OM$, $SO_2NR^9R^{10}$, $PO(OR^{16})OR^{17}$, $P^+R^9R^{11}R^{12}A^-$, $S^+R^9R^{10}A^-$, or $C(O)OM$;

wherein in $R^{6A}$ and/or $R^{7A}$, one or more carbons are optionally replaced by O, $NR^{13}$, $N^+R^{13}R^{14}A^-$, S, SO, $SO_2$, $S^+R^{13}A^-$, $PR^{13}$, $P(O)R^{13}$, $P^+R^{13}R^{14}A^-$, phenylene, amino acid, peptide, polypeptide, carbohydrate, polyether, or polyalkyl, and wherein in said polyalkyl, phenylene, amino acid, peptide, polypeptide, and carbohydrate, one or more carbons are optionally replaced by O, $NR^9$, $N^+R^9R^{10}A^-$, S, SO, $SO_2$, $S^+R^9A^-$, $PR^9$, $P^+R^9R^{10}A^-$, or $P(O)R^9$;

(b) alkyl, aryl, cycloalkyl, heterocycle, polyalkyl, acyloxy, polyether, halogen, $OR^{13}NR^{13}R^{14}NR^{13}$ $NR^{14}R^{15}$, $N^+R^9R^{11}R^{12}A^-$, $SR^{13}S^+R^{13}R^{14}$, $CO_2R^{13}$, $NR^{14}C(O)R^{13}$, and $NR^{14}C(O)R^{13}$;

wherein alkyl, aryl, cycloalkyl, heterocycle, polyalkyl, acyloxy, and polyether, can be further substituted with $OR^9$, $NR^9R^{10}$, $N^+R^9R^{11}R^{12}A^-$, $SR^9$, $S(O)R^9$, $SO_2R^9$, $SO_3R^9$, oxo, $CO_2R^9$, CN, halogen, $CONR^9R^{10}SO_2OM$, $SO_2NR^9R^{10}$, $PO(OR^{16})OR^{17}$, $P^+R^9R^{11}R^{12}A^-$, $S^+R^9R^{10}A^-$, or $C(O)OM$;

wherein $R^7$, $R^8$, $R^9$, $R^{10}$, $R^{11}$, $R^{12}$, $R^{13}$, $R^{14}$, $R^{15}$ and $A^-$ are as previously defined and $R^{16}$ and $R^{17}$ are independently selected from the group consisting of hydrogen and alkyl, and optionally $R^{13}=R^{14}=$methyl;

wherein in $R^{6A}$ and/or $R^{7A}$, one or more carbons are optionally replaced by O, $NR^{13}$, $N^+R^{13}R^{14}A^-$, S, SO, $SO_2$, $S^+R^{13}A^-$, $PR^{13}$, $P(O)R^{13}$, $P^+R^{13}R^{14}A^-$, phenylene, amino acid, peptide, polypeptide, carbohydrate, polyether, or polyalkyl; and wherein in said polyalkyl, phenylene, amino acid, peptide, polypeptide, and carbohydrate, one or more carbons are optionally replaced by O, $NR^9$, $N^+R^9R^{10}A^-$, S, SO, $SO_2$, $S^+R^9A^-$, $PR^9$, $P^+R^9R^{10}A^-$, or $P(O)R^9$;

(c) polyether, $OR^{13}$, $NR^{13}R^{14}$ and $N^+R^9R^{11}R^{12}A^-$;

(d) polyether, $OR^{13}$ and $NR^{13}R^{14}$.

According to another embodiment, the class of ASBT inhibitor compounds are as previously defined by Formulas I-1 to I-8 except that:

j is 2;

$R^{2A}$ and $R^{2B}$ are hydrogen;

wherein $R^{3A}$ and $R^{3B}$ are independently selected from the group consisting of hydrogen and alkyl; and wherein $R^{5A}$, $R^{5B}$, $R^{6A}$ and $R^{7A}$ are independently selected from the group consisting of hydrogen and phenyl optionally substituted at the meta or para position with $R^5$ selected from the group consisting of members (1)–(70) denoted in Table 1 below. It is noted that when $R^5$ is a bridging linkage, dimeric or polymeric compounds of the type {-thiepene-bridge-thiepene-} are formed wherein the thiepene is selected from the group consisting of Formulas I-1 to I-24 and exemplary bridging $R^5$ groups include, but are not limited to, (7), (17) and (24) in Table 1 below.

TABLE 1

TABLE 1-continued
| $R^5$ |
| --- |
| (2) 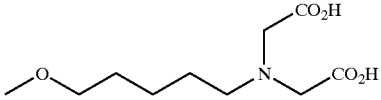 |
| (3) 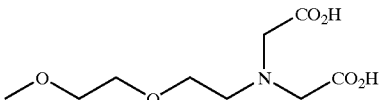 |
| (4) 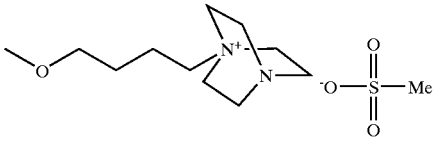 |
| (5) 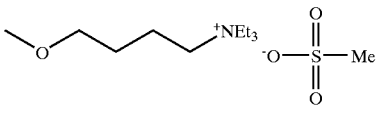 |
| (6) 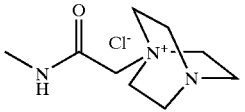 |
| (7) 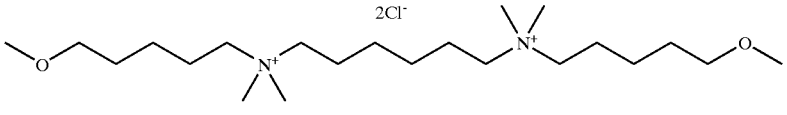 |
| (8) 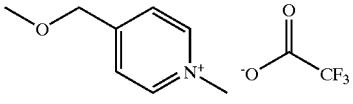 |
| (9) 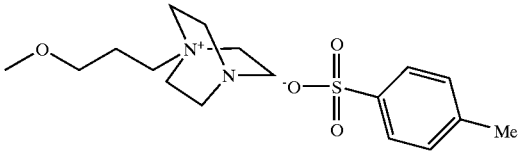 |
| (10) 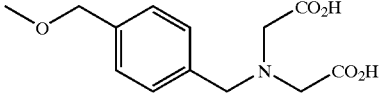 |
| (11) 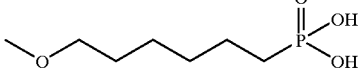 |
| (12) 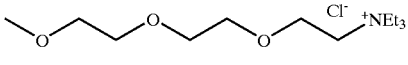 |
| (13) 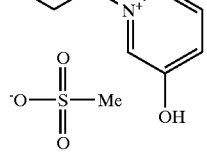 |

TABLE 1-continued

| R⁵ |
|---|
| (14) structure: methoxymethyl-pyridine-CH₂-N(CH₂CO₂H)₂ |
| (15) structure: N-methylbenzamide-CH₂-N⁺(DABCO) Cl⁻ |
| (15a) structure: methylureido-phenyl-CH₂-N⁺(DABCO) Cl⁻ |
| (16) structure: methoxymethyl-phenyl-CH₂-N⁺(DABCO) Cl⁻ |
| (17) MeO-CH₂-O-R-O-Me, R = 1000 MW PEG |
| (18) structure: 4-(methylamino)-1-methylpyridinium tosylate |
| (19) structure: MeNH-SO₂-N(CH₂CO₂H)₂ |
| (20) structure: MeO-(CH₂)₄-tetrazole |
| (21) structure: MeO-(CH₂)₄-S-tetrazole-CH₂CO₂H |
| (22) MeO-CH₂-C(O)-NH-CH₂-CO₂H |
| (23) MeO-CH₂-C₆H₄-CO₂H |

TABLE 1-continued

| $R^5$ |

(24) [Structure: methyl carbamate attached to a hexaazamacrocyclic cage complex with metal center M]

M = Co<sup>II, III</sup>, Mn<sup>II, III</sup>, Fe<sup>II, III</sup>, Ni<sup>II, III</sup>, Cr<sup>III</sup>, Cu<sup>II</sup>, Zn<sup>II</sup>, Cd<sup>II</sup>, Ga<sup>II</sup>, In<sup>III</sup>, V<sup>IV</sup>, Ru<sup>II</sup>, Pr<sup>IV</sup>, Rh<sup>III</sup> or Ir<sup>III</sup>

(25) [Structure: N-methyl amide of 5-(polyhydroxyhexylamino)pentanoic acid]

(26) [Structure: N-methyl amide linked via butyl chain to amide of gluconic acid derivative]

(27) [Structure: N-methyl gluconamide]

(28) [Structure: N-methyl amide with long alkyl chain linked to gluconamide]

(29) [Structure: N-methyl amide with butyl linker to pyranose sugar]

(30) [Structure: N-methyl amide with butyl linker to glucuronic acid pyranose]

(31) [Structure: N-methyl glycosylamine pyranose]

TABLE 1-continued

R⁵

(32) – (40) [chemical structures]

TABLE 1-continued

| R⁵ |
|---|
| (41) structure: methyl ester-(CH₂)₃-pyranose ring with OH, OH, OH, CH₂OH |
| (42) structure: methyl ester-(CH₂)₃-pyranose ring with OH, OH, OH, COOH |
| (43) structure: methoxy-pyranose with OH, OH, OH, CH₂OH |
| (44) structure: methoxy-pyranose with OH, OH, OH, COOH |
| (45) structure: methyl ester-(CH₂)₉-NH-pyranose with OH, OH, OH, COOH |
| (46) structure: methyl ester-(CH₂)₉-NH-pyranose with OH, OH, OH, CH₂OH |
| (47) structure: methyl ester-(CH₂)₃-N-pyranose with OH, OH, OH, COOH |
| (48) structure: methyl ester-(CH₂)₃-N-pyranose with OH, OH, OH, CH₂OH |

TABLE 1-continued
| $R^5$ |
|---|
| (49) 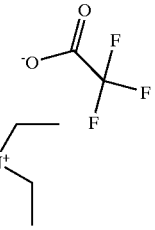 |
| (50) 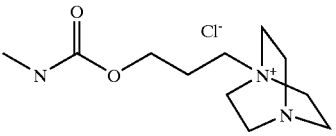 |
| (51) 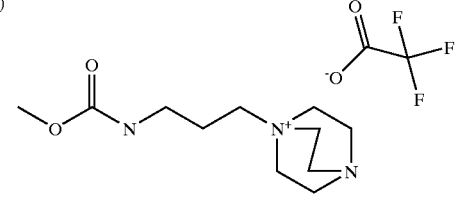 |
| (52) 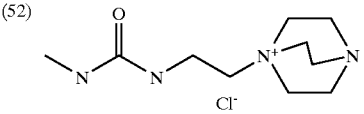 |
| (53) 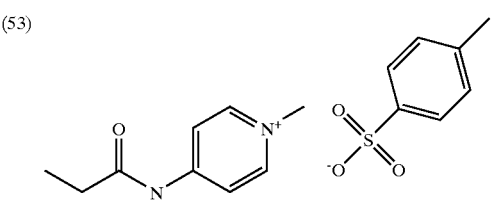 |
| (54) 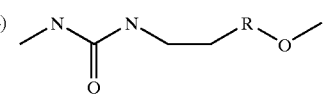 |
| (55) 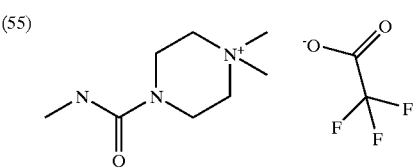 |
| (56) 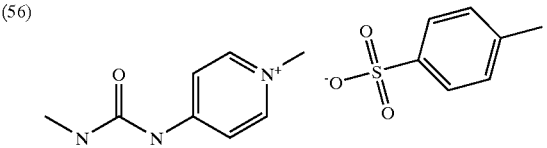 |

TABLE 1-continued

| R⁵ |
|---|
| (57) Structure: CH₃-N(CH₂COOH)(CH₂COOH) |
| (58) N-methyl phthalimide with two COOH groups on benzene ring |
| (59) Pyridine with 2-COOH, 6-acetyl, and 4-O-(CH₂)₄-OCH₃ substituents |
| (60) CH₃O-CH₂CH₂-O-CH₂CH₂-CH(COOH)₂ |
| (61) (CH₃)₃N⁺-CH₂CH₃  I⁻ |
| (62) (CH₃CH₂)₄N⁺  Br⁻ |
| (63) Ethyltriphenylphosphonium  Br⁻ |

TABLE 1-continued

R⁵

(64) 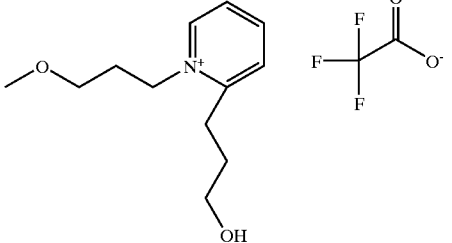

(65) 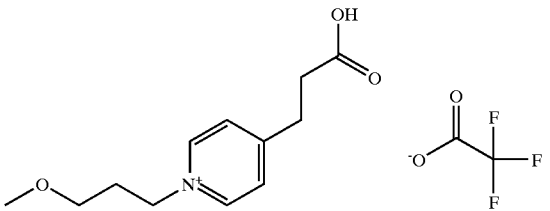

(66) 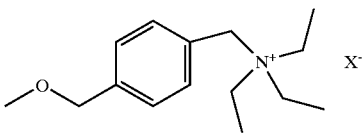

(67) 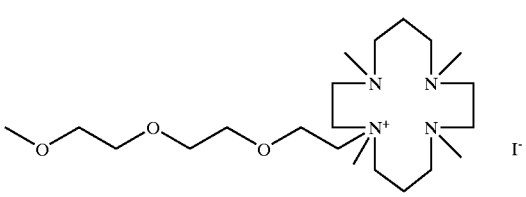

(68) 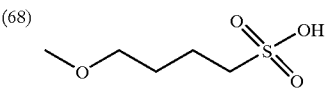

(69) 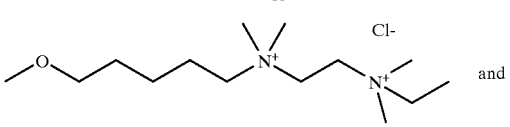 and

(70) 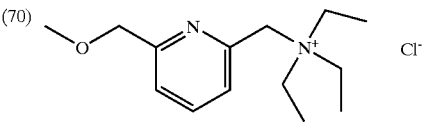

Also, in tails (1)–(70) the specified anion may be replaced by another pharmaceutically acceptable anion (e.g., A⁻ which anion is as previously described). Optionally, $R^5$ may be selected from the following: (1)–(24), (25)–(48) or (49)–(70) from Table 1. Further, $R^5$ may be acidic or contain a quaternary ammonium nitrogen. Even further, $R^5$ may be selected from the following: (1)–(5), (6)–(10), (11)–(15a), (16)–(20), (21)–(25), (26)–(30), (31)–(35), (36)–(40), (41)–(45), (46)–(50), (51)–(55), (56)–(60), (61)–(65), (66)–(70), or combinations thereof from Table 1.

Other exemplary embodiments of ASBT inhibitors of the present invention are represented by Formulas I-9 to I-16 below.

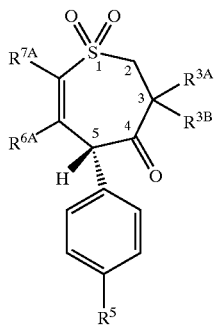

I-9

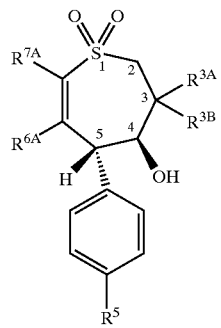

I-13

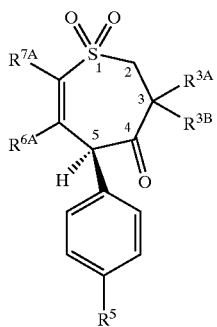

I-10

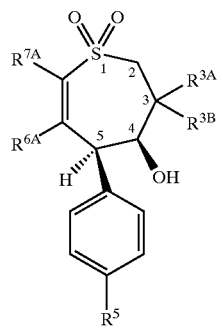

I-14

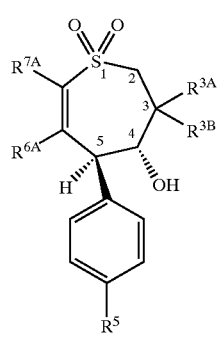

I-15

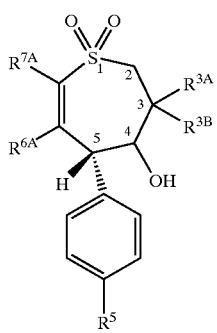

I-11

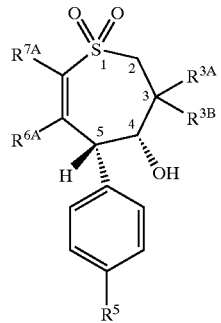

I-16

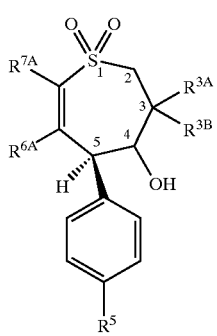

I-12 wherein $R^{3A}$ and $R^{3B}$ are independently selected from hydrogen and alkyl, wherein $R^{6A}$ and $R^{7A}$ are the same as previously defined, and wherein $R^5$ is selected from the members (1)–(70) of Table 1 above. Note that while $R^5$ is described as being attached to the para-position of the phenyl ring, $R^5$ may be attached to either the ortho or the meta position of the subject phenyl ring described above (e.g., where appropriate, in any of Formulas I-9 to I-16 above and in any of Formulas I-17 to I-24 depicted below.). Preferably, the $R^5$ substituent is at the meta- or the para-position of the $C_5$-phenyl group.

Additional exemplary embodiments of ASBT inhibitors of the present invention are represented by formulas I-17 to I-24 below:

I-17
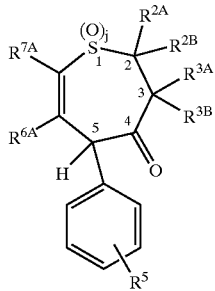

I-18
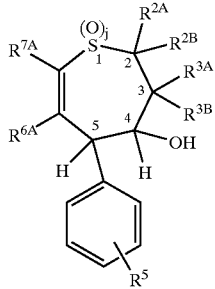

I-19
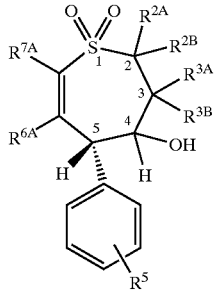

I-20
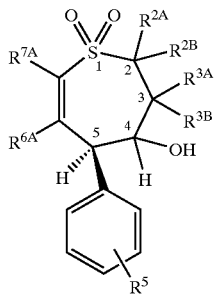

I-21
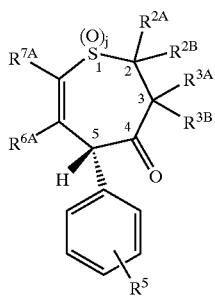

I-22
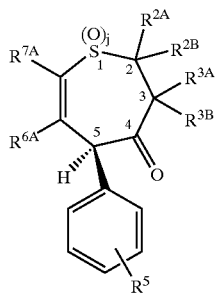

I-23
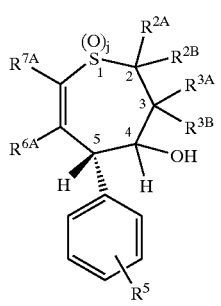

I-24
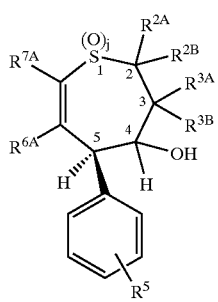

wherein $R^{2A}$, $R^{2B}$, $R^{3A}$, $R^{3B}$, $R^5$, $R^{6A}$, $R^{7A}$ and j are as previously described. Optionally, $R^{2A}=R^{2B}=H$ and/or $R^{3A}=R^{3B}$ and/or j=2.

The novel alkyl/aryl hydroxy or keto thiepine compounds of the present invention are safe and effective antihyperlipidemic agents. These compounds generally exhibit at least one desirable characteristic which includes, but is not limited to: (a) improved potency, (b) improved solubility profile, (c) improved compatibility with conventional routes of oral administration, (d) improved safety profile, and (e) elimination of a chiral center at the 4-position ring carbon in the case of the novel di-fluorinated benzothiepenes of the present invention.

The compounds of the present invention are useful for, but not limited to, the treatment of one or more hyperlipidemic condition(s) including the prophylactic treatment of hyperlipidemia in a subject. The methods, compounds, pharmaceutical compositions and kits of the present invention also are useful for the prophylaxis and/or treatment of gallstones. Besides being useful for human treatment, the above-described compounds (e.g., I-1 to I-24) also are useful for veterinary treatment of companion animals (e.g., horses, dogs, cats, etc.), exotic animals and farm animals, including mammals, rodents, and the like. Even though the invention is described in terms of human biology, it will be understood by those of ordinary skill that the present invention is applicable to other mammals, as well.

The above-noted ASBT inhibitors of the present invention may be made according to the exemplary chemical Schemes 1 and 2 below:

SCHEME 1

$R^{3A}$, $R^{3B}$ = Bu, Et, Me, etc.
$R^5$ = alkyl, heterocyclyl, -R-ionic group, etc.
$R^{6A}$, $R^{7A}$ = Me, Et, Bu, etc.

$R^{5'}$ = H, OMe, $NR_2$, halogen, etc

[1] Pure Appl Chem, 53, 2333 (1981).
[2] J. Am. Chem. Soc., 100, 2252 (1978); 108, 7791 (1986)
[3] Tetrahedron Lett., 30(16), 2057–60; 1989
[4] J. Org. Chem., 50, 4218 (1985)
[5] J. Org. Chem., 53, 5789 (1988).
[6] J. Organomet. Chem., 438 (1–2), 11 (1992).
[7] J. Organomet. Chem., 319 (2), 161 (1987).
[8] Provisional Application No. 60/330,892; See Ex. 1457–1459.

In Scheme 1, commercially available compound 1 will be reacted with zinc activated with 1,2-dibromoethane in THF, according to the procedure described in *J. Org. Chem.*, 53, 5789 (1988), to give the corresponding benzylic zinc bromide (not shown). This intermediate will be reacted with $Hg_2Cl_2$ in THF, according to the procedure described in *J. Organomet. Chem.*, 438 (1–2), 11 (1992), except that said intermediate above is substituted for the corresponding compound in said reference, to give the corresponding dibenzylicmercurial intermediate (not shown). This intermediate will be reacted with aluminum granules in toluene or xylene, according to the procedure described in *J. Organomet. Chem.*, 319 (2), 161 (1987), except that said intermediate above is substituted for the corresponding compound in said reference, to give compound 2.

Compound 3a may be synthesized exactly according to the procedures provisional application No. 60/330,892 filed on Nov. 2, 2001 entitled Novel Mono- and Di-fluorinated Benzothiepine Compounds as Inhibitors of Apical Sodium Co-dependent Bile Acid Transport (ASBT) and Taurocholate Uptake, Examples 1457–1459 for $R^{3A}=R^{3B}=Bu$. For other R groups, the same procedure will be employed, except that other known 1,3-diols will be substituted for 2,2-dibutylpropane-1,3-diol in Example 1457. Compound 3a is then reacted with MeOH and HCl to give the corresponding dimethylacetal 3.

Compound 4 will be prepared according to the procedure described in *Sulfur Lett.*, 8(1), 31–5; 1988, except that compound 3 above is substituted for the corresponding compound in said reference.

Commercially available compound 5 will be reacted with $Al(R^{5'}\text{-benzyl})_3$ and $Cp_2ZrCl_2$, according to the procedure described in *Pure Appl Chem*, 53, 2333 (1981), except that compound 2 and alkyne 5 are substituted for the corresponding compounds in said reference, to give the corresponding trisubstituted alkene intermediate (not shown). This intermediate will be reacted with $I_2$, according to the procedure described in *J. Am. Chem. Soc.*, 100, 2252 (1978); 108, 7791 (1986), except that said intermediate will be substituted for the corresponding compound in said reference, to give compound 6.

Compound 6 will be reacted with Li or BuLi to give the corresponding lithioalkene intermediate (not shown). This intermediate will be reacted with X—S—S—X or X—S-Ts (prepared according to reference 4), according to the procedure described in *Tetrahedron Lett.*, 30(16), 2057–2060; 1989, to give compound 7.

Compound 7 will be oxidized with mCPBA or oxone to give the corresponding sulfone intermediate (not shown). This intermediate will be hydrolyzed with aq. HCl to give compound 8.

Compound 9 will be prepared in accordance with step 6 of Example 1398a as described in U.S. Pat. No. 5,994,391 except that Compound 8 above is substituted for the corresponding compound used in step 6 of Example 1398a.

Compound 10 will be prepared according to procedures outlined for Example 1426 as described in U.S. Pat. No. 5,994,391 except that Compound 9 above is substituted for the corresponding compound used in Example 1426. Each of the patents, patent applications, publications or other references noted herein are incorporated by reference in their entirety into this application for all purposes.

SCHEME 1A

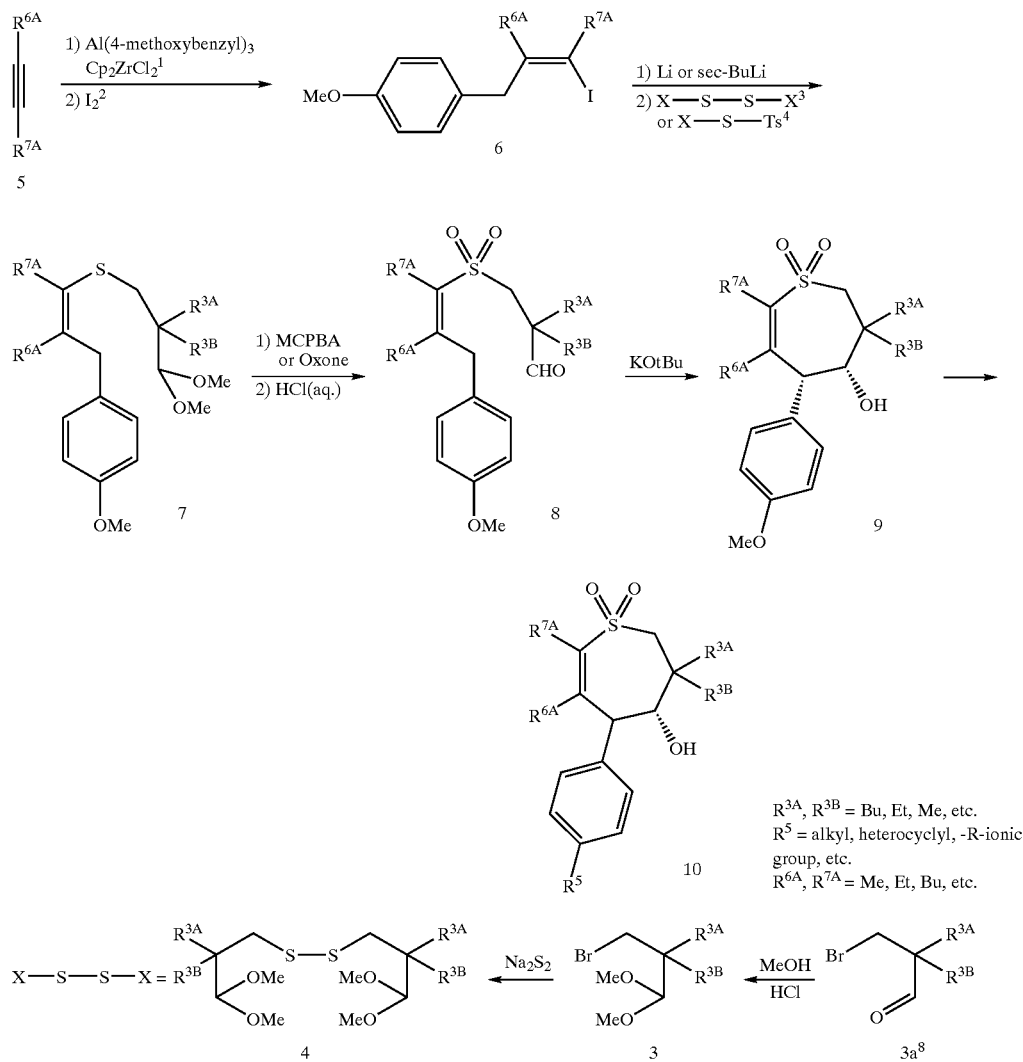

-continued

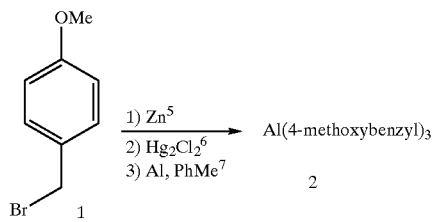

[1] Pure Appl Chem, 53, 2333 (1981)
[2] J. Am. Chem. Soc., 100, 2252 (1978); 108, 7791 (1986)
[3] Tetrahedron Lett., 30(16), 2057–60; 1989
[4] J. Org. Chem., 50, 4218 (1985)
[5] J. Org. Chem., 53, 5789 (1988).
[6] J. Organomet. Chem., 438 (1–2), 11 (1992).
[7] J. Organomet. Chem., 319 (2), 161 (1987).
[8] Provisional Application No. 60/330,892; See Ex. 1457–1459.

In Scheme 1A, commercially available compound 1 will be reacted with zinc activated with 1,2-dibromoethane in THF, according to the procedure described in *J. Org. Chem.*, 53, 5789 (1988), to give the corresponding benzylic zinc bromide (not shown). This intermediate will be reacted with $Hg_2Cl_2$ in THF, according to the procedure described in *J. Organomet. Chem.*, 438 (1–2), 11 (1992), except that said intermediate above is substituted for the corresponding compound in said reference, to give the corresponding dibenzylicmercurial intermediate (not shown). This intermediate will be reacted with aluminum granules in toluene or xylene, according to the procedure described in *J. Organomet. Chem.*, 319 (2), 161 (1987)., except that said intermediate above is substituted for the corresponding compound in said reference, to give compound 2.

Compound 3a may be synthesized exactly according to the procedures in Mono & difluoro patent C-3385, Examples 1457–1459 for $R^{3A}=R^{3B}=Bu$. For other R groups, the same procedure will be employed, except that other known 1,3-diols will be substituted for 2,2-dibutylpropane-1,3-diol in Example 1457. Compound 3a is then reacted with MeOH and HCl to give the corresponding dimethylacetal 3.

Compound 4 will be prepared according to the procedure described in *Sulfur Lett.*, 8(1), 31–5; 1988, except that compound 3 above is substituted for the corresponding compound in said reference.

Commercially available compound 5 will be reacted with Al(4-methoxybenzyl)$_3$ and $Cp_2ZrCl_2$, according to the procedure described in *Pure Appl Chem*, 53, 2333 (1981), except that compound 2 and alkyne 5 are substituted for the corresponding compounds in said reference, to give the corresponding trisubstituted alkene intermediate (not shown). This intermediate will be reacted with $I_2$, according to the procedure described in *J. Am. Chem. Soc.*, 100, 2252 (1978); 108, 7791 (1986), except that said intermediate will be substituted for the corresponding compound in said reference, to give compound 6.

Compound 6 will be reacted with Li or BuLi to give the corresponding lithioalkene intermediate (not shown). This intermediate will be reacted with X—S—S—X or X—S-Ts (prepared according to reference 4), according to the procedure described in *Tetrahedron Lett.*, 30(16), 2057–2060; 1989, to give compound 7.

Compound 7 will be oxidized with mCPBA or oxone to give the corresponding sulfone intermediate (not shown). This intermediate will be hydrolyzed with aq. HCl to give compound 8.

Compound 9 will be prepared in accordance with step 6 of Example 1398a as described in U.S. Pat. No. 5,994,391 except that Compound 8 above is substituted for the corresponding compound used in step 6 of Example 1398a.

Compound 10 will be prepared according to procedures outlined for Example 1426 as described in U.S. Pat. No. 5,994,391 except that Compound 9 above is substituted for the corresponding compound used in Example 1426.

SCHEME 1B

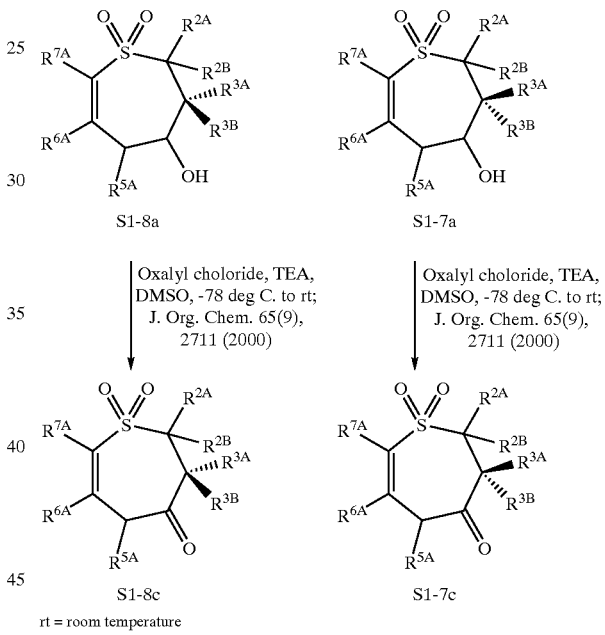

rt = room temperature

It is noted that optically active compounds of the present invention can be prepared by using optically active starting materials of compound 3 or by resolution of compounds S1-7a and S1-8a. Resolution of compounds S1-7a and S1-8a can be accomplished with optical resolution agents well known in the art and described in J. Org. Chem., 39 (26), 3904–3906 (1974), J. Org. Chem., 42 (16), 2781–2782 (1977) and J. Org. Chem., 44 (26), 4891–4896 (1979).

According to Scheme 1B, compounds S1-7a and/or S1-8a should first be converted to the ketones S1-7c and/or S1-8c by treatment with oxalyl chloride, triethanolamine (TEA) and dimethyl sulfoxide (DMSO) as indicated in J. Org. Chem., 65 (9), 2711–2715 (2000).

Also, optically active compounds S1-7a, S1-8a, S1-7c and S1-8c can be obtained by using optically active starting materials of compound 3 or by using previously described optical resolving agents to separate optically active compounds S1-7a and S1-8a or S1-7c and S1-8c from each other, respectively. Thereafter, separated compounds S1-7a and S1-8a should be converted to S1-7c and S1-8c, respectively, as noted above.

SCHEME 1C

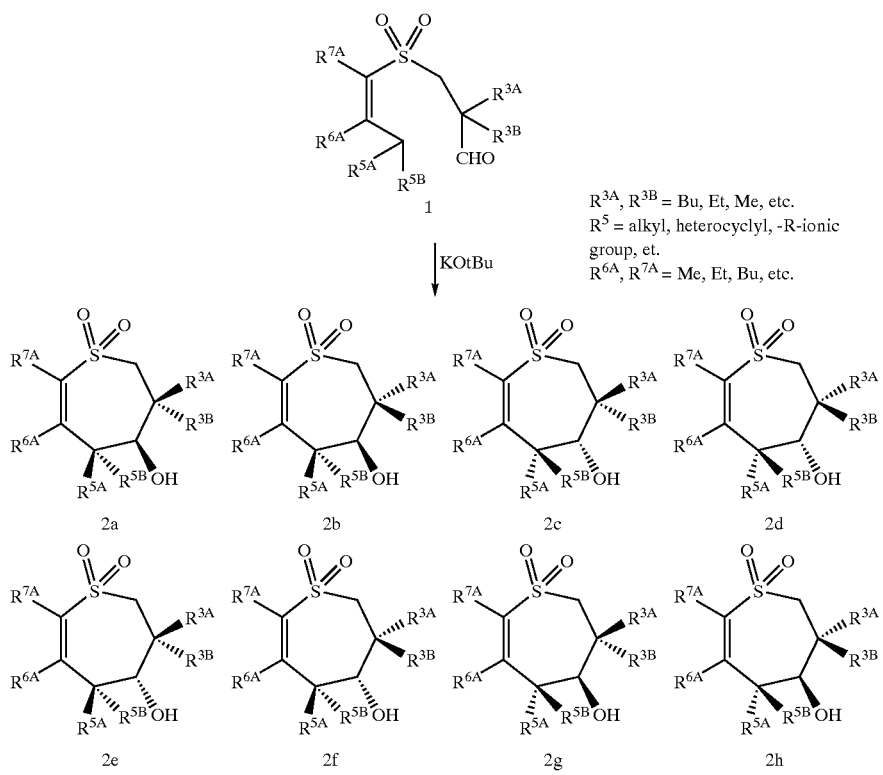

$R^{3A}, R^{3B}$ = Bu, Et, Me, etc.
$R^5$ = alkyl, heterocyclyl, -R-ionic group, et.
$R^{6A}, R^{7A}$ = Me, Et, Bu, etc.

In Scheme 1C, compounds 2a–2h will be prepared in accordance with step 6 of Example 1398a as described in U.S. Pat. No. 5,994,391 except that Compound 1 above is substituted for the corresponding compound used in step 6 of Example 1398a. Compounds 2a–2h will be separated from each other using optical resolving agents.

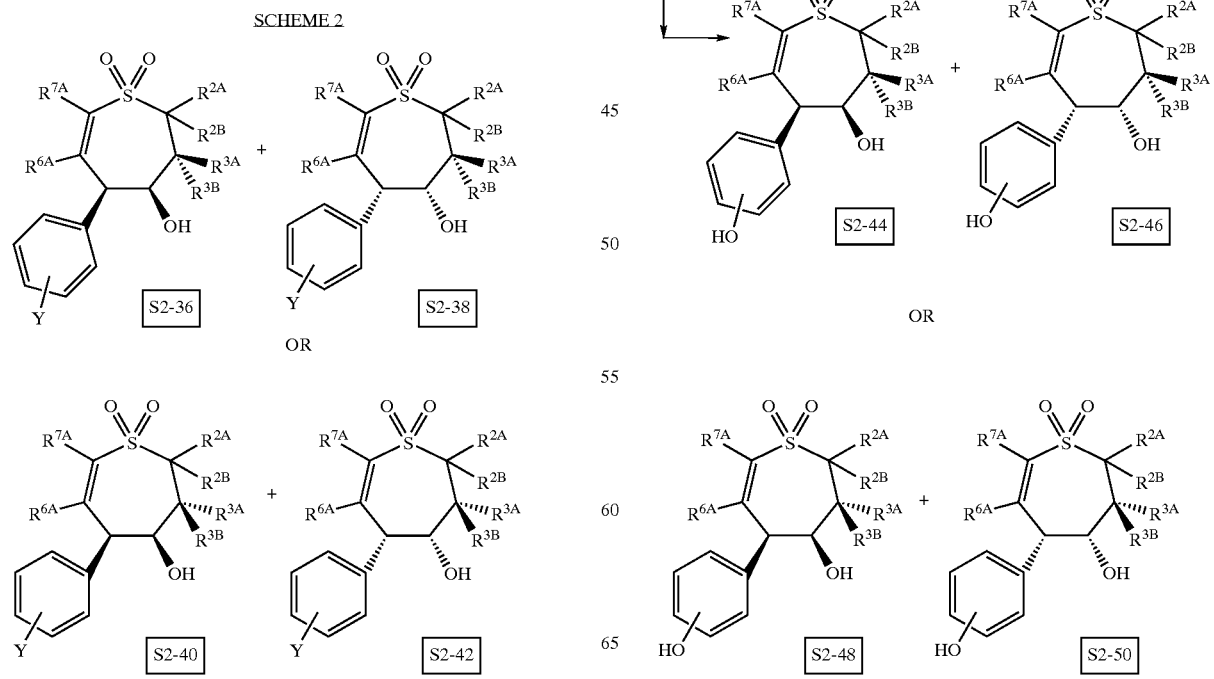

(where Y = MeO for each of S2-36, S2-38, S2-40 and S2-42)

-continued

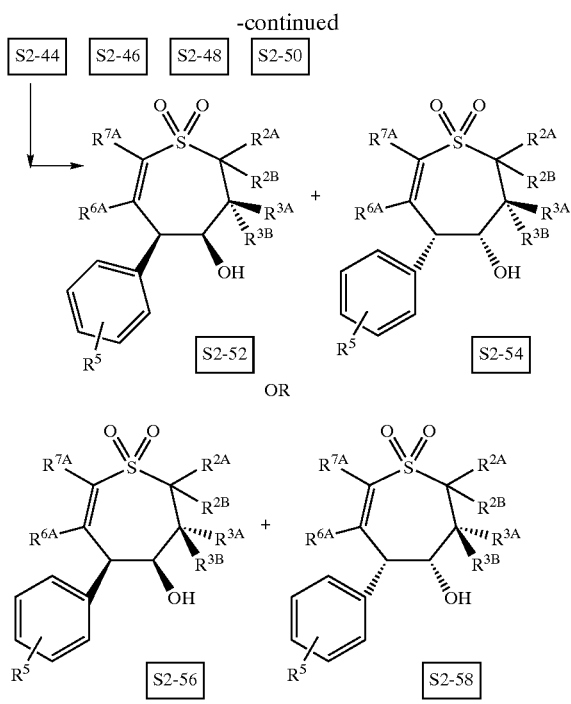

$R^5$ = substituents (1)–(70) noted in Table 1 for each of S2-52, S2-54, S2-56 and S2-58

In Scheme 2, compound S2-36, S2-38, S2-40 and S2-42 are formed according to Scheme 1 using the appropriate chiral materials or by resolving the chiral compounds S2-36, S2-38, S2-40 and S2-42 using the previously noted optical resolution agents. Further, in Scheme 2, Y typically is OMe. However, Y may be another alkoxy, or a halogen (F, Cl, Br, and I).

Exemplary conversion of S2-36, S2-38, S2-40 and S2-42 (e.g., wherein Y=OMe) into S2-44, S2-46, S2-48 and S2-50 is accomplished according to the procedure outlined in Step 9 of Example 1401 of provisional application No. 60/330,892 filed on Nov. 2, 2001. In particular, the methoxy compounds S2-36, S2-38, S2-40 and/or S2-42 (e.g., Y=OMe) and $CHCl_3$ are placed in a flask purged with $N_2$. The reaction mixture is then cooled to −78° C. and boron tribromide ($BBr_3$) is added. The mixture is allowed to warm to room temperature. After about 4 hours, the reaction mixture is cooled to 0° C. and then quenched with 10% $K_2CO_3$. Thereafter (about 10 min. later), the layers are separated and the aqueous layers extracted twice with ethyl ether. The $CHCl_3$ and ether extracts are combined, washed with saturated aqueous NaCl, dried (MgSO4), filtered and concentrated in vacuo to yield the products S2-44, S2-46, S2-48 and/or S2-50.

Compounds S2-44, S2-46, S2-48 and S2-50 are then converted to compounds S2-52, S2-54, S2-56 and S2-58 (wherein $R^5$ is a moiety selected from members (1)–(70) depicted in Table 1 above) according to the procedures for adding the same groups described and outlined in the Examples of provisional application No. 60/330,892 filed on Nov. 2, 2001.

An additional Scheme for forming compounds S3-11c and S3-11d analogous to compounds S1-7a and S1-8a is provided in Scheme 3 below. Scheme 4 below outlines the procedures for forming other compounds S6-15c and S6-15d analogous to compounds S3-11c and S3-11d, where the stereochemistry at the C-3 carbon is varied when $R^{3A} \neq R^{3B}$. Once formed, compounds S3-11c, S3-11d, S6-15c and S6-15d are subjected to the procedures previously described and outlined in Scheme 2 for the attachment of $R^5$. Scheme 3 and 4 are as follows:

SCHEME 3

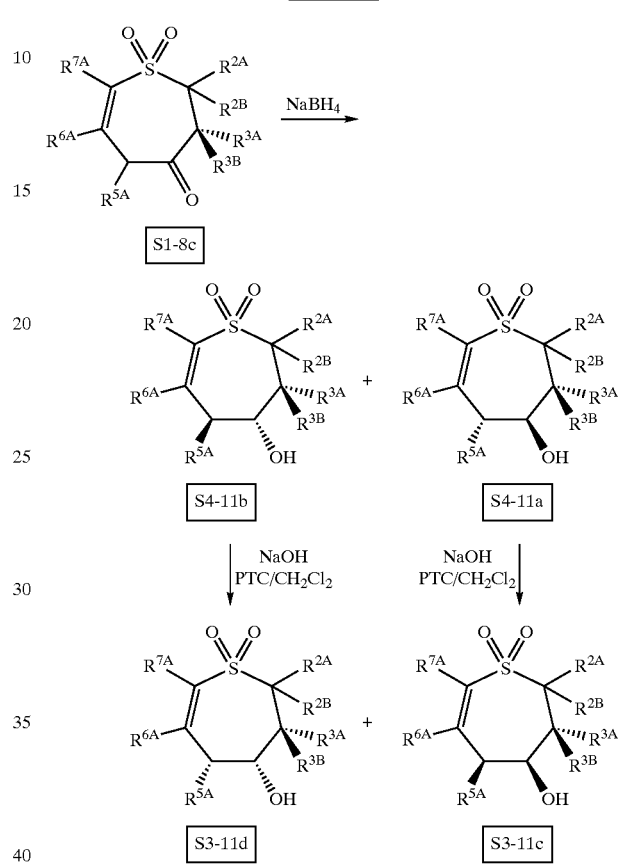

SCHEME 4

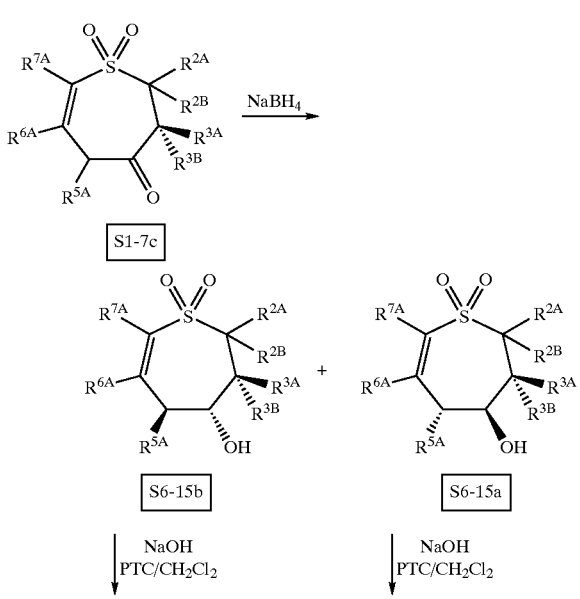

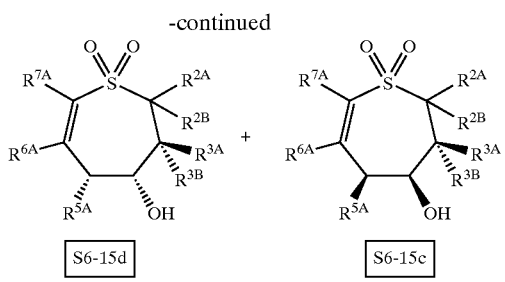

S6-15d  S6-15c

In Scheme 3, compound S1-8c is reduced with NaBH$_4$ to yield compounds S4-11a and/or S4-11b (made with chiral starting materials or optical resolving agents). Both S4-1a and S4-11b depict the R$^{5A}$ group and the OH group on opposite sides. Compounds S4-11a and S4-11b can be converted to compounds S3-11c and S3-11d, respectively, by treating the former compounds (S4-11a and/or S4-11b) in methylene chloride with 40–50% sodium hydroxide in the presence of a phase transfer catalyst (PTC). The transformation of S4-11a and S4-11b to S3-11c and S3-11d, respectively, can also be carried out with potassium t-butoxide in tetahydrofuran (THF).

In Scheme 4, compound S1-7c (formed according to Scheme 1B) is reduced with sodium borohydride to give compounds S6-15a and/or S6-15b. Note that compounds S6-15a and S6-15b are formed by utilizing chiral starting materials or by using optical resolving agents. Thereafter, compounds S6-15a and S6-15b can be converted to compounds S6-15c and S6-15d, respectively, by reaction in methylene chloride with 40–50% sodium hydroxide in the presence of a phase transfer agent (PTC) as previously described in connection with Scheme 3.

Additional embodiments of the claimed invention include compounds of formulas I-1 to I-24 wherein the substituents are as described below. For example, (a) R$^{2A}$ and R$^{2B}$ are independently selected from the group consisting of hydrogen and alkyl;

(b) R$^{3A}$ and R$^{3B}$ are independently selected from the groups consisting of hydrogen; alkyl; cycloalkyl; alkenyl; cycloalkenyl; alkynyl; aryl; heterocyclyl; arylalkyl; heterocyclylalkyl; alkoxyalkyl; alkoxyalkenyl; alkoxyalkynyl; aryloxyalkyl; aryloxyalkenyl; aryloxyalkynyl; heterocylcyloxyalkyl; heterocycloxyalkenyl; heterocyclyloxyalkynyl; alkylaryl; and (polyalkyl)aryl; or R$^{3A}$ and R$^{3B}$ taken together with the carbon to which they are attached form C$_3$–C$_{10}$ cycloalkyl or C$_3$–C$_{10}$ cycloalkenyl;

wherein the R$^{3A}$ and R$^{3B}$ alkyl; cycloalkyl; alkenyl; cycloalkenyl; alkynyl; aryl; heterocyclyl; arylalkyl; heterocyclylalkyl; alkoxyalkyl; alkoxyalkenyl; alkoxyalkynyl; aryloxyalkyl; aryloxyalkenyl; aryloxyalkynyl; heterocylcyloxyalkyl; heterocycloxyalkenyl; heterocyclyloxyalkynyl; alkylaryl; and (polyalkyl)aryl radicals optionally may be substituted with one or more radicals selected from the group consisting of —CN; halogen; oxo; —OR$^9$; —NR$^9$R$^{10}$; —N$^+$R$^9$R$^{10}$R$^W$A$^-$; —SR$^9$; —S$^+$R$^9$R$^{10}$A$^-$; —PR$^9$R$^{10}$; —P$^+$R$^9$R$^{10}$R$^W$A$^+$; —S(O)R$^9$; —SO$_2$R$^9$; —SO$_3$R$^9$; —CO$_2$R$^9$; and —CONR$^9$R$^{10}$; and wherein the R$^{3A}$ and R$^{3B}$ alkyl; cycloalkyl; alkenyl; cycloalkenyl; alkynyl; aryl; heterocyclyl; arylalkyl; heterocyclylalkyl; alkoxyalkyl; alkoxyalkenyl; alkoxyalkynyl; aryloxyalkyl; aryloxyalkenyl; aryloxyalkynyl; heterocylcyloxyalkyl; heterocycloxyalkenyl; heterocyclyloxyalkynyl; alkylaryl; and (polyalkyl)aryl radicals optionally may have one or more carbons replaced by —O—; —NR$^9$—; —N$^+$R$^9$R$^{10}$A$^-$—; —S—; —SO—; —SO$_2$—; —S$^+$R$^9$A$^-$—; —PR$^9$—; —P(O)R$^9$—; —P$^+$R$^9$R$^{10}$A$^-$; or phenylene;

(c) R$^{4A}$ and R$^{4B}$ are independently selected from the group consisting of hydrogen; alkyl; alkenyl; alkynyl; aryl; heterocyclyl; —OR$^9$—; —NR$^9$R$^{10}$; —SR$^9$; —S(O)R$^9$; —SO$_2$R$^9$; and —SO$_3$R$^9$; or R$^{4A}$ and R$^{4B}$ together form =O; =NOR$^9$; =S; =NNR$^9$R$^{10}$; =NR$^9$; or =CR$^{11}$R$^{12}$;

(d) R$^{5A}$ and R$^5$ are independently selected from the group consisting of alkyl; cycloalkyl; alkenyl; alkynyl; aryl; heterocyclyl; quaternary heterocyclyl; —OR$^9$; —SR$^9$; —S(O)R$^9$; —SO$_2$R$^9$; and —SO$_3$R$^9$;

wherein the R$^{5A}$ and R$^5$ alkyl; cycloalkyl; alkenyl; alkynyl; aryl; heterocyclyl; and quaternary heterocyclyl radicals optionally may be substituted with one or more radicals independently selected from the group consisting of halogen; —CN; —NO$_2$; oxo; alkyl; polyalkyl; haloalkyl; hydroxyalkyl; cycloalkyl; alkenyl; alkynyl; aryl; heterocyclyl; quaternary heterocyclyl; arylalkyl; heterocyclylalkyl; polyether; —OR$^{13}$; —NR$^{13}$R$^{14}$; —SR$^{13}$; —S(O)R$^{13}$; —SO$_2$R$^{13}$; —SO$_3$R$^{13}$; —NR$^{13}$OR$^{14}$; —NR$^{13}$NR$^{14}$R$^{15}$; —CO$_2$R$^{13}$; —OM; —SO$_2$OM; —SO$_2$NR$^{13}$R$^{14}$; —C(O)NR$^{13}$R$^{14}$; —C(O)OM; —COR$^{13}$; —NR$^{13}$C(O)R$^{14}$; —NR$^{13}$C(O)NR$^{14}$R$^{15}$; —NR$^{13}$CO$_2$R$^{14}$; —OC(O)R$^{13}$; —OC(O)NR$^{13}$R$^{14}$; —NR$^{13}$SOR$^{14}$; —NR$^{13}$SO$_2$R$^{14}$; —NR$^{13}$SONR$^{14}$R$^{15}$; —NR$^{13}$SO$_2$NR$^{14}$R$^{15}$; —PR$^{13}$R$^{14}$; —P(O)R$^{13}$R$^{14}$; —P$^+$R$^{13}$R$^{14}$R$^{15}$A$^-$; —P(OR$^{13}$)OR$^{14}$; —S$^+$R$^{13}$R$^{14}$A$^-$; and —N$^+$R$^{13}$R$^{14}$R$^{15}$A$^-$; and wherein the alkyl, polyalkyl, haloalkyl, hydroxyalkyl, cycloalkyl, alkenyl, alkynyl, aryl, heterocyclyl, quaternary heterocyclyl, arylalkyl, heterocyclylalkyl, and polyether substituents of the R$^{5A}$ and R$^5$ radicals optionally may be further substituted with one or more radicals selected from the group consisting of —CN; halogen; hydroxy; oxo; alkyl; cycloalkyl; alkenyl; alkynyl; aryl; heterocyclyl; arylalkyl; heterocyclylalkyl; quaternary heterocyclyl; —OR$^{19}$; —NR$^{19}$R$^{20}$; —SR$^{19}$; —S(O)R$^{19}$; —SO$_2$R$^{19}$; —SO$_3$R$^{19}$; —CO$_2$R$^{19}$; —CONR$^{19}$R$^{20}$; —N$^+$R$^9$R$^{19}$R$^{20}$A$^-$; —P(O)R$^{19}$R$^{20}$; —P$^+$R$^{19}$R$^{20}$; —P$^+$R$^9$R$^{19}$R$^{20}$A$^-$; and —P(O)(OR$^{19}$)OR$^{20}$; and wherein the alkyl, polyalkyl, haloalkyl, hydroxyalkyl, cycloalkyl, alkenyl, alkynyl, aryl, heterocyclyl, quaternary heterocyclyl, arylalkyl, heterocyclylalkyl, and polyether substituents of the R$^{5A}$ and R$^5$ radicals optionally may have one or more carbons replaced by —O—; —NR$^{19}$—; —N$^+$R$^{19}$R$^{20}$A$^-$—; —S—; —SO—; —SO$_2$—; —S$^{19}$A$^-$—; —P(O)R$^{19}$—; —P$^+$R$^{19}$R$^{20}$A$^-$—; or phenylene;

(e) R$^{5B}$ is selected from the group consisting of hydrogen; alkyl; cycloalkyl; alkenyl; alkynyl; aryl; heterocyclyl; quaternary heterocyclyl; —OR$^9$; —SR$^9$; —S(O)R$^9$; —SO$_2$R$^9$; and —SO$_3$R$^9$;

wherein the R$^{5B}$ alkyl; cycloalkyl; alkenyl; alkynyl; aryl; heterocyclyl; and quaternary heterocyclyl radical optionally may be substituted with one or more radicals independently selected from the group consisting of halogen; —CN; —NO$_2$; oxo; alkyl; polyalkyl; haloalkyl; hydroxyalkyl; cycloalkyl; alkenyl; alkynyl; aryl; heterocyclyl; quaternary heterocyclyl; arylalkyl; heterocyclylalkyl; polyether; —OR$^{13}$; —NR$^{13}$R$^{14}$;

—$SR^{13}$; —$S(O)R^{13}$; —$SO_2R^{13}$; —$SO_3R^{13}$; $NR^{13}OR^{14}$; —$NR^{13}NR^{14}R^{15}$; —$CO_2R^{13}$; —OM; —$SO_2OM$; —$SO_2NR^{13}R^{14}$; —$C(O)NR^{13}R^{14}$; —$C(O)OM$; —$COR^{13}$; —$NR^{13}C(O)R^{14}$; —$NR^{13}C(O)NR^{14}R^{15}$; —$NR^{13}CO_2R^{14}$; —$OC(O)R^{13}$; —$OC(O)NR^{13}R^{14}$; —$NR^{13}SOR^{14}$; —$NR^{13}SO_2R^{14}$; —$NR^{13}SONR^{14}R^{15}$; —$NR^{13}SO_2NR^{14}R^{15}$; —$PR^{13}R^{14}$; —$P(O)R^{13}R^{14}$; —$P^+R^{13}R^{14}R^{15}A^-$; —$P(OR^{13})OR^{14}$; —$S^+R^{13}R^{14}$ $A^-$; and —$N^+R^{13}R^{14}R^{15}A^-$; and wherein the alkyl, polyalkyl, haloalkyl, hydroxyalkyl, cycloalkyl, alkenyl, alkynyl, aryl, heterocyclyl, quaternary heterocyclyl, arylalkyl, heterocyclylalkyl, and polyether substituents of the $R^{5B}$ radical optionally may be further substituted with one or more radicals selected from the group consisting of —CN; halogen; hydroxy; oxo; alkyl; cycloalkyl; alkenyl; alkynyl; aryl; heterocyclyl; arylalkyl; heterocyclylalkyl; quaternary heterocyclyl; —$OR^{19}$; —$NR^{19}R^{20}$; —$SR^{19}$; —$S(O)R^{19}$; —$SO_2R^{19}$; —$SO_3R^{19}$; —$CO_2R^{19}$; —$CONR^{19}R^{20}$; —$N^+R^9R^{19}R^{20}A^-$; —$P(O)R^{19}R^{20}$; —$PR^{19}R^{20}$; —$P^+R^9R^{19}R^{20}A^-$; and —$P(O)(OR^{19})OR^{20}$; and wherein the alkyl, polyalkyl, haloalkyl, hydroxyalkyl, cycloalkyl, alkenyl, alkynyl, aryl, heterocyclyl, quaternary heterocyclyl, arylalkyl, heterocyclylalkyl, and polyether substituents of the $R^{5B}$ radical optionally may have one or more carbons replaced by —O—; —$NR^{19}$—; —$N^+R^{19}R^{20}A^-$—; —S—; —SO—; —$SO_2$—; —$S^+R^{19}A^-$—; —$PR^{19}$—; —$P(O)R^{19}$—; —$P^+R^{19}R^{20}A^-$—; or phenylene;

(f) wherein the $R^{6A}$ and $R^{7A}$ radicals are independently selected from the group consisting of hydrogen; halogen; —CN; —$NO_2$; alkyl; cycloalkyl; polyalkyl; haloalkyl; hydroxyalkyl; alkenyl; alkynyl; aryl; aryl-$R^5$; heterocyclyl; quaternary heterocyclyl; arylalkyl; heterocyclylalkyl; polyether; acyloxy; —$OR^{13}$; —$NR^{13}R^{14}$; —$SR^{13}$; —$S(O)R^{13}$; —$S(O)_2R^{13}$; —$SO_3R^{13}$; —$S^+R^{13}R^{14}A^-$; —$NR^{13}OR^{14}$; —$NR^{13}NR^{14}R^{15}$; —$CO_2R^{13}$; —OM; —$SO_2OM$; —$SO_2NR^{13}R^{14}$; —$NR^{14}C(O)R^{13}$; —$C(O)NR^{13}R^{14}$; —$C(O)OM$; —$COR^{13}$; —$OR^{18}$; —$S(O)_nNR^{13}R^{14}$; —$NR^{13}R^{18}$; —$NR^{18}OR^{14}$; —$N^+R^{13}R^{14}R^{15}A^-$; —$PR^{13}R^{14}$; —$P(O)R^{13}R^{14}$; —$P^+R^{13}R^{14}R^{15}A^-$; amino acid residue; peptide residue; polypeptide residue; and carbohydrate residue;

wherein the $R^{6A}$ and $R^{7A}$ alkyl; cycloalkyl; polyalkyl; haloalkyl; hydroxyalkyl; alkenyl; alkynyl; aryl; aryl-$R^5$; heterocyclyl; arylalkyl; heterocyclylalkyl; polyether; and acyloxy radicals optionally may be further independently substituted with one or more radicals selected from the group consisting of halogen; —CN; oxo; —$OR^{16}$; —$NR^9R^{10}$; —$N^+R^9R^{10}R^WA^-$; —$SR^{16}$; —$S(O)R^9$; —$SO_2R^9$; —$SO_3R^{16}$; —$CO_2R^{16}$; —$CONR^9R^{10}$; —$SO_2NR^9R^{10}$; —$PO(OR^{16})OR^{17}$; —$P^9R^{10}$; —$P^+R^9R^{11}R^{12}A^-$; —$S^+R^9R^{10}A^-$; and carbohydrate residue;

wherein the $R^{6A}$ and $R^{7A}$ quaternary heterocyclyl radical optionally may be independently substituted with one or more radicals selected from the group consisting of halogen; —CN; —$NO_2$; oxo; alkyl; cycloalkyl; polyalkyl; haloalkyl; hydroxyalkyl; alkenyl; alkynyl; aryl; heterocyclyl; arylalkyl; aryl-$R^5$; heterocyclylalkyl; polyether; —$OR^{13}$; —$NR^{13}R^{14}$; —$SR^{13}$; —$S(O)R^{13}$; —$SO_2R^{13}$; —$SO_3R^{13}$; $NR^{13}OR^{14}$; —$NR^{13}NR^{14}R^{15}$; —$CO_2R^{13}$; —OM; —$SO_2OM$; —$SO_2NR^{13}R^{14}$; —$C(O)NR^{13}R^{14}$; —$C(O)OM$; —$COR^{13}$; —$P(O)R^{13}R^{14}$; —$P^{13}R^{14}$; —$P^+R^{13}R^{14}R^{15}A^-$; —$P(OR^{13})OR^{14}$; —$S^+R^{13}R^{14}A^-$; —$N^+R^{13}R^{14}R^{15}A^-$; and carbohydrate residue;

wherein the $R^{6A}$ and $R^{7A}$ radicals comprising carbon optionally may independently have one or more carbons replaced by —O—; —$NR^{13}$—; —$N^+R^{13}R^{14}A^-$—; —S—; —SO—; —$SO_2$—; —$S^+R^{13}A^-$—; —$PR^{13}$—; —$P(O)R^{13}$—; —$PR^{13}R^{14}$; —$P^+R^{13}R^{14}A^-$—; phenylene; amino acid residue; peptide residue; polypeptide residue; carbohydrate residue; polyether; or polyalkyl; wherein said phenylene; amino acid residue; peptide residue; polypeptide residue; carbohydrate residue; and polyalkyl optionally may have one or more carbons replaced by —O—; —$NR^9$—; —$N^+R^9R^{10}A^-$—; —S—; —SO—; —$SO_2$—; —$S^+R^9A^-$; —$PR^9$—; —$P^+R^9R^{10}A^-$—; or —$P(O)R^9$; or the $R^{6A}$ and $R^{7A}$ groups together with the carbon atoms to which they are attached form a $C_4$–$C_{12}$ mono- or bi-cyclic carbocyclic or heterocyclic ring; a mono- or bi-cyclic carbocyclic ring; or a mono- or bi-cyclic heterocyclic ring;

wherein the mono- or bi-cyclic carbocyclic or heterocyclic rings optionally may be further substituted with one or more radicals selected from the group consisting of halogen; hydroxy; cyano; nitro; oxo; thioxo; alkyl; haloalkyl; alkoxy; aryl; heterocyclyl; $OR^{16}$; —$NR^9R^{10}$; —$N^+R^9R^{10}R^WA^-$; —$SR^{16}$; —$S(O)R^9$; —$SO_2R^9$; —$SO_3R^{16}$; —$CO_2R^{16}$; —$CONR^9R^{10}$; —$SO_2NR^9R^{10}$; —$PO(OR^{16})OR^{17}$; —$P^9R^{10}$; —$P^+R^9R^{11}R^{12}A^-$; —$S^+R^9R^{10}A^-$; and carbohydrate residue;

(g) wherein $R^9$, $R^{10}$, and $R^W$ are independently selected from the group consisting of hydrogen; alkyl; cycloalkyl; alkenyl; alkynyl; aryl; heterocyclyl; alkylammoniumalkyl; arylalkyl; heterocyclylalkyl; carboxyalkyl; alkoxyalkyl; carboalkoxyalkyl; carboxyaryl; carboxyheterocyclyl; amino; alkylamino; carboxyalkylamino; alkoxyalkylamino; and acyl;

(h) wherein $R^{11}$ and $R^{12}$ are independently selected from the group consisting of hydrogen; —CN; halogen; oxo; alkyl; alkenyl; alkynyl; aryl; heterocyclyl; arylalkyl; heterocyclylalkyl; carboxyalkyl; alkoxyalkyl; carboalkoxyalkyl; cycloalkyl; cycloalkenyl; haloalkyl; hydroxyalkyl; cyanoalkyl; —$OR^9$; —$NR^9R^{10}$; —$SR^9$; —$S(O)R^9$; —$SO_2R^9$; —$SO_3R^9$; —$CO_2R^9$; and —$CONR^9R^{10}$; or $R^{11}$ and $R^{12}$ together with the carbon atom to which they are attached form a cyclic ring; and (i) wherein $R^{13}$, $R^{14}$, and $R^{15}$ are independently selected from the group consisting of hydrogen; alkyl; haloalkyl; cycloalkyl; polyalkyl; alkenyl; alkynyl; aryl; heterocyclyl; quaternary heterocyclyl; arylalkyl; heterocyclylalkyl; quaternary heterocyclylalkyl; alkylarylalkyl; alkylheterocyclylalkyl; alkylammoniumalkyl; aminoalkyl; aminocarbonylalkyl; alkylaminocarbonylalkyl; carboxyalkylaminocarbonylalkyl; and polyether; or $R^{13}$ and $R^{14}$ together with the nitrogen atom to which they are attached form a mono- or polycyclic heterocyclyl that is optionally substituted with one or more radicals selected from the group consisting of oxo, carboxy, and quaternary salts; or wherein $R^{14}$ and $R^{15}$ together with the nitrogen atom to which they are attached form a cyclic ring; and wherein the $R^{13}$, $R^{14}$, and $R^{15}$ alkyl; haloalkyl; cycloalkyl; polyalkyl; alkenyl; alkynyl; aryl; heterocyclyl; quaternary heterocyclyl; arylalkyl; heterocyclylalkyl; quaternary heterocyclylalkyl; alkylarylalkyl; alkylheterocyclylalkyl; alkylammoniumalkyl; aminoalkyl; aminocarbonylalkyl; alkylaminocarbonylalkyl; carboxyalkylaminocarbonylalkyl; and polyether radicals optionally may be substituted with one or more radicals selected from the group consisting of halogen; —CN; sulfo; oxo; alkyl; haloalkyl; hydroxyalkyl; sulfoalkyl; alkenyl; alkynyl; aryl; heterocyclyl; quaternary heterocyclyl; quaternary heterocyclylalkyl; carboxy; carboxyalkyl; guanidinyl; —OR$^{16}$; —NR$^9$R$^{10}$; —N$^+$R$^9$R$^{10}$R$^W$A$^-$; —SR$^{16}$; —S(O)R$^9$; —SO$_2$R$^9$; —SO$_3$R$^{16}$; —CO$_2$R$^{16}$; —CONR$^9$R$^{10}$; —SO$_2$NR$^9$R$^{10}$; —PO(OR$^{16}$)OR$^{17}$; —P$^9$R$^{10}$; —P$^+$R$^9$R$^{10}$R$^{11}$A$^-$; —S$^+$R$^9$R$^{10}$A$^-$; and carbohydrate residue; and wherein the R$^{13}$, R$^{14}$, and R$^{15}$ alkyl; haloalkyl; cycloalkyl; polyalkyl; alkenyl; alkynyl; aryl; heterocyclyl; quaternary heterocyclyl; arylalkyl; heterocyclylalkyl; quaternary heterocyclylalkyl; alkylarylalkyl; alkylheterocyclylalkyl; alkylammoniumalkyl; aminoalkyl; aminocarbonylalkyl; alkylaminocarbonylalkyl; carboxyalkylaminocarbonylalkyl; and polyether radicals optionally may have one or more carbons replaced by —O—; —NR$^9$—; —N$^+$R$^9$R$^{10}$A$^-$—; —S—; —SO—; —SO$_2$—; —S$^+$R$^9$A$^-$—; —PR$^9$—; —P$^+$R$^9$R$^{10}$A$^-$—; —P(O)R$^9$—; phenylene; carbohydrate residue; amino acid residue; peptide residue; or polypeptide residue; and (j) wherein R$^{16}$ and R$^{17}$ are independently selected from the group consisting of R$^9$ and M; and (k) wherein R$^{18}$ is selected from the group consisting of alkyl; alkenyl; alkynyl; aryl; heterocyclyl; quaternary heterocyclyl; arylalkyl; heterocyclylalkyl; acyl; alkoxycarbonyl; arylalkoxycarbonyl; and heterocyclylalkoxycarbonyl; and wherein the R$^{18}$ alkyl; alkenyl; alkynyl; aryl; heterocyclyl; quaternary heterocyclyl; arylalkyl; heterocyclylalkyl; acyl; alkoxycarbonyl; arylalkoxycarbonyl; and heterocyclylalkoxycarbonyl radical optionally may be substituted with one or more radicals selected from the group consisting of halogen; —CN; NO$_2$; oxo; —OR$^9$; —NR$^9$R$^{10}$; —N$^+$R$^9$R$^{11}$R$^{12}$A$^-$; —SR$^9$; —S(O)R$^9$; —SO$_2$R$^9$; —SO$_3$R$^9$; —CO$_2$R$^9$; —CONR$^9$R$^{10}$; —SO$_2$OM; —SO$_2$NR$^9$R$^{10}$; —PR$^9$R$^{10}$; —P(OR$^{13}$)OR$^{14}$; —PO(OR$^{16}$)OR$^{17}$; and —C(O)OM; and (l) wherein R$^{19}$ and R$^{20}$ are independently selected from the group consisting of hydrogen; alkyl, alkenyl; alkynyl; aryl; and heterocyclyl; and (m) wherein M is a pharmaceutically acceptable cation, wherein A$^-$ is a pharmaceutically acceptable anion; or a pharmaceutically acceptable salt, solvate, or prodrug thereof.

According to another embodiment, the invention includes compounds of formulas I-1 to I-24 having the following substituents:

(a1) R$^{2A}$ and R$^{2B}$ are independently selected from the group consisting of hydrogen and alkyl;

(b1) R$^{3A}$ and R$^{3B}$ are independently selected from the group consisting of hydrogen; alkyl; cycloalkyl; alkenyl; alkynyl; arylalkyl; alkoxyalkyl; alkoxyalkenyl; alkoxyalkynyl; alkylaryl; and (polyalkyl)aryl; or R$^{3A}$ and R$^{3B}$ taken together with the carbon to which they are attached form C$_3$–C$_7$ cycloalkyl or C$_3$–C$_7$ cycloalkenyl;

wherein the R$^{3A}$ and R$^{3B}$ alkyl; cycloalkyl; alkenyl; alkynyl; arylalkyl; alkoxyalkyl; alkoxyalkenyl; alkoxyalkynyl; alkylaryl; and (polyalkyl)aryl radicals optionally may be substituted with one or more radicals selected from the group consisting of —CN; halogen; oxo; —OR$^9$; —NR$^9$R$^{10}$; —N$^+$R$^9$R$^{10}$R$^W$A$^-$; —SR$^9$; —S$^+$R$^9$R$^{10}$A$^-$; —PR$^9$R$^{10}$; —P$^+$R$^9$R$^{10}$R$^W$A$^-$; —S(O)R$^9$; —SO$_2$R$^9$; —SO$_3$R$^9$; —CO$_2$R$^9$; and —CONR$^9$R$^{10}$; and wherein the R$^{3A}$ and R$^{3B}$ alkyl; cycloalkyl; alkenyl; alkynyl; arylalkyl; alkoxyalkyl; alkoxyalkenyl; alkoxyalkynyl; alkylaryl; and (polyalkyl)aryl radicals optionally may have one or more carbons replaced by —O—; —NR$^9$—; —N$^+$R$^9$R$^{10}$A$^-$—, —S—; —SO—; —SO$_2$—; —S$^+$R$^9$A$^-$—, —PR$^9$—; —P(O)R$^9$—; —P$^+$R$^9$R$^{10}$A$^-$—, or phenylene;

(c1) R$^{4A}$ and R$^{4B}$ are independently selected from the group consisting of hydrogen; alkyl; alkenyl; alkynyl; aryl; heterocyclyl; —OR$^9$; —NR$^9$R$^{10}$; —SR$^9$; —S(O)R$^9$; —SO$_2$R$^9$; and —SO$_3$R$^9$; or R$^{4A}$ and R$^{4B}$ together form =O; =NOR$^9$; =S; =NNR$^9$R$^{10}$; =NR$^9$; or =CR$^{11}$R$^{12}$;

(d1) R$^{5A}$ is selected from the group consisting of alkyl; cycloalkyl; alkenyl; alkynyl; aryl; heterocyclyl; quaternary heterocyclyl; —OR$^9$; —SR$^9$; —S(O)R$^9$; —SO$_2$R$^9$; and —SO$_3$R$^9$;

wherein the alkyl, polyalkyl, haloalkyl, hydroxyalkyl, cycloalkyl, alkenyl, alkynyl, aryl, heterocyclyl, quaternary heterocyclyl, arylalkyl, heterocyclylalkyl, and polyether substituents of the R$^{5A}$ radical optionally may be further substituted with one or more radicals selected from the group consisting of —CN; halogen; hydroxy; oxo; alkyl; cycloalkyl; alkenyl; alkynyl; aryl; heterocyclyl; arylalkyl; heterocyclylalkyl; quaternary heterocyclyl; —OR$^{19}$; —NR$^{19}$R$^{20}$; —SR$^{19}$; —S(O)R$^{19}$; —SO$_2$R$^9$; —SO$_3$R$^9$; —CO$_2$R$^{19}$; —CONR$^{19}$R$^{20}$; —N$^+$R$^9$R$^{19}$R$^{20}$A$^-$; —P(O)R$^{19}$R$^{20}$; —PR$^{19}$R$^{20}$; —P$^+$R$^9$R$^{19}$R$^{20}$A$^-$; and —P(O)(OR$^{19}$)OR$^{20}$; and wherein the alkyl, polyalkyl, haloalkyl, hydroxyalkyl, cycloalkyl, alkenyl, alkynyl, aryl, heterocyclyl, quaternary heterocyclyl, arylalkyl, heterocyclylalkyl, and polyether substituents of the R$^{5A}$ radical optionally may have one or more carbons replaced by —O—; —NR$^{19}$—; —N$^+$R$^{19}$R$^{20}$A$^-$—; —S—; —SO—; —SO$_2$—; —S$^+$R$^{19}$A$^-$—; —PR$^{19}$—; —P(O)R$^{19}$—; —P$^+$R$^{19}$R$^{20}$A$^-$—; or phenylene;

(e1) R$^{5B}$ is selected from the group consisting of hydrogen; alkyl; cycloalkyl; alkenyl; alkynyl; aryl; heterocyclyl; quaternary heterocyclyl; —OR$^9$; —SR$^9$; —S(O)R$^9$; —SO$_2$R$^9$; and —SO$_3$R$^9$;

wherein the R$^{5B}$ alkyl; cycloalkyl; alkenyl; alkynyl; aryl; heterocyclyl; and quaternary heterocyclyl radical optionally may be substituted with one or more radicals independently selected from the group consisting of halogen; —CN; —NO$_2$; oxo; alkyl; polyalkyl; haloalkyl; cycloalkyl; alkenyl; alkynyl; aryl; heterocyclyl; quaternary heterocyclyl; arylalkyl; heterocyclylalkyl; polyether; —OR$^{13}$; —NR$^{13}$R$^{14}$; —SR$^{13}$; —S(O)R$^{13}$; —SO$_2$R$^{13}$; —SO$_3$R$^{13}$; —NR$^{13}$OR$^{14}$; —NR$^{13}$NR$^{14}$R$^{15}$; —CO$_2$R$^{13}$; —OM; —SO$_2$OM; —SO$_2$NR$^{13}$R$^{14}$; —C(O)NR$^{13}$R$^{14}$; —C(O)OM; —COR$^{13}$; —NR$^{13}$C(O)R$^{14}$; —NR$^{13}$C(O)NR$^{14}$R$^{15}$; —NR$^{13}$CO$_2$R$^{14}$; —OC(O)R$^{13}$; —OC(O)NR$^{13}$R$^{14}$; —NR$^{13}$SOR$^{14}$; —NR$^{13}$SO$_2$R$^{14}$; —NR$^{13}$SONR$^{14}$R$^{15}$; —NR$^{13}$SO$_2$NR$^{14}$R$^{15}$; —PR$^{13}$R$^{14}$; —P(O)R$^{13}$R$^{14}$; —P$^+$R$^{13}$R$^{14}$R$^{15}$A$^-$; —P(OR$^{13}$)OR$^{14}$; —S$^+$R$^{13}$R$^{14}$A$^-$; and —N$^+$R$^{13}$R$^{14}$R$^{15}$A$^-$; and wherein the alkyl, polyalkyl, haloalkyl, hydroxyalkyl, cycloalkyl, alkenyl, alkynyl, aryl, heterocyclyl, quaternary heterocyclyl, arylalkyl, heterocyclylalkyl, and polyether substituents of the $R^{5B}$ radical optionally may be further substituted with one or more radicals selected from the group consisting of —CN; halogen; hydroxy; oxo; alkyl; cycloalkyl; alkenyl; alkynyl; aryl; heterocyclyl; arylalkyl; heterocyclylalkyl; quaternary heterocyclyl; —OR$^{19}$; —NR$^{19}$R$^{20}$; —SR$^{19}$; —S(O)R$^{19}$; —SO$_2$R$^{19}$; —SO$_3$R$^{19}$; —CO$_2$R$^{19}$; —CONR$^{19}$R$^{20}$; —N$^+$R$^9$R$^{19}$R$^{20}$A$^-$; —P(O)R$^{19}$R$^{20}$; —PR$^{19}$R$^{20}$; —P$^+$R$^9$R$^{19}$R$^{20}$A$^-$; and —P(O)(OR$^{19}$)OR$^{20}$; and wherein the alkyl, polyalkyl, haloalkyl, hydroxyalkyl, cycloalkyl, alkenyl, alkynyl, aryl, heterocyclyl, quaternary heterocyclyl, arylalkyl, heterocyclylalkyl, and polyether substituents of the $R^{5B}$ radical optionally may have one or more carbons replaced by —O—; —NR$^{19}$—; —N$^+$R$^{19}$R$^{20}$A$^-$—; —S—; —SO—; —SO$_2$—; —S$^+$R$^{19}$A$^-$—; —PR$^{19}$—; —P(O)R$^{19}$—; —P$^+$R$^{19}$R$^{20}$A$^-$—; or phenylene;

(f1) wherein the $R^{6A}$ and $R^{7A}$ radicals are independently selected from the group consisting of hydrogen; halogen; —CN; —NO$_2$; alkyl; cycloalkyl; polyalkyl; haloalkyl; alkenyl; alkynyl; aryl; aryl-R$^5$; heterocyclyl; quaternary heterocyclyl; arylalkyl; polyether; acyloxy; —OR$^{13}$; —NR$^{13}$R$^{14}$; —SR$^{13}$; —S(O)R$^{13}$; —S(O)$_2$R$^{13}$; —SO$_3$R$^{13}$; —S$^+$R$^{13}$R$^{14}$A$^-$; —NR$^{13}$OR$^{14}$; —NR$^{13}$NR$^{14}$R$^{15}$; —CO$_2$R$^{13}$; —OM; —SO$_2$OM; —SO$_2$NR$^{13}$R$^{14}$; —NR$^{14}$C(O)R$^{13}$; —C(O)NR$^{13}$R$^{14}$; —C(O)OM; —COR$^{13}$; —OR$^{18}$; —S(O)$_n$NR$^{13}$R$^{14}$; —NR$^{13}$R$^{18}$; —NR$^{18}$OR$^{14}$; —N$^+$R$^{13}$R$^{14}$R$^{15}$A$^-$; —PR$^{13}$R$^{14}$; —P(O)R$^{13}$R$^{14}$; —P$^+$R$^{13}$R$^{14}$R$^{15}$A$^-$; amino acid residue; peptide acid residue; polypeptide acid residue; and carbohydrate acid residue;

wherein the $R^{6A}$ and $R^{7A}$ alkyl; cycloalkyl; polyalkyl; haloalkyl; hydroxyalkyl; alkenyl; alkynyl; aryl; aryl-R$^5$; heterocyclyl; arylalkyl; heterocyclylalkyl; polyether; and acyloxy radicals optionally may be further independently substituted with one or more radicals selected from the group consisting of halogen; —CN; oxo; —OR$^{16}$; —NR$^9$R$^{10}$; —N$^+$R$^9$R$^{10}$R$^W$A$^-$; —SR$^{16}$; —S(O)R$^9$; —SO$_2$R$^9$; —SO$_3$R$^{16}$; —CO$_2$R$^{16}$; —CONR$^9$R$^{10}$; —SO$_2$NR$^9$R$^{10}$; —PO(OR$^{16}$)OR$^{17}$; —PR$^9$R$^{10}$; —P$^+$R$^9$R$^{11}$R$^{12}$A$^-$; —S$^+$R$^9$R$^{10}$A$^-$; and carbohydrate residue;

wherein the $R^{6A}$ and $R^{7A}$ quaternary heterocyclyl radical optionally may be independently substituted with one or more radicals selected from the group consisting of halogen; —CN; —NO$_2$; oxo; alkyl; cycloalkyl; polyalkyl; haloalkyl; hydroxyalkyl; alkenyl; alkynyl; aryl; aryl-R$^5$; heterocyclyl; arylalkyl; heterocyclylalkyl; polyether; —OR$^{13}$; —NR$^{13}$R$^{14}$; —SR$^{13}$; —S(O)R$^{13}$; —SO$_2$R$^{13}$; —SO$_3$R$^{13}$; —NR$^{13}$OR$^{14}$; —NR$^{13}$NR$^{14}$R$^{15}$; —CO$_2$R$^{13}$; —OM; —SO$_2$OM; —SO$_2$NR$^{13}$R$^{14}$; —C(O)NR$^{13}$R$^{14}$; —C(O)OM; —COR$^{13}$; —P(O)R$^{13}$R$^{14}$; —PR$^{13}$R$^{14}$; —P$^+$R$^{13}$R$^{14}$R$^{15}$A$^-$; —P(OR$^{13}$)OR$^{14}$; —S$^+$R$^{13}$R$^{14}$A$^-$; and —N$^+$R$^{13}$R$^{14}$R$^{15}$A$^-$; and carbohydrate residue;

wherein the $R^{6A}$ and $R^{7A}$ radicals comprising carbon optionally may independently have one or more carbons replaced by —O—; —NR$^{13}$—; —N$^+$R$^{13}$R$^{14}$A$^-$—; —S—; —SO—; —SO$_2$—; —S$^+$R$^{13}$A$^-$—; —PR$^{13}$—; —P(O)R$^{13}$—; —PR$^{13}$—; —P$^+$R$^{13}$R$^{14}$A$^-$—; phenylene; amino acid; peptide; polypeptide; carbohydrate; polyether; or polyalkyl; wherein said phenylene; amino acid; peptide; polypeptide; carbohydrate; and polyalkyl optionally may have one or more carbons replaced by —O—; —NR$^9$—; —N$^+$R$^9$R$^{10}$A$^-$—; —S—; —SO—; —SO$_2$—; —S$^+$R$^9$A$^-$; —PR$^9$—; —P$^+$R$^9$R$^{10}$A$^-$—; or —P(O)R$^9$—; or the $R^{6A}$ and $R^{7A}$ groups together with the carbon atoms to which they are attached form a $C_4$-$C_{10}$ mono- or bi-cyclic carbocyclic or heterocyclic ring;

wherein the mono- or bi-cyclic carbocyclic or heterocyclic rings optionally may be further substituted with one or more radicals selected from the group consisting of halogen; hydroxy; cyano; nitro; oxo; thioxo; alkyl; haloalkyl; alkoxy; aryl; heterocyclyl; OR$^{16}$; —NR$^9$R$^{10}$; —N$^+$R$^9$R$^{10}$R$^W$A$^-$; —SR$^{16}$; —S(O)R$^9$; —SO$_2$R$^9$; —SO$_3$R$^{16}$; —CO$_2$R$^{16}$; —CONR$^9$R$^{10}$; —SO$_2$NR$^9$R$^{10}$; —PO(OR$^{16}$)OR$^{17}$; —P$^9$R$^{10}$; —P$^+$R$^9$R$^{11}$R$^{12}$A$^-$; —S$^+$R$^9$R$^{10}$A$^-$; and carbohydrate residue;

(g1) wherein $R^9$, $R^{10}$, and $R^W$ are independently selected from the group consisting of hydrogen; alkyl; cycloalkyl; alkenyl; alkynyl; aryl; heterocyclyl; alkylammoniumalkyl; arylalkyl; heterocyclylalkyl; carboxyalkyl; alkoxyalkyl; carboalkoxyalkyl; carboxyaryl; carboxyheterocyclyl; amino; alkylamino; carboxyalkylamino; alkoxyalkylamino; and acyl;

(h1) wherein $R^{11}$ and $R^{12}$ are independently selected from the group consisting of hydrogen; —CN; halogen; oxo; alkyl; alkenyl; alkynyl; aryl; heterocyclyl; arylalkyl; heterocyclylalkyl; carboxyalkyl; alkoxyalkyl; carboalkoxyalkyl; cycloalkyl; cycloalkenyl; haloalkyl; hydroxyalkyl; cyanoalkyl; —OR$^9$; —NR$^9$R$^{10}$; —SR$^9$; —S(O)R$^9$; —SO$_2$R$^9$; —SO$_3$R$^9$; —CO$_2$R$^9$; and —CONR$^9$R$^{10}$; or $R^{11}$ and $R^{12}$ together with the carbon atom to which they are attached form a cyclic ring; and (i1) wherein $R^{13}$, $R^{14}$, and $R^{15}$ are independently selected from the group consisting of hydrogen; alkyl; haloalkyl; cycloalkyl; polyalkyl; alkenyl; alkynyl; aryl; heterocyclyl; quaternary heterocyclyl; arylalkyl; heterocyclylalkyl; quaternary heterocyclylalkyl; alkylarylalkyl; alkylheterocyclylalkyl; alkylammoniumalkyl; aminoalkyl; aminocarbonylalkyl; alkylaminocarbonylalkyl; carboxyalkylaminocarbonylalkyl; and polyether; or $R^{13}$ and $R^{14}$ together with the nitrogen atom to which they are attached form a mono- or polycyclic heterocyclyl that is optionally substituted with one or more radicals selected from the group consisting of oxo, carboxy, and quaternary salts; or wherein $R^{14}$ and $R^{15}$ together with the nitrogen atom to which they are attached form a cyclic ring; and wherein the $R^{13}$, $R^{14}$, and $R^{15}$ alkyl; haloalkyl; cycloalkyl; polyalkyl; alkenyl; alkynyl; aryl; heterocyclyl; quaternary heterocyclyl; arylalkyl; heterocyclylalkyl; quaternary heterocyclylalkyl; alkylarylalkyl; alkylheterocyclylalkyl; alkylammoniumalkyl; aminoalkyl; aminocarbonylalkyl; alkylaminocarbonylalkyl; carboxyalkylaminocarbonylalkyl; and polyether radicals optionally may be substituted with one or more radicals selected from the group consisting of halogen; —CN; sulfo; oxo; alkyl; haloalkyl; hydroxyalkyl; sulfoalkyl; alkenyl; alkynyl; aryl; heterocyclyl; quaternary heterocyclyl; quaternary heterocyclylalkyl; carboxy; carboxyalkyl; guanidinyl; —OR$^{16}$; —NR$^9$R$^{10}$; —N$^+$R$^9$R$^{10}$R$^W$A$^-$; —SR$^{16}$; —S(O)R$^9$; —SO$_2$R$^9$; —SO$_3$R$^{16}$; —CO$_2$R$^{16}$; —CONR$^9$R$^{10}$; —SO$_2$NR$^9$R$^{10}$; —PO(OR$^{16}$)OR$^{17}$; —P$^9$R$^{10}$; —P$^+$R$^9$R$^{10}$R$^{11}$A$^-$; —S$^+$R$^9$R$^{10}$A$^-$; and carbohydrate residue; and wherein the $R^{13}$, $R^{14}$, and $R^{15}$ alkyl; haloalkyl; cycloalkyl; polyalkyl; alkenyl; alkynyl; aryl; heterocyclyl; quaternary heterocyclyl; arylalkyl; heterocyclylalkyl; quaternary heterocyclylalkyl; alkylarylalkyl; alkylheterocyclylalkyl; alkylammoniumalkyl; aminoalkyl; aminocarbonylalkyl; alkylaminocarbonylalkyl; carboxyalkylaminocarbonylalkyl; and polyether radicals optionally may have one or more carbons replaced by —O—; —NR$^9$—; —N$^+$R$^9$R$^{10}$A$^-$—; —S—; —SO—; —SO$_2$—; —S$^+$R$^9$A$^-$—; —PR$^9$—; —P$^+$R$^9$R$^{10}$A$^-$—; —P(O)R$^9$—; phenylene; carbohydrate residue; amino acid residue; peptide residue; or polypeptide residue; and (j1) wherein R$^{16}$ and R$^{17}$ are independently selected from the group consisting of R$^9$ and M; and (k1) wherein R$^{18}$ is selected from the group consisting of alkyl; alkenyl; alkynyl; aryl; heterocyclyl; quaternary heterocyclyl; arylalkyl; heterocyclylalkyl; acyl; alkoxycarbonyl; arylalkoxycarbonyl; and heterocyclylalkoxycarbonyl; and wherein the R$^{18}$ alkyl; alkenyl; alkynyl; aryl; heterocyclyl; quaternary heterocyclyl; arylalkyl; heterocyclylalkyl; acyl; alkoxycarbonyl; arylalkoxycarbonyl; and heterocyclylalkoxycarbonyl radical optionally may be substituted with one or more radicals selected from the group consisting of halogen; —CN; NO$_2$; oxo; —OR$^9$; —NR$^9$R$^{10}$; —N$^+$R$^9$R$^{11}$R$^{12}$A$^-$; —SR$^9$; —S(O)R$^9$; —SO$_2$R$^9$; —SO$_3$R$^9$; —CO$_2$R$^9$; —CONR$^9$R$^{10}$; —SO$_2$OM; —SO$_2$NR$^9$R$^{10}$; —PR$^9$R$^{10}$; —P(OR$^{13}$)OR$^{14}$; —PO(OR$^{16}$)OR$^{17}$; and —C(O)OM; and (l1) wherein R$^{19}$ and R$^{20}$ are independently selected from the group consisting of hydrogen; alkyl, alkenyl; alkynyl; aryl; and heterocyclyl; and (m1) same as (m) above.

According to another embodiment the compounds of formulas I-1 to I-24 have the following substituents:

(a2) R$^{2A}$ and R$^{2B}$ are independently selected from the group consisting of hydrogen and (C$_1$–C$_7$)alkyl;

(b2) R$^{3A}$ and R$^{3B}$ taken together with the carbon to which they are attached form (C$_3$–C$_7$)cycloalkyl;

wherein the R$^{3A}$ and R$^{3B}$ (C$_1$–C$_{10}$)alkyl; (C$_3$–C$_{10}$)cycloalkyl; (C$_2$–C$_{10}$)alkenyl; (C$_2$–C$_{10}$)alkynyl; aryl (C$_1$–C$_{10}$)alkyl; (C$_1$–C$_{10}$)alkoxy(C$_1$–C$_{10}$)alkyl; (C$_1$–C$_{10}$)alkoxy(C$_2$–C$_{10}$)alkenyl; (C$_1$–C$_{10}$)alkoxy (C$_2$–C$_{10}$)alkynyl; (C$_1$–C$_{10}$)alkylaryl; and (polyalkyl) aryl radicals optionally may be independently substituted with one or more radicals selected from the group consisting of —CN; halogen; oxo; —OR$^9$; —NR$^9$R$^{10}$; —N$^+$R$^9$R$^{10}$R$^W$A$^-$; —SR$^9$; —S$^+$R$^9$R$^{20\ A-}$; —PR$^9$R$^{10}$; —P$^+$R$^9$R$^{10}$R$^W$A$^-$; —S(O)R$^9$; —SO$_2$R$^9$; —SO$_3$R$^9$; —CO$_2$R$^9$; and —CONR$^9$R$^{10}$;

wherein the R$^{3A}$ and R$^{3B}$ (C$_1$–C$_{10}$)alkyl; (C$_3$–C$_{10}$)cycloalkyl; (C$_2$–C$_{10}$)alkenyl; (C$_2$–C$_{10}$)alkynyl; aryl (C$_1$–C$_{10}$)alkyl; (C$_1$–C$_{10}$)alkoxy(C$_1$–C$_{10}$)alkyl; (C$_1$–C$_{10}$)alkoxy(C$_2$–C$_{10}$)alkenyl; (C$_1$–C$_{10}$)alkoxy (C$_2$–C$_{10}$)alkynyl; (C$_1$–C$_{10}$)alkylaryl; and (polyalkyl) aryl radicals optionally may have one or more carbons independently replaced by —O—; —NR$^9$—; —N$^+$R$^9$R$^{10}$A$^-$; —S—; —SO—; —SO$_2$—; —S$^+$R$^9$A$^-$—; —PR$^9$; —P(O)R$^9$—; —P$^+$R$^9$R$^{10}$A$^-$; or phenylene;

(c2) R$^{4A}$ and R$^{4B}$ are independently selected from the group consisting of hydrogen; (C$_1$–C$_{10}$)alkyl; (C$_2$–C$_{10}$)alkenyl; (C$_2$–C$_{10}$)alkynyl; aryl; heterocyclyl; —OR$^9$; —NR$^9$R$^{10}$; —SR$^9$; —S(O)R$^9$; —SO$_2$R$^9$; and —SO$_3$R$^9$; or R$^{4A}$ and R$^{4B}$ together form =O; =NOR$^9$; =S; =NNR$^9$R$^{10}$; =NR$^9$; or =CR$^{11}$R$^{12}$; or (d2) R$^{5A}$ is selected from the group consisting of (C$_1$–C$_{10}$) alkyl; (C$_3$–C$_{10}$)cycloalkyl; (C$_2$–C$_{10}$)alkenyl; (C$_2$–C$_{10}$) alkynyl; aryl; heterocyclyl; quaternary heterocyclyl; —OR$^9$; —SR$^9$; —S(O)R$^9$; —SO$_2$R$^9$; and —SO$_3$R$^9$;

wherein the R$^{5A}$ C$_1$–C$_{10}$)alkyl; (C$_3$–C$_{10}$)cycloalkyl; (C$_2$–C$_{10}$)alkenyl; (C$_2$–C$_{10}$)alkynyl; aryl; heterocyclyl; and quaternary heterocyclyl radical optionally may be substituted with one or more radicals independently selected from the group consisting of halogen; —CN; —NO$_2$; oxo; (C$_1$–C$_{10}$)alkyl; polyalkyl; halo(C$_1$–C$_{10}$) alkyl; (C$_3$–C$_{10}$)cycloalkyl; (C$_2$–C$_{10}$)alkenyl; (C$_2$–C$_{10}$) alkynyl; aryl; heterocyclyl; quaternary heterocyclyl; aryl(C$_1$–C$_{10}$)alkyl; heterocyclyl(C$_1$–C$_{10}$)alkyl; polyether; —OR$^{13}$; NR$^{13}$R$^{14}$; —SR$^{13}$; —S(O)R$^{13}$; —SO$_2$R$^{13}$; —SO$_2$R$^{13}$; —NR$^{13}$OR$^{14}$; —NR$^{13}$NR$^{14}$R$^{15}$; —CO$_2$R$^{13}$; —OM; —SO$_2$OM; —SO$_2$NR$^{13}$R$^{14}$; —C(O)NR$^{13}$R$^{14}$; —C(O)OM; —COR$^{13}$; —NR$^{13}$C(O)R$^{14}$; —NR$^{13}$C(O)NR$^{14}$R$^{15}$; —NR$^{13}$CO$_2$R$^{14}$; —OC(O)R$^{13}$; —OC(O)NR$^{13}$R$^{14}$; —NR$^{13}$SOR$^{14}$; —NR$^{13}$SO$_2$R$^{14}$; —NR$^{13}$SONR$^{14}$R$^{15}$; —NR$^{13}$SO$_2$NR$^{14}$R$^{15}$; —P(O)R$^{13}$R$^{14}$; —PR$^{13}$R$^{14}$; —P$^+$R$^{13}$R$^{14}$R$^{15}$A$^-$; —P(OR$^{13}$)OR$^{14}$; —S$^+$R$^{13}$R$^{14}$A$^-$; and —N$^+$R$^{13}$R$^{14}$R$^{15}$A$^-$; and wherein the (C$_1$–C$_{10}$)alkyl, polyalkyl, halo(C$_1$–C$_{10}$)alkyl, hydroxy(C$_1$–C$_{10}$)alkyl, (C$_3$–C$_{10}$)cycloalkyl, (C$_2$–C$_{10}$) alkenyl, (C$_2$–C$_{10}$)alkynyl, aryl, heterocyclyl, quaternary heterocyclyl, aryl(C$_1$–C$_{10}$)alkyl, heterocyclyl (C$_1$–C$_{10}$)alkyl, and polyether substituents of the R$^{5A}$ radical optionally may be further substituted with one or more radicals selected from the group consisting of —CN; halogen; hydroxy; oxo; (C$_1$–C$_{10}$)alkyl; (C$_3$–C$_{10}$)cycloalkyl; (C$_2$–C$_{10}$)alkenyl; (C$_2$–C$_{10}$) alkynyl; aryl; heterocyclyl; aryl(C$_1$–C$_{10}$)alkyl; heterocyclyl(C$_1$–C$_{10}$)alkyl; quaternary heterocyclyl; —OR$^{19}$; —NR$^{19}$R$^{20}$; —SR$^{19}$; —S(O)R$^{19}$; —SO$_2$R$^{19}$; SO$_3$R$^{19}$; —CO$_2$R$^{19}$; —CONR$^{19}$R$^{20}$; —N$^+$R$^9$R$^{19}$R$^{20}$A$^-$; —P(O)R$^{19}$R$^{20}$; —R$^{20}$; —P$^+$R$^9$R$^{19}$R$^{20}$A$^-$; and —P(O)(OR$^{19}$)OR$^{20}$; and wherein the (C$_1$–C$_{10}$)alkyl, polyalkyl, halo(C$_1$–C$_{10}$)alkyl, hydroxy(C$_1$–C$_{10}$)alkyl, (C$_3$–C$_{10}$)cycloalkyl, (C$_2$–C$_{10}$) alkenyl, (C$_2$–C$_{10}$)alkynyl, aryl, heterocyclyl, quaternary heterocyclyl, aryl(C$_1$–C$_{10}$)alkyl, heterocyclyl (C$_1$–C$_{10}$)alkyl, and polyether substituents of the R$^{5A}$ radical optionally may have one or more carbons replaced by —O—; —NR$^{19}$—; —N$^+$R$^{19}$R$^{20}$A$^-$—; —S—; —SO—; —SO$_2$—; —S$^+$R$^{19}$A$^-$—; —PR$^{19}$—; —P(O)R$^{19}$—; —P$^+$R$^{19}$R$^{20}$A$^-$—; or phenylene;

(e2) R$^{5B}$ is selected from the group consisting of hydrogen; (C$_1$–C$_{10}$)alkyl; (C$_3$–C$_{10}$)cycloalkyl; (C$_2$–C$_{10}$) alkenyl; (C$_2$–C$_{10}$)alkynyl; aryl; heterocyclyl; quaternary heterocyclyl; —OR$^9$; —SR$^9$; —S(O)R$^9$; —SO$_2$R$^9$; and —SO$_3$R$^9$;

wherein the R$^{5B}$ (C$_1$–C$_{10}$)alkyl; (C$_3$–C$_{10}$)cycloalkyl; (C$_2$–C$_{10}$)alkenyl; (C$_2$–C$_{10}$)alkynyl; aryl; heterocyclyl; and quaternary heterocyclyl radical optionally may be substituted with one or more radicals independently selected from the group consisting of halogen; —CN; —NO$_2$; oxo; (C$_1$–C$_{10}$)alkyl; polyalkyl; halo(C$_1$–C$_{10}$) alkyl; (C$_3$–C$_{10}$)cycloalkyl; (C$_2$–C$_{10}$)alkenyl; (C$_2$–C$_{10}$) alkynyl; aryl; heterocyclyl; quaternary heterocyclyl; aryl(C$_1$–C$_{10}$)alkyl; heterocyclyl(C$_1$–C$_{10}$)alkyl; polyether; —OR$^{13}$; —NR$^{13}$R$^{14}$; —SR$^{13}$; —S(O)R$^{13}$; —SO$_2$R$^{13}$; —SO$_2$R$^{13}$; —NR$^{13}$OR$^{14}$; —NR$^{13}$NR$^{14}$R$^{15}$; —CO$_2$R$^{13}$; —OM; —SO$_2$OM; —SO$_2$NR$^{13}$R$^{14}$; —C(O)NR$^{13}$R$^{14}$; —C(O)OM; —COR$^{13}$; —NR$^{13}$C(O)R$^{14}$; —NR$^{13}$C(O)NR$^{14}$R$^{15}$;

—NR$^{13}$CO$_2$R$^{14}$; —OC(O)R$^{13}$; —OC(O)NR$^{13}$R$^{14}$; —NR$^{13}$SOR$^{14}$; —NR$^{13}$SO$_2$R$^{14}$; —NR$^{13}$SONR$^{14}$R$^{15}$; —NR$^{13}$SO$_2$NR$^{14}$R$^{15}$; —P(O)R$^{13}$R$^{14}$; —PR$^{13}$R$^{14}$; —P$^+$R$^{13}$R$^{14}$R$^{15}$A$^-$; —P(OR$^3$)OR$^{14}$; —S$^+$R$^{13}$R$^{14}$A$^-$; and —N$^+$R$^{13}$R$^{14}$R$^{15}$A$^-$;

wherein the (C$_1$–C$_{10}$)alkyl, polyalkyl, halo(C$_1$–C$_{10}$)alkyl, hydroxy(C$_1$–C$_{10}$)alkyl, (C$_3$–C$_{10}$)cycloalkyl, (C$_2$–C$_{10}$)alkenyl, (C$_2$–C$_{10}$)alkynyl, aryl, heterocyclyl, quaternary heterocyclyl, aryl(C$_1$–C$_{10}$)alkyl, heterocyclyl (C$_1$–C$_{10}$)alkyl, and polyether substituents of the R$^{5B}$ radical optionally may be further substituted with one or more radicals selected from the group consisting of —CN; halogen; hydroxy; oxo; (C$_1$–C$_{10}$)alkyl; (C$_3$–C$_{10}$)cycloalkyl; (C$_2$–C$_{10}$)alkenyl; (C$_2$–C$_{10}$) alkynyl; aryl; heterocyclyl; aryl(C$_1$–C$_{10}$)alkyl; heterocyclyl(C$_1$–C$_{10}$)alkyl; quaternary heterocyclyl; —OR$^{19}$; —NR$^{19}$R$^{20}$; —SR$^{19}$; —S(O)R$^{19}$; —SO$_2$R$^{19}$; —SO$_3$R$^{19}$; —CO$_2$R$^{19}$; —CONR$^{19}$R$^{20}$; —N$^+$R$^9$R$^{19}$R$^{20}$A$^-$; —P(O)R$^{19}$R$^{20}$; —PR$^{19}$R$^{20}$; —P$^+$R$^9$R$^{19}$R$^{20}$A$^-$; and —P(O)(OR$^{19}$)OR$^{20}$;

wherein the (C$_1$–C$_{10}$)alkyl, polyalkyl, halo(C$_1$–C$_{10}$)alkyl, hydroxy(C$_1$–C$_{10}$)alkyl, (C$_3$–C$_{10}$)cycloalkyl, (C$_2$–C$_{10}$) alkenyl, (C$_2$–C$_{10}$)alkynyl, aryl, heterocyclyl, quaternary heterocyclyl, aryl(C$_1$–C$_{10}$)alkyl, heterocyclyl (C$_1$–C$_{10}$)alkyl, and polyether substituents of the R$^{5B}$ radical optionally may have one or more carbons replaced by —O—; —N$^+$R$^9$R$^{20}$A$^-$—; —S—; —SO—; —SO$_2$—; —S$^+$R$^{19}$A$^-$—; —PR$^{19}$—; —P(O)R$^{19}$—; —P$^+$R$^{19}$R$^{20}$A$^-$—; or phenylene;

(f2) wherein the R$^{6A}$ and R$^{7A}$ radicals are independently selected from the group consisting of hydrogen; halogen; —CN; —NO$_2$; (C$_1$–C$_{10}$)alkyl; (C$_3$–C$_{10}$) cycloalkyl; polyalkyl; halo(C$_1$–C$_{10}$)alkyl; (C$_2$–C$_{10}$) alkenyl; (C$_2$–C$_{10}$)alkynyl; aryl; aryl-R$^5$; heterocyclyl; quaternary heterocyclyl; aryl(C$_1$–C$_{10}$)alkyl; polyether; acyloxy; —OR$^{13}$; —NR$^{13}$R$^{14}$; —SR$^{13}$ —S(O)R$^{13}$; —S(O)2R$^{13}$; —SO$_3$R$^{13}$; —S$^+$R$^{13}$R$^{14}$A$^-$; —NR$^{13}$OR$^{14}$; —NR$^{13}$NR$^{14}$R$^{15}$; —CO$_2$R$^{13}$; —OM; —SO$_2$OM; —SO$_2$NR$^{13}$R$^{14}$; —NR$^{14}$C(O)R$^{13}$; —C(O)NR$^{13}$R$^{14}$; —C(O)OM; —COR$^{13}$; —OR$^{18}$; —S(O)$_n$NR$^{13}$R$^{14}$; —NR$^{13}$R$^{18}$; —NR$^{18}$OR$^{14}$; N$^+$R$^{13}$R$^{14}$R$^{15}$A$^-$; —PR$^{13}$R$^{14}$; —P(O)R$^{13}$R$^{14}$; —P$^+$R$^{13}$R$^{14}$R$^{15}$A$^-$; amino acid residue; peptide acid residue; polypeptide acid residue; and carbohydrate acid residue;

wherein the R$^{6A}$ and R$^{7A}$ (C$_1$–C$_{10}$)alkyl; (C$_3$–C$_{10}$) cycloalkyl; polyalkyl; halo(C$_1$–C$_{10}$)alkyl; hydroxy (C$_1$–C$_{10}$)alkyl; (C$_2$–C$_{10}$)alkenyl; (C$_2$–C$_{10}$)alkynyl; aryl; heterocyclyl; aryl(C$_1$–C$_{10}$)alkyl; heterocyclyl (C$_1$–C$_{10}$)alkyl; polyether; and acyloxy radicals optionally may be further independently substituted with halogen; —CN; oxo; —OR$^{16}$; —NR$^9$R$^{10}$; —N$^+$R$^9$R R$^{12}$A$^-$; —SR$^{16}$; —S(O)R$^9$; —SO$_2$R$^9$; —SO$_3$R$^{16}$; —CO$_2$R$^{16}$; —CONR$^9$R$^{10}$; —SO$_2$NR$^9$R$^{10}$; —PO(OR$^6$) OR$^{17}$; —PR$^9$R$^{10}$; —P$^+$R$^9$R$^{11}$R$^{12}$A$^-$; or —S$^+$R$^9$R$^{10}$A$^-$;

wherein the R$^{6A}$ and R$^{7A}$ quaternary heterocyclyl radical optionally may be independently subtituted with one or more radicals selected from the group consisting of halogen; —CN; —NO$_2$; oxo; (C$_1$–C$_{10}$)alkyl; (C$_3$–C$_{10}$) cycloalkyl; polyalkyl; halo(C$_1$–C$_{10}$)alkyl; hydroxy (C$_1$–C$_{10}$)alkyl; (C$_2$–C$_{10}$)alkenyl; (C$_2$–C$_{10}$)alkynyl; aryl; heterocyclyl; aryl(C$_1$–C$_{10}$)alkyl; heterocyclyl (C$_1$–C$_{10}$)alkyl; polyether; OR$^{13}$; NR$^{13}$R$^{14}$; —SR$^{13}$; —S(O)R$^3$; —SO$_2$R$^{13}$; —SO$_3$R$^{13}$; —NR$^{13}$OR$^{14}$; —NR$^{13}$NR$^{14}$R$^{15}$; —CO$_2$R$^{13}$; —OM; —SO$_2$OM; —SO$_2$NR$^{13}$R$^{14}$; —C(O)NR$^{13}$R$^{14}$; —C(O)OM; —COR$^{13}$; —P(O)R$^{13}$R$^{14}$; —PR$^{13}$R$^{14}$; —P$^+$R$^{13}$R$^{14}$R$^{15}$A$^-$; —P(OR$^{13}$)OR$^{14}$; —S$^+$R$^{13}$R$^{14}$A$^-$; and —N$^+$R$^{13}$R$^{14}$R$^{15}$A$^-$; and wherein the R$^{6A}$ and R$^{7A}$ radicals comprising carbon optionally may independently have one or more carbons replaced by —O—; —NR$^{13}$—; —N$^+$R$^{13}$R$^{14}$A$^-$—; —S—; —SO—; —SO$_2$—; —S$^+$R$^{13}$A$^-$—; —PR$^{13}$—; —P(O)R$^{13}$—; —PR$^{13}$—; —P$^+$R$^{13}$R$^{14}$A$^-$—; phenylene; amino acid residue; peptide residue; polypeptide residue; carbohydrate residue; polyether; or polyalkyl; wherein said phenylene; amino acid residue; peptide residue; polypeptide residue; carbohydrate residue; and polyalkyl optionally may have one or more carbons replaced by —O—; —NR$^9$—; —N$^+$R$^9$R$^{10}$A$^-$—; —S—; —SO—; —SO$_2$—; —S$^+$R$^9$A$^-$; —PR$^9$—; —P$^+$R$^9$R$^{10}$A$^{31}$; or —P(O)R$^9$—; or the R$^{6A}$ and R$^{7A}$ groups together with the carbon atoms to which they are attached form a C$_4$–C$_{10}$ mono- or bi-cyclic carbocyclic or heterocyclic ring;

wherein the mono- or bi-cyclic carbocyclic or heterocyclic rings optionally may be further substituted with one or more radicals selected from the group consisting of halogen; hydroxy; cyano; nitro; oxo; thioxo; (C$_1$–C$_{10}$)alkyl; halo(C$_1$–C$_{10}$)alkyl; (C$_1$–C$_{10}$)alkoxy; aryl; —OR$^{16}$; —NR$^9$R$^{10}$; —N$^+$R$^9$R$^{10}$R$^W$A$^-$; —SR$^{16}$; —S(O)R$^9$; —SO$_2$R$^9$; —SO$_3$R$^{16}$; —CO$_2$R$^{16}$; —CONR$^9$R$^{10}$; —SO$_2$NR$^9$R$^{10}$; —PO(OR$^{16}$)OR$^{17}$; —P$^9$R$^{10}$; —P$^+$R$^9$R$^{11}$R$^{12}$A$^-$; —S$^+$R$^9$R$^{10}$A$^-$; and carbohydrate residue;

(g2) wherein R$^9$, R$^{10}$, and R$^W$ are independently selected from the group consisting of hydrogen; (C$_1$–C$_{10}$)alkyl; (C$_3$–C$_{10}$)cycloalkyl; (C$_2$–C$_{10}$)alkenyl; (C$_2$–C$_{10}$) alkynyl; aryl; heterocyclyl; ammonium(C$_1$–C$_{10}$)alkyl; (C$_1$–C$_{10}$)alkylammonium(C$_1$–C$_{10}$)alkyl; aryl(C$_1$–C$_{10}$) alkyl; heterocyclyl(C$_1$–C$_{10}$)alkyl; carboxy(C$_1$–C$_{10}$) alkyl; carbo(C$_1$–C$_{10}$)alkoxy(C$_1$–C$_{10}$)alkyl; carboxyheterocyclyl; carboxy(C$_1$–C$_{10}$)alkylamino; and acyl; and (h2) wherein R$^{11}$ and R$^{12}$ are independently selected from the group consisting of hydrogen; —CN; halogen; oxo; (C$_1$–C$_{10}$)alkyl; (C$_2$–C$_{10}$)alkenyl; (C$_2$–C$_{10}$)alkynyl; aryl; heterocyclyl; aryl(C$_1$–C$_{10}$)alkyl; carboxy (C$_1$–C$_{10}$)alkyl; carbo(C$_1$–C$_{10}$)alkoxy(C$_1$–C$_{10}$)alkyl; (C$_3$–C$_{10}$)cycloalkyl; cyano(C$_1$–C$_{10}$)alkyl; —OR$^9$; —NR$^9$R$^{10}$; —SR$^9$; —S(O)R$^9$; —SO$_2$R$^9$; —SO$_3$R$^9$; —CO$_2$R$^9$; and —CONR$^9$R$^{10}$; or R$^{11}$ and R$^{12}$ together with the carbon atom to which they are attached form a cyclic ring;

(i2) wherein R$^{13}$, R$^{14}$, and R$^{15}$ are independently selected from the group consisting of hydrogen; (C$_1$–C$_{10}$)alkyl; halo(C$_1$–C$_{10}$)alkyl; (C$_3$–C$_{10}$)cycloalkyl; polyalkyl; (C$_2$–C$_{10}$)alkenyl; (C$_2$–C$_{10}$)alkynyl; heterocyclyl; quaternary heterocyclyl; aryl(C$_1$–C$_{10}$)alkyl; heterocyclyl (C$_1$–C$_{10}$)alkyl; quaternary heterocyclyl(C$_1$–C$_{10}$)alkyl; (C$_1$–C$_{10}$)alkylaryl(C$_1$–C$_{10}$)alkyl; (C$_1$–C$_{10}$) alkylheterocyclyl(C$_1$–C$_{10}$)alkyl; (C$_1$–C$_{10}$) alkylammonium(C$_1$–C$_{10}$)alkyl; carboxy (C$_1$–C$_{10}$alkylaminocarbonyl(C$_1$–C$_{10}$)alkyl; (C$_1$–C$_{10}$) alkyl; and polyether; or wherein R$^{13}$ and R$^{14}$ together with the nitrogen atom to which they are attached from a mono- or polycyclic heterocyclyl that is optionally subtituted with one or more radicals selected from the group consisting of oxo, carboxy, and quaternary salts; or wherein R$^{14}$ and R$^{15}$ together with the nitrogen atom to which they are attached from a cyclic ring; and wherein the $R^{13}$, $R^{14}$, and $R^{15}$ $(C_1–C_{10})$alkyl; halo $(C_1–C_{10})$alkyl; $(C_3–C_{10})$cycloalkyl; polyalkyl; $(C_2–C_{10})$alkenyl; $(C_2–C_{10})$alkynyl; aryl; heterocyclyl; quaternary heterocyclyl; aryl$(C_1–C_{10})$alkyl; heterocyclyl$(C_1–C_{10})$alkyl; quaternary heterocyclyl $(C_1–C_{10})$alkyl; $(C_1–C_{10})$alkylaryl$(C_1–C_{10})$alkyl; $(C_1–C_{10})$alkylheterocyclyl$(C_1–C_{10})$alkyl; $(C_1–C_{10})$alkylammonium$(C_1–C_{10})$alkyl; aminocarbonyl $(C_1–C_{10})$alkyl; $(C_1–C_{10})$alkylaminocarbonyl$(C_1–C_{10})$alkyl; carboxy$(C_1–C_{10})$alkylaminocarbonyl$(C_1–C_{10})$alkyl; and polyether radicals optionally may be substituted with one or more radicals selected from the group consisting of halogen; —CN; sulfo; oxo; $(C_1–C_{10})$alkyl; sulfo$(C_1–C_{10})$alkyl; heterocyclyl; quaternary heterocyclyl; quaternary heterocyclyl$(C_1–C_{10})$alkyl; carboxy; carboxy$(C_1–C_{10})$alkyl; guanidinyl; —$OR^{16}$; —$NR^9R^{10}$; —$N^+R^9R^{10}R^WA^-$; —$SR^{16}$; —$S(O)R^9$; —$SO_2R^9$; —$SO_3R^{16}$; —$CO_2R^{16}$; —$CONR^9R^{10}$; —$SO_2NR^9R^{10}$; —$PO(OR^6)OR^{17}$; —$PR^9R^{10}$; —$P^+R^9R^{10}R^{11}A^-$; —$S^+R^9R^{10}A^-$; and carbohydrate residue;

wherein the $R^{13}$, $R^{14}$; and $R^{15}$ $(C_1–C_{10})$alkyl; halo $(C_1–C_{10})$alkyl; $(C_3–C_{10})$cycloalkyl; polyalkyl; $(C_2–C_{10})$alkenyl; $(C_2–C_{10})$alkynyl; aryl; heterocyclyl; quaternary heterocyclyl; aryl$(C_1–C_{10})$alkyl; heterocyclyl$(C_1–C_{10})$alkyl; quaternary heterocyclyl $(C_1–C_{10})$alkyl; $(C_1–C_{10})$alkylaryl$(C_1–C_{10})$alkyl; $(C_1–C_{10})$alkylheterocyclyl$(C_1–C_{10})$alkyl; $(C_1–C_{10})$alkylammonium$(C_1–C_{10})$alkyl; aminocarbonyl $(C_1–C_{10})$alkyl; $(C_1–C_{10}$alkylaminocarbonyl$(C_1–C_{10})$alkyl; carboxy$(C_1–C_{10})$alkylaminocarbonyl$(C_1–C_{10})$alkyl; and polyether radicals optionally may have one or more carbons replaced by —O—; —$NR^9$—; —$N^+R^9R^{10}A^-$—; —S—; —SO—; —$SO_2$—; —$S^+R^9A^-$—; —$PR^9$—; —$P^+R^9R^{10}A^-$—; —$P(O)R^9$—; phenylene; carbohydrate residue; amino acid residue; peptide residue; or polypeptide residue;

(j2) wherein $R^{16}$ and $R^{17}$ are independently selected from the group consisting of $R^9$ and M;

(k2) wherein $R^{18}$ is selected from the group consisting of $(C_1–C_{10})$alkyl; heterocyclyl; quaternary heterocyclyl; aryl$(C_1–C_{10})$alkyl; acyl; and aryl$(C_1–C_{10})$alkoxycarbonyl; wherein the $R^{18}$ $(C_1–C_{10})$alkyl; heterocyclyl; quaternary heterocyclyl; aryl$(C_1–C_{10})$alkyl; acyl; and aryl$(C_1–C_{10})$alkoxycarbonyl radical optionally may be substituted with one or more radicals selected from the group consisting of halogen; —CN; oxo; —$OR^9$; —$NR^9R^{10}$; —$N^+R^9R^{11}R^{12}A^-$; —$SR^9$; —$S(O)R^9$; —$SO_2R^9$; —$SO_3R^9$; —$CO_2R^9$; —$CONR^9R^{10}$; —$SO_2OM$; —$SO_2NR^9R^{10}$; —$PR^9R^{10}$; —$P(OR^{13})OR^{14}$; —$PO(OR^{16})OR^{17}$; and —C(O)OM;

(l2) wherein $R^{19}$ and $R^{20}$ are independently selected from the group consisting of hydrogen and $(C_1–C_{10})$alkyl; and (m2) same as (m1) above;

(n2) provided that aryl is selected from the group consisting of optionally substituted phenyl, biphenyl and naphthyl;

(o2) provided that heterocyclyl is selected from the group consisting of optionally substituted heterocyclyl comprising a 4 to 10 membered ring and comprising one or more ring atoms that are heteroatoms selected from the group consisting of oxygen, nitrogen, sulfur and phosphorus.

According to another embodiment, the substituents on the compounds of formulas I-1 to I-24 are as follows:

(a3) $R^{2A}$ and $R^{2B}$ are independently selected from the group consisting of hydrogen and $(C_1–C_{10})$alkyl;

(b3) $R^{3A}$ and $R^{3B}$ are independently selected from the group consisting of hydrogen and $(C_1–C_{10})$alkyl; or $R^{3A}$ and $R^{3B}$ taken together with the carbon to which they are attached form $(C_3–C_7)$cycloalkyl;

(c3) $R^{4A}$ and $R^{4B}$ are independently selected from the group consisting of hydrogen and —$OR^9$;

(d3) $R^{5A}$ is selected from phenyl, wherein said phenyl is optionally substituted with one or more radicals independently selected from the group consisting of $R^5$ halogen; hydroxy; —$NO_2$; $(C_1–C_{10})$alkyl; halo $(C_1–C_{10})$alkyl; aryl$(C_1–C_{10})$alkyl; heterocyclyl $(C_1–C_{10})$alkyl; polyether; —$OR^{13}$; —$NR^{13}R^{14}$; and —$NR^{13}C(O)R^{14}$;

(e3) $R^{5B}$ is hydrogen;

(f3) wherein the $R^{6A}$ and $R^{7A}$ radicals are independently selected from the group consisting of hydrogen; —$NO_2$; $(C_1–C_{10})$alkyl; halo$(C_1–C_{10})$alkyl; —$OR^{13}$; —$NR^{13}R^{14}$; or the $R^{6A}$ and $R^{7A}$ groups together with the carbon atoms to which they are attached form a $C_5–C_8$ mono-cyclic carbocyclic or heterocyclic ring;

wherein the mono-cyclic carbocyclic or heterocyclic rings optionally may be further substituted with one or more radicals selected from the group consisting of halogen; hydroxy; cyano; nitro; oxo; thioxo; $(C_1–C_{10})$alkyl; halo $(C_1–C_{10})$alkyl; $(C_1–C_{10})$alkoxy; aryl; $OR^{16}$; —$NR^9R^{11}$; —$N^+R^9R^{10}R^WA^-$; —$SR^{16}$; —$S(O)R^9$; —$SO_2R^9$; —$SO_2R^{16}$; —$CO_2R^6$; —$CONR^9R^{10}$; —$SO_2NR^9R^{10}$; —$PO(OR^{16})OR^7$; —$P^9R^{10}$; —$P^+R^9R^{11}R^{12}A^-$; —$S^+R^9R^{10}A^-$; and carbohydrate residue;

(g3) wherein $R^9$, $R^{10}$ and $R^W$ are independently selected from the group consisting of hydrogen; $(C_1–C_{10})$alkyl; heterocyclyl; ammonium$(C_1–C_{10})$alkyl; $(C_1–C_{10})$alkylammonium$(C_1–C_{10})$alkyl; aryl$(C_1–C_{10})$alkyl; heterocyclyl$(C_1–C_{10})$alkyl; carboxy$(C_1–C_{10})$alkyl; carbo$(C_1–C_{10})$alkoxy$(C_1–C_{10})$alkyl; carboxyheterocyclyl; carboxy$(C_1–C_{10})$alkylamino; and acyl;

(h3) wherein $R^{11}$ and $R^{12}$ are independently selected from the group consisting of hydrogen; $(C_1–C_{10})$alkyl; heterocyclyl; aryl$(C_1–C_{10})$alkyl; carboxy$(C_1–C_{10})$alkyl; and carbo$(C_1–C_{10})$alkoxy$(C_1–C_{10})$alkyl; or $R^{11}$ and $R^{12}$ together with the carbon atom to which they are attached form a cyclic ring;

(i3) wherein $R^{13}$, $R^{14}$, and $R^{15}$ are independently selected from the group consisting of hydrogen; $(C_1–C_{10})$alkyl; halo$(C_1–C_{10})$alkyl; heterocyclyl; quaternary heterocyclyl; aryl$(C_1–C_{10})$alkyl; heterocyclyl$(C_1–C_{10})$alkyl; quaternary heterocyclyl$(C_1–C_{10})$alkyl; $(C_1–C_{10})$alkylheterocyclyl$(C_1–C_{10})$alkyl; $(C_1–C_{10})$alkylammonium$(C_1–C_{10})$alkyl; and polyether; or wherein the $R^{13}$, $R^{14}$, and $R^{15}$ $(C_1–C_{10})$alkyl; halo $(C_1–C_{10})$alkyl; heterocyclyl; quaternary heterocyclyl; aryl$(C_1–C_{10})$alkyl; heterocyclyl$(C_1–C_{10})$alkyl; quaternary heterocyclyl$(C_1–C_{10})$alkyl; $(C_1–C_{10})$alkylheterocyclyl$(C_1–C_{10})$alkyl; $(C_1–C_{10})$alkylammonium$(C_1–C_{10})$alkyl; and polyether radicals optionally may be substituted with one or more radicals selected from the group consisting of halogen; $(C_1–C_{10})$alkyl; heterocyclyl; quaternary heterocyclyl; quaternary heterocyclyl$(C_1–C_{10})$alkyl; carboxy; carboxy$(C_1–C_{10})$alkyl; —$OR^{16}$; —$NR^9R^{10}$; —$N^+R^9R^{10}R^WA^-$; and —$CONR^9R^{10}$;

(j3) wherein $R^{16}$ is selected from the group consisting of $R^9$ and M;

(k3) same as (k2) above;

(l3) same as (l2) above;

(m3) same as (m2) above;

(n3) provided that aryl is selected from the group consisting of optionally substituted phenyl, biphenyl and naphthyl;

(o3) provided that heterocyclyl is selected from the group consisting of optionally substituted heterocyclyl comprising a 5 to 8 membered ring and comprising one or more ring atoms that are heteroatoms selected from the group consisting of oxygen, nitrogen, sulfur and phosphorus.

According to another embodiment, the substituents of formulas I-1 to I-24 are as follows:

(a4) $R^{2A}$ and $R^{2B}$ are independently selected from the group consisting of hydrogen, methyl, ethyl, n-propyl, isopropyl, n-butyl, isobutyl, sec-butyl, tert-butyl, pentyl and hexyl; and (b4) $R^{3A}$ and $R^{3B}$ are independently selected from the group consisting of hydrogen, methyl, ethyl, n-propyl, isopropyl, n-butyl, isobutyl, sec-butyl, tert-butyl, pentyl, hexyl, phenoxymethylene, phenoxyethylene, phenoxypropylene, pyridinyloxymethylene, pyridinyloxyethylene; methylpyridinyloxymethylene, methylpyridinyloxyethylene, pyrimidinyloxymethylene, and pyrimidinyloxyethylene; or $R^{3A}$ and $R^{3B}$ taken together with the carbon to which they are attached form cyclopropyl, cyclobutyl, cyclopentyl, or cyclohexyl;

(c4) $R^{4A}$ and $R^{4B}$ are independently selected from the group consisting of hydrogen, hydroxy, methyl, ethyl, phenyl, pyridinyl, amino, methylamino, dimethylamino, ethylamino and diethylamino;

(d4) same as (d3) above;

(e4) $R^{5B}$ is hydrogen;

(f4) wherein the $R^{6A}$ and $R^{7A}$ radicals are independently selected from the group consisting of hydrogen, hydroxy, methyl, ethyl, n-propyl, isopropyl, n-butyl, isobutyl, tert-butyl, sec-butyl, methoxy, ethoxy, n-propoxy, isopropoxy, methylthio, methylsulfinyl, methylsulfonyl, ethylthio, ethylsulfinyl, ethylsulfonyl, amino, hydroxyamino, methylamino, dimethylamino, ethylamino, diethylamino, trimethylammonium, triethylammonium, N-methyl-N-carboxymethylamino, N,N-dimethyl-N-carboxymethyl-ammonium, methylcarbonylamino, chloromethylcarbonylamino, fluoromethylcarbonylamino, bromomethylcarbonylamino, iodomethylcarbonylamino, ethylcarbonylamino, n-propylcarbonylamino, n-butylcarbonylamino, n-pentylcarbonylamino, n-hexylcarbonylamino, benzyloxycarbonylamino, aminoimidocarbonylamino, morpholinyl, N-methyl-morpholinium, azetidinyl, N-methyl-azetidinium, pyrrolidine, N-methyl-pyrrolidinium, piperazinyl, N-methylpiperazinyl, N,N'-dimethyl-piperazinium, piperidinyl, methylpiperidinyl, N-methyl-piperidinium, and thienyl; or the $R^{6A}$ and $R^{7A}$ groups together with the carbon atoms to which they are attached form a $C_4$–$C_{10}$ mono- or bi-cyclic carbocyclic or heterocyclic ring;

wherein said mono- or bi-cyclic carbocyclic or heterocyclic ring is selected from the group consisting of cyclobutyl, cyclopentyl, cyclohexyl, cyclopentenyl, cyclohexenyl, phenyl, naphthyl, tetrahydronaphthyl, indenyl, indanyl, biphenyl, pyrrolyl, imidazolyl, pyrazolyl, pyridyl, pyrazinyl, pyrimidyl, pyridazinyl, triazolyl, tetrazolyl, indolizinyl, indolyl, isoindolyl, purinyl, quinolyl, isoquinolyl, phthalazinyl, naphthyridinyl, quinoxalinyl, quinazolinyl, cinnolinyl, pteridinyl, furanyl, pyranyl, thiophenyl, dithiolyl, oxazolyl, isoxazolyl, oxadiazolyl, oxatriazolyl, dioxazolyl, oxazinyl, isooxazinyl, oxathiolyl, thiazolyl, isothiazolyl, thiodiazolyl, oxathiazolyl, oxathiazinyl, chromanyl, thiochromanyl, pyrrolidinyl, imidazolidinyl, dihydrothiophenyl, dihydropyranyl, dihydrofuranyl, dihydrothiazolyl, dihydroindolyl, pyrrolinyl, piperidinyl, piperazinyl, morpholinyl, benzoxazolyl, benzodioxolyl, benzodioxanyl, benzoxadiazolyl, dihydrobenzofuryl, benzothienyl, benzothiazolyl, benzothiadiazolyl, benzopyran, benzothiopyran, benzimidazolyl, benzotriazolyl, tetrazolopyridazinyl cyclohexofuryl, and cyclohexenofuryl wherein the mono- or bi-cyclic carbocyclic or heterocyclic rings optionally may be further substituted with one or more radicals selected from the group consisting of halogen; hydroxy; cyano; nitro; oxo; thioxo; methyl; ethyl; propyl; butyl; pentyl; hexyl; methoxy; ethoxy; propoxy; butoxy; pentoxy; hexyloxy; amino; methylamino; dimethylamino; ethylamino; and diethylamino; or a pharmaceutically acceptable salt, solvate, or prodrug thereof;

(g4) same as (g3) above;

(h4) same as (h3) above;

(i4) same as (i3) above;

(j4) same as (j3) above;

(k4) same as (k3) above;

(l4) same as (l3) above;

(m4) same as (m3) above;

(n4) same as (n3) above;

(o4) same as (o3) above).

According to another embodiment, the subsituents on compounds of formulas I-1 to I-24 are as follows:

(a5) $R^{2A}$ and $R^{2B}$ are hydrogen; or (b5) $R^{3A}$ and $R^{3B}$ are independently selected from the group consisting of hydrogen, methyl, ethyl, n-propyl, isopropyl, n-butyl, isobutyl, sec-butyl, tert-butyl, pentyl, and hexyl;

(c5) $R^{4A}$ and $R^{4B}$ are independently selected from the group consisting of hydrogen, and hydroxy;

(d5) same as (d4) above;

(e5) $R^{5B}$ is hydrogen;

(f5) wherein the $R^{6A}$ and $R^{7A}$ radicals are independently selected from the group consisting of hydrogen, hydroxy, methyl, ethyl, n-propyl, isopropyl, n-butyl, isobutyl, tert-butyl, sec-butyl, methoxy, ethoxy, n-propoxy, isopropoxy, methylthio, methylsulfinyl, methylsulfonyl, ethylthio, ethylsulfinyl, ethylsulfonyl, amino, hydroxyamino, methylamino, dimethylamino, ethylamino, diethylamino; and aryl-$R^5$; or the $R^{6A}$ and $R^{7A}$ groups together with the carbon atoms to which they are attached form a $C_5$–$C_{10}$ mono- or bi-cyclic carbocyclic or heterocyclic ring;

wherein said mono- or bi-cyclic carbocyclic or heterocyclic ring is selected from the group consisting of cyclopentyl, cyclohexyl, cyclopentenyl, cyclohexenyl, phenyl, naphthyl, tetrahydronaphthyl, indenyl, indanyl, biphenyl, pyrrolyl, imidazolyl, pyrazolyl, pyridyl, pyrazinyl, pyrimidyl, pyridazinyl, triazolyl, tetrazolyl, indolizinyl, indolyl, isoindolyl, purinyl, quinolyl, isoquinolyl, phthalazinyl, naphthyridinyl, quinoxalinyl, quinazolinyl, cinnolinyl, pteridinyl, furanyl, pyranyl, thiophenyl, dithiolyl, oxazolyl, isoxazolyl, oxadiazolyl, oxatriazolyl, dioxazolyl, oxazinyl, isooxazinyl, oxathiolyl, thiazolyl, isothiazolyl, thiodiazolyl, oxathiazolyl, oxathiazinyl, chromanyl, thiochromanyl, pyrrolidinyl, imidazolidinyl, dihydrothiophenyl, dihydropyranyl, dihydrofuranyl, dihydrothiazolyl, dihydroindolyl, pyrrolinyl, piperidinyl, piperazinyl, morpholinyl, benzoxazolyl, benzodioxolyl, benzodioxanyl, benzoxadiazolyl, dihydrobenzofuryl, benzothienyl, benzothiazolyl, benzothiadiazolyl, benzopyran, benzothiopyran, benzimidazolyl, benzotriazolyl, tetrazolopyridazinyl cyclohexofuryl, and cyclohexenofuryl.

wherein the mono- or bi-cyclic carbocyclic or heterocyclic rings optionally may be further substituted with one or more radicals selected from the group consisting of halogen; hydroxy; cyano; nitro; oxo; thioxo; methyl; ethyl; propyl; butyl; pentyl; hexyl; methoxy; ethoxy; propoxy; butoxy; pentoxy; hexyloxy; amino; methylamino; dimethylamino; ethylamino; and diethylamino;

(g5) same as (g4) above;

(h5) same as (h4) above;

(i5) same as (i4) above;

(j5) same as (j4) above;

(k5) same as (k4) above;

(l5) same as (l4) above; or (m5) wherein $A^-$ is a pharmaceutically acceptable anion; or a pharmaceutically acceptable salt, solvate, or prodrug thereof;

(n5) same as (n4) above;

(o5) same as (o4) above.

According to another embodiment, the substituents on compounds I-1 to I-24 are as follows:

(a6) same as (a1) above;

(b6) same as (b1) above;

(c6) same as (c1) above;

(d6) $R^{5A}$ is selected from the group consisting of aryl; heterocyclyl; and quaternary heterocyclyl;

wherein the $R^{5A}$ aryl; heterocyclyl; and quaternary heterocyclyl radical optionally may be substituted with one or more radicals independently selected from the group consisting of halogen; —CN; —NO$_2$; oxo; alkyl; polyalkyl; haloalkyl; cycloalkyl; alkenyl; alkynyl; aryl; heterocyclyl; quaternary heterocyclyl; arylalkyl; heterocyclylalkyl; polyether; —OR$^{13}$; —NR$^{13}$R$^{14}$; —SR$^{13}$; —S(O)R$^{13}$; —SO$_2$R$^{13}$; —SO$_3$R$^{13}$; —NR$^{13}$OR$^{14}$; —NR$^{13}$NR$^{14}$R$^{15}$; —CO$_2$R$^{13}$; —OM; —SO$_2$OM; —SO$_2$NR$^{13}$R$^{14}$; —C(O)NR$^{13}$R$^{14}$; —C(O)OM; —COR$^{13}$; —NR$^{13}$C(O)R$^{14}$; —NR$^{13}$C(O)NR$^{14}$R$^{15}$; —NR$^{13}$CO$_2$R$^{14}$; —OC(O)R$^{13}$; —OC(O)NR$^{13}$R$^{14}$; —NR$^{13}$SOR$^{14}$; —NR$^{13}$SO$_2$R$^{14}$; —NR$^{13}$SONR$^{14}$R$^{15}$; —NR$^{13}$SO$_2$NR$^{14}$R$^{15}$; —PR$^{13}$R$^{14}$; —P(O)R$^{13}$R$^{14}$; —P$^+$R$^{13}$R$^{14}$R$^{15}$A$^-$; —P(OR$^{13}$)OR$^{14}$; —S$^+$R$^{13}$R$^{14}$A$^-$; and —N$^+$R$^{13}$R$^{14}$R$^{15}$A$^-$;

wherein the alkyl, polyalkyl, haloalkyl, hydroxyalkyl, cycloalkyl, alkenyl, alkynyl, aryl, heterocyclyl, quaternary heterocyclyl, arylalkyl, heterocyclylalkyl, and polyether substituents of the $R^{5A}$ radical optionally may be further substituted with one or more radicals selected from the group consisting of —CN; halogen; hydroxy; oxo; alkyl; cycloalkyl; alkenyl; alkynyl; aryl; heterocyclyl; arylalkyl; heterocyclylalkyl; quaternary heterocyclyl; —OR$^{19}$; —NR$^{19}$R$^{20}$; —SR$^{19}$; —S(O)R$^{19}$; —SO$_2$R$^{19}$; —SO$_3$R$^{19}$; —CO$_2$R$^9$; —CONR$^{19}$R$^{20}$; —N$^+$R$^9$R$^{19}$R$^2$A$^-$; —P(O)R$^9$R$^{20}$; —PR$^{19}$R$^{20}$; —P$^+$R$^9$R$^{19}$R$^{20}$A$^-$; and —P(O)(OR$^{19}$)OR$^{20}$;

wherein the alkyl, polyalkyl, haloalkyl, hydroxyalkyl, cycloalkyl, alkenyl, alkynyl, aryl, heterocyclyl, quaternary heterocyclyl, arylalkyl, heterocyclylalkyl, and polyether substituents of the $R^{5A}$ radical optionally may have one or more carbons replaced by —O—; —NR$^{19}$—; —N$^+$R$^{19}$R$^{20}$A$^-$—; —S—; —SO—; —SO$_2$—; —S$^+$R$^{19}$A$^-$—; —PR$^{19}$—; —P(O)R$^9$—; —P$^+$R$^{19}$R$^{20}$A$^-$—; or phenylene;

(e6) same as (e1) above;

(f6) same as (f5) above;

(g6) wherein $R^9$, $R^{10}$, and $R^W$ are independently selected from the group consisting of hydrogen; alkyl; cycloalkyl; alkenyl; alkynyl; aryl; heterocyclyl; alkylammoniumalkyl; arylalkyl; heterocyclylalkyl; carboxyalkyl; carboalkoxyalkyl; carboxyheterocyclyl; carboxyalkylamino; and acyl;

(h6) wherein $R^{11}$ and $R^{12}$ are independently selected from the group consisting of hydrogen; —CN; halogen; oxo; alkyl; alkenyl; alkynyl; aryl; heterocyclyl; arylalkyl; carboxyalkyl; carboalkoxyalkyl; cycloalkyl; cyanoalkyl; —OR$^9$; —NR$^9$R$^{10}$; —SR$^9$; —S(O)R$^9$; —SO$_2$R$^9$; —SO$_2$R$^9$; —CO$_2$R$^9$; and —CONR$^9$R$^{10}$; or $R^{11}$ and $R^{12}$ together with the carbon atom to which they are attached form a cyclic ring;

(i6) wherein $R^{13}$, $R^{14}$, and $R^{15}$ are independently selected from the group consisting of hydrogen; alkyl; haloalkyl; cycloalkyl; polyalkyl; alkenyl; alkynyl; aryl; heterocyclyl; quaternary heterocyclyl; arylalkyl; heterocyclylalkyl; quaternary heterocyclylalkyl; alkylarylalkyl; alkylheterocyclylalkyl; alkylammoniumalkyl; carboxyalkylaminocarbonylalkyl; and polyether; or wherein $R^{13}$ and $R^{14}$ together with the nitrogen atom to which they are attached form a mono- or polycyclic heterocyclyl that is optionally substituted with one or more radicals selected from the group consisting of oxo, carboxy, and quaternary salts; or wherein $R^{14}$ and $R^{15}$ together with the nitrogen atom to which they are attached form a cyclic ring; and wherein the $R^{13}$, $R^{14}$, and $R^{15}$ alkyl; haloalkyl; cycloalkyl; polyalkyl; alkenyl; alkynyl; aryl; heterocyclyl; quaternary heterocyclyl; arylalkyl; heterocyclylalkyl; quaternary heterocyclylalkyl; alkylarylalkyl; alkylheterocyclylalkyl; alkylammoniumalkyl; aminocarbonylalkyl; alkylaminocarbonylalkyl; carboxyalkylaminocarbonylalkyl; and polyether radicals optionally may be substituted with one or more radicals selected from the group consisting of halogen; —CN; sulfo; oxo; alkyl; sulfoalkyl; heterocyclyl; quaternary heterocyclyl; quaternary heterocyclylalkyl; carboxy; carboxyalkyl; guanidinyl; —OR$^6$; —NR$^9$R$^{10}$; —N$^+$R$^9$R$^{10}$R$^W$A$^-$; —SR$^{16}$; —S(O)R$^9$; —SO$_2$R$^9$; —SO$_2$R$^{16}$; —CO$_2$R$^{16}$; —CONR$^9$R$^{10}$; —SO$_2$NR$^9$R$^{10}$; —PO(OR$^{16}$)OR$^7$; —PR$^9$R$^{10}$; —P$^+$R$^9$R$^{10}$R$^{11}$A$^-$; —S$^+$R$^9$R$^{10}$A$^-$; and carbohydrate residue;

wherein the $R^{13}$, $R^{14}$, and $R^{15}$ alkyl; haloalkyl; cycloalkyl; polyalkyl; alkenyl; alkynyl; aryl; heterocyclyl; quaternary heterocyclyl; arylalkyl; heterocyclylalkyl; quaternary heterocyclylalkyl; alkylarylalkyl; alkylheterocyclylalkyl; alkylammoniumalkyl; aminocarbonylalkyl; alkylaminocarbonylalkyl; carboxyalkylaminocarbonylalkyl; and polyether radicals optionally may have one or more carbons replaced by —O—; —NR$^9$—; —N$^+$R$^9$R$^{10}$A$^-$—; —S—; —SO—; —SO$_2$—; —S$^+$R$^9$A$^-$—; —PR$^9$—; —P$^{+R9}$R$^{10}$A$^-$; —P(O)R$^9$—; phenylene; carbohydrate residue; amino acid residue; peptide residue; or polypeptide residue;

(j6) wherein R$^{16}$ and R$^{17}$ are independently selected from the group consisting of R$^9$ and M; and (k6) wherein R$^{18}$ is selected from the group consisting of alkyl; alkenyl; alkynyl; aryl; heterocyclyl; quaternary heterocyclyl; arylalkyl; heterocyclylalkyl; acyl; alkoxycarbonyl; arylalkoxycarbonyl; and heterocyclylalkoxycarbonyl;

wherein the R$^{18}$ alkyl; alkenyl; alkynyl; aryl; heterocyclyl; quaternary heterocyclyl; arylalkyl; heterocyclylalkyl; acyl; alkoxycarbonyl; arylalkoxycarbonyl; and heterocyclylalkoxycarbonyl radical optionally may be substituted with one or more radicals selected from the group consisting of halogen; —CN; oxo; —OR$^9$; —NR$^9$R$^{10}$; —N$^+$R$^9$R$^{11}$R$^{12}$A$^-$; —SR$^9$; —S(O)R$^9$; —SO$_2$R$^9$; —SO$_3$R$^9$; —CO$_2$R$^9$; —CONR$^9$R$^{10}$; —SO$_2$OM; —SO$_2$NR$^9$R$^{10}$; —PR$^9$R$^{10}$; —P(OR$^{13}$)OR$^{14}$; —PO(OR$^{16}$)OR$^{17}$; and —C(O)OM;

(l6) wherein R$^{19}$ and R$^{20}$ are independently selected from the group consisting of hydrogen and alkyl; and (m6) same as (m1) above;

According to another embodiment, the substituents of compounds of formulas I-1 to I-24 are as follows:

(a7) same as (a1) above;

(b7) same as (b1) above;

(c7) R$^{5A}$ has the formula

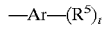

wherein t is an integer from 0 to 5; Ar is selected from the group consisting of phenyl; thiophenyl; pyridyl; piperazinyl; piperonyl; pyrrolyl; naphthyl; furanyl; anthracenyl; quinolinyl; isoquinolinyl; quinoxalinyl; imidazolyl; pyrazolyl; oxazolyl; isoxazolyl; pyrimidinyl; thiazolyl; triazolyl; isothiazolyl; indolyl; benzoimidazolyl; benzoxazolyl; benzothiazolyl; and benzoisothiazolyl;

one or more R$^5$ are independently selected from the group consisting of halogen; —CN; —NO$_2$; oxo; alkyl; polyalkyl; haloalkyl; cycloalkyl; alkenyl; alkynyl; aryl; heterocyclyl; quaternary heterocyclyl; arylalkyl; heterocyclylalkyl; polyether; —OR$^{13}$; —NR$^{13}$R$^{14}$; —SR$^{13}$; —S(O)R$^{13}$; —SO$_2$R$^{13}$; —SO$_3$R$^{13}$; —NR$^{13}$OR$^{14}$; —NR$^{13}$NR$^{14}$R$^{15}$; —CO$_2$R$^{13}$; —OM; —SO$_2$OM; —SO$_2$NR$^{13}$R$^{14}$; —C(O)NR$^{13}$R$^{14}$; —C(O)OM; —COR$^{13}$; —NR$^{13}$C(O)R$^{14}$; —NR$^{13}$C(O)NR$^{14}$R$^{15}$; —NR$^{13}$CO$_2$R$^{14}$; —OC(O)R$^{13}$; —OC(O)NR$^{13}$R$^{14}$; —NR$^{13}$SOR$^{14}$; —NR$^{13}$SO$_2$R$^{14}$; —NR$^{13}$SONR$^{14}$R$^{15}$; —NR$^{13}$SO$_2$NR$^{14}$R$^{15}$; —PR$^{13}$R$^{14}$; —P(O)R$^{13}$R$^{14}$; —P$^+$R$^{13}$R$^{14}$R$^{15}$A$^-$; —P(OR$^{13}$)OR$^{14}$; —S$^+$R$^{13}$R$^{14}$A$^-$; and —N$^+$R$^{13}$R$^{14}$R$^{15}$A$^-$; and wherein the alkyl, polyalkyl, haloalkyl, hydroxyalkyl, cycloalkyl, alkenyl, alkynyl, aryl, heterocyclyl, quaternary heterocyclyl, arylalkyl, heterocyclylalkyl, and polyether substituents of the R$^5$ radical optionally may be further substituted with one or more radicals selected from the group consisting of —CN; halogen; hydroxy; oxo; alkyl; cycloalkyl; alkenyl; alkynyl; aryl; heterocyclyl; arylalkyl; heterocyclylalkyl; quaternary heterocyclyl; —OR$^{19}$; —NR$^{19}$R$^{20}$; —SR$^1$; —S(O)R$^{19}$; —SO$_2$R$^{19}$; —SO$_3$R$^{19}$; —CO$_2$R$^{19}$; —CONR$^{19}$R$^{20}$; —N$^+$R$^9$R$^{19}$R$^{20}$A$^-$; —P(O)R$^{19}$R$^{20}$; —PR$^{19}$R$^{20}$; —P$^+$R$^9$R$^{19}$R$^{20}$A$^-$; and —P(O)(OR$^{19}$)OR$^{20}$;

wherein the alkyl, polyalkyl, haloalkyl, hydroxyalkyl, cycloalkyl, alkenyl, alkynyl, aryl, heterocyclyl, quaternary heterocyclyl, arylalkyl, heterocyclylalkyl, and polyether substituents of the R$^5$ radical optionally may have one or more carbons replaced by —O—; —NR$^{19}$—; —N$^+$R$^{19}$R$^{20}$A$^-$—; —S—; —SO—; —SO$_2$—; —S$^+$R$^{19}$A$^-$; —PR$^{19}$——; —P(O)R$^{19}$—; —P$^+$R$^{19}$R$^{20}$A$^-$—; or phenylene;

(d7) same as (d1) above;

(e7) same as (e1) above;

(f7) same as (f1) above;

(g7) wherein R$^9$, R$^{10}$, and R$^W$ are independently selected from the group consisting of hydrogen; alkyl; cycloalkyl; alkenyl; alkynyl; aryl; heterocyclyl; alkylammoniumalkyl; arylalkyl; heterocyclylalkyl; carboxyalkyl; carboalkoxyalkyl; carboxyheterocyclyl; carboxyalkylamino; and acyl;

(h7) wherein R$^{11}$ and R$^{12}$ are independently selected from the group consisting of hydrogen; —CN; halogen; oxo; alkyl; alkenyl; alkynyl; aryl; heterocyclyl; arylalkyl; carboxyalkyl; carboalkoxyalkyl; cycloalkyl; cyanoalkyl; —OR$^9$; —NR$^9$R$^{10}$; —SR$^9$; —S(O)R$^9$; —SO$_2$R$^9$; —SO$_3$R$^9$; —CO$_2$R$^9$; and —CONR$^9$R$^{10}$; or R$^{11}$ and R$^{12}$ together with the carbon atom to which they are attached form a cyclic ring; and (i7) wherein R$^{13}$, R$^{14}$, and R$^{15}$ are independently selected from the group consisting of hydrogen; alkyl; haloalkyl; cycloalkyl; polyalkyl; alkenyl; alkynyl; aryl; heterocyclyl; quaternary heterocyclyl; arylalkyl; heterocyclylalkyl; quaternary heterocyclylalkyl; alkylarylalkyl; alkylheterocyclylalkyl; alkylammoniumalkyl; carboxyalkylaminocarbonylalkyl; and polyether; or wherein R$^{13}$ and R$^{14}$ together with the nitrogen atom to which they are attached form a mono- or polycyclic heterocyclyl that is optionally substituted with one or more radicals selected from the group consisting of oxo, carboxy, and quaternary salts; or wherein R$^{14}$ and R$^{15}$ together with the nitrogen atom to which they are attached form a cyclic ring; and wherein the R$^{13}$, R$^{14}$, and R$^{15}$ alkyl; haloalkyl; cycloalkyl; polyalkyl; alkenyl; alkynyl; aryl; heterocyclyl; quaternary heterocyclyl; arylalkyl; heterocyclylalkyl; quaternary heterocyclylalkyl; alkylarylalkyl; alkylheterocyclylalkyl; alkylammoniumalkyl; aminocarbonylalkyl; alkylaminocarbonylalkyl; carboxyalkylaminocarbonylalkyl; and polyether radicals optionally may be substituted with one or more radicals selected from the group consisting of halogen; —CN; sulfo; oxo; alkyl; sulfoalkyl; heterocyclyl; quaternary heterocyclyl; quaternary heterocyclylalkyl; carboxy; carboxyalkyl; guanidinyl; —OR$^{16}$; —NR$^9$R$^{10}$; —N$^+$R$^9$R$^{10}$R$^W$A$^-$; —SR$^{16}$; —S(O)R$^9$; —SO$_2$R$^9$; —SO$_3$R$^{16}$; —CO$_2$R$^{16}$; —CONR$^9$R$^{10}$; —SO$_2$NR$^9$R$^{10}$; —PO(OR$^{16}$)OR$^{17}$; —PR$^9$R$^{10}$; —P$^+$R$^9$R$^{10}$R$^{11}$A$^-$; —S$^+$R$^9$R$^{10}$A$^-$; and carbohydrate residue; and wherein the $R^{13}$, $R^{14}$, and $R^{15}$ alkyl; haloalkyl; cycloalkyl; polyalkyl; alkenyl; alkynyl; aryl; heterocyclyl; quaternary heterocyclyl; arylalkyl; heterocyclylalkyl; quaternary heterocyclylalkyl; alkylarylalkyl; alkylheterocyclylalkyl; alkylammoniumalkyl; aminocarbonylalkyl; alkylaminocarbonylalkyl; carboxyalkylaminocarbonylalkyl; and polyether radicals optionally may have one or more carbons replaced by —O—; —$NR^9$—; —$N^+R^9R^{10}A^-$—; —S—; —SO—; —$SO_2$—; —$S^+R^9A^-$—; —$PR^9$—; —$P^{+R9}R^{10}A^-$—; —$P(O)R^9$—; phenylene; carbohydrate residue; amino acid residue; peptide residue; or polypeptide residue;

(j7) wherein $R^{16}$ and $R^{17}$ are independently selected from the group consisting of $R^9$ and M;

(k7) wherein $R^{18}$ is selected from the group consisting of alkyl; alkenyl; alkynyl; aryl; heterocyclyl; quaternary heterocyclyl; arylalkyl; heterocyclylalkyl; acyl; alkoxycarbonyl; arylalkoxycarbonyl; and heterocyclylalkoxycarbonyl;

wherein the $R^{18}$ alkyl; alkenyl; alkynyl; aryl; heterocyclyl; quaternary heterocyclyl; arylalkyl; heterocyclylalkyl; acyl; alkoxycarbonyl; arylalkoxycarbonyl; and heterocyclylalkoxycarbonyl radical optionally may be substituted with one or more radicals selected from the group consisting of halogen; —CN; oxo; —$OR^9$; —$NR^9R^{10}$; —$N^+R^9R^{11}R^{12}A^-$; —$SR^9$; —$S(O)R^9$; —$SO_2R^9$; —$SO_3R^9$; —$CO_2R^9$; —$CONR^9R^{10}$; —$SO_2OM$; —$SO_2NR^9R^{10}$; —$PR^9R^{10}$; —$P(OR^{13})OR^{14}$; —$PO(OR^{16})OR^{17}$; and —C(O)OM;

(l7) wherein $R^{19}$ and $R^{20}$ are independently selected from the group consisting of hydrogen and alkyl; and (m7) same as (m1) above;

According to another embodiment, the substituents of compounds of formulas I-1 to I-24 are as follows:

(a8) same as (a7) above;
(b8) same as (b7) above;
(c8) wherein $R^{5A}$ is:

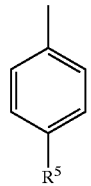

II wherein $R^5$ is as defined in (c7) above and t is 1, 2, 3, 4 or 5;

(d8) same as (d7) above;
(e8) same as (e7) above;
(f8) same as (f7) above;
(g8) same as (g7) above;
(h8) same as (h7) above;
(i8) same as (i7) above;
(j8) same as (j7) above;
(k8) same as (k7) above;
(l8) same as (l7) above; and
(m8) same as (m7) above.

According to another embodiment, the substituents of compounds of formulas I-1 to I-24 are as follows:

(a9) same as (a8) above;
(b9) same as (b8) above;

(c9) wherein $R^{5A}$ is:

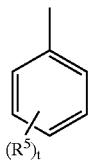

IIA wherein $R^5$ is as defined in (c8) above;
(d9) same as (d8) above;
(e9) same as (e8) above;
(f9) same as (f8) above;
(g9) same as (g8) above;
(h9) same as (h8) above;
(i9) same as (i8) above;
(j9) same as (j8) above;
(k9) same as (k8) above;
(l9) same as (l8) above;
(m9) same as (m8) above.

According to another embodiment, the substituents of compounds of formulas I-1 to I-24 are as follows:

(a10) same as (a8) above;
(b10) same as (b8) above;
(c10) wherein $R^{5A}$ is:

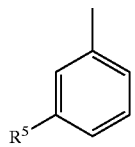

IIB wherein $R^W$ is as defined in (c8) above;
(d10) same as (d9) above;
(e10) same as (e9) above;
(f10) same as (f9) above;
(g10) same as (g9) above;
(h10) same as (h9) above;
(i10) same as (i9) above;
(j10) same as (j9) above;
(k10) same as (k9) above;
(l10) same as (l9) above;
(m10) same as (m9) above.

Preferably, in each of the various embodiments of the invention described above, in each of Formulas I-1 to I-24 and in each of the benzothiepine intermediates and products (containing a thiepene 7 membered ring described in Schemes 1, 1A, 1B, 1C, 2, 3, 4, and 5 herein), at least one or more of the following conditions are satisfied:

(1) j is 1 or 2. Preferably, j is 2; and/or
(2) The substituents at the 2-position of the benzothiepine are independently selected from the group consisting of hydrogen and alkyl. Preferably, these substituents are hydrogen; and/or
(3) The substituents at the 3-position of the benzothiepine are independently selected from the group consisting of hydrogen and alkyl. Preferably, these substituents are independently selected from the group consisting of $C_{1-6}$ alkyls. More preferably, these substituents are selected from the group consisting of ethyl, propyl and butyl. Still more preferably, either (a) one of these 3-position substituents is ethyl and the other is n-butyl, or (b) both of these 3-position substituents are n-butyl; and/or (4) The substituents at the 5-position of the benzothiepene is aryl or substituted aryl. Preferably, the aryl is phenyl that is optionally substituted at the meta and/or the para position. More preferably, the substitution at the meta and/or the para position of the phenyl is glucuronidated or monosubstituted with a radical selected from the group consisting of $-R^5$, $-OR^{13}$, $-NR^{13}C(O)R^{14}$, $-NR^{13}C(O)NR^{14}R^{15}$, $-NR^{13}CO_2R^{14}$, $-OC(O)R^{13}$, $-OC(O)NR^{13}R^{14}$, $-NR^{13}SOR^{14}$, $-NR^{13}SO_2R^{14}$, $-NR^{13}SONR^{14}R^{15}$, and $-NR^{13}SO_2NR^{14}R^{15}$ wherein $R^5$, $R^{13}$, $R^{14}$ and $R^{15}$ are as previously defined; and/or (6) Only one of $R^{5A}$ or $R^{5B}$ is hydrogen; and/or (7) Substituents $R^{6A}$ and $R^{7A}$ are independently selected from the group consisting of halogen, $-OR^{13}$ and $-NR^{13}R^{14}$, wherein $R^{13}$ and $R^{14}$ are as previously defined. Preferably, the substituents $R^{6A}$ and $R^{7A}$ are independently selected from the group consisting of halogen, hydroxy, alkoxy, amino, alkylamino and dialkylamino. Still more preferably, the substituents $R^{6A}$ and $R^{7A}$ are independently selected from the group consisting of chloro, methoxy and dimethylamino.

Alternative Forms of Novel Compounds

Also included in the family of compounds of Formulas I-1 to I-24 are (a) the stereoisomers thereof, (b) the pharmaceutically-acceptable salts thereof, (c) the tautomers thereof, (d) the protected acids and the conjugate acids thereof, and (e) the prodrugs thereof.

(a) The Stereoisomers

The stereoisomers of these compounds may include, but are not limited to, enantiomers, diastereomers, racemic mixtures and combinations thereof. Such stereoisomers can be prepared and separated using conventional techniques, either by reacting enantiomeric starting materials, or by separating isomers of compounds of the present invention. Isomers may include geometric isomers. Examples of geometric isomers includes, but are not limited to, cis isomers or trans isomers across a double bond. Other isomers are contemplated among the compounds of the present invention. The isomers may be used either in pure form or in admixture with other isomers of the inhibitors described above.

(b) The Pharmaceutically-acceptable Salts

Pharmaceutically-acceptable salts of the compounds of the present invention (Formulas I-1 to I-24) include salts commonly used to form alkali metal salts or form addition salts of free acids or free bases. The nature of the salt is not critical, provided that it is pharmaceutically-acceptable. Suitable pharmaceutically-acceptable acid addition salts of compounds of Formulas I-1 to I-24 may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids. Examples of organic and sulfonic classes of organic acids includes, but are not limited to, formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicyclic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, N-hydroxybutyric, salicyclic, galactaric and galacturonic acid and combinations thereof.

Suitable pharmaceutically-acceptable base addition salts of compounds of Formulas I-1 to I-24 include metallic salts, such as salts made from aluminum, calcium, lithium, magnesium, potassium, sodium and zinc, or salts made from organic bases including primary, secondary and tertiary amines, substituted amines including cyclic amines, such as caffeine, arginine, diethylamine, N-ethyl piperidine, histidine, glucamine, isopropylamine, lysine, morpholine, N-ethyl morpholine, piperazine, piperidine, triethylamine, and trimethylamine. The above salts may be prepared by conventional means from the corresponding compounds of the invention by reacting, for example, the appropriate acid or base with the compounds of Formulas I-1 to I-24.

(c) The Tautomers

Tautomrers of the aforementioned compounds (Formulas I-1 to I-24) are encompassed by the present invention. Thus, for example, (even though not shown) a carbonyl includes its hydroxy tautomer.

(d) The Protected Acids and the Coniugate Acids

The protected acids of these compounds (Formulas I-1 to I-24) include, but are not limited to, protected acids such as esters, hydroxyamino derivatives, amides and sulfonamides. Thus, for example, primary and secondary amines can be reacted with carboxylic acid substituted forms of the compounds of Formulas I-1 to I-24 to form amides which can be useful as prodrugs. Preferred amines are heterocyclicamines, including optionally substituted aminothiazoles, optionally substituted amino-isoxazoles, optionally substituted aminopyridines, optionally substituted aniline derivatives, optionally substituted sulfonamides, optionally substituted aminocarboxylic acids, and the like. The esters, hydroxyamino derivatives and sulfonamides can be prepared from the acids by methods known to one skilled in the art.

(e) The Prodrugs

The present invention includes the prodrugs of the compounds of Formulas I-1 to I-24.

Dosages and Treatment Regimen

Dosage levels of the compounds of Formulae I-1 to I-24 typically are from about 0.001 mg to about 10,000 mg daily, preferably from about 0.005 mg to about 1,000 mg daily, more preferably from about 0.008 mg to about 100 mg daily, and even more preferably from about 0.05 mg to about 50 mg daily. On the basis of mg/kg daily dose, either given in a single or divided doses, dosages typically range from about 0.001/75 mg/kg to about 10,000/75 mg/kg, preferably from about 0.005/75 mg/kg to about 1,000/75 mg/kg, more preferably from about 0.008/75 to about 100/75 mg/kg, and even more preferably from about 0.05/75 mg/kg to about 50/75 mg/kg.

The total daily dose of each drug can be administered to the patient in a single dose, or in multiple subdoses. Typically, subdoses can be administered two to six times per day, preferably two to four times per day, and even more preferably two to three times per day. Doses can be in immediate release form or sustained release form sufficiently effective to obtain the desired control over the hyperlipidemic condition.

The dosage regimen to prevent, treat, give relief from, or ameliorate a hyperlipidemic condition or disorder, or to otherwise protect against or treat high cholesterol blood (or plasma) levels with the combinations and compositions of the present invention is selected in accordance with a variety of factors. These factors include, but are not limited to, the type, age, weight, sex, diet, and medical condition of the subject, the severity of the disease, the route of administration, pharmacological considerations such as the activity, efficacy, pharmacokinetics and toxicology profiles of the particular inhibitors employed, whether a drug delivery system is utilized, and whether the inhibitors are administered with other active ingredients. Thus, the dosage regimen actually employed may vary widely and therefore deviate from the preferred dosage regimen set forth above.

Initial treatment of a patient suffering from a hyperlipidemic condition or disorder can begin with the dosages indicated above. Treatment generally should be continued as necessary over a period of several weeks to several months or years until the hyperlipidemic condition or disorder has been controlled or eliminated. Patients undergoing treatment with the combinations of the compounds disclosed herein can be routinely monitored, for example, by measuring serum LDL and total cholesterol levels by any of the methods well-known in the art, to determine the effectiveness of the combination therapy. Continuous and intermittent analysis of such data permits modification of the treatment regimen during therapy so that optimal therapeutically effective amounts of each type of inhibitor are administered at any time for an appropriate duration of time. In this way, the treatment regimen/dosing schedule can be rationally modified over the course of therapy so that the lowest amount of inhibitor that exhibits satisfactory therapeutic effectiveness is administered, and so that administration is continued only so long as is necessary to successfully treat or otherwise ameliorate the hyperlipidemic condition. Of course, maintenance dosing to keep the hyperlipidemic condition under the desired control may be instituted as necessary.

Pharmaceutical Compositions

For the prophylaxis or treatment of the conditions and disorders referred to above, the compounds of this invention (Formulas I-1 to I-24) can be administered as the compound per se. Alternatively, pharmaceutically-acceptable salts are particularly suitable for medical applications because of their greater aqueous solubility relative to that of the parent compound.

The compounds of the present invention also can be administered with an acceptable carrier in the form of a pharmaceutical composition. The carrier must be acceptable in the sense of being compatible with the other ingredients of the composition and must not be intolerably deleterious to the recipient. The carrier can be a solid or a liquid, or both, and preferably is formulated with the compound as a unit-dose composition, for example, a tablet, which can contain from about 0.05% to about 95% by weight of the active compound(s) based on a total weight of the dosage form. Other pharmacologically active substances can also be present, including other compounds useful in the treatment of a hyperlipidemic condition.

The active compounds of the present invention may be administered by any suitable route, preferably in the form of a pharmaceutical composition adapted to such a route, and in a therapeutically effective dose for the treatment intended. The active compounds and compositions, for example, may be administered orally, sublingually, nasally, pulmonarily, mucosally, parenterally, intravascularly, intraperitoneally, subcutaneously, intramuscularly or topically. Unit dose formulations, particularly orally administrable unit dose formulations such as tablets or capsules, generally contain, for example, from about 0.001 to about 500 mg, preferably from about 0.005 mg to about 100 mg, and more preferably from about 0.01 to about 50 mg, of the active ingredient. In the case of pharmaceutically acceptable salts, the weights indicated above for the active ingredient refer to the weight of the pharmaceutically active ion derived from the salt.

For oral administration, the pharmaceutical composition may be in the form of, for example, a tablet, a capsule, a suspension, an emulsion, a paste, a solution, a syrup or other liquid form. The pharmaceutical composition is preferably made in the form of a dosage unit containing a particular amount of the active ingredient. If administered by mouth, the compounds may be admixed with, for example, lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration.

Oral delivery of the compounds of the present invention can include formulations, as are well known in the art, to provide immediate delivery or prolonged or sustained delivery of the drug to the gastrointestinal tract by any number of mechanisms. Immediate delivery formulations include, but are not limited to, oral solutions, oral suspensions, fast-dissolving tablets or capsules, sublingual tablets, disintegrating tablets and the like. Prolonged or sustained delivery formulations include, but are not limited to, pH sensitive release of the active ingredient from the dosage form based on the changing pH of the small intestine, slow erosion of a tablet or capsule, retention in the stomach based on the physical properties of the formulation, bioadhesion of the dosage form to the mucosal lining of the intestinal tract, or enzymatic release of the active drug from the dosage form. The intended effect is to extend the time period over which the active drug molecule is delivered to the site of action (for example, the ileum for ASBT inhibitors) by manipulation of the dosage form. Thus, enteric-coated and enteric-coated controlled release formulations are within the scope of the present invention. Suitable enteric coatings include cellulose acetate phthalate, polyvinylacetate phthalate, hydroxypropylmethyl-cellulose phthalate and anionic polymers of methacrylic acid and methacrylic acid methyl ester. Such prolonged or sustained delivery formulations preferably are in a dispersed form at the time they reach the ileum. Other examples of suitable coatings include products known as Eudragit S provided in a thickness sufficient to release the active ingredient in the desired location of the GI tract. Preferably, in the case of an Eudragit S coating, the coating has a thickness from about 10 to about 50 microns, more preferably from about 20 to 45 microns, even more preferably from about 25 to about 43 microns and most preferably from about 30 to about 40 microns. The coating of Eudragit S may be combined with other coating materials known as Eudragit L. Formulations of ASBT inhibitor(s), such as tablets coated with Eudragit S and/or Eudragit L, can be readily formed by those of ordinary skill.

Pharmaceutical compositions suitable for oral administration can be presented in discrete units, such as capsules, cachets, lozenges, or tablets, each containing a predetermined amount of at least one compound of the present invention; as a powder or granules; as a solution or a suspension in an aqueous or non-aqueous liquid; or as an oil-in-water or water-in-oil emulsion. As indicated, such compositions can be prepared by any suitable method of pharmacy which includes the step of bringing into association the inhibitor(s) and the carrier (which can constitute one or more accessory ingredients). In general, the compositions are prepared by uniformly and intimately admixing the inhibitor(s) with a liquid or finely divided solid carrier, or both, and then, if necessary, shaping the product. For example, a tablet can be prepared by compressing or molding a powder or granules of the inhibitors, optionally with one or more accessory ingredients. Compressed tablets can be prepared by compressing, in a suitable machine, the compound in a free-flowing form, such as a powder or granules optionally mixed with a binder, lubricant, inert diluent and/or surface active/dispersing agent(s). Molded tablets can be made, for example, by molding the powdered compound in a suitable machine.

Liquid dosage forms for oral administration can include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

Pharmaceutical compositions suitable for buccal (sublingual) administration include lozenges comprising a compound of the present invention in a flavored base, usually sucrose, and acacia or tragacanth, and pastilles comprising the inhibitors in an inert base such as gelatin and glycerin or sucrose and acacia.

Formulations for parenteral administration, for example, may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Pharmaceutically acceptable carriers encompass all the foregoing and the like. The pharmaceutical compositions of the invention can be prepared by any of the well-known techniques of pharmacy, such as admixing the components. The above considerations in regard to effective formulations and administration procedures are well known in the art and are described in standard textbooks. Formulation of drugs is discussed in, for example, Hoover, John E., *Remington's Pharmaceutical Sciences*, Mack Publishing Co., Easton, Pa. (1975); Liberman, et al., Eds., *Pharmaceutical Dosage Forms*, Marcel Decker, New York, N.Y. (1980); and Kibbe, et al., Eds., *Handbook of Pharmaceutical Excipients* (3$^{rd}$ Ed.), American Pharmaceutical Association, Washington (1999); *U.S. Pharamacopeia* (Twenty-First Revision—USP XXI) National Formulary (Sixteenth Edition—XVI), United States Pharmacopeial Convention, Inc., Rockville, Md. (1985) and its later editions; and *Remington's Pharmaceutical Sciences*, 16$^{th}$ Edition, Arthur Osol, Editor and Chairman of the Editorial Board, Mack Publishing Co., Easton, Pa. (1980) and its later editions.

Methods of Use

The present invention also includes methods for the treatment of one or more hyperlipidemic condition(s) in a subject. One such method comprises the step of administering to a subject in need thereof, a therapeutically effective amount of one or more compounds of Formulas I-1 to I-24.

The present invention further includes methods for the treatment of gallstones in a subject. An exemplary method for the treatment of gallstones comprises the step of administering to a subject in need thereof, a therapeutically effective amount of one or more compound(s) of Formulas I-1 to I-24.

The methods and compounds of the present invention may be used alone or in conjunction with additional therapies and/or compounds known to those skilled in the art in the prevention or treatment of hyperlipidemia. Alternatively, the methods and compounds described herein may be used, partially or completely, in conjunctive therapy. By way of example, the compounds may be administered alone or in conjunction with other anti-hyperlipidemic agents, such as together with HMG-Co-A reductase inhibitors, bile acid sequestering agents, fibric acid derivatives, nicotinic acid, and/or probucol. The above-noted combination therapeutic agents may be provided in a kit.

Terms

As used herein, various terms are defined below.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

The term "subject" as used herein includes mammals (e.g., humans and animals).

The term "treatment" includes any process, action, application, therapy, or the like, for improving the subject's medical condition, directly or indirectly, including, but not limited to, hyperlipidemia or conditions associated with hyperlipidemia.

The terms "prophylaxis" and "prevention" include either preventing the onset of a clinically evident hyperlipidemic condition or disorder altogether or preventing the onset of a preclinically evident stage of a hyperlipidemic condition or disorder in an individual. These terms encompass the prophylactic treatment of a subject at risk of developing a hyperlipidemic condition or disorder such as, but not limited to, atherosclerosis and hypercholesterolemia.

The term "combination therapy" or "co-therapy" means the administration of two or more therapeutic agents to treat a hyperlipidemic condition and/or disorder, for example atherosclerosis and hypercholesterolemia. Such administration encompasses co-administration of two or more therapeutic agents in a substantially simultaneous manner, such as in a single capsule having a fixed ratio of active ingredients or in multiple, separate capsules for each inhibitor agent. In addition, such administration encompasses use of each type of therapeutic agent in a sequential manner. In either case, the treatment regimen will provide beneficial effects of the drug combination in treating the hyperlipidemic condition.

The phrase "therapeutically-effective" means the amount of each agent administered that will achieve the goal of improvement in hyperlipidemic condition or disorder severity, while avoiding or minimizing adverse side effects associated with the given therapeutic treatment.

The term "pharmaceutically acceptable" means that the subject item is appropriate for use in a pharmaceutical product.

The term "prodrug" includes a compound that is a drug precursor that, following administration to a subject and subsequent absorption, is converted to an active species in vivo. Conversion to the active, species in vivo is typically via some process, such as metabolic conversion. An example of a prodrug is an acylated form of the active compound.

The term "ASBT inhibitor" includes a compound capable of inhibiting absorption of bile acids from the intestine into the circulatory system of a mammal, indicating that of a human. This includes increasing the fecal excretion of bile acids, as well as reducing the blood plasma or serum concentrations of cholesterol and cholesterol ester, and more specifically, reducing LDL and VLDL cholesterol.

Where the term "alkyl" is used, either alone or within other terms such as "haloalkyl", and "hydroxyalkyl", it includes linear or branched radicals having one to about twenty carbon atoms, preferably, one to about twelve carbon atoms, more preferably, "lower alkyl" radicals having one to about six carbon atoms and, even more preferably, lower alkyl radicals having one to three carbon atoms. Examples of such radicals include, but are not limited to, methyl, ethyl, n-propyl, isopropyl, n-butyl, isobutyl, sec-butyl, tert-butyl, pentyl, iso-amyl, hexyl and the like.

Where the term "alkenyl" is used, either alone or within other terms such as "arylalkenyl", it includes linear or branched radicals having at least one carbon-carbon double bond in a radical having from two to about twenty carbon atoms, preferably, from two to about twelve carbon atoms, and more preferably "lower alkenyl" radicals having from two to about six carbon atoms. Examples of alkenyl radicals include, but are not limited to, ethenyl, propenyl, allyl, propenyl, butenyl and 4-methylbutenyl.

The terms "alkenyl" and "lower alkenyl", include radicals having "cis" and "trans" orientations, or alternatively, "E" and "Z" orientations.

The term "alkynyl" includes, but is not limited to, linear or branched radicals having from two to about twenty carbon atoms or, preferably, from two to about twelve carbon atoms, more preferably "lower alkynyl" radicals having from two to about ten carbon atoms, most preferably lower alkynyl radicals having from two to about six carbon atoms. Examples of such radicals include propargyl, butynyl, and the like.

The term "cycloalkyl" includes, but is not limited to, saturated carbocyclic radicals having from three to about twelve carbon atoms, more preferably "lower cycloalkyl" radicals having from three to about ten carbon atoms. Examples of such radicals include cyclopropyl, cyclobutyl, cyclopentyl and cyclohexyl. The term "cycloalkyl" additionally encompasses spiro systems wherein the cycloalkyl ring has a carbon ring atom in common with the seven-membered heterocyclic ring of the benzothiepene.

The term "cycloalkenyl" includes, but is not limited to, unsaturated carbocyclic radicals having at least one double bond and having from three to twelve carbon atoms and more preferably "lower cycloalkenyl" radicals having from four to about ten carbon atoms. Cycloalkenyl radicals that are partially unsaturated carbocyclic radicals that contain two double bonds (that may or may not be conjugated) can be called "cycloalkyldienyl". Examples of cycloalkenyl radicals includes, but is not limited to, cyclobutenyl, cyclopentenyl and cyclohexenyl.

The terms "halo" and "halogen" include, but are not limited to, halogen atoms such as fluorine, chlorine, bromine or iodine. The term "haloalkyl" includes radicals wherein any one or more of the alkyl carbon atoms is substituted with a halogen atom. Specifically embraced are monohaloalkyl, dihaloalkyl and polyhaloalkyl radicals. A monohaloalkyl radical, for one example, may have either an iodo, bromo, chloro or fluoro atom within the radical. Dihalo and polyhaloalkyl radicals may have two or more of the same or different halogen atoms. "Lower haloalkyl" includes radicals having one to six carbon atoms. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl" includes alkyl radicals having all hydrogen atoms replaced with fluoro atoms. Examples include trifluoromethyl and pentafluoroethyl.

The term "hydroxyalkyl" includes, but is not limited to, linear or branched alkyl radicals preferably having from one to about ten carbon atoms, more preferably "lower hydroxyalkyl" radicals having from one to six carbon atoms and even more preferably lower hydroxyalkyl radicals having from one to three carbon atoms wherein one or more of the carbon atoms are substituted with one or more hydroxyl radicals. Examples of such radicals include hydroxymethyl, hydroxyethyl, hydroxypropyl, hydroxybutyl and hydroxyhexyl.

The term "aryl" includes, but is not limited to, a carbocyclic aromatic system containing one or more rings wherein such rings may be attached together in a pendent manner or may be fused. The term "aryl" includes aromatic radicals such as cyclopentodienyl phenyl, naphthyl, tetrahydronaphthyl, indanyl, biphenyl, and anthracenyl. Further, "aryl" group may optionally have from one to three substituents such as lower alkyl, hydroxy, halo, haloalkyl, nitro, cyano, alkoxy and lower alkylamino.

The term "heterocyclyl" includes, but is not limited to, saturated, partially saturated and unsaturated heteroatom-containing ring-shaped radicals, where the heteroatoms may be nitrogen, sulfur, oxygen or combinations thereof. Preferred heterocyclyls include, but are not limited to, 3–10 membered ring heterocyclyl, particularly 5–8 membered ring heterocyclyl. Examples of saturated heterocyclic radicals include saturated 3 to 6-membered heteromonocyclic groups containing 1 to 4 nitrogen atoms (e.g., pyrrolidinyl, imidazolidinyl, piperidino, piperazinyl); saturated 3 to 6-membered heteromonocyclic groups containing from 1 to 2 oxygen atoms and from 1 to 3 nitrogen atoms (e.g., morpholinyl); saturated 3 to 6-membered heteromonocyclic groups containing 1 to 2 sulfur atoms and 1 to 3 nitrogen atoms (e.g., thiazolidinyl). Examples of partially saturated heterocyclyl radicals include dihydrothiophene, dihydropyran, dihydrofuran and dihydrothiazole. Examples of unsaturated heterocyclic radicals, also termed "heteroaryl" radicals, include unsaturated 5 to 6 membered heteromonocyclyl groups containing 1 to 4 nitrogen atoms, for example, pyrrolinyl, imidazolyl, pyrazolyl, 2-pyridyl, 3-pyridyl, 4-pyridyl, pyrimidyl, pyrazinyl, pyridazinyl, triazolyl (e.g., 4H-1,2,4-triazolyl, 1H-1,2,3-triazolyl, 2H-1,2,3-triazolyl); unsaturated condensed heterocyclic groups containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl (e.g., tetrazolo [1,5-b]pyridazinyl); unsaturated 3 to 6-membered heteromonocyclic groups containing an oxygen atom, for example, pyranyl, 2-furyl, 3-furyl, etc.; unsaturated 5 to 6-membered heteromonocyclic groups containing a sulfur atom, for example, 2-thienyl, 3-thienyl, etc.; unsaturated 5- to 6-membered heteromonocyclic groups containing 1 to 2 oxygen atoms and 1 to 3 nitrogen atoms, for example, isoxazolyl, oxadiazolyl (e.g., 1,2,4-oxadiazolyl, 1,3,4-oxadiazolyl, 1,2,5-oxadiazolyl); unsaturated condensed heterocyclic groups containing 1 to 2 oxygen atoms and 1 to 3 nitrogen atoms (e.g., benzoxazolyl, benzoxadiazolyl); unsaturated 5 to 6-membered heteromonocyclic groups containing 1 to 2 sulfur atoms and 1 to 3 nitrogen atoms, for example, thiazolyl, thiadiazolyl (e.g., 1,2,4-thiadiazolyl, 1,3,4-thiadiazolyl, 1,2,5-thiadiazolyl); unsaturated condensed heterocyclic groups containing 1 to 2 sulfur atoms and 1 to 3 nitrogen atoms (e.g., benzothiazolyl, benzothiadiazolyl) and the like. The term also includes radicals where heterocyclic radicals are fused with aryl radicals. Examples of such fused bicyclic radicals include benzofuran, benzothiophene, and the like. The "heterocyclyl" group may optionally have 1 to 3 substituents such as lower alkyl, hydroxy, oxo, amino and lower alkylamino. The term "heterocyclyl" includes all positioned isomers.

"Heteroaryl" radicals can include, but are not limited to, fused or unfused radicals, particularly 3–10 membered fused or unfused radicals. Preferred examples of heteroaryl radicals include benzofuryl, 2,3-dihydrobenzofuryl, benzothienyl, indolyl, dihydroindolyl, chromanyl, benzopyran, thiochromanyl, benzothiopyran, benzodioxolyl, benzodioxanyl, pyridyl, thienyl, thiazolyl, furyl, and pyrazinyl. More preferred heteroaryl radicals are 5- or 6-membered heteroaryl, containing one or two heteroatoms selected from sulfur, nitrogen and oxygen such as thienyl, furanyl, thiazolyl, imidazolyl, pyrazolyl, isoxazolyl, isothiazolyl, pyridyl, piperidinyl or pyrazinyl. The term "heteroaryl" includes, but is not limited to, a fully unsaturated heterocyclyl. The term "heteroaryl" includes all positional isomers.

In either the "heterocyclyl" or the "heteroaryl" radical, the point of attachment to the molecule of interest can be at the heteroatom or elsewhere within the ring.

The term "triazolyl" includes, but is not limited to, all positional isomers. In all other heterocyclyl and heteroaryl which contain more than one ring heteroatom and for which isomers are possible, such isomers are included in the definition of said heterocyclyl and heteroaryl.

The term "quaternary heterocyclyl" includes, but is not limited to, a heterocyclyl in which one or more of the heteroatoms, for example, nitrogen, sulfur, phosphorus or oxygen, has such a number of bonds that it is positively charged (and therefore the term is intended to encompass both ternary and quaternary positively charged structures). The point of attachment of the quaternary heterocyclyl to the molecule of interest can be at a heteroatom or elsewhere.

The term "quaternary heteroaryl" includes, but is not limited to, a heteroaryl in which one or more of the heteroatoms, for example, nitrogen, sulfur, phosphorus or oxygen, has such a number of bonds that it is positively charged (and therefore the term is intended to encompass both ternary and quaternary positively charged structures). The point of attachment of the quaternary heteroaryl to the molecule of interest can be at a heteroatom or elsewhere.

The term "oxo" includes, but is not limited to, an oxygen with two bonds.

The term "polyalkyl" includes, but is not limited to, a branched or straight hydrocarbon chain having a molecular weight up to about 20,000 gms, more preferably up to about 10,000 gms, and most preferably up to about 5,000 gms.

The term "polyether" includes, but is not limited to, a polyalkyl wherein one or more carbons are replaced by oxygen, wherein the polyether has a molecular weight up to about 20,000 gms, more preferably up to about 10,000 gms, and most preferably up to about 5,000 gms.

The term "polyalkoxy" includes, but is not limited to, a polymer of alkylene oxides, wherein the polyalkoxy has a molecular weight up to about 20,000 gms, more preferably up to about 10,000 gms, and most preferably up to about 5,000 gms.

The term "carbohydrate residue" includes , but is not limited to, residues derived from carbohydrates, but is not limited to, mono-, di-, tri-, tetra- and polysaccharides wherein the polysaccharides can have a molecular weight of up to about 20,000 gms, for example, hydroxypropylmethylcellulose or chitosan residue; compounds derived from aldoses and ketoses with from 3 to 7 carbon atoms and which belong to the D- or L-series; aminosugars; sugar alcohols; and saccharic acids. Nonlimiting specific examples of such carbohydrates include glucose, mannose, fructose, galactose, ribose, erythrose, glycerinaldehyde, sedoheptulose, glucosamine, galactosamine, glucoronic acid, galacturonic acid, gluconic acid, galactonic acid, mannoic acid, glucamine, 3-amino-1,2-propanediol, glucaric acid and galactaric acid.

The term "peptide residue" includes, but is not limited to, polyamino acid residue containing up to about 100 amino acid units.

The term "polypeptide residue" includes, but is not limited to, a polyamino acid residue containing from about 100 amino acid units to about 1000 amino acid units, more preferably from about 100 amino acid units to about 750 amino acid units, and even more preferably from about 100 amino acid units to about 500 amino acid units.

The term "alkylammoniumalkyl" includes, but is not limited to, an —$NH_2$ group or a mono-, di- or tri-substituted amino group, any of which is bonded to an alkyl wherein said alkyl is bonded to the molecule of interest.

The term "sulfo" includes, but is not limited to, a —$SO_2$— group, a —$SO_3H$ group, and its salts.

The term "sulfoalkyl" includes, but is not limited to, an alkyl group to which a sulfonate group is bonded, wherein said alkyl is bonded to the molecule of interest.

The term "aralkyl" includes, but is not limited to, aryl-substituted alkyl radicals, preferably "lower aralkyl" radicals having aryl radicals attached to alkyl radicals having from one to six carbon atoms, and even more preferably lower aralkyl radicals having phenyl attached to alkyl portions having from one to three carbon atoms. Examples of such radicals include benzyl, diphenylmethyl and phenylethyl. The aryl in said aralkyl may be optionally substituted with halo, alkyl, alkoxy, halkoalkyl and haloalkoxy. The term "arylalkenyl" includes aryl-substituted alkenyl radicals. Preferable arylalkenyl radicals are "lower arylalkenyl" radicals having aryl radicals attached to alkenyl radicals having from one to ten carbon atoms.

The term "heterocyclylalkyl" includes, but is not limited to, an alkyl radical that is substituted with one or more heterocyclyl groups. Preferable heterocyclylalkyl radicals are "lower heterocyclylalkyl" radicals having from one or more heterocyclyl groups attached to an alkyl radical having from one to ten carbon atoms.

The term "heteroarylalkyl" includes, but is not limited to, an alkyl radical that is substituted with one or more heteroaryl groups. Preferable heteroarylalkyl radicals are "lower heteroarylalkyl" radicals having from one or more heteroaryl groups attached to an alkyl radical having from one to ten carbon atoms.

The term "quaternary heterocyclylalkyl" includes, but is not limited to, an alkyl radical that is substituted with one or more quaternary heterocyclyl groups. Preferable quaternary heterocyclylalkyl radicals are "lower quaternary heterocyclylalkyl" radicals having from one or more quaternary heterocyclyl groups attached to an alkyl radical having from one to ten carbon atoms.

The term "quaternary heteroarylalkyl" includes, but is not limited to, an alkyl radical that is substituted with one or more quaternary heteroaryl groups. Preferable quaternary heteroarylalkyl radicals are "lower quaternary heteroarylalkyl" radicals having from one or more quaternary heteroaryl groups attached to an alkyl radical having from one to ten carbon atoms.

The term "alkylheteroarylalkyl" includes, but is not limited to, a heteroarylalkyl radical that is substituted with one or more alkyl groups. Preferable alkylheteroarylalkyl radicals are "lower alkylheteroarylalkyl" radicals with alkyl portions having from one to ten carbon atoms.

The term "alkoxy" includes, but is not limited to, an alkyl radical which is attached to the molecule of interest by oxygen, such as a methoxy radical. More preferred alkoxy radicals are "lower alkoxy" radicals having from one to six carbon atoms. Examples of such radicals include methoxy, ethoxy, propoxy, iso-propoxy, butoxy and tert-butoxy.

The term "carboxy" includes, but is not limited to, the carboxy group, —CO2H, and its salts.

The term "carboxyalkyl" includes, but is not limited to, an alkyl radical that is substituted with one or more carboxy groups. Preferable carboxyalkyl radicals are "lower carboxyalkyl" radicals having one or more carboxy groups attached to an alkyl radical having from one to six carbon atoms.

The term "carboxyheterocyclyl" includes, but is not limited to, a heterocyclyl radical that is substituted with one or more carboxy groups.

The term "carboxyheteroaryl" includes, but is not limited to, a heteroaryl radical that is substituted with one or more carboxy groups.

The term "carboalkoxyalkyl" includes, but is not limited to, an alkyl radical that is substituted with one or more alkoxycarbonyl groups. Preferable carboalkoxyalkyl radicals are "lower carboalkoxyalkyl" radicals having one or more alkoxycarbonyl groups attached to an alkyl radical having from one to six carbon atoms.

The term "carboxyalkylamino" includes, but is not limited to, an amino radical that is mono- or di-substituted. When used in combination, for example "alkylaryl" or "arylalkyl," the individual terms "alkyl" and "aryl" listed above have the meaning indicated above.

The term "acyl" includes, but is not limited to, an organic acid group in which the hydroxy of the carboxy group has been removed. Examples of acyl groups include, but are not limited to, acetyl and benzoyl.

The term "hydrocarbyl" refers to radicals consisting exclusively of the elements carbon and hydrogen. These radicals include, for example, alkyl, cycloalkyl, alkenyl, cycloalkenyl, alkynyl, and aryl moieties. These radicals also include alkyl, cycloalkyl, alkenyl, cycloalkenyl, alkynyl, and aryl moieties substituted with other aliphatic or cyclic hydrocarbon groups, such as alkaryl, alkenaryl and alkynaryl. Preferably, these moieties comprise 1 to 20 carbon atoms, 1–10 carbons or 1–6 carbons.

The term "a substituted hydrocarbyl" refers to a hydrocarbyl radical that is substituted with a group comprising at least one atom other than carbon, such as but not limited to, halogen, oxygen, nitrogen, sulfur and phosphorus. Examples of such substituted hydrocarbyl include hydrocarbyl radicals substituted with groups such as, but not limited to, lower alkoxy such as methoxy, ethoxy, and butoxy; halogen such as chloro and fluoro; ethers; acetals; ketals; esters; heterocyclyl such as furyl and thienyl; alkanoxy; hydroxy; protected hydroxy; acyl; acyloxy; nitro; cyano; amino; and amido. Substituted hydrocarbyl also includes hydrocarbyl radicals in which a carbon chain atom is replaced with a heteroatom such as nitrogen, oxygen, sulfur, or a halogen.

The term "sugar protecting group" means a protecting group on one or more hydroxy groups of a given sugar. Examples of such "sugar protecting groups" include, but are not limited to, acetyl, trialkylsilyl, alkyl (e.g., methyl), alkoxy (e.g., methoxy, ethoxy), tetrahydropyranyl (THP), etc.

Abbreviations used herein have the following meanings:

| TERM | DEFINITION |
| --- | --- |
| THF | tetrahydrofuran |
| PTC | phase transfer catalyst |
| Aliquart 336 | methyltricaprylylammonium chloride |
| MCPBA | m-chloroperbenzoic acid |
| Celite | a brand of diatomaceous earth filtering aid |
| DMF | Dimethylformamide |
| DME | -ethylene glycol dimethyl ether |
| BOC | t-butoxycarbonyl group |
| Me | Methyl |
| Et | Ethyl |
| Bu | Butyl |
| EtOAc | Ethyl acetate |
| Et$_2$O | diethyl ether |
| CH$_2$Cl$_2$ | methylene chloride |
| MgSO$_4$ | magnesium sulfate |
| NaOH | sodium hydroxide |
| CH$_3$OH | Methanol |
| HCl | hydrochloric acid |
| NaCl | sodium chloride |
| NaH | sodium hydride |
| LAH | lithium aluminum hydride |
| LiOH | lithium hydroxide |
| Na$_2$SO$_3$ | sodium sulfite |
| NaHCO$_3$ | sodium bicarbonate |
| DMSO | Dimethylsulfoxide |
| KOSiMe$_3$ | potassium trimethylsilanolate |
| PEG | polyethylene glycol |
| MS | Mass spectrometry |
| HRMS | high resolution mass spectrometry |
| ES | Electrospray |
| NMR | nuclear magnetic resonance spectroscopy |
| GC | gas chromatography |
| MPLC | medium pressure liquid chromatography |
| HPLC | high pressure liquid chromatography |
| RPHPLC | reverse phase high pressure liquid chromatography |
| RT | Room temperature |
| h or hr | hour(s) |
| Min | minute(s) |

Biological Evaluation

The inhibitor concentration of the compounds of the present invention is to be determined by the following assays. These assays are to be performed in vitro and in animal models.

In Vitro Assay of Compounds that Inhibit ASBT-Mediated Uptake of [14C]-Taurocholate (TC) in H14 Cells Seed baby hamster kidney cells (BHK) transfected with the cDNA of human ASBT (H14 cells) in 96 well Top-Count tissue culture plates at 60,000 cells/well (run assays within 24 hours of seeding), 30,000 cells/well (run assays within 48 hours of seeding), and 10,000 cells/well (run assays within 72 hours of seeding).

On the day of assay, gently wash the cell monolayer once with 100 mL assay buffer (Dulbecco's Modified Eagle's medium with 4.5 g/L glucose plus 0.2% (w/v) fatty acid free bovine serum albumin ((FAF) BSA). To each well, add 50 mL of a two-fold concentrate of test compound in assay buffer along with 50 mL of 6 mM [$^{14}$C]-taurocholate in assay buffer (final concentration of 3 mM [$^{14}$C]-taurocholate). Incubate the cell culture plates for 2 hours at 37° C. prior to gently washing each well twice with 100 mL 4° C. Dulbecco's phosphate-buffered saline (PBS) containing 0.2% (w/v) (FAF)BSA. Then gently wash wells once with 100 mL 4° C. PBS without (FAF)BSA. To each 200 mL of liquid, add scintillation counting fluid. Heat seal the plates and shake for 30 minutes at room temperature prior to measuring the amount of radioactivity in each well on a Packard Top-Count instrument.

In Vitro Assay of Compounds that Inhibit Uptake of [$^{14}$C]-Alanine

The alanine uptake assay is performed in an identical fashion to the taurocholate assay, except that labeled alanine is substituted for the labeled taurocholate.

In Vivo Assay of Compounds that Inhibit Rat Ileal Uptake of [$^{14}$C]-Taurocholate into Bile (See Une et al. "Metabolism of 3α,7β-dihydroxy-7β-methyl-5β-cholanoic acid and 3α,7β-dihydroxy-7α-methyl-5β-cholanoic acid in hamsters", *Biochimica et Biophysica Acta*, Vol. 833, pp. 196–202 (1985)).

Anesthetize male wistar rats (200–300 g) with inactin @ 100 mg/kg. Cannulate bile ducts with a 10" length of PE10 tubing. Expose the small intestine and lay out on a gauze pad. Insert a canulae (⅛" luer lock, tapered female adapter) at 12 cm from the junction of the small intestine and the cecum. Cut a slit at 4 cm from this same junction (utilizing a 8 cm length of ileum). Use 20 mL of warm Dulbecco's phosphate buffered saline, pH 6.5 ("PBS") to flush out the intestine segment. Cannulate the distal opening with a 20 cm length of silicone tubing (0.02" I.D.×0.037" O.D.). Hook up the proximal cannulae to a peristaltic pump and wash the intestine for 20 minutes with warm PBS at 0.25 ml/minute. Continuously monitor the temperature of the gut segment.

At the start of the experiment, load 2.0 mL of control sample ([$^{14}$C]-taurocholate @ 0.05 ml/mL with 5 mM cold taurocholate) into the gut segment with a 3 mL syringe and begin bile sample collection. Infuse control sample at a rate of 0.25 ml/minute for 21 minutes. Collect bile sample fractions every 3 minutes for the first 27 minutes of the procedure. After the 21 minutes of sample infusion, wash out the ileal loop with 20 mL of warm PBS (using a 30 mL syringe), and then wash out the loop for 21 minutes with warm PBS at 0.25 ml/minutes. Initiate a second perfusion as described above but with test compound being administered as well (21 minutes administration followed by 21 minutes of wash out) and sample bile every 3 minutes for the first 27 minutes. If necessary, conduct a third perfusion as above that containing the control sample.

Measurement of Hepatic Cholesterol Concentration (HEPATIC CHOL)

Weigh liver tissue and homogenize in chloroform:methanol (2:1). After homogenization and centrifugation, separate the supernatant and dry under nitrogen. Dissolve the residue in isopropanol and measure the cholesterol content enzymatically, using a combination of cholesterol oxidase and peroxidase, as described by Allain, C. A., et al., *Clin. Chem.* 20, 470 (1974).

Measurement of Hepatic HMG CoA-Reductase Activity (HMG COA)

Prepare Hepatic microsomes by homogenizing liver samples in a phosphate/sucrose buffer, followed by centrifugal separation. Resuspend the final pelleted material in buffer and assay an aliquot for HMG CoA reductase activity by incubating for 60 minutes at 37° C. in the presence of $^{14}$C-HMG-CoA (Dupont-NEN). Stop the reaction by adding 6N HCl followed by centrifugation. Separate an aliquot of the supernatant by thin-layer chromatography, and scrape off the plate the spot corresponding to the enzyme product. Extract and determine radioactivity by scintillation counting. (See Akerlund, J. and Bjorkhem, I., *J. Lipid Res.* 31, 2159(1990)).

Determination of Serum Cholesterol (SER.CHOL, HDL-CHOL TGI and VLDL+LDL)

Measure total serum cholesterol (SER.CHOL) enzymatically using a commercial kit from Wako Fine Chemicals (Richmond, Va.); Cholesterol C11, Catalog No. 276-64909. Assay HDL cholesterol (HDL-CHOL) using this same kit after precipitation of VLDL and LDL with Sigma Chemical Co. HDL Cholesterol reagent, Catalog No. 352-3 (dextran sulfate method). Enzymatically assay total serum triglycerides (blanked) (TGI) with Sigma Chemical Co. GPO-Trinder, Catalog No. 337-B. Calculate VLDL and LDL (VLDL+LDL) cholesterol concentrations as the difference between total and HDL cholesterol.

Measurement of Hepatic Cholesterol 7α-Hydroxylase Activity (7α-OHase)

Prepare hepatic microsomes by homogenizing liver samples in a phosphate/sucrose buffer, followed by centrifugal separation. Resuspend the final pelleted material in buffer and assay an aliquot for cholesterol 7α-hydroxylase activity by incubating for 5 minutes at 37° C. in the presence of NADPH. Following extraction into petroleum ether, evaporate the organic solvent and dissolve the residue in acetonitrile/methanol. Separate the enzymatic product by injecting an aliquot of the extract onto a $C_{18}$ reversed phase HPLC column and quantitate the eluted material using UV detection at 240 nm. (See Horton, J. D., et al., *J. Clin. Invest.* 93, 2084(1994).)

Rat Gavage Assay

Administer ASBT inhibitors to male Wister rats (275–300 g) using an oral gavage procedure. Administer drug or vehicle (0.2% Tween 80 in water) once a day (9:00–10:00 a.m.) for 4 days at varying dosages in a final volume of 2 mL per kilogram of body weight. Collect total fecal samples during the final 48 hours of the treatment period and analyze for bile acid content using an enzymatic assay as described below. Determine compound efficacy by comparison of the increase in fecal bile acid (FBA) concentration in treated rats to the mean FBA concentration of rats in the vehicle group.

Measurement of Fecal Bile Acid Concentration (FBA)

Collect total fecal output from individually housed hamsters is collected for 24 or 48 hours, dried under a stream of nitrogen, pulverized and weighed. Approximately 0.1 gram is weighed out and extracted into an organic solvent (butanol/water). Following separation and drying, the residue is dissolved in methanol and the amount of bile acid present is measured enzymatically using the 3α-hydroxysteroid steroid dehydrogenase reaction with bile acids to reduce AND. (See Mashige, F., et al., *Clin. Chem.* 27, 1352 (1981)).

[$^3$H]Taurocholate Uptake in Rabbit Brush Border Membrane Vesicles (BBMV)

Prepare rabbit Ileal brush border membranes from frozen ileal mucosa by the calcium precipitation method describe by Malathi et al. (See *Biochimica Biophysica Acta*, 554, 259 (1979)). The method for measuring taurocholate is essentially as described by Kramer et al. (Reference: (1992) *Biochimica Biophysica Acta*, 1111, 93) except the assay volume is 200 μL instead of 100 μL. Briefly, incubate at room temperature a 190 μL solution containing 2 μM [$^3$H]-taurocholate (0.75 μCi), 20 mM tris, 100 mM sodium chloride, 100 mM mannitol pH 7.4 for 5 seconds with 10 μL of brush border membrane vesicles (60–120 μg protein). Initiate the incubation by the addition of BBMV while vortexing and stop the reaction by the addition of 5 μL of ice cold buffer (20 mM Hepes-tris, 150 mM KCl) followed immediately by filtration through a nylon filter (0.2 μm pore) and an additional 5 mL wash with stop buffer.

Acyl-CoA; Cholesterol Acyl Transferase (ACAT)

Prepare hamster liver and rat intestinal microsomes from tissue as described previously (See *J. Biol. Chem.* 255, 9098 (1980)) and use as a source of ACAT enzyme. The assay consists of a 2.0 mL incubation containing 24 μM Oleoyl-CoA (0.05 μCi) in a 50 mM sodium phosphate, 2 mM DTT pH 7.4 buffer containing 0.25% BSA and 200 μg of microsomal protein. Initiate the assay by the addition of oleoyl-CoA. Allow the reaction to proceed for 5 minutes at 37° C. and terminate it by the addition of 8.0 mL of chloroform/methanol (2:1). To the extraction, add 125 μg of cholesterol oleate in chloroform methanol to act as a carrier and the organic and separate the aqueous phases of the extraction by centrifugation after thorough vortexing. Take the chloroform phase to dryness and then spot on a silica gel 60 thin layer chromatography plate and develop in hexane/ethyl ether (9:1). Determine the amount of cholesterol ester formed by measuring the amount of radioactivity incorporated into the cholesterol oleate spot on the thin layer chromatography plate with a Packard instaimager.

As various changes could be made in the above methods and apparatus without departing from the scope of the invention, it is intended that all matter contained in the above description be interpreted as illustrative and not in a limiting sense. All documents, books, patents, references and publications mentioned in this application are expressly incorporated by reference in their entirety as if fully set forth at length.

Dog Model for the Evaluation of Lipid-lowering Drugs

Obtain male beagle dogs weighing 6–12 kg from a vendor, such as Marshall farms. Feed each dog once a day for two hours and give water ad libitum. Randomly assign dogs to dosing groups consisting of 6 to 12 dogs each, corresponding to: vehicle, i.g.; 1 mg/kg, i.g.; 2 mg/kg, i.g.; 4 mg/kg, i.g.; 2 mg/kg, p.o. (powder in capsule). Perform intra-gastric dosing of a therapeutic compound dissolved in aqueous solution (for example, 0.2% Tween 80 solution (polyoxyethylene mono-oleate, Sigma Chemical Co., St. Louis, Mo.)) using a gavage tube. Prior to initiating dosing, draw blood samples from the cephalic vein before the morning feeding in order to evaluate serum cholesterol (total and HDL) and triglycerides. For several consecutive days, dose animals in the morning prior to feeding. Thereafter, allow animals to eat for two hours before remaining food is removed. Collect feces over a 2-day period at the end of the study and analyze for bile acid or lipid content. Collect blood samples at the end of the treatment period for comparison with pre-study serum lipid levels. Determine statistical significance using the standard Student's T-test, with $p<0.05$.

Dog Serum Lipid Measurement

Collect blood from the cephalic veins of fasted dogs using serum separator tubes (Vacutainer SST, Becton Dickinson and Co., Franklin Lakes, N.J.). Centrifuge the blood at 2000 rpm for 20 minutes and decant the serum.

Measure total cholesterol in a 96-well format using a Wako enzymatic diagnostic kit (Cholesterol CII) (Wako Chemicals, Richmond, Va.), utilizing the cholesterol oxidase reaction to produce hydrogen peroxide, which is measured calorimetrically. Prepare a standard curve from 0.5 to 10 mg cholesterol in the first two columns of the plate. Add the serum samples (20–40 mL, depending on the expected lipid concentration) or known serum control samples to individual wells in duplicate. Add water to bring the volume to 100 mL in each well. Add a 100-m 1 aliquot of color reagent to each well, and read the plates at 500 nm after a 15-minute incubation at 37° C. HDL cholesterol was assayed using Sigma kit No. 352-3 (Sigma Chemical Co., St. Louis, Mo.), which utilizes dextran sulfate and $Mg^{2+}$ to selectively precipitate LDL and VLDL. Add a volume of 150 mL of each serum sample to individual microfuge tubes, followed by 15 mL of HDL cholesterol reagent (Sigma 352-3). Mix samples and centrifuge at 5000 rpm for 5 minutes. Then mix a 50 mL aliquot of the supernatant with 200 mL of saline and assay using the same procedure as for total cholesterol measurement.

Measure triglycerides using Sigma kit No. 337 in a 96-well plate format. This procedure will measure the release glycerol from triglycerides with lipoprotein lipase. Use standard solutions of glycerol (Sigma 339-11) ranging from 1 to 24 mg to generate the standard curve. Add serum samples (20–40 mL, depending on the expected lipid concentration) to wells in duplicate. Add water to bring the volume to 100 mL in each well and then add 100 mL of color reagent to each well. After mixing and a 15-minutes of incubation, read the plates at 540 nm and calculate the triglyceride values from the standard curve. Run a replicate plate using a blank enzyme reagent to correct for any endogenous glycerol in the serum samples.

Dog Fecal Bile Acid Measurement

Collect fecal samples to determine the fecal bile acid (FBA) concentration for each animal. Obtain fecal collections during the final 48 hours of the study, for two consecutive 24-hour periods between 9:00 a.m. and 10:00 a.m. each day, prior to dosing and feeding. Weigh the separate two-day collections from each animal, combine and homogenize with distilled water in a processor (Cuisinart) to generate a homogeneous slurry. Extract a sample of 1.4 g of the homogenate in a final concentration of 50% tertiary butanol/distilled water (2:0.6) for 45 minutes in a 37° C. water bath and centrifuge for 13 minutes at 2000×G.

Determine the concentration of bile acids (mmoles/day) using a 96-well enzymatic assay system. Add a 20-mL aliquot of the fecal extract to two sets each of triplicate wells in a 96-well assay plate. Analyze a standardized sodium taurocholate solution and a standardized fecal extract solution (previously made from pooled samples and characterized for its bile acid concentration) for assay quality control. Similarly add aliquots of sodium taurocholate (20 mL), serially diluted to generate a standard curve, to two sets of triplicate wells. Add a 230-mL reaction mixture containing IM hydrazine hydrate, 0.1 M pyrophosphate and 0.46 mg/ml AND to each well. Then add a 50-mL aliquot of 3α-hydroxysteroid dehydrogenase enzyme (HSD; 0.8 units/ml) or assay buffer (0.1 M sodium pyrophosphate) to one of the two sets of triplicates. Obtain all reagents from Sigma Chemical Co., St. Louis, Mo. Following 60 minutes of incubation at room temperature, measure the optical density at 340 nm and calculate the mean of each set of triplicate samples. Use the difference in optical density HSD enzyme to determine the bile acid concentration (mM) of each sample, based on the sodium taurocholate standard curve. Use the bile acid concentration of the extract, the weight of the fecal homogenate (grams) and the body weight of the animal to calculate the corresponding FBA concentration in mmoles/kg/day for each animal. Substrate the mean FBA concentration (mmoles/kg/day) of the vehicle group from the FBA concentration of each treatment group to determine the increase (delta value) in FBA concentration as a result of the treatment.

Below are various illustrative examples for making various compounds in connection with the invention. The following examples and specific embodiments are provided for illustrative purposes and not intended to limit the scope of the invention.

Additional schemes for forming compounds of the present invention are provided below.

Scheme 5

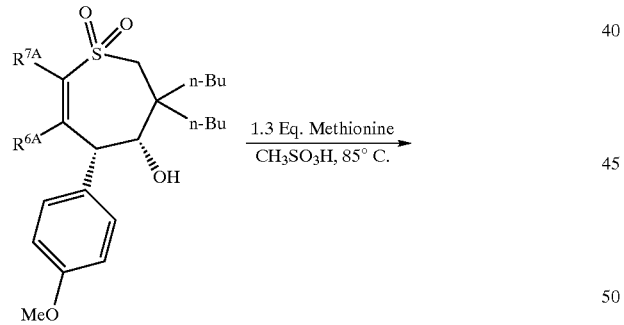

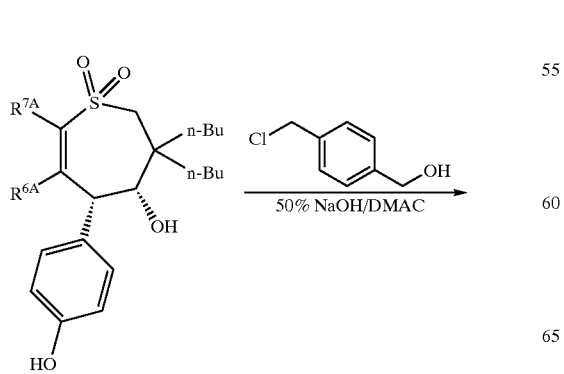

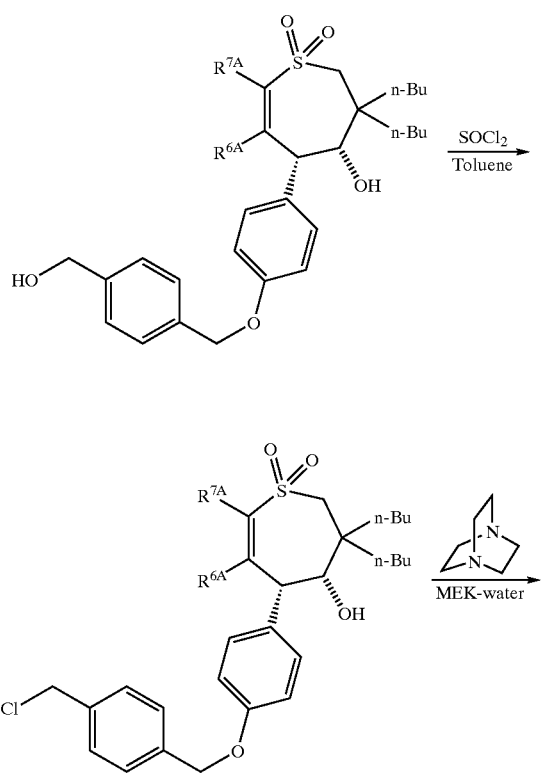

Scheme 6

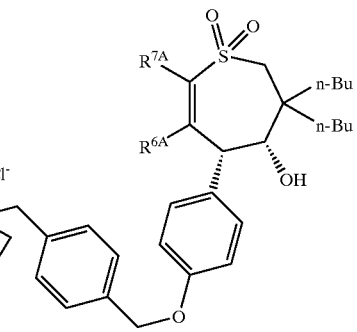

29x

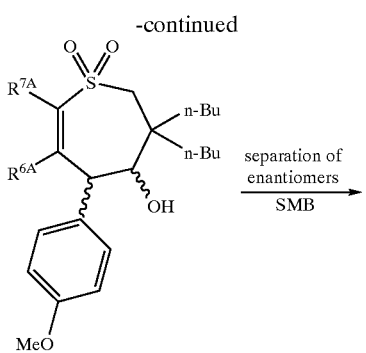

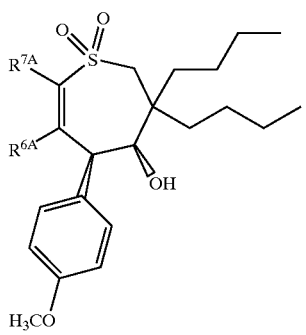

Generally, the process methods of the present invention can be performed as follows.

EXAMPLE 1462

Preparation of Syn-24x

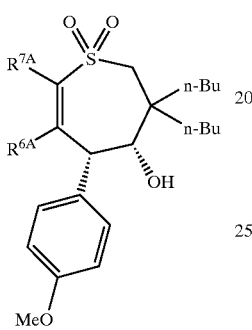

Purge a 250 ml round bottom glass reactor fitted with mechanical agitator and a heating/cooling bath with nitrogen. Charge forty-five grams of potassium t-butoxide/THF solution to the reactor and start agitation. In a separate container, dissolve 38 mmoles of 29x in 25 grams of THF. Charge the 29x/THF solution into the reactor through a addition funnel over about 2.0 hours. Control the reactor temperature between about 16–20° C. Quench the reaction with 54 grams of 7.4% ammonium chloride aqueous solution over a period of about 30 minutes while keeping the reactor temperature at 16–24° C. Gently stir the mixture until all salt is dissolved (about 10 minutes). Stop agitation and allow the phases to separate. Drain the aqueous layer. Concentrate the organic layer in vacuo to give syn-24x as a 50/50 mixture of R,R and S,S isomers.

EXAMPLE 1463a

Conditions for Optical Resolution of Compound (4R,5R)-24x

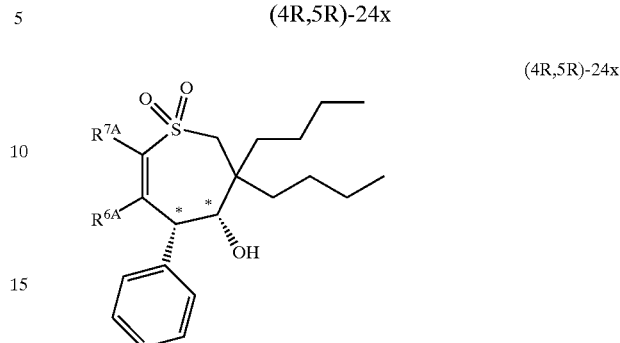

The following simulated moving bed chromatography (SMB) conditions are to be used to separate the (4R,5R) and (4S,5S) enantiomers of compound 24x.

| Column (CSP): | Daicel Chiralpak AS |
|---|---|
| Mobile Phase: | acetonitrile (100%) |
| Column Length: | 11 cm (9 cm for column 6) |
| Column I.D.: | 20.2 cm |
| Number of Columns: | 6 columns |
| Feed Concentration: | 39 grams/liter |
| Eluent Flowrate: | 182 L/hour |
| Feed Flowrate: | 55 L/hour |
| Extract Flowrate: | 129.4 L/hour |
| Raffinate Flowrate: | 107.8 L/hour |
| Recycling Flowrate: | 480.3 L/hour |
| Period: | 0.6 minute |
| Temperature: | Ambient |

EXAMPLE 1463b

Alternate Conditions for Optical Resolution of Compound (4R,5R)-24x

The following simulated moving bed chromatography (SMB) conditions are to be used to separate the (4R,5R) and (4S,5S) enantiomers of compound 24x.

| Column (CSP): | di-methyl phenyl derivative of tartaric acid (Kromasil DMB) |
|---|---|
| Mobile Phase: | toluene/methyl tert-butyl ether (70/30) |
| Column Length: | 6.5 cm |
| Column I.D.: | 2.12 cm |
| Number of Columns: | 8 columns |
| Zones: | 2-3-2-1 |
| Feed Concentration: | 6.4 weight percent |
| Fluent Flowrate: | 20.3 g/minute |
| Feed Flowrate: | 0.7 g/minute |
| Extract Flowrate: | 5.0 g/minute |
| Raffinate Flowrate: | 16.0 g/minute |
| Period: | 8 minute |
| Temperature: | Ambient |

EXAMPLE 1463c

Alternate Conditions for Optical Resolution of Compound (4R,5R)-24x

The following simulated moving bed chromatography (SMB) conditions are to be used to separate the (4R,5R) and (4S,5S) enantiomers of compound 24x.

| | |
|---|---|
| Column (CSP): | di-methyl phenyl derivative of tartaric acid (Kromasil DMB) |
| Mobile Phase: | toluene (100%) |
| Column Length: | 6.5 cm |
| Column I.D.: | 2.12 cm |
| Number of Columns: | 8 columns |
| Zones: | 2-3-2-1 |
| Feed Concentration: | 64 weight percent |
| Eluent Flowrate: | 20.3 g/minute |
| Feed Flowrate: | 0.5 g/minute |
| Extract Flowrate: | 4.9 g/minute |
| Raffinate Flowrate: | 15.9 g/minute |
| Period: | 8 minute |
| Temperature: | Ambient |

EXAMPLE 1463d

Racemization of Compound (4S,5S)-24x

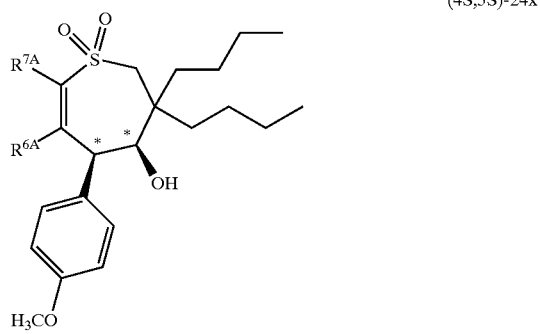

(4S,5S)-24x

Purge a 250 mL round bottom glass reactor fitted with mechanical agitator and a heating/cooling bath with nitrogen gas. In a flask, add 38 mmoles of (4S,5S)-24x and dissolve in 50 g of dry THF. Charge this solution into the reactor and bring to about 23–25° C. with agitation. To the reactor, charge 45 g of potassium t-butoxide/THF solution (1 M, Aldrich) through an addition funnel over about 0.5 hour. Stir the slurry at about 24–26° C. for about 1–1.5 hours. Quench the reaction with 54 g of 7.5% aqueous ammonium chloride while keeping the reactor temperature at about 23–26° C. Charge with the first ca. 20% of the ammonium chloride solution slowly until the slurry turns thin and the rest of the ammonium chloride solution is charged over about 0.5 hour. Stir the mixture gently until all the salt is dissolved. Stop the agitation and allow the phases to separate. Remove the aqueous layer. Concentrate the organic layer in vacuo to give racemic (4S,5S)-24x.

EXAMPLE 1464

Preparation of (4R,5R)-28x

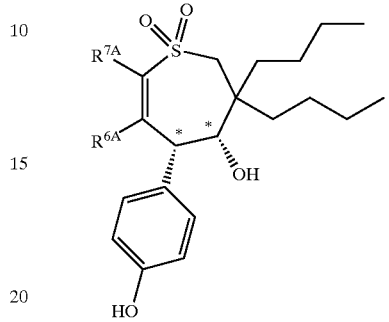

(4R,5R)-28x

Fit a 1000 mL 4 neck Reliance jacketed reactor flask with a mechanical stirrer, a nitrogen inlet, an addition funnel, condenser or distillation head with receiver, a therrmocouple, and a Teflon paddle agitator. Purge the flask with nitrogen gas and charge with 87 mmoles of (4R,5R)-24x and 18.7 grams of methionine followed by 240 grams of methanesulfonic acid. Heat the mixture to 75° C. and stir for 8 hrs. Then cool the mixture to 25° C. and charge with 480 mL of 3-pentanone. Next, charge the flask with 320 mL of dilution water and stir for 15 minutes. Separate the aqueous layer and add to the organic layer, 250 mL of saturated sodium bicarbonate. Stir the mixture for 15 minutes and the separate aqueous layer. Concentrate the organic layer in vacuo to give (4R,5R)-28x.

EXAMPLE 1464a

Alternate Preparation of (4R,5R)-28x

Fit a 1000 mL 4 neck Ace jacketed reactor flask with a mechanical stirrer, a nitrogen inlet, an addition funnel, condenser or distillation head with receiver, a thermocouple, and a Teflon paddle agitator. Purge the flask with nitrogen gas and charge with 84.4 mmoles of (4R,5R)-24x and 17.8 grams of methionine followed by 178.6 grams of methanesulfonic acid. Heat the mixture to 80° C. and stir for 12 hrs. Cool the mixture to 15° C. and charge with 241.1 mL of water over 30 minutes. Then charge the reactor with 361.7 mL of 3-pentanone. Next, stir the flask for 15 minutes. Separate the aqueous layer and, add to the organic layer, 361.7 mL of saturated sodium bicarbonate. Stir the mixture for 15 minutes and separate the aqueous layer. Concentrate the organic layer in vacuo to give (4R,5R)-28x.

EXAMPLE 1465

Preparation of 1-(Chloromethyl)-4-(hydroxymethyl)benzene, 55x

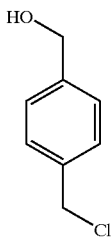

A reaction flask fitted with a nitrogen inlet and outlet, a reflux condenser, and a magnetic stirrer was purged with nitrogen. The flask was charged with 25 g of 4-(chloromethyl)benzoic acid. The flask was charged with 75 mL of THF at ambient temperature. Stirring caused a suspension to form. An endothermic reaction ensued in which the temperature of the reaction mixture dropped 22° C. to 14° C. To the reaction mixture 175 mL of borane-THF adduct was added via a dropping funnel over about 30 minutes. During this exothermic addition, an ice-bath was used for external cooling to keep the temperature below 30° C. The reaction mixture was stirred at 20° C. for 1 h and it was then cooled to 0° C. The reaction mixture was quenched by slow addition of 1M sulfuric acid. The resulting reaction mixture was diluted with 150 mL of t-butyl methyl ether (TBME) and stirred for at least 20 min to destroy boric acid esters. The layers were separated and the aqueous layer was washed with another portion of 50 mL of TBME. The combined organic layers were washed twice with 100 mL of saturated sodium bicarbonate solution. The organic layer was dried over 11 g of anhydrous sodium sulfate and filtered. The solvents were evaporated on a rotary evaporator at 45° C. (bath temperature) and <350 mbar yielding a colorless oil. The oil was seeded with crystals and the resulting solid 55x was dried under vacuum. Yield: 19.7 g (86%). Assay by GC (HP-5 25 meter column, 1 mL $N_2$/min at 100° C., FID detection at 300° C., split 50:1).

EXAMPLE 1466

Preparation of 41x

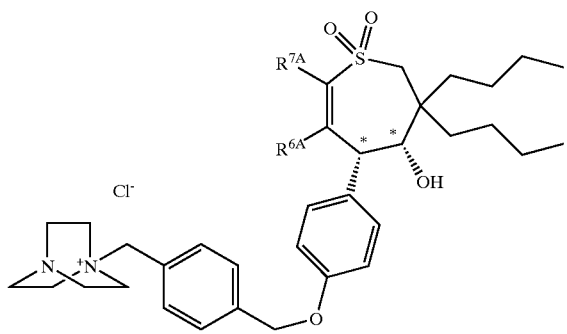

Step 1. Preparation of (4R,5R)-26x.

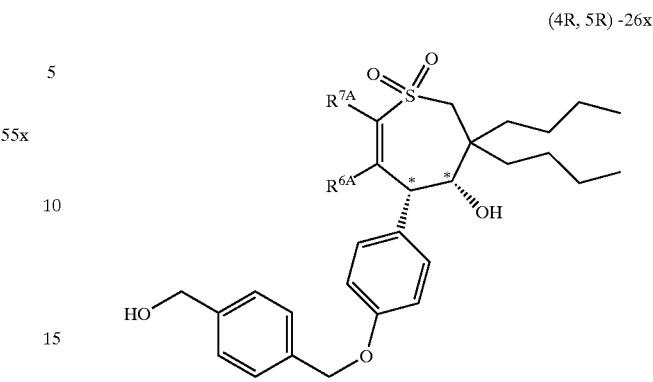

Fit a 1000 mL 4 neck jacketed Ace reactor flask with a mechanical stirrer, a nitrogen inlet, an addition funnel or condenser or distilling head with receiver, a thermocouple, four internal baffles and a 28 mm Teflon turbine agitator. Purge the flask with nitrogen gas and charge with 54.4 mmoles of (4R,5R)-28x and 125 mL of N,N-dimethylacetamide (DMAC). To this, add 4.2 grams of 50% sodium hydroxide. Heat the mixture to 50° C. and stir for 15 minutes. To the flask add 8.3 grams of 55x dissolved in 10 mL of DMAC, all at once. Hold the temperature at 50° C. for 24 hrs. To the flask, add 250 mL of toluene followed by 125 mL of dilution water. Stir the mixture for 15 minutes and allow the layers to separate at 50° C. Then charge the flask with 125 mL of saturated sodium chloride solution and stir 15 minutes. Layers should separate cleanly in 30 seconds at 50° C. Distill off approximately half of the solvent under vacuum at 50° C. The residual reaction mixture should contain (4R,5R)-26x.

Step 2. Preparation of (4R,5R)-27x.

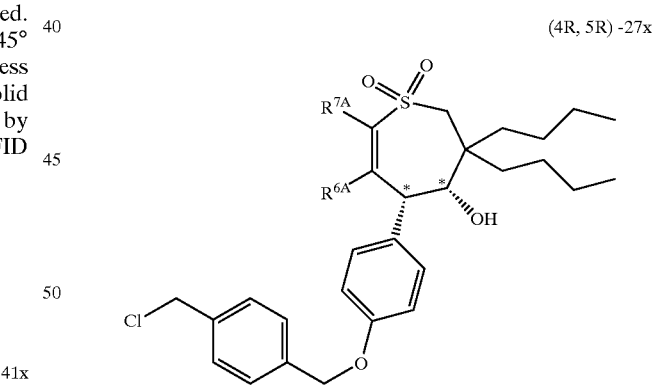

Charge toluene back to the reaction mixture of Step 1 and cool the mixture to 35° C. Then, to the mixture, add 7.0 grams of thionyl chloride over 5 minutes. The reaction should be exothermic and the temperature reached should be about 39° C. The reaction should turn cloudy on first addition of thionyl chloride, then partially clear and then finally turn cloudy. Stir the mixture for 0.5 hr and then wash with 0.25N NaOH. The mixture should appear to form a small amount of solids that diminish on stirring, and the layers should cleanly separate. Distill the solvent to a minimum stir volume under vacuum at 50° C. The residual reaction mixture should contain (4R,5R)-27x.

Step 3. Preparation of 41x

To the reaction mixture of Step 2, charge with 350 mL of methyl ethyl ketone (MEK) followed by 10.5 mL water and 6.4 grams of diazabicyclo[2.2.2]octane (DABCO) dissolved in 10 mL of MEK. Heat the mixture to reflux, until HPLC showed <0.5% of (4R,5R)-27x. Concentrate the reaction mixture in vacuo to give 41x.

All patents, publications, textbooks, articles and any other publications referenced in this application are incorporated herein by reference in their entirety for all purposes.

What is claimed is:

1. A compound comprising a benzothiepene of Formula I-1 or I-2:

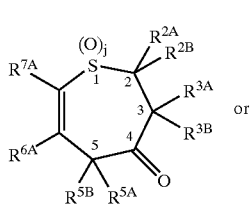

I-1

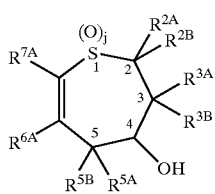

I-2 or a pharmaceutically acceptable salt, solvate, or prodrug thereof wherein j is 0, 1 or 2;

wherein $R^{2A}$ and $R^{2B}$ are independently selected from the group consisting of hydrogen and hydrocarbyl;

wherein $R^{3A}$, $R^{3B}$, $R^{5A}$, and $R^{5B}$ are independently selected from the group consisting of hydrogen, alkyl; cycloalkyl; alkenyl; alkynyl; heterocyclyl; quaternary heterocyclyl, oxo; aryl-$R^5$; —$OR^9$; —$NR^9R^{10}$; —$SR^9$; —$S(O)R^9$; —$SO_2R^9$; and —$SO_3R^9$;

wherein $R^9$ and $R^{10}$ are independently selected from the group consisting of hydrogen; hydrocarbyl; amino; and hydrocarbylamino;

wherein $R^5$ is selected from the group consisting of hydrogen; hydrocarbyl, heterocyclyl; quaternary heterocyclyl; —$OR^9$; —$SR^9$; —$S(O)R^9$; —$SO_2R^9$; and —$SO_3R^9$;

wherein when $R^5$ is said cycloalkyl, aryl or heterocyclyl, said cycloalkyl, aryl or heterocyclyl are optionally substituted with —NH—X—R or —O—X—R;

wherein X is selected from the group consisting of —(C=O)$_s$-alkyl-; —(C=O)$_s$-alkyl-NH—; —(C=O)$_s$-alkyl-O—; —(C=O)$_s$-alkyl-(C=O)$_t$; and a covalent bond, wherein s and t are independently 0 or 1;

wherein R is selected from the group consisting of monosaccharides, disaccharides, and polysaccharides, wherein said monosaccharides, disaccharides, and polysaccharides are optionally protected with one or more sugar protecting groups;

wherein $R^9$ and $R^{10}$ are as previously defined;

wherein, when $R^5 \neq H$, $R^5$ is optionally substituted with one or more radicals independently selected from the group consisting of halogen; —$NO_2$; —CN; oxo; hydrocarbyl; —$OR^{13}$; —$NR^{13}R^{14}$; —$SR^{13}$; —$S(O)R^{13}$; —$SO_2R^{13}$; —$SO_3R^{13}$; —$NR^{13}OR^{14}$; —$NR^{13}NR^{14}R^{15}$; —$CO_2R^{13}$; —OM; —$SO_2OM$; —$SO_2NR^{13}R^{14}$; —$C(O)NR^{13}R^{14}$; —$C(O)OM$; —$COR^{13}$; —$NR^{13}C(O)R^{14}$; —$NR^{13}C(O)NR^{14}R^{15}$; —$NR^{13}CO_2R^{14}$; —$OC(O)R^{13}$; —$OC(O)NR^{13}R^{14}$; —$NR^{13}SOR^{14}$; —$NR^{13}SO_2R^{14}$; —$NR^{13}SONR^{14}R^{15}$; —$NR^{13}SO_2NR^{14}R^{15}$; —$PR^{13}R^{14}$; —$P(O)R^{13}R^{14}$; —$P^+R^{13}R^{14}R^{15}A^-$; —$P(OR^{13})OR^{14}$; —$S^+R^{13}R^{14}A^-$; and —$N^+R^{13}R^{14}R^{15}A^-$;

wherein $R^{13}$, $R^{14}$, and $R^{15}$ are independently selected from the group consisting of hydrogen and hydrocarbyl;

wherein $A^-$ is a pharmaceutically acceptable anion;

wherein M is a pharmaceutically acceptable cation;

wherein $R^{6A}$ and $R^{7A}$ radicals are independently selected from the group consisting of hydrogen; halogen; —CN; —$NO_2$; hydrocarbyl; —$R^5$; -aryl-$R^5$; —$OR^{13}$; —$NR^{13}R^{14}$; —$SR^{13}$; —$S(O)R^{13}$; —$S(O)_2R^{13}$; —$SO_3R^{13}$; —$S^+R^{13}R^{14}A^-$; —$NR^{13}OR^{14}$; —$NR^{13}NR^{14}R^{15}$; —OM; —$SO_2OM$; —$SO_2NR^{13}R^{14}$; —$NR^{14}C(O)R^{13}$; —$C(O)OM$; —$S(O)NR^{13}R^{14}$; —$N^+R^{13}R^{14}R^{15}A-$; —$PR^{13}R^{14}$; —$P(O)R^{13}R^{14}$; —$P^+R^{13}R^{14}R^{15}A^-$; amino acid residue; peptide residue; polypeptide residue; and carbohydrate residue;

wherein $R^{13}$, $R^{14}$, $R^{15}$, $A^-$, and M are as defined above; and wherein, in each instance, said hydrocarbyl may be optionally substituted with one or more groups comprising one or more heteroatoms, and wherein, in each instance, said hydrocarbyl optionally may have one or more carbon atoms replaced by one or more heteroatoms independently selected from the group consisting of oxygen, nitrogen, sulfur, phosphorus and combinations thereof.

2. The compound of claim 1 or a pharmaceutically acceptable salt, solvate or prodrug thereof, wherein $R^{2A}$ and $R^{2B}$ are independently selected from the group consisting of hydrogen and alkyl, $R^{3A}$ and $R^{3B}$ are independently selected from the group consisting of hydrogen, alkyl, alkenyl, alkynyl, cycloalkyl, cycloalkylalkyl, aryl and arakyl and $R^5$ is selected from the group consisting of alkyl, cycloalkyl, alkenyl, alkynyl and aryl.

3. The compound of claim 1 or a pharmaceutically acceptable salt, solvate or prodrug thereof, wherein $R^{5A}$ is aryl optionally substituted with said radical $R^5$ selected from the group consisting of (1)–(69) and (70):

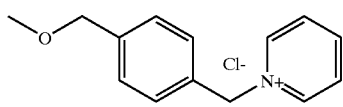

(1)

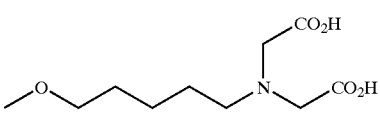

(2)

-continued
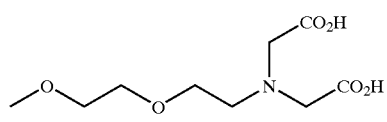
(3)
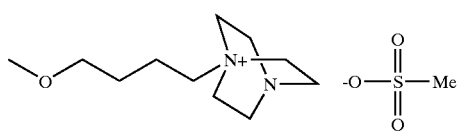
(4)
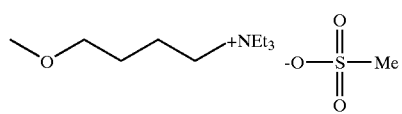
(5)
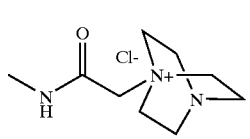
(6)
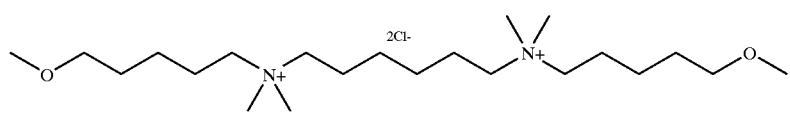
(7)
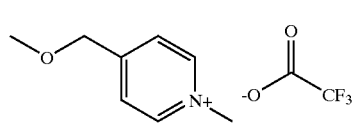
(8)
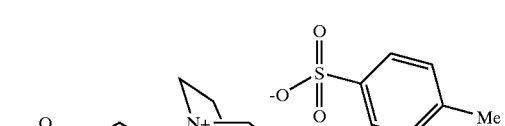
(9)
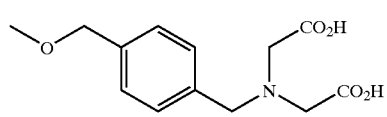
(10)
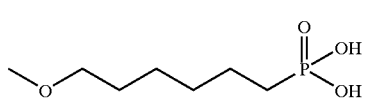
(11)
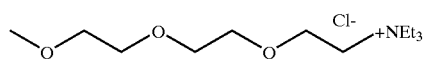
(12)
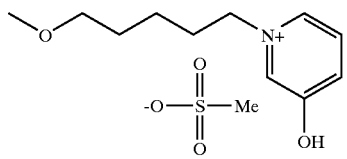
(13)
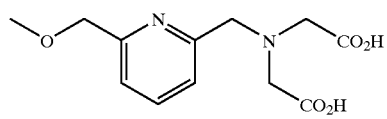
(14)
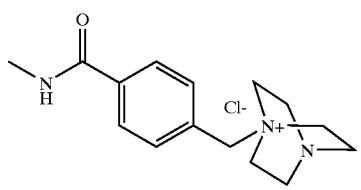
(15)
(15a)
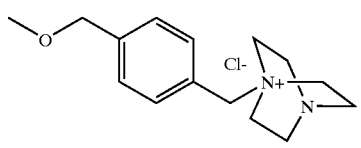
(16)
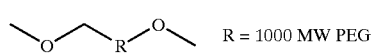
R = 1000 MW PEG
(17)
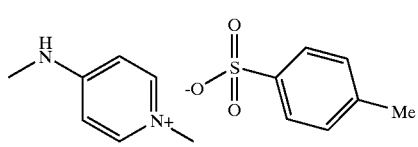
(18)
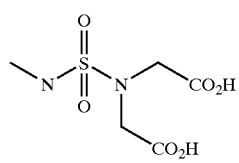
(19)
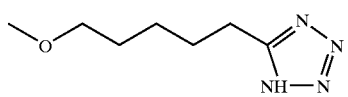
(20)

(21) 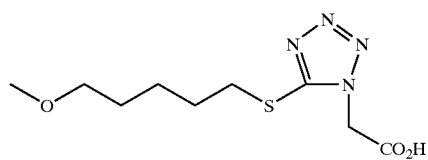
(22) 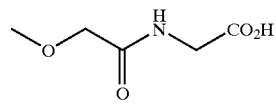
(23) 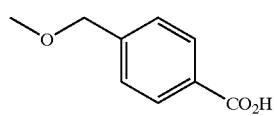
(24) 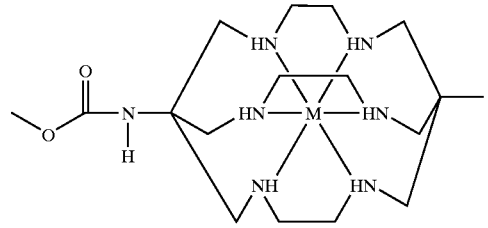
M = Co$^{II,III}$, Mn$^{II,III}$, Fe$^{II,III}$, Ni$^{II,III}$, Cr$^{III}$, Cu$^{II}$, Zn$^{II}$, Cd$^{II}$, Ga$^{III}$, In$^{III}$, V$^{IV}$, Ru$^{II}$, Pr$^{IV}$, Ph$^{III}$ or Ir$^{III}$
(25) 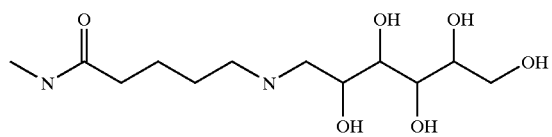
(26) 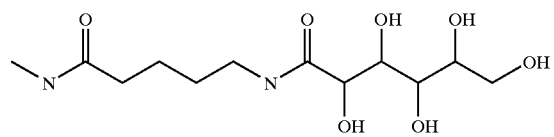
(27) 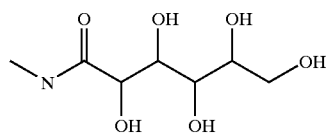
(28) 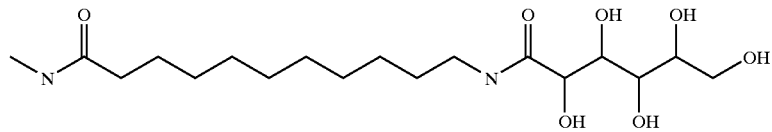
(29) 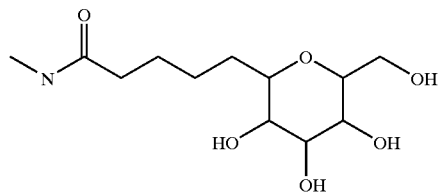
(30) 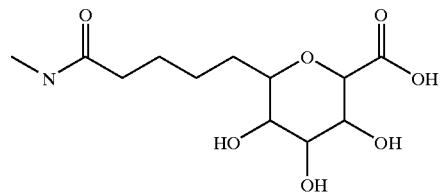
(31) 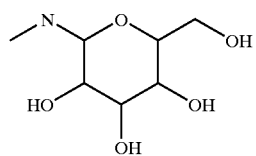
(32) 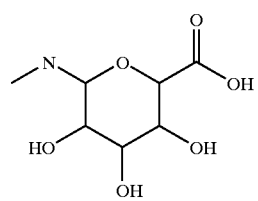
(33) 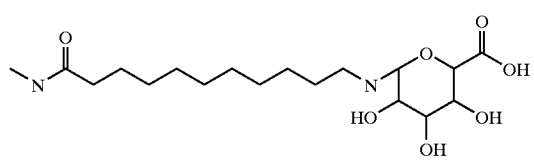
(34) 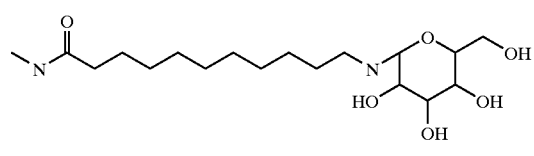

-continued
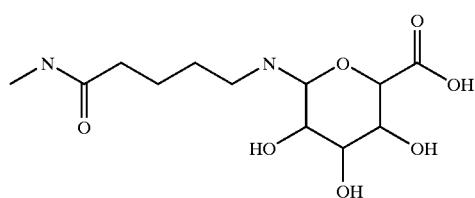
(35)
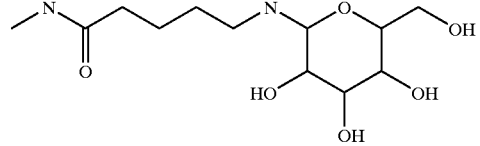
(36)
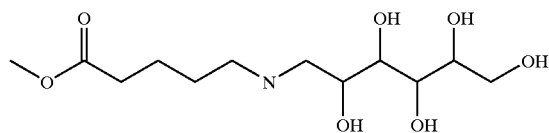
(37)
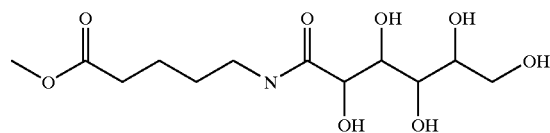
(38)
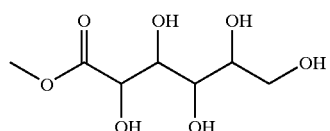
(39)
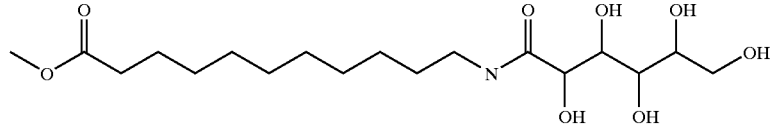
(40)
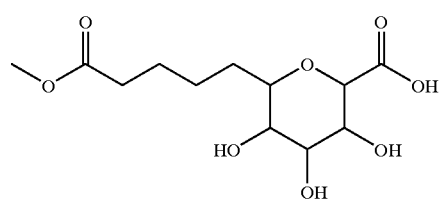
(41)
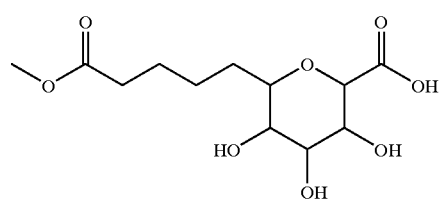
(42)
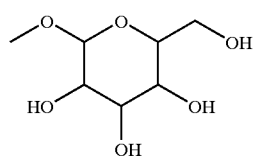
(43)
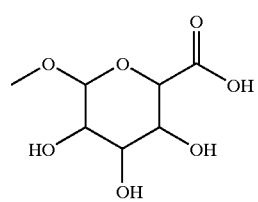
(44)
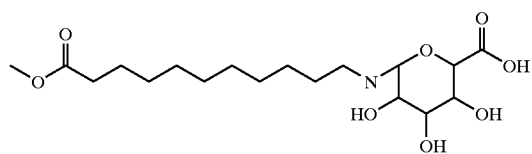
(45)
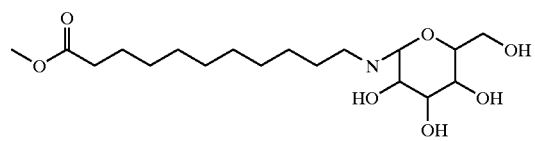
(46)
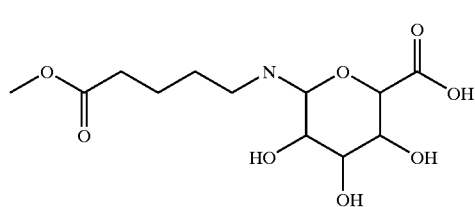
(47)
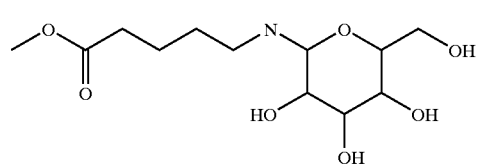
(48)

-continued
(49) 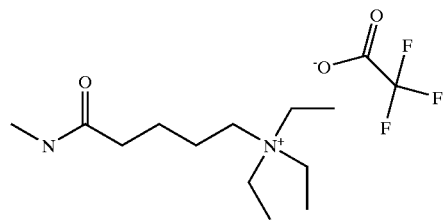
(50) 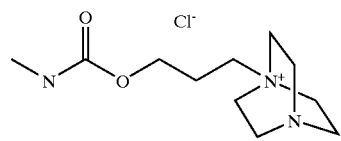
(51) 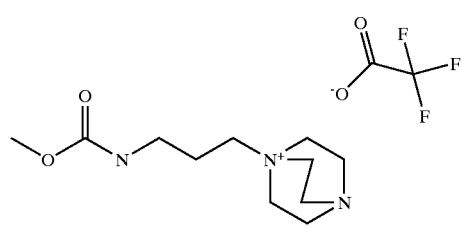
(52) 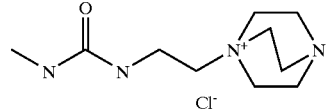
(53) 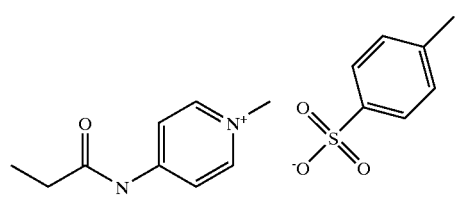
(54) 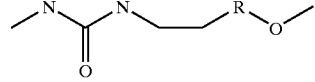
(55) 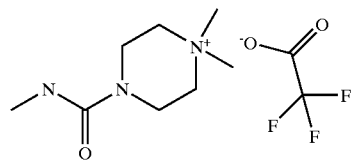
(56) 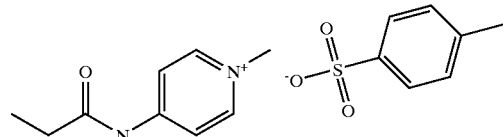
(57) 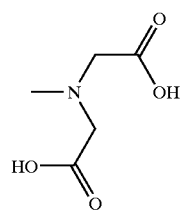
(58) 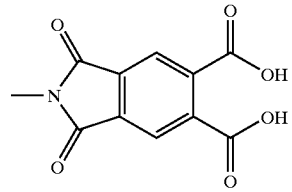
(59) 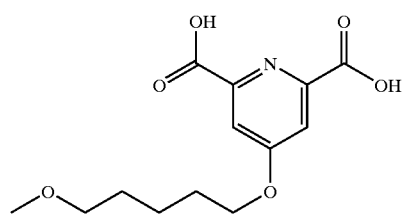
(60) 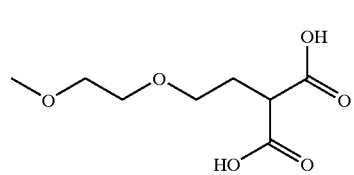
(61) 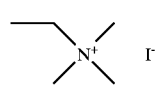
(62) 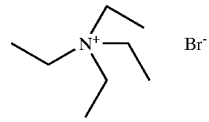

-continued

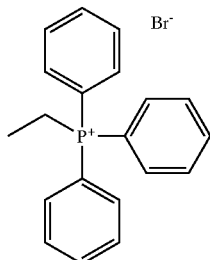
(63)

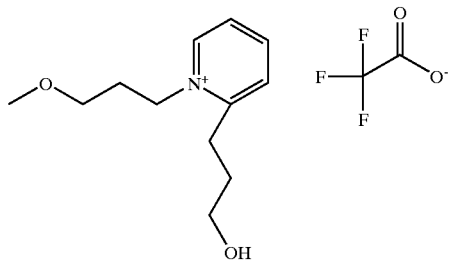
(64)

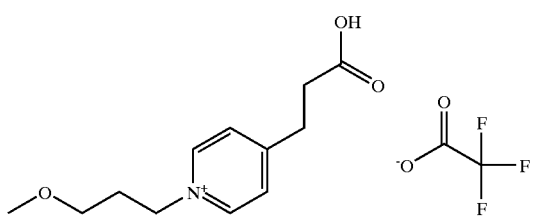
(65)

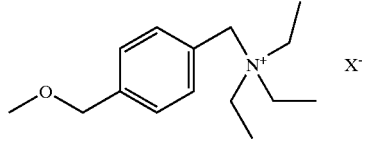
(66)

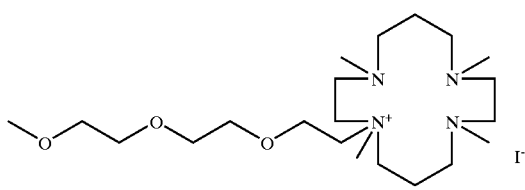
(67)

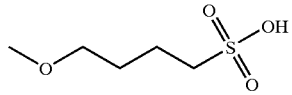
(68)

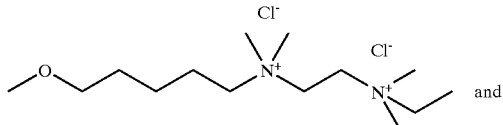 and
(69)

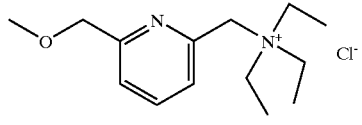
(70)

provided that when said $R^5$ is (7), (17) or (24), then said $R^{5A}$ is a left end of said $R^5$ and $R^{5B}$ is a right end of said $R^5$ or vice versa.

4. The compound of claim 3 or a pharmaceutically acceptable salt, solvate or prodrug thereof, wherein $R^{5A}$ is phenyl optionally substituted at least at either a para position or a meta position of said phenyl with said radical $R^5$.

5. The compound of claim 1 or a pharmaceutically acceptable salt, solvate or prodrug thereof, wherein j=2, $R^{2A}$ and $R^{2B}$ are independently selected from the group consisting of hydrogen and alkyl, and $R^{3A}$ and $R^{3B}$ are independently selected from the group consisting of hydrogen and alkyl.

6. The compound of claim 1 or a pharmaceutically acceptable salt, solvate or prodrug thereof, wherein j=2, at least one of $R^{2A}$ and $R^{2B}$ is hydrogen, and $R^{3A}$ and $R^{3B}$ each are alkyl.

7. The compound of claim 6 or a pharmaceutically acceptable salt, solvate or prodrug thereof, wherein $R^{2A}=R^{2B}=H$ and $R^{3A}$ and $R^{3B}$ are independently selected from the group consisting of ethyl, propyl and butyl.

8. The compound of claim 1 or a pharmaceutically acceptable salt, solvate or prodrug thereof, wherein $R^{2A}$ and $R^{2B}$ are independently selected from the group consisting of hydrogen and $C_{1-10}$ alkyl, $R^{3A}$ and $R^{3B}$ are independently selected from the group consisting of hydrogen and $C_{1-10}$ alkyl.

9. The compound of claim 1 or a pharmaceutically acceptable salt, solvate or prodrug thereof, wherein $R^{2A}$ and $R^{2B}$ are independently selected from the group consisting of hydrogen and $C_{1-6}$ alkyl, and $R^{3A}$ and $R^{3B}$ are independently selected from the group consisting of hydrogen and $C_{1-6}$ alkyl.

10. The compound of claim 1 or a pharmaceutically acceptable salt, solvate or prodrug thereof, wherein $R^{2A}$ and $R^{2B}$ are the same radical.

11. The compound of claim 10 or a pharmaceutically acceptable salt, solvate or prodrug thereof, wherein $R^{2A}$ and $R^{2B}$ are the same alkyl radical.

12. The compound of claim 10 or a pharmaceutically acceptable salt, solvate or prodrug thereof, wherein $R^{2A}$ and $R^{2B}$ are the same radical selected from the group consisting of hydrogen, $C_{1-10}$ alkyl, $C_{1-10}$ alkenyl and $C_{1-10}$ alkynyl.

13. The compound of claim 10 or a pharmaceutically acceptable salt, solvate or prodrug thereof, wherein $R^{3A}$ and $R^{3B}$ are the same radical.

14. The compound of claim 11 or a pharmaceutically acceptable salt, solvate or prodrug thereof, wherein $R^{3A}$ and $R^{3B}$ are the same alkyl radical.

15. The compound of claim 12 or a pharmaceutically acceptable salt, solvate or prodrug thereof, wherein $R^{3A}$ and $R^{3B}$ are the same radical selected from the group consisting of hydrogen, $C_{1-10}$ alkyl, $C_{1-10}$ alkenyl and $C_{1-10}$ alkynyl.

16. The compound of claim 1 or a pharmaceutically acceptable salt, solvate or prodrug thereof, wherein $R^{3A}$ and $R^{3B}$ are the same radical.

17. The compound of claim 16 or a pharmaceutically acceptable salt, solvate or prodrug thereof, wherein $R^{3A}$ and $R^{3B}$ are the same alkyl radical.

18. The compound of claim 16 or a pharmaceutically acceptable salt, solvate or prodrug thereof, wherein $R^{3A}$ and $R^{3B}$ are the same radical selected from the group consisting of hydrogen, $C_{1-10}$ alkyl, $C_{1-10}$ alkenyl and $C_{1-10}$ alkynyl.

19. The compound of claim 1 or a pharmaceutically acceptable salt, solvate or prodrug thereof, wherein $R^{2A}$ and $R^{2B}$ are the same $C_{1-20}$ hydrocarbyl radical.

20. The compound of claim 19 or a pharmaceutically acceptable salt, solvate or prodrug thereof, wherein $R^{2A}$ and $R^{2B}$ are the same $C_{1-10}$ hydrocarbyl radical.

21. The compound of claim 20 or a pharmaceutically acceptable salt, solvate or prodrug thereof, wherein $R^{2A}$ and $R^{2B}$ are the same $C_{1-6}$ hydrocarbyl radical.

22. The compound of claim 1 or a pharmaceutically acceptable salt, solvate or prodrug thereof, wherein $R^{3A}$ and $R^{3B}$ are the same $C_{1-20}$ hydrocarbyl radical.

23. The compound of claim 22 or a pharmaceutically acceptable salt, solvate or prodrug thereof, wherein $R^{3A}$ and $R^{3B}$ are the same $C_{1-10}$ hydrocarbyl radical.

24. The compound of claim 23 or a pharmaceutically acceptable salt, solvate or prodrug thereof, wherein $R^{3A}$ and $R^{3B}$ are the same $C_{1-6}$ hydrocarbyl radical.

25. The compound of claim 11 or a pharmaceutically acceptable salt, solvate or prodrug thereof, wherein $R^{2A}$ and $R^{2B}$ are each n-butyl.

26. The compound of claim 10 or a pharmaceutically acceptable salt, solvate or prodrug thereof, wherein $R^{2A}$ and $R^{2B}$ are each H.

27. The compound of claim 13 or a pharmaceutically acceptable salt, solvate or prodrug thereof, wherein $R^{3A}$ and $R^{3B}$ are each H or n-butyl.

28. The compound of claim 1 or a pharmaceutically acceptable salt, solvate or prodrug thereof, wherein said radicals $R^{6A}$ and $R^{7A}$ are independently selected from the group consisting of hydrogen, halogen, hydroxy, alkoxy, amino, alkylamino and dialkylamino.

29. The compound of claim 28 or a pharmaceutically acceptable salt, solvate or prodrug thereof, wherein said radicals $R^{6A}$ and $R^{7A}$ are independently selected from the group consisting of methoxy, ethoxy and dimethylamino.

30. The compound of claim 1 or a pharmaceutically acceptable salt, solvate or prodrug thereof, wherein j=2, one of $R^{5A}$ and $R^{5B}$ is hydrogen and the other of $R^{5A}$ and $R^{5B}$ is a phenyl radical optionally substituted at a para position of said phenyl radical with said radical $R^5$ selected from the group consisting of (1)–(69) and (70):

(1)
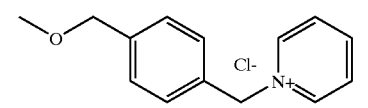

(2)
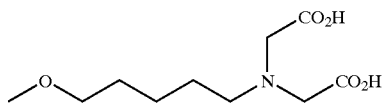

(3)
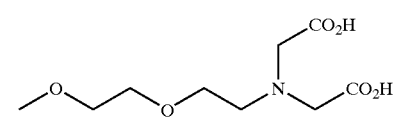

(4)
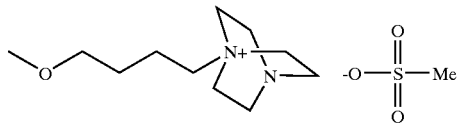

(5)
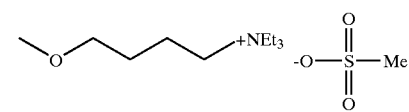

(6)
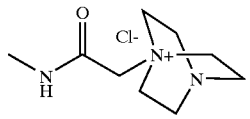

(7)
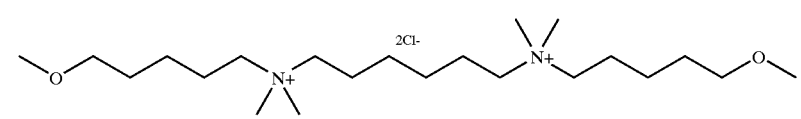

(8)
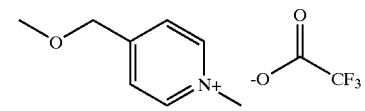

(9)
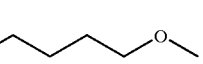

(10)
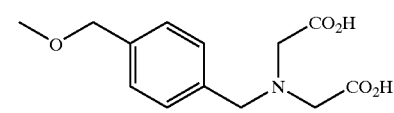

(11)
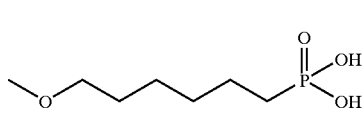

(12)
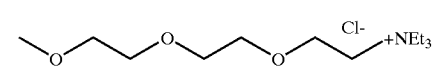

(13)
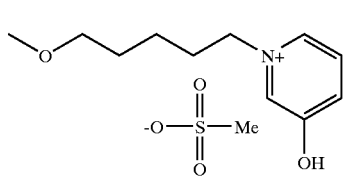

-continued
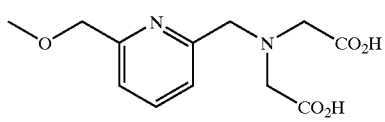
(14)
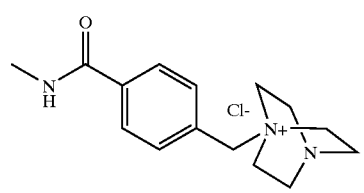
(15)
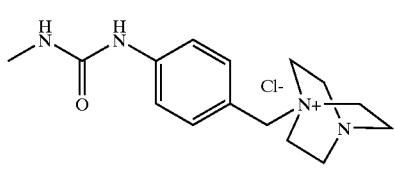
(15a)
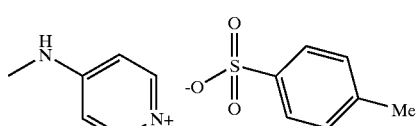
(16)
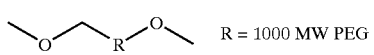
(17)
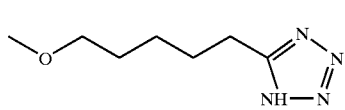
(18)
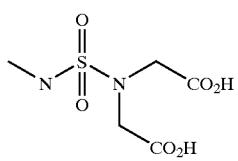
(19)
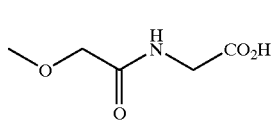
(20)
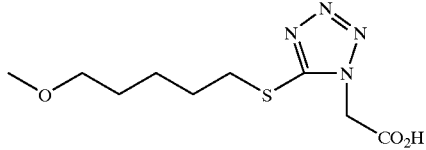
(21)
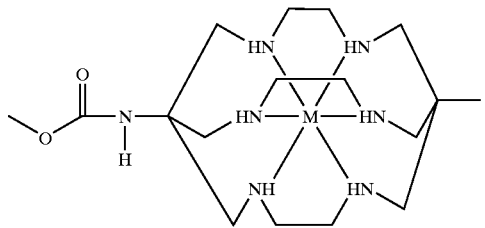
(22)
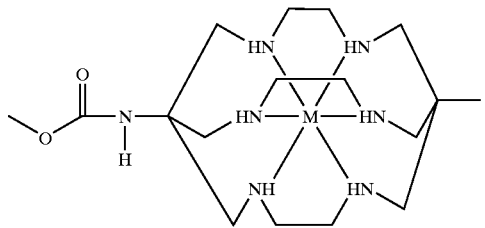
(23)
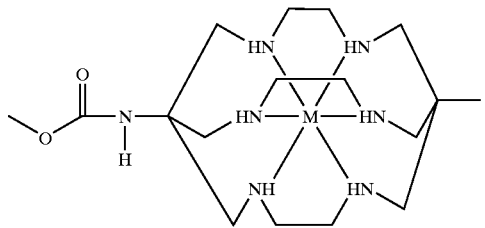
(24)
M = $Co^{II,III}$, $Mn^{II,III}$, $Fe^{II,III}$, $Ni^{II,III}$, $Cr^{III}$, $Cu^{II}$, $Zn^{II}$, $Cd^{II}$, $Ga^{III}$, $In^{III}$, $V^{IV}$, $Ru^{II}$, $Pr^{IV}$, $Ph^{III}$ or $Ir^{III}$
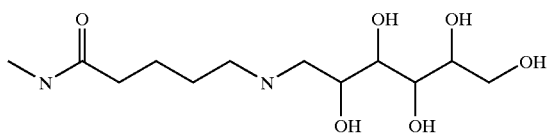
(25)
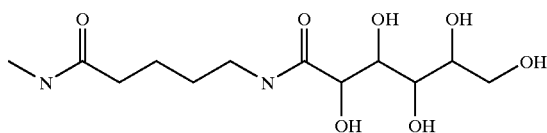
(26)
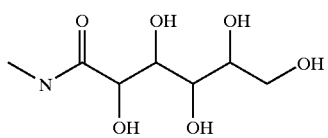
(27)
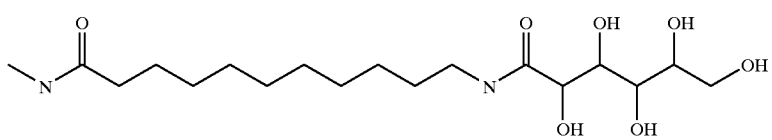
(28)

-continued
(29)
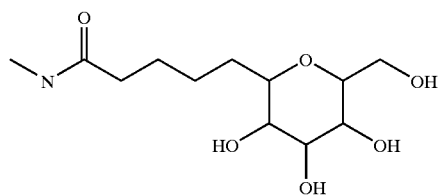
(30)
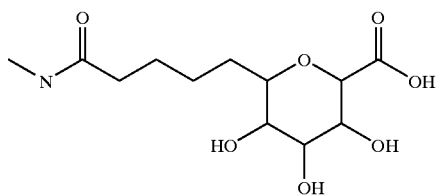
(31)
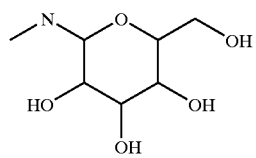
(32)
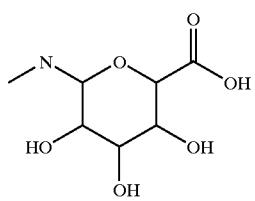
(33)
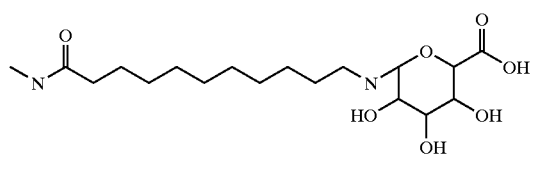
(34)
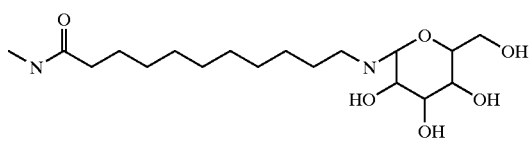
(35)
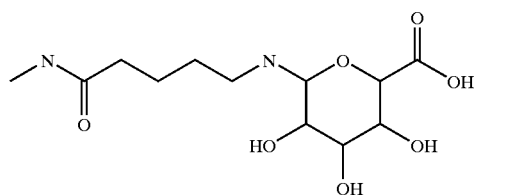
(36)
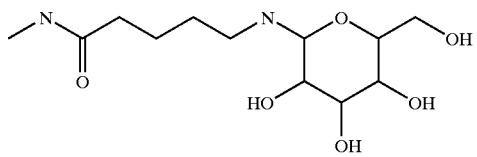
(37)
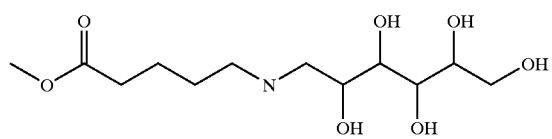
(38)
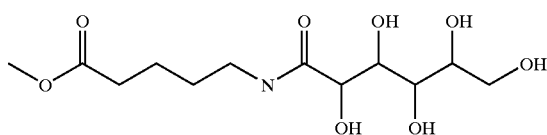
(39)
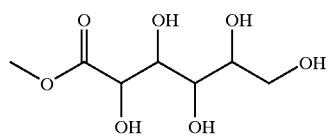
(40)
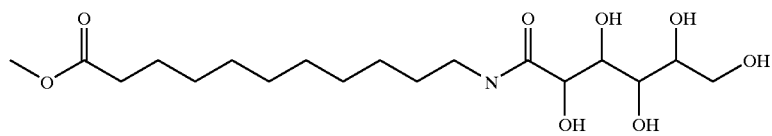
(41)
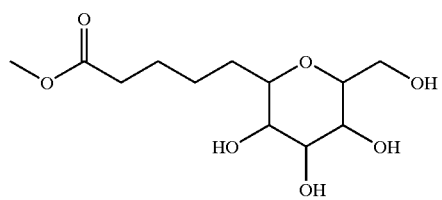
(42)
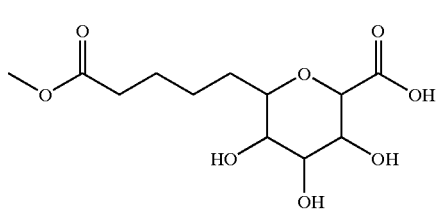
(43)
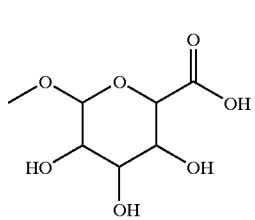
(44)

-continued
(45)
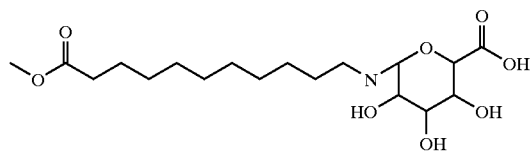
(46)
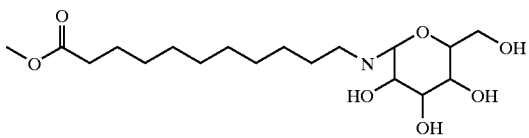
(47)
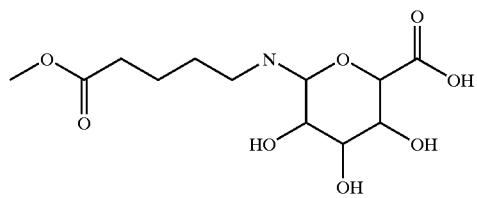
(48)
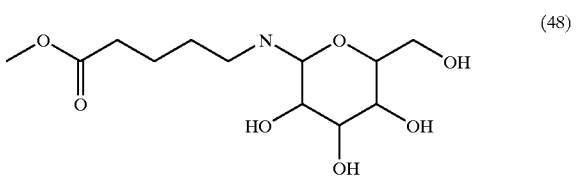
(49)
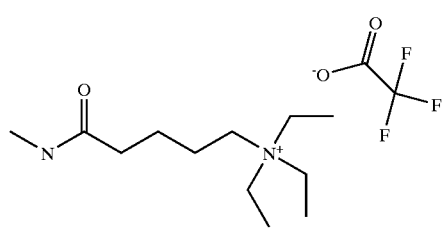
(50)
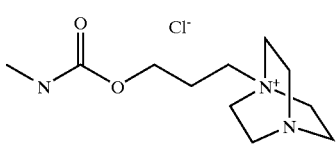
(51)
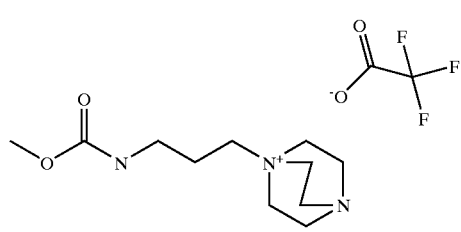
(52)
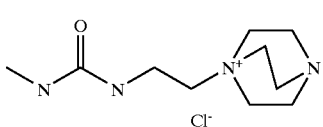
(53)
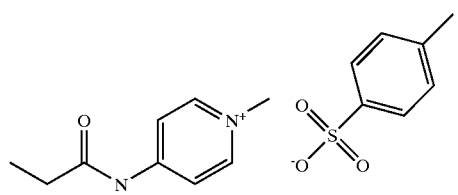
(54)
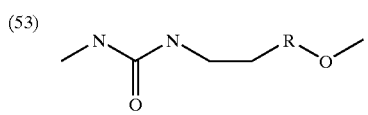
(55)
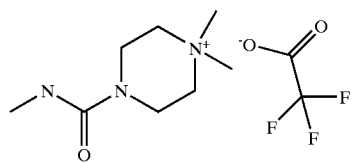
(56)
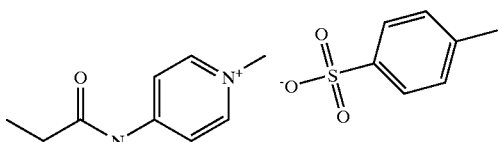
(57)
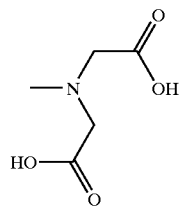
(58)
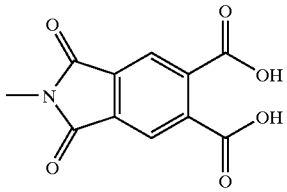
(59)
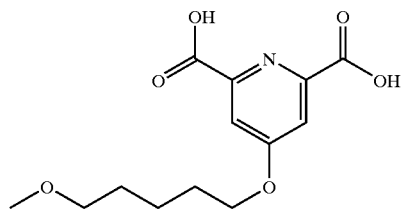
(60)
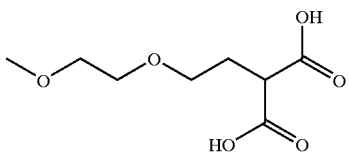

(61) 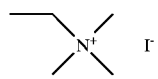

(62) 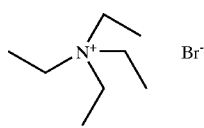

(63) 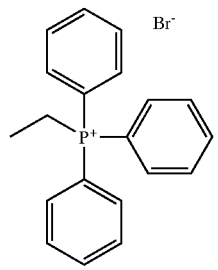

(64) 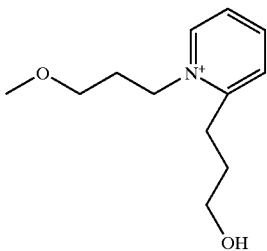

(65) 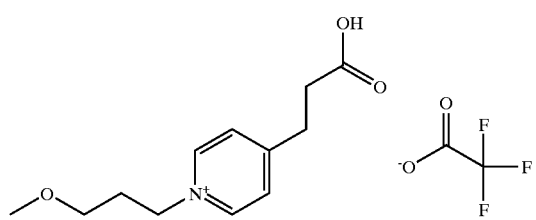

(66) 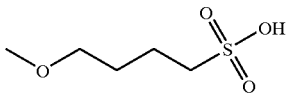

(67) 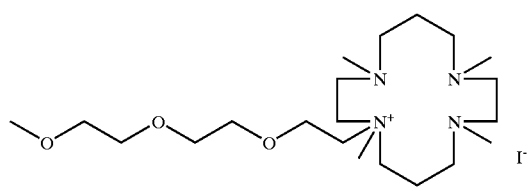

(68) 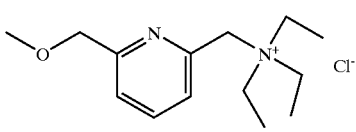

(69) 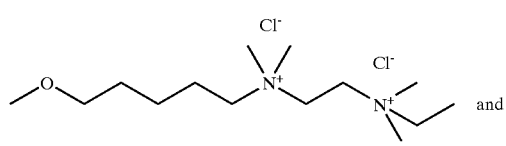 and

(70) 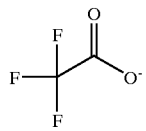

provided that when said $R^5$ is (7), (17) or (24), then said $R^{5A}$ is a left end of said $R^5$ and $R^{5B}$ is a right end of said $R^5$ or vice versa.

31. The compound of claim 1 wherein said benzothiepene comprises the compound of Formula I-17 or I-18:

I-17
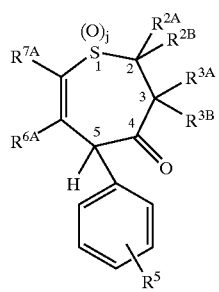

I-18
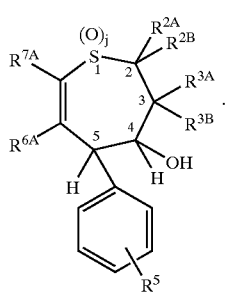

32. The compound of claim 31 wherein said $R^5$ is attached to either a para-position or a meta-position on said phenyl ring attached to the 5-position ring carbon of said benzothiepene compound of said Formulas I-17 or I-18.

33. The compound of claim 31 wherein said benzothiepene of said Formula I-17 comprises a member selected from the group consisting of Formulas I-21 and I-22:

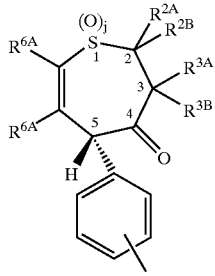

I-21

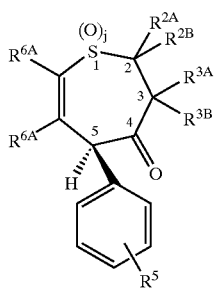

I-22

34. The compound of claim 33 wherein said benzothiepene of said Formulas I-21 and I-22 comprise Formulas I-9 and I-10, respectively, represented by:

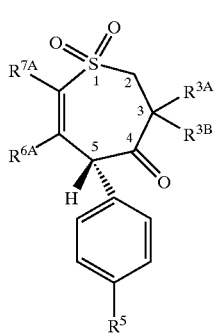

I-9

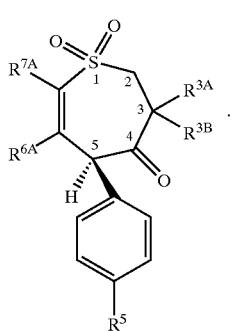

I-10

35. The compound of claim 31 wherein said benzothiepene of said Formula I-18 comprises a member selected from the group consisting of Formulas I-23, and I-24:

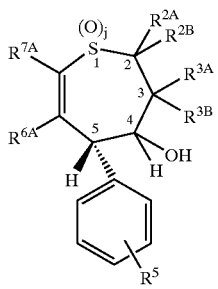

I-23

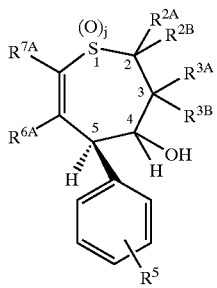

I-24

36. The compound of claim 35 wherein said benzothiepene of said Formulas I-23 and I-24 comprise Formulas I-19 and I-20, respectively, represented by:

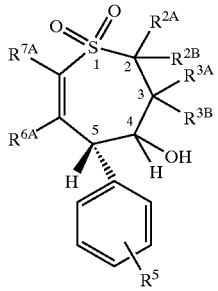

I-19

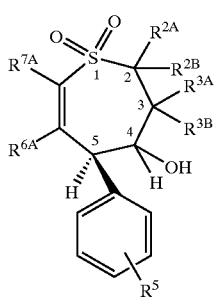

I-20

37. The compound of claim 35 wherein said $R^5$ is attached to either a meta-position or a para-position on said phenyl ring attached to said 5-position carbon ring of said benzothiepenes of said Formulas I-23 and I-24.

38. The compound of claims 31-37 wherein said $R^5$ is selected from the group consisting of (1)–(69) and (70):

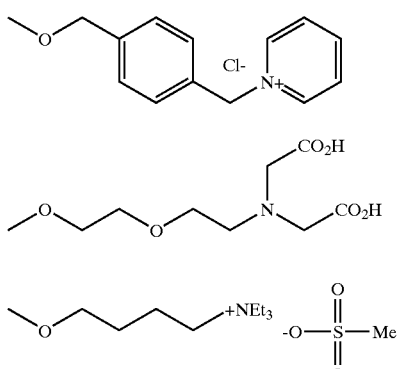
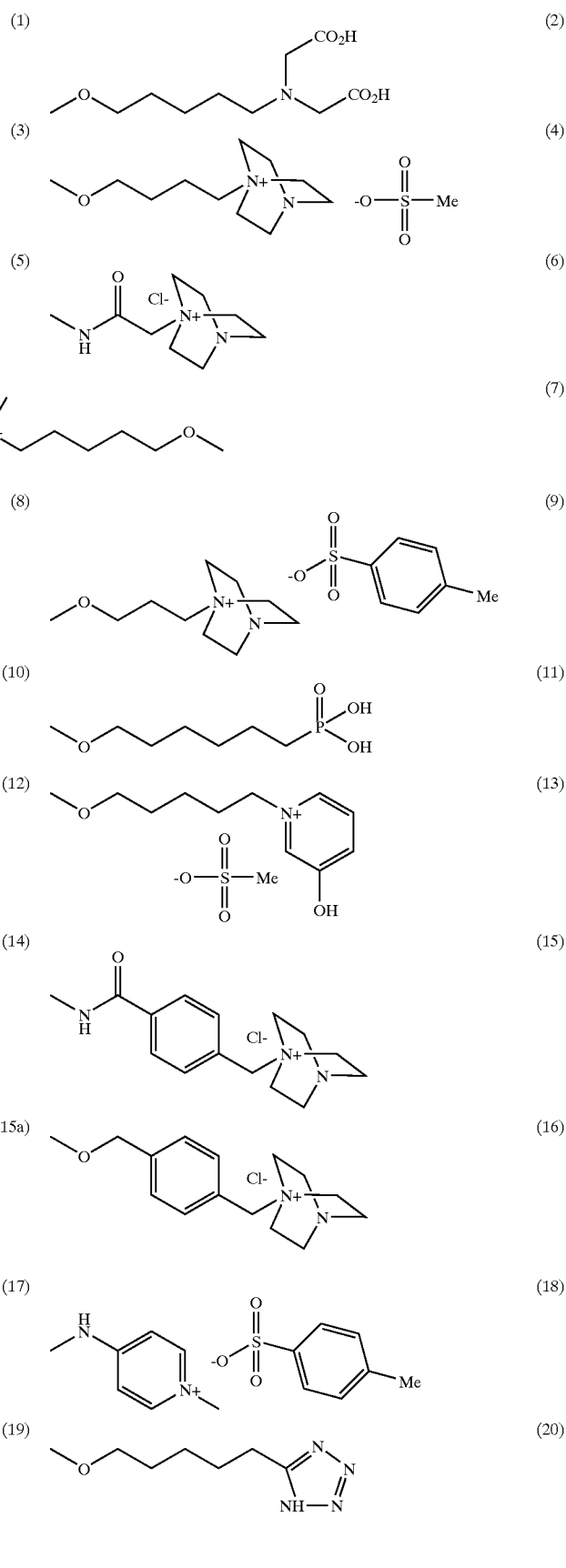

-continued
(21)
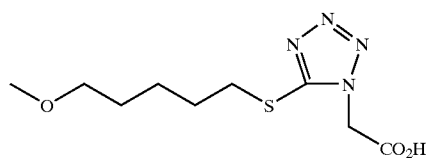
(22)
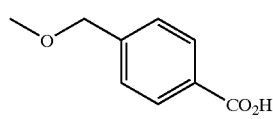
(23)
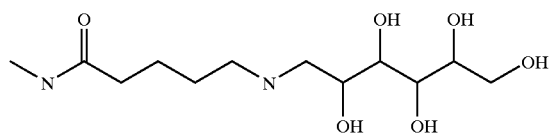
(24)
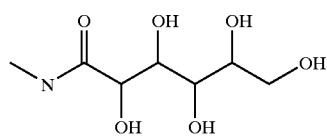
$M = Co^{II,III}, Mn^{II,III}, Fe^{II,III}, Ni^{II,III},$
$Cr^{III}, Cu^{II}, Zn^{II}, Cd^{II}, Ga^{III}, In^{III}, V^{IV},$
$Ru^{II}, Pr^{IV}, Ph^{III}$ or $Ir^{III}$
(25) (26)
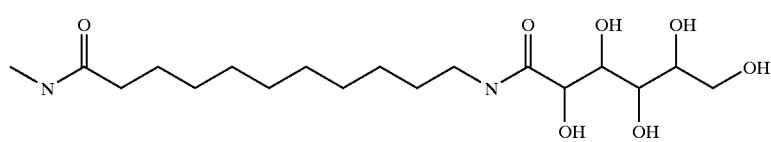
(27)
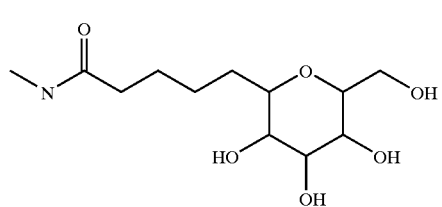
(28)
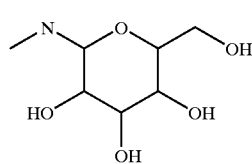
(29) (30)
(31) (32)
(33) (34)
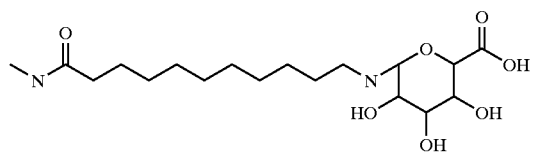

-continued
(35) 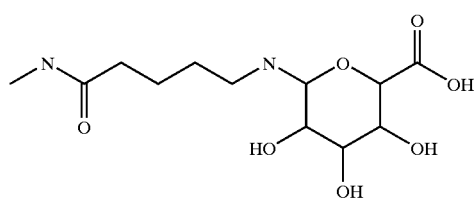
(36) 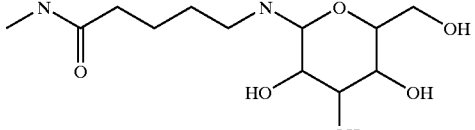
(37) 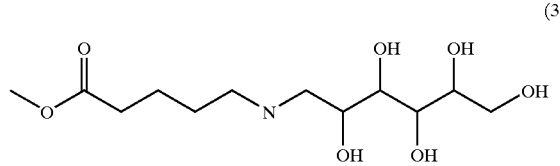
(38) 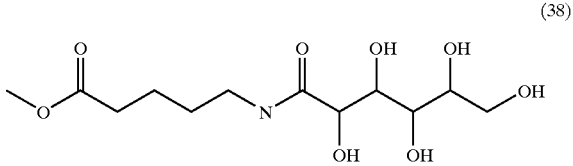
(39) 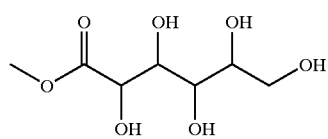
(40) 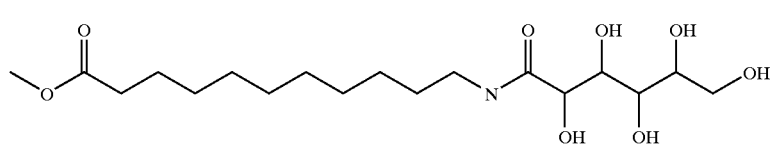
(41) 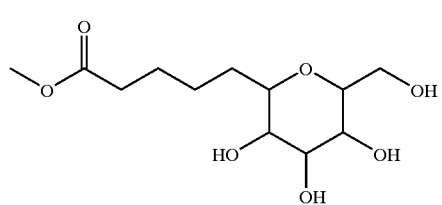
(42) 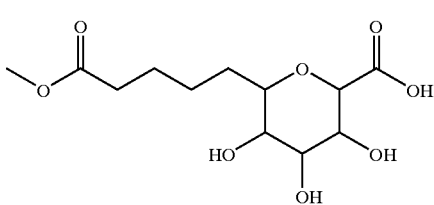
(43) 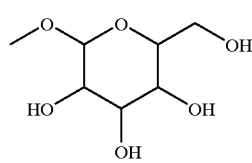
(44) 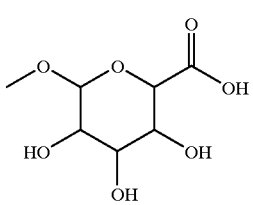
(45) 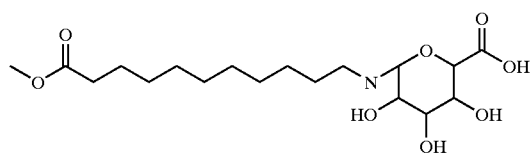
(46) 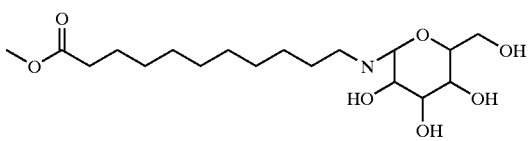
(47) 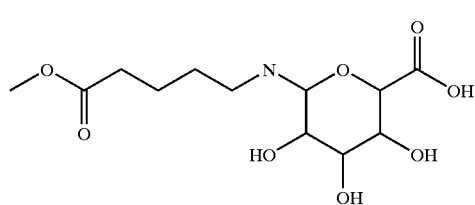
(48) 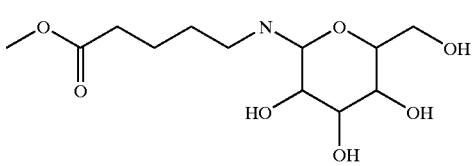

-continued
(49)
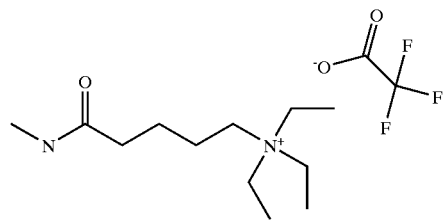
(50)
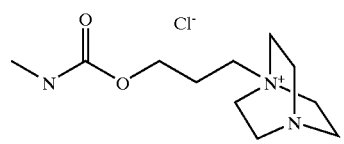
(51)
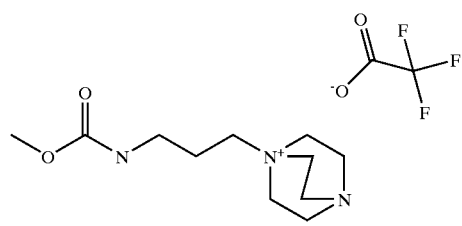
(52)
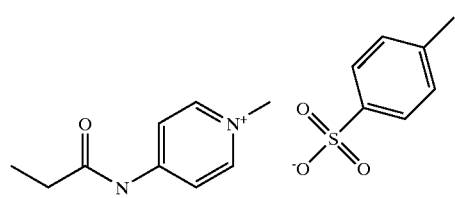
(53)
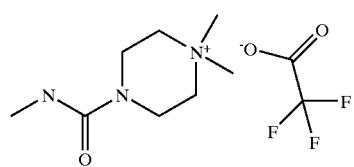
(54)
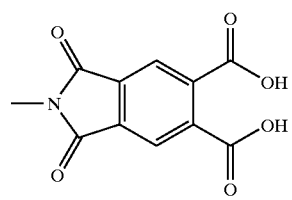
(55)
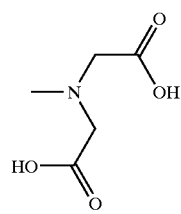
(56)
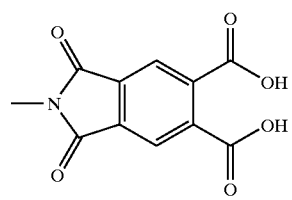
(57)
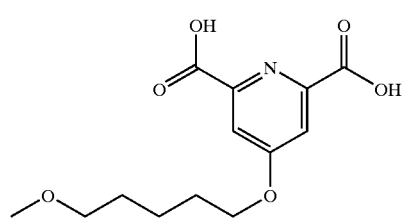
(58)
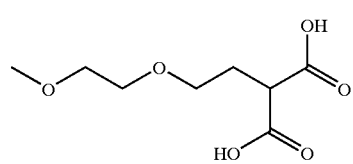
(59)
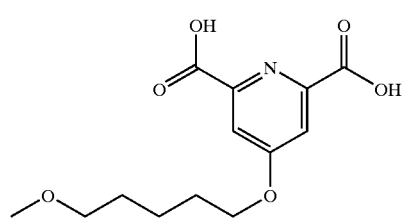
(60)
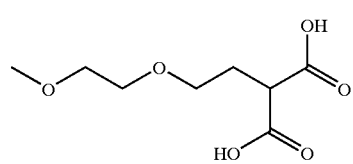
(61)
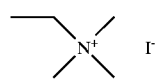
(62)
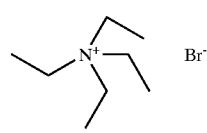

-continued

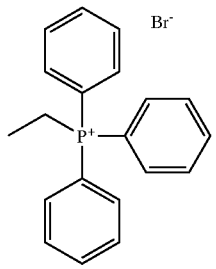 (63)

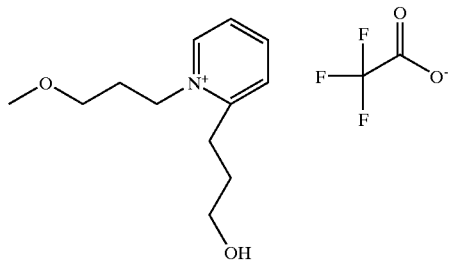 (64)

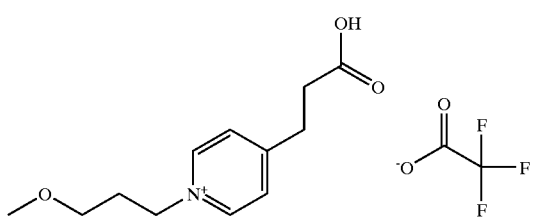 (65) (66)

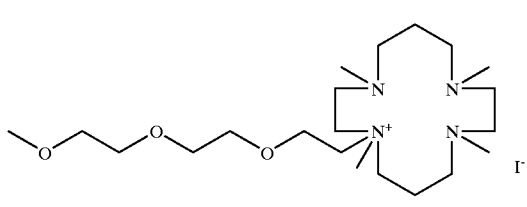 (67) (68)

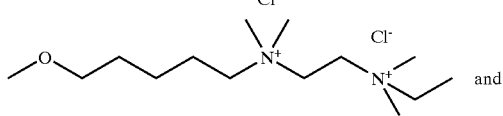 (69) (70)

wherein when said $R^5$ is said (7), said (17) or said (24), then said $R^{5A}$ represents a left-end of said $R^5$ and said $R^{5B}$ represents a right end of said $R^5$ or vice versa.

39. A method for treating a hyprelipidemic condition in a subject comprising administering to said subject in need thereof a therapeutically effective amount of a compound of Formulas I-1 or I-2, wherein said Formulas I-1 and I-2 are represented by:

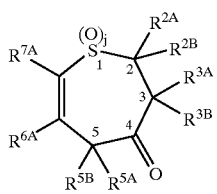 I-1

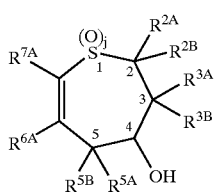 I-2 or a pharmaceutically acceptable salt, solvate, or prodrug thereof wherein j is 0, 1 or 2;

wherein $R^{2A}$ and $R^{2B}$ are independently selected from the group consisting of hydrogen and hydrocarbyl;

wherein $R^{3A}$, $R^{3B}$, $R^{5A}$, and $R^{5B}$ are independently selected from the group consisting of hydrogen, alkyl; cycloalkyl; alkenyl; alkynyl; heterocyclyl; quaternary heterocyclyl, oxo; aryl-$R^5$; —$OR^9$; —$NR^9R^{10}$; —$SR^9$; —$S(O)R^9$; —$SO_2R^9$; and —$SO_3R^9$;

wherein $R^9$ and $R^{10}$ are independently selected from the group consisting of hydrogen; hydrocarbyl; amino; and hydrocarbylamino;

wherein $R^5$ is selected from the group consisting of hydrogen; hydrocarbyl, heterocyclyl; quaternary heterocyclyl; —$OR^9$; —$SR^9$; —$S(O)R^9$; —$SO_2R^9$; and —$SO_3R^9$;

wherein when $R^5$ is said cycloalkyl, aryl or heterocyclyl, said cycloalkyl, aryl or heterocyclyl are optionally substituted with —NH—X—R or —O—X—R;

wherein X is selected from the group consisting of —(C=O)$_s$-alkyl-; —(C=O)$_s$-alkyl-NH—; —(C=O)$_s$-alkyl-O—; —(C=O)$_s$-alkyl-(C=O)$_t$; and a covalent bond, wherein s and t are independently 0 or 1;

wherein R is selected from the group consisting of monosaccharides, disaccharides, and polysaccharides, wherein said monosaccharides, disaccharides, and polysaccharides are optionally protected with one or more sugar protecting groups;

wherein $R^9$ and $R^{10}$ are as previously defined;

wherein, when $R^5 \neq H$, $R^5$ is optionally substituted with one or more radicals independently selected from the group consisting of halogen; —$NO_2$; —CN; oxo; hydrocarbyl; —$OR^{13}$; —$NR^{13}R^{14}$; —$SR^{13}$; —$S(O)R^{13}$; —$SO_2R^{13}$; —$SO_3R^{13}$; —$NR^{13}OR^{14}$; —$NR^{13}NR^{14}R^{15}$; —$CO_2R^{13}$; —OM; —$SO_2OM$; —$SO_2NR^{13}R^{14}$; —$C(O)NR^{13}R^{14}$; —C(O)OM; —$COR^{13}$; —$NR^{13}C(O)R^{14}$; —$NR^{13}C(O)NR^{14}R^{15}$; —$NR^{13}CO_2R^{14}$; —$OC(O)R^{13}$; —$OC(O)NR^{13}R^{14}$; —$NR^{13}SOR^{14}$; —$NR^{13}SO_2R^{14}$; —$NR^{13}SONR^{14}R^{15}$; —$NR^{13}SO_2NR^{14}R^{15}$; —$PR^{13}R^{14}$; —$P(O)R^{13}R^{14}$; —$P^+R^{13}R^{14}R^{15}A^-$; —$P(OR^{13})OR^{14}$; —$S^+R^{13}R^{14}A^-$; and —$N^+R^{13}R^{14}R^{15}A^-$;

wherein $R^{13}$, $R^{14}$, and $R^{15}$ are independently selected from the group consisting of hydrogen and hydrocarbyl;

wherein $A^-$ is a pharmaceutically acceptable anion;

wherein M is a pharmaceutically acceptable cation;

wherein $R^{6A}$ and $R^{7A}$ radicals are independently selected from the group consisting of hydrogen; halogen; —CN; —$NO_2$; hydrocarbyl; —$R^5$; -aryl-$R^5$; —$OR^{13}$; —$NR^{13}R^{14}$; —$SR^{13}$; —$S(O)R^3$; —$S(O)_2R^{13}$; —$SO_3R^{13}$; —$S^+R^{13}R^{14}A^-$; —$NR^{13}OR^{14}$; —$NR^{13}NR^{14}R^{15}$; —OM; —$SO_2OM$; —$SO_2NR^{13}R^{14}$; —$NR^{14}C(O)R^{13}$; —C(O)OM; —$S(O)NR^{13}R^{14}$; —$N^+R^{13}R^{14}R^{15}A^-$; —$PR^{13}R^{14}$; —$P(O)R^{13}R^{14}$; —$PR^{13}R^{14}R^{15}A^-$; amino acid residue; peptide residue; polypeptide residue; and carbohydrate residue;

wherein $R^{13}$, $R^{14}$, $R^{15}$, A, and M are as defined above; and wherein, in each instance, said hydrocarbyl may be optionally substituted with one or more groups comprising one or more heteroatoms, and wherein, in each instance, said hydrocarbyl optionally may have one or more carbon atoms replaced by one or more heteroatoms independently selected from the group consisting of oxygen, nitrogen, sulfur, phosphorus and combinations thereof.

40. A method of treating gallstones or a condition associated therewith in a subject comprising administering to said subject in need thereof a therapeutically effective amount of a compound of Formulas I-1 or I-2 represented by:

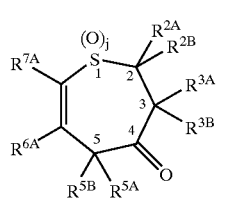

I-1

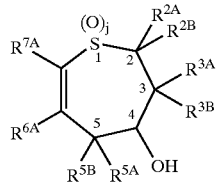

I-2 or a pharmaceutically acceptable salt, solvate, or prodrug thereof wherein j is 0, 1 or 2;

wherein $R^{2A}$ and $R^{2B}$ are independently selected from the group consisting of hydrogen and hydrocarbyl;

wherein $R^{3A}$, $R^{3B}$, $R^{5A}$, and $R^{5B}$ are independently selected from the group consisting of hydrogen, alkyl; cycloalkyl; alkenyl; alkynyl; heterocyclyl; quaternary heterocyclyl, oxo; aryl-$R^5$; —$OR^9$; —$NR^9R^{10}$; —$SR^9$; —$S(O)R^9$; —$SO_2R^9$; and —$SO_3R^9$;

wherein $R^9$ and $R^{10}$ are independently selected from the group consisting of hydrogen; hydrocarbyl; amino; and hydrocarbylamino;

wherein $R^5$ is selected from the group consisting of hydrogen; hydrocarbyl, heterocyclyl; quaternary heterocyclyl; —$OR^9$; —$SR^9$; —$S(O)R^9$; —$SO_2R^9$; and —$SO_3R^9$;

wherein when $R^5$ is said cycloalkyl, aryl or heterocyclyl, said cycloalkyl, aryl or heterocyclyl are optionally substituted with —NH—X—R or O—X—R;

wherein X is selected from the group consisting of —(C=O)$_s$-alkyl-; —(C=O)$_s$-alkyl-NH—; —(C=O)$_s$-alkyl-O—; —(C=O)$_s$-alkyl-(C=O)$_t$; and a covalent bond, wherein s and t are independently 0 or 1;

wherein R is selected from the group consisting of monosaccharides, disaccharides, and polysaccharides, wherein said monosaccharides, disaccharides, and polysaccharides are optionally protected with one or more sugar protecting groups;

wherein $R^9$ and $R^{10}$ are as previously defined;

wherein, when $R^5 \neq H$, $R^5$ is optionally substituted with one or more radicals independently selected from the group consisting of halogen; —$NO_2$; —CN; oxo; hydrocarbyl; —$OR^{13}$; —$NR^{13}R^{14}$; —$SR^{13}$; —$S(O)R^{13}$; —$SO_2R^{13}$; —$SO_3R^{13}$; —$NR^{13}OR^{14}$; —$NR^{13}NR^{14}R^{15}$; —$CO_2R^{13}$; —OM; —$SO_2OM$; —$SO_2NR^{13}R^{14}$; —$C(O)NR^{13}R^{14}$; —C(O)OM; —$COR^{13}$; —$NR^{13}C(O)R^{14}$; —$NR^{13}C(O)NR^{14}R^{15}$; —$NR^{13}CO_2R^{14}$; —$OC(O)R^{13}$; —$OC(O)NR^{13}R^{14}$; —$NR^{13}SOR^{14}$; —$NR^{13}SO_2R^{14}$; —$NR^{13}SONR^{14}R^{15}$; —$NR^{13}SO_2NR^{14}R^{15}$; —$PR^{13}R^{14}$; —$P(O)R^{13}R^{14}$; —$P^+R^{13}R^{14}R^{15}A^-$; —$P(OR^{13})OR^{14}$; —$S^+R^{13}R^{14}A^-$; and —$N^+R^{13}R^{14}R^{15}A^-$;

wherein $R^{13}$, $R^{14}$, and $R^{15}$ are independently selected from the group consisting of hydrogen and hydrocarbyl;

wherein $A^-$ is a pharmaceutically acceptable anion;

wherein M is a pharmaceutically acceptable cation;

wherein $R^{6A}$ and $R^{7A}$ radicals are independently selected from the group consisting of hydrogen; halogen; —CN; —$NO_2$; hydrocarbyl; —$R^5$; -aryl-$R^5$; —$OR^{13}$; —$NR^{13}R^{14}$; —$SR^{13}$; —$S(O)R^{13}$; —$S(O)_2R^{13}$; —$SO_3R^{13}$; —$S^+R^{13}R^{14}A^-$; —$NR^{13}OR^{14}$; —$NR^{13}NR^{14}R^{15}$; —OM; —$SO_2OM$; —$SO_2NR^{13}R^{14}$; —$NR^{14}C(O)R^{13}$; —C(O)OM; —$S(O)NR^{13}R^{14}$; —$N^+R^{13}R^{14}R^{15}A^-$; —$PR^{13}R^{14}$; —$P(O)R^{13}R^{14}$; —$P^+R^{13}R^{14}R^{15}A^-$; amino acid residue; peptide residue; polypeptide residue; and carbohydrate residue;

wherein $R^{13}$, $R^{14}$, $R^{15}$, $A^-$, and M are as defined above; and wherein, in each instance, said hydrocarbyl may be optionally substituted with one or more groups comprising one or more heteroatoms, and wherein, in each instance, said hydrocarbyl optionally may have one or more carbon atoms replaced by one or more heteroatoms independently selected from the group consisting of oxygen, nitrogen, sulfur, phosphorus and combinations thereof.

41. The method of claim 39, wherein said subject is a mammal.

42. The method of claim 41, wherein said subject is a human.

43. The method of claim 40 wherein said subject is a mammal.

44. The method of claim 43, wherein said mammal is a human.

45. The method of claim 39, wherein said therapeutically effective amount is administered in a single dose or in multiple divided doses.

46. The method of claim 40, wherein said therapeutically effective amount is administered in a single dose or in multiple divided doses.

47. A method for treating a hyperlipidemic condition in a subject comprising administering to said subject in need thereof a therapeutically effective amount of a compound of Formulas I-17 or I-18 represented by:

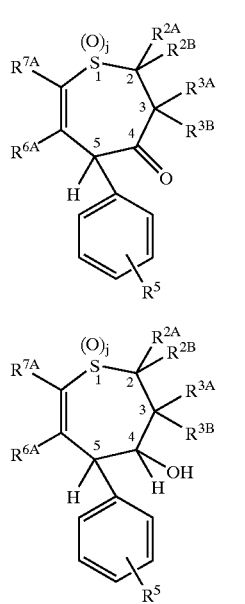

I-17

I-18 or a pharmaceutically acceptable salt, solvate, or prodrug thereof wherein j is 0, 1 or 2;

wherein $R^{2A}$ and $R^{2B}$ are independently selected from the group consisting of hydrogen and hydrocarbyl;

wherein $R^{3A}$, $R^{3B}$, $R^{5A}$, and $R^{5B}$ are independently selected from the group consisting of hydrogen, alkyl; cycloalkyl; alkenyl; alkynyl; heterocyclyl; quaternary heterocyclyl, oxo; aryl-$R^5$; —$OR^9$; —$NR^9R^{10}$; —$SR^9$; —$S(O)R^9$; —$SO_2R^9$; and —$SO_3R^9$;

wherein $R^9$ and $R^{10}$ are independently selected from the group consisting of hydrogen; hydrocarbyl; amino; and hydrocarbylamino;

wherein $R^5$ is selected from the group consisting of hydrogen; hydrocarbyl, heterocyclyl; quaternary heterocyclyl; —$OR^9$; —$SR^9$; —$S(O)R^9$; —$SO_2R^9$; and —$SO_3R^9$;

wherein when $R^5$ is said cycloalkyl, aryl or heterocyclyl, said cycloalkyl, aryl or heterocyclyl are optionally substituted with —NH—X—R or —O—X—R;

wherein X is selected from the group consisting of —(C=O)$_s$-alkyl-; —(C=O)$_s$-alkyl-NH—; —(C=O)$_s$-alkyl-O—; —C=O)$_s$-alkyl-(C=O)$_t$; and a covalent bond, wherein s and t are independently 0 or 1;

wherein R is selected from the group consisting of monosaccharides, disaccharides, and polysaccharides, wherein said monosaccharides, disaccharides, and polysaccharides are optionally protected with one or more sugar protecting groups;

wherein $R^9$ and $R^{10}$ are as previously defined;

wherein, when $R^5 \neq H$, $R^5$ is optionally substituted with one or more radicals independently selected from the group consisting of halogen; —$NO_2$; —CN; oxo; hydrocarbyl; —$OR^{13}$; —$NR^{13}R^{14}$; —$SR^{13}$; —$S(O)R^{13}$; —$SO_2R^{13}$; —$SO_3R^{13}$; —$NR^{13}OR^{14}$; —$NR^{13}NR^{14}R^{15}$; —$CO_2R^{13}$; —OM; —$SO_2OM$; —$SO_2NR^{13}OR^{14}$; —$C(O)NR^{13}R^{14}$; —$C(O)OM$; —$COR^{13}$; —$NR^{13}C(O)R^{14}$; —$NR^{13}C(O)NR^{13}R^{14}$; —$NR^{13}CO_2R^{14}$; —$OC(O)R^{13}$; —$OC(O)NR^{13}R^{14}$; —$NR^{13}SOR^{14}$; —$NR^{13}SO_2R^{14}$; —$NR^{13}SONR^{14}R^{15}$; —$NR^{13}SO_2NR^{14}R^{15}$; —$PR^{13}R^{14}$; —$P(O)R^{13}R^{14}$; —$P^+R^{13}R^{14}R^{15}A^-$; —$P(OR^{13})OR^{14}$; —$S^+R^{13}R^4A^-$; and —$N^+R^{13}R^{14}R^{15}A^-$;

wherein $R^{13}$, $R^{14}$, and $R^{15}$ are independently selected from the group consisting of hydrogen and hydrocarbyl;

wherein $A^-$ is a pharmaceutically acceptable anion;

wherein M is a pharmaceutically acceptable cation;

wherein $R^{6A}$ and $R^{7A}$ radicals are independently selected from the group consisting of hydrogen; halogen; —CN; —$NO_2$; hydrocarbyl; —$R^5$; aryl-$R^5$; —$OR^{13}$; —$NR^{13}R^{14}$; —$SR^{13}$; —$S(O)R^{13}$; —$S(O)_2R^{13}$; —$SO_3R^{13}$; —$S^+R^{13}R^{14}$; —$NR^{13}NR^{14}R^{15}$; —OM; —$SO_2OM$; —$SO_2NR^{13}R^{14}$; —$NR^{14}C(O)R^{13}$; —$C(O)OM$; —$S(O)NR^{13}R^{14}$; —$N^+R^{13}R^{14}R^{15}A^-$; —$PR^{13}R^{14}$; —$P(O)R^{13}R^{14}$; —$P^+R^{13}R^{14}R^{15}A^-$; amino acid residue; peptide residue; polypeptide residue; and carbohydrate residue;

wherein $R^{13}$, $R^{14}$, $R^{15}$, $A^-$, and M are as defined above; and wherein, in each instance, said hydrocarbyl may be optionally substituted with one or more groups comprising one or more heteroatoms, and wherein, in each instance, said hydrocarbyl optionally may have one or more carbon atoms replaced by one or more heteroatoms independently selected from the group consisting of oxygen, nitrogen, sulfur, phosphorus and combinations thereof.

48. The method of claim 47 wherein said Formula I-17 comprises a member selected from the group consisting of I-21 and I-22 represented by:

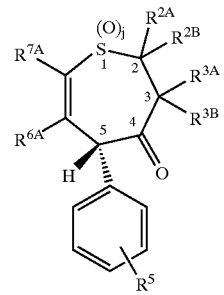

I-21

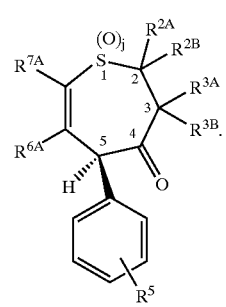

I-22

49. The method of claim 48 wherein said Formulas I-21 and I-22 comprise Formulas I-9 and I-10, respectively, represented by:

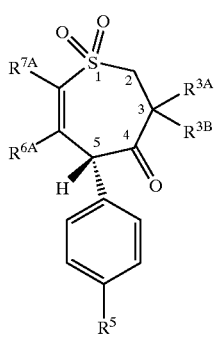

I-9

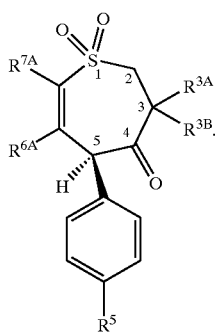

I-10

50. The method of claim 47 wherein said Formula I-18 comprises a member selected from the group consisting of I-19 and I-20 represented by:

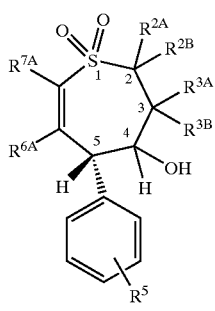

I-19

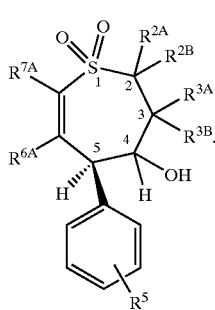

I-20

51. The method of claim 50 wherein said Formulas I-19 and I-20 comprise Formulas I-11 and I-12, respectively, represented by:

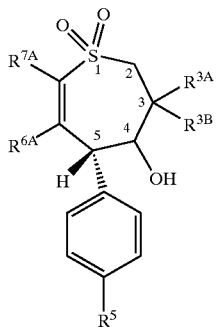

I-11

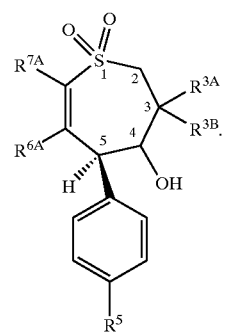

I-12

52. The method of claim 51 where said Formula I-11 comprises a member selected from the group consisting of Formulas I-13 and I-16 represented by:

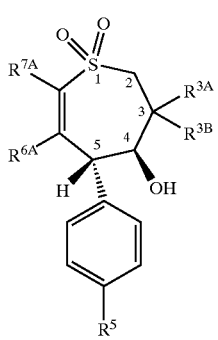

I-13

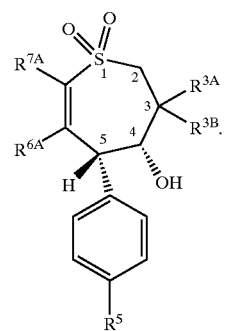

I-16

53. The method of claim 51 wherein said Formula I-12 comprises a member selected from the group consisting of Formulas I-14 and I-15 represented by:
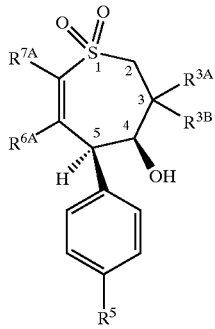
I-14
-continued
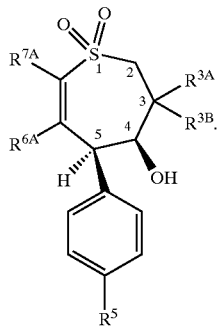
I-15
54. The method of claims 47 to 53 wherein said $R^5$ is a member selected from the group consisting of (1)–(69) and (70):
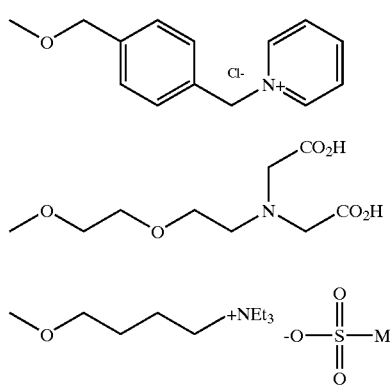
(1), (3), (5), (8), (10), (12), (14)
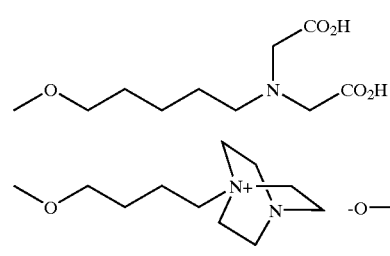
(2)
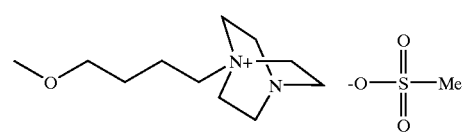
(4)
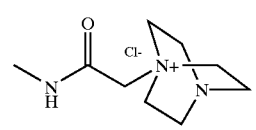
(6)
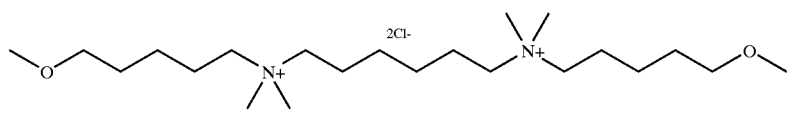
(7)
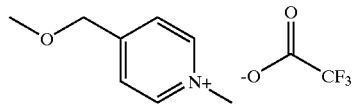
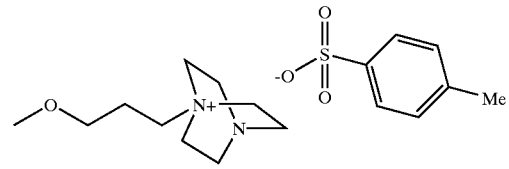
(9)
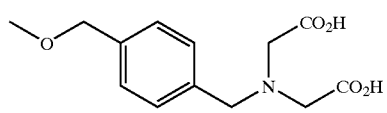
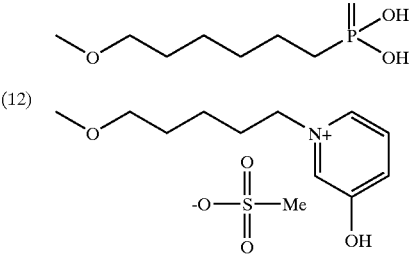
(11), (13)
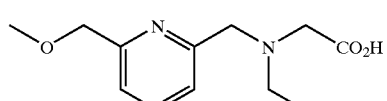
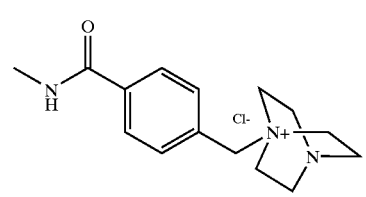
(15)

-continued
(15a)
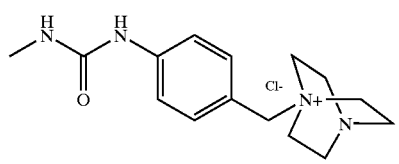
(16)
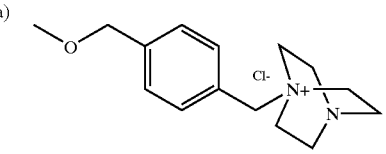
(17)
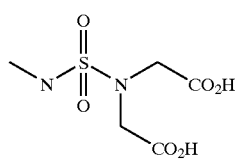  R = 1000 MW PEG
(18)
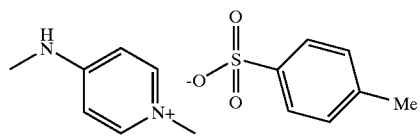
(19)
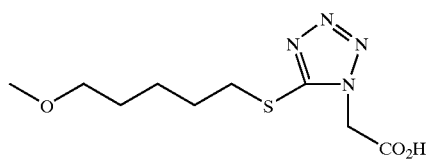
(20)
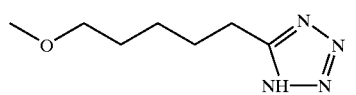
(21)
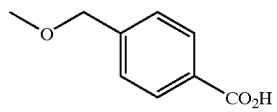
(22)
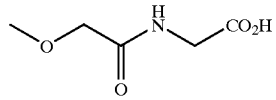
(23)
(24)
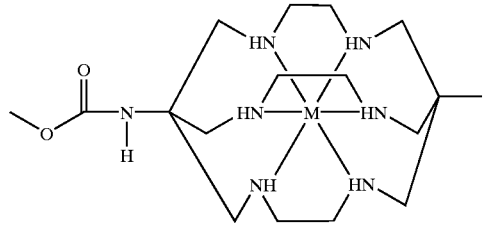
M = $Co^{II,III}$, $Mn^{II,III}$, $Fe^{II,III}$, $Ni^{II,III}$, $Cr^{III}$, $Cu^{II}$, $Zn^{II}$, $Cd^{II}$, $Ga^{III}$, $In^{III}$, $V^{IV}$, $Ru^{II}$, $Pr^{IV}$, $Ph^{III}$ or $Ir^{III}$
(25)
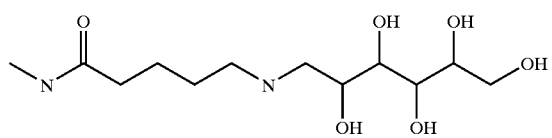
(26)
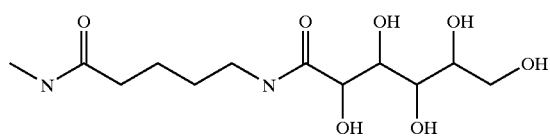
(27)
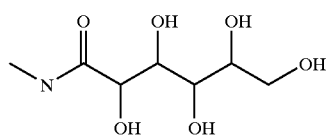
(28)
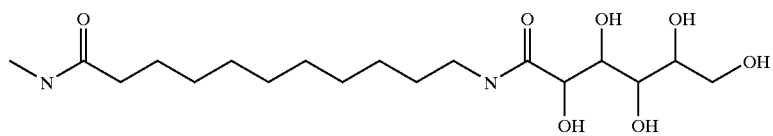
(29)
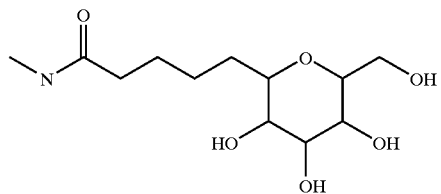
(30)
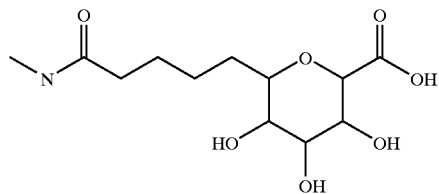

-continued

-continued

-continued

(63) 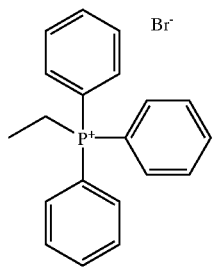

(64) 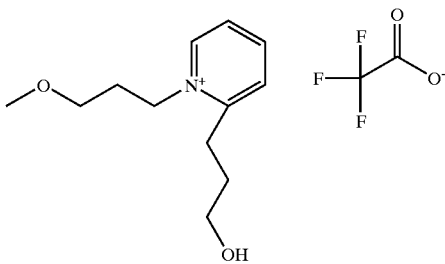

(65) 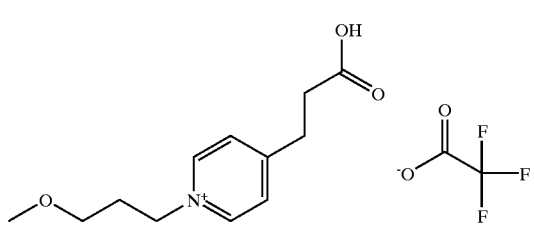

(66)

(67) 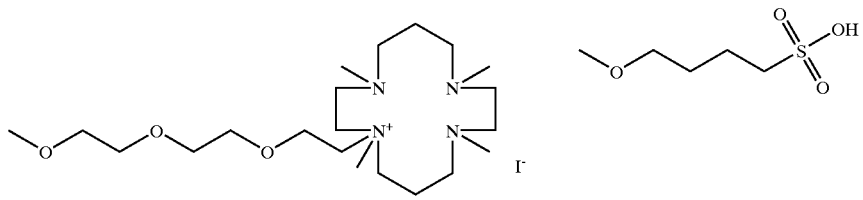

(68)

(69) 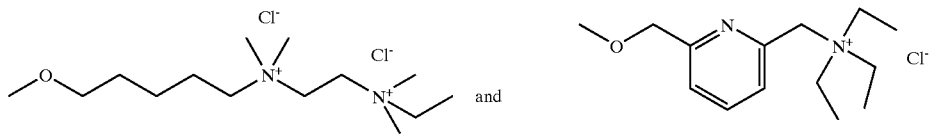 and (70)

provided that when said R⁵ is (7), (17) or (24), then said $R^{5A}$ is a left end of said $R^5$ and said $R^{5B}$ is a right end of said $R^5$ or vice versa.

55. A method for treating gallstones or a condition associated therewith in a subject in need thereof, said method comprising administering a therapeutically effective amount of a compound of Formulas I-17 or I-18 represented by:

I-17 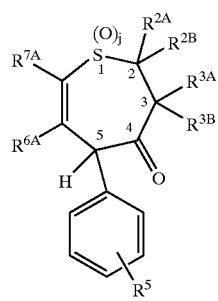

-continued

I-18 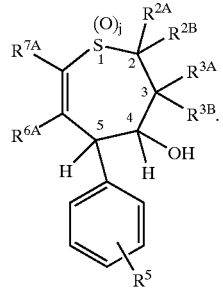

or a pharinaceutically acceptable salt, solvate, or prodrug thereof wherein j is 0, 1 or 2;

wherein $R^{2A}$ and $R^{2B}$ are independently selected from the group consisting of hydrogen and hydrocarbyl;

wherein $R^{3A}$, $R^{3B}$, $R^{5A}$, and $R^{5B}$ are independently selected from the group consisting of hydrogen, alkyl; cycloalkyl; alkenyl; alkynyl; heterocyclyl; quaternary heterocyclyl, oxo; aryl-$R^5$; —$OR^9$; —$NR^9R^{10}$; —$SR^9$; —$S(O)R^9$; —$SO_2R^9$; and —$SO_3R^9$;

wherein $R^9$ and $R^{10}$ are independently selected from the group consisting of hydrogen; hydrocarbyl; amino; and hydrocarbylamino;

wherein $R^5$ is selected from the group consisting of hydrogen; hydrocarbyl, heterocyclyl; quaternary heterocyclyl; —$OR^9$; —$SR^9$; —$S(O)R^9$; —$SO_2R^9$; and —$SO_3R^9$;

wherein when $R^5$ is said cycloalkyl, aryl or heterocyclyl, said cycloalkyl, aryl or heterocyclyl are optionally substituted with —NH—X—R or —O—X—R;

wherein X is selected from the group consisting of —(C=O)$_s$-alkyl-; —(C=O)$_s$-alkyl-NH—; —(C=O)$_s$-alkyl-O—; —(C=O)$_s$-alkyl-(C=O)$_t$; and a covalent bond, wherein s and t are independently 0 or 1;

wherein R is selected from the group consisting of monosaccharides, disaccharides, and polysaccharides, wherein said monosaccharides, disaccharides, and polysaccharides are optionally protected with one or more sugar protecting groups;

wherein $R^9$ and $R^{10}$ are as previously defined;

wherein, when $R^5 \neq H$, $R^5$ is optionally substituted with one or more radicals independently selected from the group consisting of halogen; —$NO_2$; —CN; oxo; hydrocarbyl; —$OR^{13}$; —$NR^{13}R^{14}$; —$SR^{13}$; —$S(O)R^{13}$; —$SO_2R^{13}$; —$SO_3R^{13}$; —$NR^{13}OR^{14}$; —$NR^{13}NR^{14}R^{15}$; —$CO_2R^{13}$; —OM; —$SO_2OM$; —$SO_2NR^{13}R^{14}$; —$C(O)NR^{13}R^{14}$; —C(O)OM; —$COR^{13}$; —$NR^{13}C(O)R^{14}$; —$NR^{13}C(O)NR^{14}R^{15}$; —$NR^{13}CO_2R^{14}$; —$OC(O)R^{13}$; —$OC(O)NR^{13}R^{14}$; —$NR^{13}SOR^{14}$; —$NR^{13}SO_2R^{14}$; —$NR^{13}SONR^{14}R^{15}$; —$NR^{13}SO_2NR^{14}R^{15}$; —$PR^{13}R^{14}$; —$P(O)R^{13}R^{14}$; —$P^+R^{13}R^{14}R^{15}A^-$; —$P(OR^{13})OR^{14}$; —$S^+R^{13}R^{14}A^-$; and —$N^+R^{13}R^{14}R^1A^-$;

wherein $R^{13}$, $R^{14}$, and $R^{15}$ are independently selected from the group consisting of hydrogen and hydrocarbyl;

wherein $A^-$ is a pharmaceutically acceptable anion;

wherein M is a pharmaceutically acceptable cation;

wherein $R^{6A}$ and $R^{7A}$ radicals are independently selected from the group consisting of hydrogen; halogen; —CN; —$NO_2$; hydrocarbyl; —$R^5$; aryl-$R^5$; —$OR^{13}$; —$NR^{13}R^{14}$; —$SR^{13}$; —$S(O)R^{13}$; —$S(O)_2R^{13}$; —$SO_3R^{13}$; —$S^+R^{13}R^{14}$; —$NR^{13}NR^{14}R^{15}$; —OM; —$SO_2OM$; —$SO_2NR^{13}R^{14}$; —$NR^{14}C(O)R^{13}$; —C(O)OM; —$S(O)NR^{13}R^{14}$; —$N^+R^{13}R^{14}R^{15}A^-$; —$PR^{13}R^{14}$; —$P(O)R^{13}R^{14}$; —$P^+R^{13}R^{14}R^{15}A^-$; and acid residue; peptide residue; polypeptide residue; and carbohydrate residue;

wherein $R^{13}$, $R^{14}$, $R^{15}$, $A^-$, and M are as defined above; and wherein, in each instance, said hydrocarbyl may be optionally substituted with one or more groups comprising one or more heteroatoms, and wherein, in each instance, said hydrocarbyl optionally may have one or more carbon atoms replaced by one or more heteroatoms independently selected from the group consisting of oxygen, nitrogen, sulfur, phosphorus and combinations thereof.

56. The method of claim 55 wherein said Formula I-17 comprises a member selected from the group consisting of I-21 and I-22 represented by:

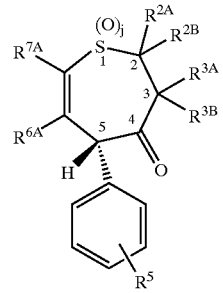

I-21

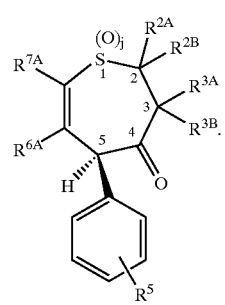

I-22

57. The method of claim 56 wherein said Formulas I-21 and I-22 comprise Formulas I-9 and I-10, respectively, represented by:

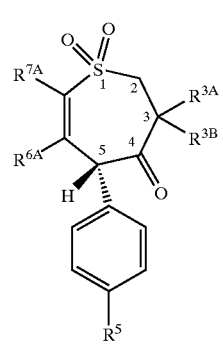

I-9

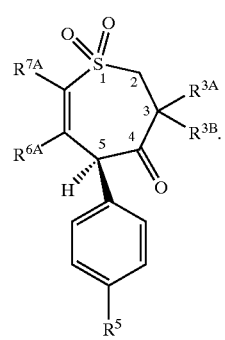

I-10

58. The method of claim 57 wherein said Formula I-18 comprises a member selected from the group consisting of I-19 and I-20 represented by:

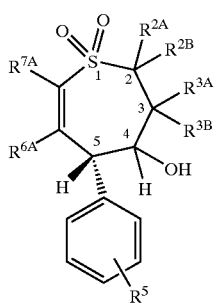

I-19

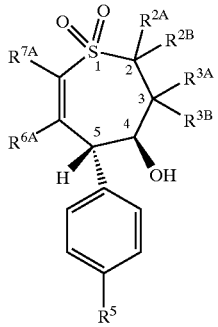

I-13

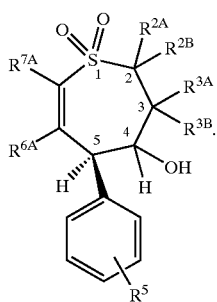

I-20

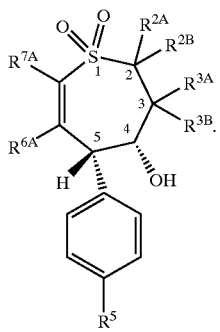

I-16

59. The method of claim 58 wherein said Formulas I-19 and I-20 comprise Formulas I-11 and I-12, respectively, represented by:

61. The method of claim 59 wherein said Formula I-12 comprises a member selected from the group consisting of Formulas I-14 and I-15 represented by:

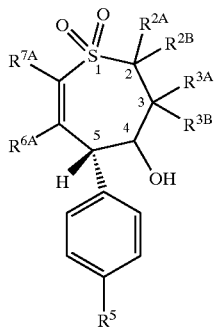

I-11

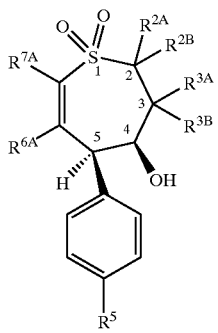

I-14

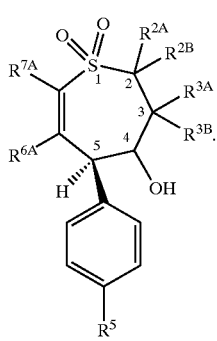

I-12

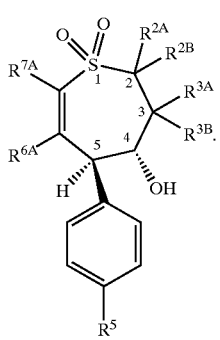

I-15

60. The method of claim 59 wherein said Formula I-11 comprises a member selected from the group consisting of Formulas I-13 and I-16 represented by:

62. The method of claims 55 to 61 wherein said $R^5$ is a member selected from the group consisting of (1)–(69) and (70):

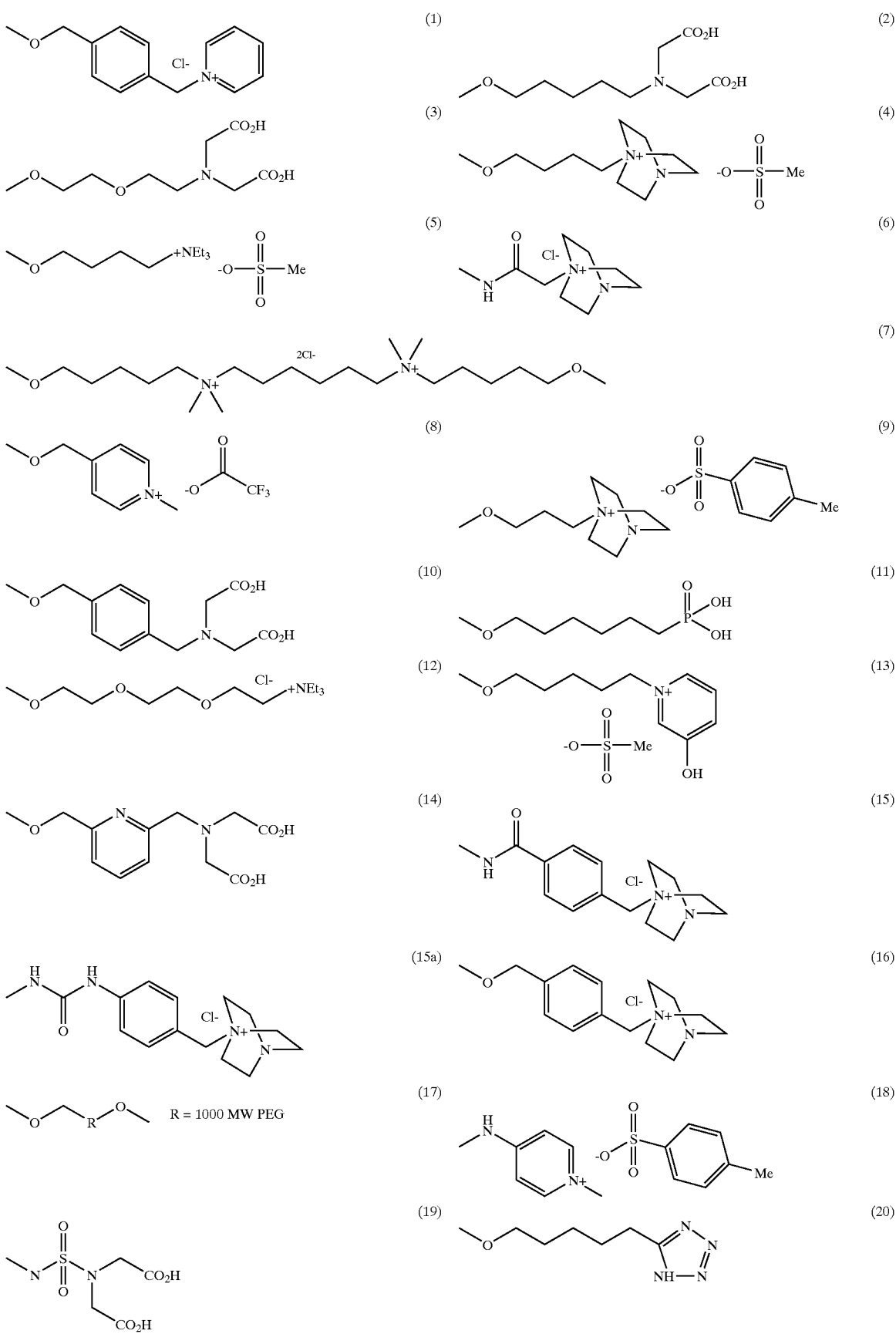

(21)
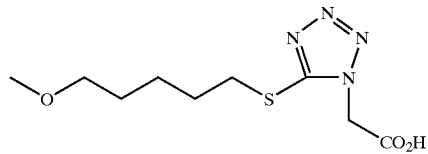
(22)
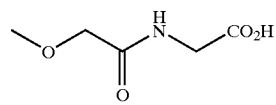
(23)
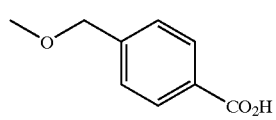
(24)
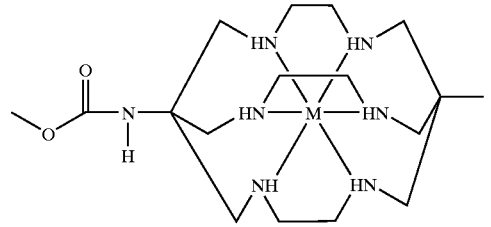
M = Co$^{II,III}$, Mn$^{II,III}$, Fe$^{II,III}$, Ni$^{II,III}$, Cr$^{III}$, Cu$^{II}$, Zn$^{II}$, Cd$^{II}$, Ga$^{III}$, In$^{III}$, V$^{IV}$, Ru$^{II}$, Pr$^{IV}$, Ph$^{III}$ or Ir$^{III}$
(25)
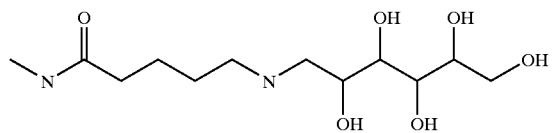
(26)
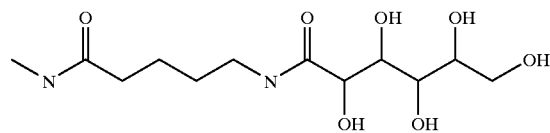
(27)
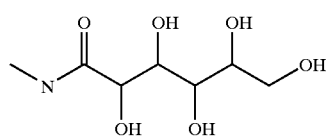
(28)
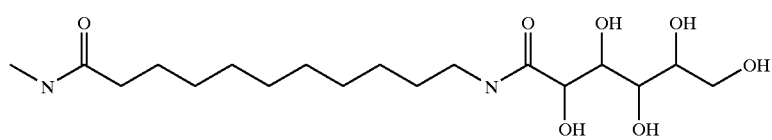
(29)
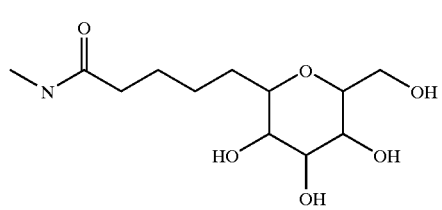
(30)
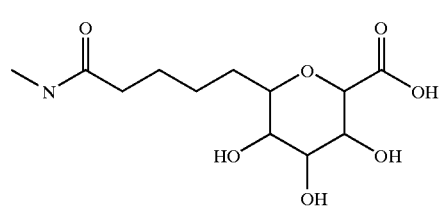
(31)
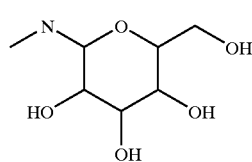
(32)
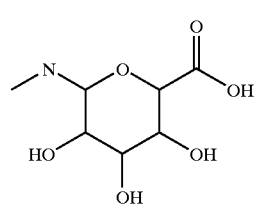
(33)
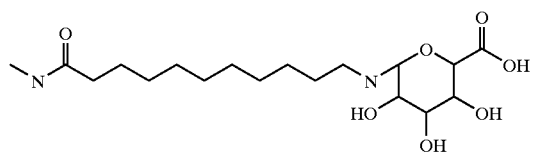
(34)
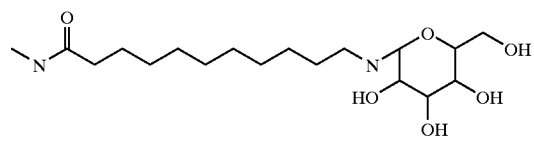

-continued
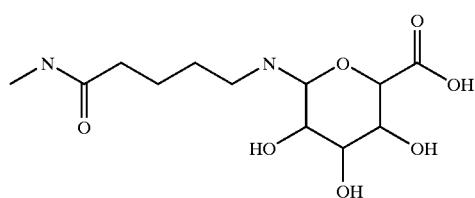 (35)
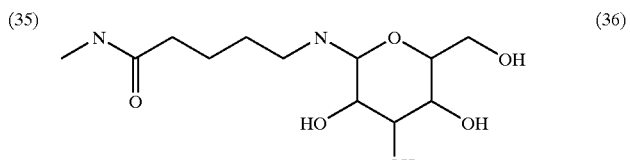 (36)
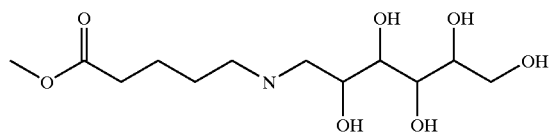 (37)
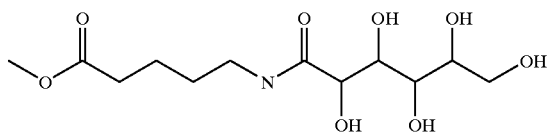 (38)
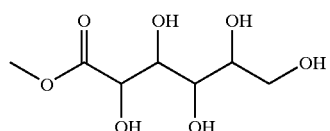 (39)
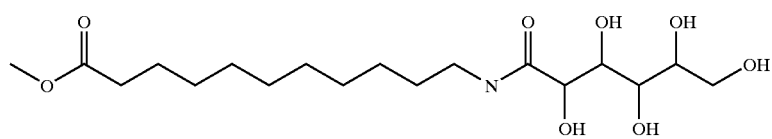 (40)
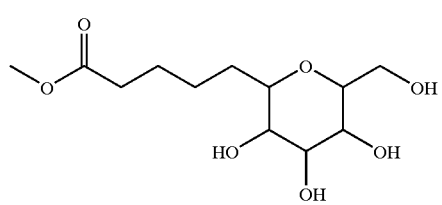 (41)
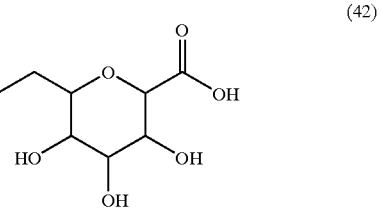 (42)
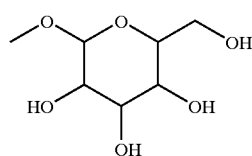 (43)
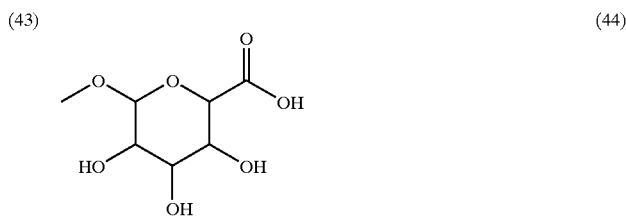 (44)
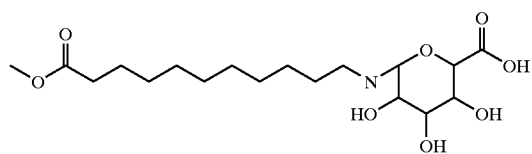 (45)
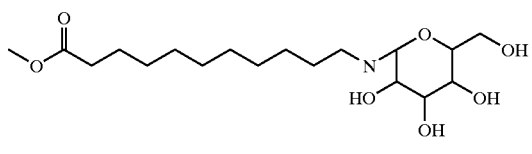 (46)
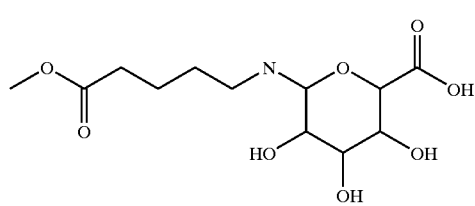 (47)
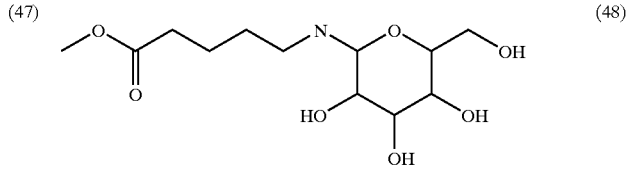 (48)

-continued
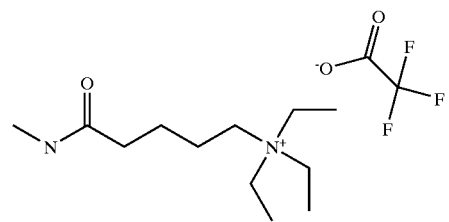 (49)
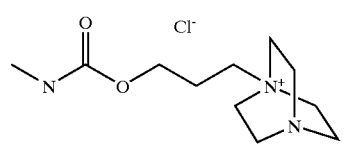 (50)
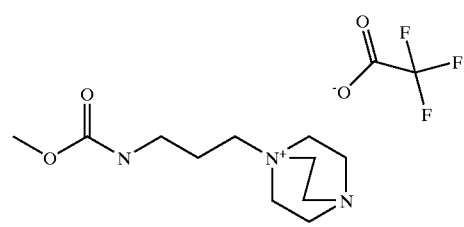 (51)
(52)
(53)
(54)
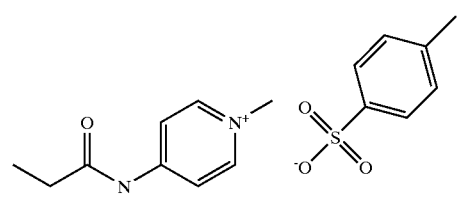 (55)
(56)
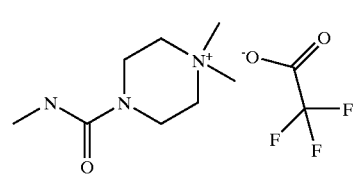 (57)
(58)
(59)
(60)
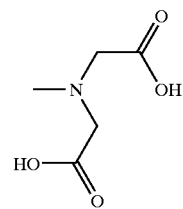 (61)
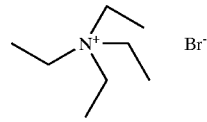 (62)

-continued

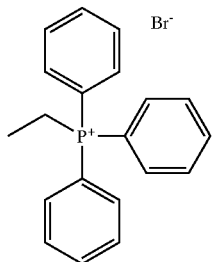 (63)

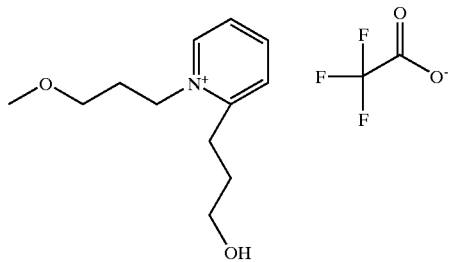 (64)

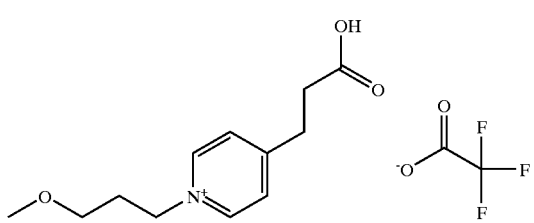 (65)

(66)

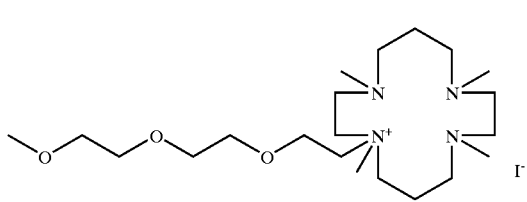 (67)

(68)

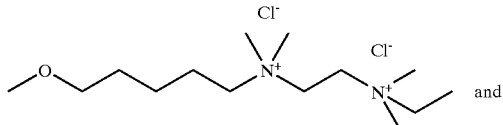 (69)

(70)

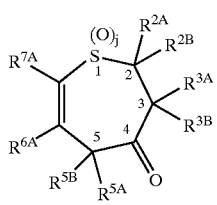

provided that when said $R^5$ is (7), (17) or (24), then said $R^{5A}$ is a left end of said $R^5$ and said $R^{5B}$ is a right end of said $R^5$ or vice versa.

63. A method of forming a compound of the Formula I-1:

I-1 or a pharmaceutically acceptable salt, solvate, or prodrug thereof wherein j is 0, 1 or 2;

wherein $R^{2A}$ and $R^{2B}$ are independently selected from the group consisting of hydrogen and hydrocarbyl;

wherein $R^{3A}$, $R^{3B}$, $R^{5A}$, and $R^{5B}$ are independently selected from the group consisting of hydrogen, alkyl; cycloalkyl; alkenyl; alkynyl; heterocyclyl; quaternary heterocyclyl, oxo; aryl-$R^5$; —$OR^9$; —$NR^9R^{10}$; —$SR^9$; —$S(O)R^9$; —$SO_2R^9$; and —$SO_3R^9$;

wherein $R^9$ and $R^{10}$ are independently selected from the group consisting of hydrogen; hydrocarbyl; amino; and hydrocarbylamino;

wherein $R^5$ is selected from the group consisting of hydrogen; hydrocarbyl; heterocyclyl; quaternary heterocyclyl; —$OR^9$; —$SR^9$; —$S(O)R^9$; —$SO_2R^9$; and —$SO_3R^9$;

wherein when $R^5$ is said cycloalkyl, aryl or heterocyclyl, said cycloalkyl, aryl or heterocyclyl are optionally substituted with —NH—X—R or —O—X—R;

wherein X is selected from the group consisting of —(C=O)$_s$-alkyl-; —(C=O)$_s$-alkyl-NH—; —(C=O)$_s$-alkyl-O—; —(C=O)$_s$-alkyl-(C=O)$_t$; and a covalent bond, wherein s and t are independently 0 or 1;

wherein R is selected from the group consisting of monosaccharides, disaccharides, and polysaccharides, wherein said monosaccharides, disaccharides, and polysaccharides are optionally protected with one or more sugar protecting groups;

wherein $R^9$ and $R^{10}$ are as previously defined;

wherein, when $R^5 \neq H$, $R^5$ is optionally substituted with one or more radicals independently selected from the group consisting of halogen; —$NO_2$; —CN; oxo; hydrocarbyl; —$OR^{13}$; —$NR^{13}R^{14}$; —$SR^{13}$; —$S(O)R^{13}$; —$SO_2R^{13}$; —$SO_3R^{13}$; —$NR^{13}OR^{14}$; —$NR^{13}NR^{14}R^{15}$; —$CO_2R^{13}$; —OM; —$SO_2OM$; —$SO_2NR^{13}R^{14}$; —$C(O)NR^{13}R^{14}$; —C(O)OM; —$COR^{13}$; —$NR^{13}C(O)R^{14}$; —$NR^{13}C(O)NR^{14}R^{15}$; —NR $CO_2R^{14}$; —$OC(O)R^{13}$; —$OC(O)NR^{13}R^{14}$; —$NR^{13}SOR^{14}$; —$NR^{13}SO_2R^{14}$; —$NR^{13}SONR^{14}R^{15}$; —$NR^{13}SO_2NR^{14}R^{15}$; —$PR^{13}R^{14}$; —$P(O)R^{13}R^{14}$;

—P$^+$R$^{13}$R$^{14}$R$^{15}$A$^-$;  —P(OR$^{13}$)OR$^{14}$;
—S$^+$R$^{13}$R$^{1414}$A$^-$; and —N$^+$R$^{13}$R$^{14}$R$^{15}$A$^-$;

wherein R$^{13}$, R$^{14}$, and R$^{15}$ are independently selected from the group consisting of hydrogen and hydrocarbyl;

wherein A$^-$ is a pharmaceutically acceptable anion;

wherein M is a pharmaceutically acceptable cation;

wherein R$^{6A}$ and R7$^A$ radicals are independently selected from the group consisting of hydrogen; halogen; —CN; —NO$_2$; hydrocarbyl; —R$^5$; aryl-R$^5$; —OR$^{13}$; —NR$^{13}$R$^{14}$; —SR$^{13}$; —S(O)R$^{13}$; —S(O)$_2$R$^{13}$; —SO$_3$R$^{13}$; —S$^+$R$^{13}$R$^{14}$A$^-$; —NR$^{13}$OR$^{14}$; —NR$^{13}$NR$^{14}$R$^{15}$; —OM; —SO$_2$OM; —SO$_2$NR$^{13}$R$^{14}$; —NR$^{14}$C(O)R$^{13}$; —C(O)OM; —S(O)NR$^{13}$R$^{14}$; —N$^+$R$^{13}$R$^{14}$R$^{15}$A$^-$; —PR$^{13}$R$^{14}$; —P(O)R$^{13}$R$^{14}$; —P$^+$R$^{13}$R$^{14}$R$^{15}$A$^-$; acid residue; peptide residue; polypeptide residue; and carbohydrate residue;

wherein R$^{13}$, R$^{14}$, R$^{15}$, A$^-$, and M are as defined above; and wherein, in each instance, said hydrocarbyl may be optionally substituted with one or more groups comprising one or more heteroatoms, and wherein, in each instance, said hydrocarbyl optionally may have one or more carbon atoms replaced by one or more heteroatoms independently selected from the group consisting of oxygen, nitrogen, sulfur, phosphorus and combinations thereof, said method comprising the steps of:

(a) forming a compound of Formula S1-78a:

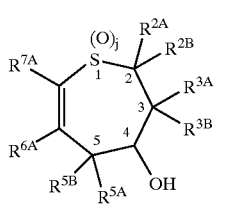

S1-78a wherein R$^{2A}$, R$^{2B}$, R$^{3A}$, R$^{3B}$, R$^{5A}$, R$^{5B}$, R$^{6A}$, R$^{7A}$ and j are as previously defined; and (b) treating said compound of Formula S1-78a with oxalyl chloride to form said compound of Formula I-1.

64. The method of claim 63 wherein said treating step (b) is carried out in an inert solvent.

65. The method of claim 64 wherein said treating step (b) is carried out in said inert solvent cooled to from about −50° C. to about −78° C.

66. A method of forming a compound of Formula I-18:

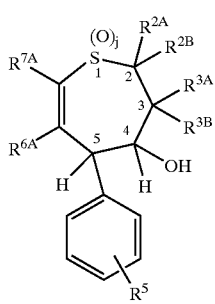

I-18 or a pharmaceutically acceptable salt, solvate, or prodrug thereof wherein j is 0, 1 or 2;

wherein R$^{2A}$ and R$^{2B}$ are independently selected from the group consisting of hydrogen and hydrocarbyl;

wherein R$^{3A}$ and R$^{3B}$, R$^{5A}$, and R$^{5B}$ are independently selected from the group consisting of hydrogen, alkyl; cycloalkyl; alkenyl; alkynyl; heterocyclyl; quaternary heterocyclyl, oxo; aryl-R$^5$; —OR$^9$; —NR$^9$R$^{10}$; —SR$^9$; —S(O)R$^9$; —SO$_2$R$^9$; and —SO$_3$R$^9$;

wherein R$^9$ and R$^{10}$ are independently selected from the group consisting of hydrogen; hydrocarbyl; amino; and hydrocarbylamino;

wherein R$^5$ is selected from the group consisting of hydrogen; hydrocarbyl; heterocyclyl; quaternary heterocyclyl; —OR$^9$; —SR$^9$; —S(O)R$^9$; —SO$_2$R$^9$; and —SO$_3$R$^9$;

wherein when R$^5$ is said cycloalkyl, aryl or heterocyclyl, said cycloalkyl, aryl or heterocyclyl are optionally substituted with —NH—X—R or —O—X—R;

wherein X is selected from the group consisting of —(C=O)$_s$-alkyl-;  —(C=O)$_s$-alkyl-NH—; —(C=O)$_s$-alkyl-O—; —(C=O)$_s$-alkyl-(C=O)$_t$; and a covalent bond, wherein s and t are independently 0 or 1;

wherein R is selected from the group consisting of monosaccharides, disaccharides, and polysaccharides, wherein said monosaccharides, disaccharides, and polysaccharides are optionally protected with one or more sugar protecting groups;

wherein R$^9$ and R$^{10}$ are as previously defined;

wherein, when R$^5$≠H, R$^5$ is optionally substituted with one or more radicals independently selected from the group consisting of halogen; —NO$_2$; —CN; oxo; hydrocarbyl; —OR$^{13}$; —NR$^{13}$R$^{14}$; —SR$^{13}$; —S(O)R$^{13}$; —SO$_2$R$^{13}$; —SO$_3$R$^{13}$; —NR$^{13}$OR$^{14}$; —NR$^{13}$NR$^{14}$R$^{15}$; —CO$_2$R$^{13}$; —OM; —SO$_2$OM; —SO$_2$NR$^{13}$R$^{14}$; —C(O)NR$^{13}$R$^{14}$; —C(O)OM; —COR$^{13}$; —NR$^{13}$C(O)R$^{14}$; —NR$^{13}$C(O)NR$^{14}$R$^{15}$; —NR$^{13}$CO$_2$R$^{14}$; —OC(O)R$^{13}$; —OC(O)NR$^{13}$R$^{14}$; —NR$^{13}$SOR$^{14}$; —NR$^{13}$SO$_2$R$^{14}$; —NR$^{13}$SONR$^{14}$R$^{15}$; —NR$^{13}$SO$_2$NR$^{14}$R$^{15}$; —PR$^{13}$R$^{14}$; —P(O)R$^{13}$R$^{14}$; —P$^+$R$^{13}$R$^{14}$R$^{15}$A$^-$; —P(OR$^{13}$)OR$^{14}$; —S$^+$R$^{13}$R$^{14}$A$^-$; and —N$^+$R$^{13}$R$^{14}$R$^{15}$A$^-$;

wherein R$^{13}$, R$^{14}$, and R$^{15}$ are independently selected from the group consisting of hydrogen and hydrocarbyl;

wherein A$^-$ is a pharmaceutically acceptable anion;

wherein M is a pharmaceutically acceptable cation;

wherein R$^{6A}$ and R$^{7A}$ radicals are independently selected from the group consisting of hydrogen; halogen; —CN; —NO$_2$; hydrocarbyl; —R$^5$; aryl-R$^5$; —OR$^{13}$; —NR$^{13}$R$^{14}$; —SR$^{13}$; —S(O)R$^{13}$; —S(O)$_2$R$^{13}$; —SO$_3$R$^{13}$; —S$^+$R$^{13}$R$^{14}$A$^-$; —NR$^{13}$OR$^{14}$; —NR$^{13}$NR$^{14}$R$^{15}$; —OM; —SO$_2$OM; —SO$_2$NR$^{13}$R$^{14}$; —NR$^{14}$C(O)R$^{13}$; —C(O)OM; —S(O)NR$^{13}$R$^{14}$; —N$^+$R$^{13}$R$^{14}$R$^{15}$A—; —PR$^{13}$R$^{14}$; —P(O)R$^3$R$^{14}$; —P$^+$R$^{13}$R$^{14}$R$^{15}$A$^-$; amino acid residue; peptide residue; polypeptide residue; and carbohydrate residue;

wherein R$^{13}$, R$^{14}$, R$^{15}$, A$^-$, and M are as defined above; and wherein, in each instance, said hydrocarbyl may be optionally substituted with one or more groups comprising one or more heteroatoms, and wherein, in each instance, said hydrocarbyl optionally may have one or more carbon atoms replaced by one or more heteroatoms independently selected from the group consisting of oxygen, nitrogen, sulfur, phosphorus and combinations thereof, said method comprising the steps of:

(a) forming a compound of Formula S2-36384042:

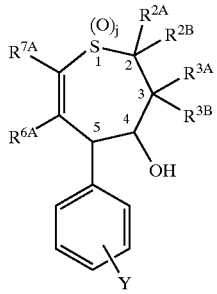

S2-36384042 wherein $R^{2A}$, $R^{2B}$, $R^{3A}$, $R^{3B}$, $R^{6A}$, $R^{7A}$ and j are as previously defined; wherein Y=alkoxy or halo (b) treating said compound of Formula S2-36384042 with $BBr_3$ and then quenching with 10% $K_2CO_3$ to form S2-44464850:

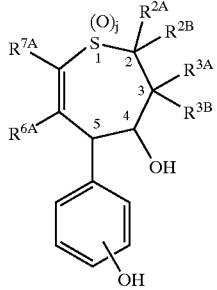

S2-44464850 and (c) replacing the aryl hydroxy group with $R^5$ to form compound I-18.

67. The method of claim 66 wherein said treating step (b) is carried out in an inert solvent.

68. The method of claim 67 wherein said treating step (b) is carried out in said inert solvent cooled to from about −50° C. −78° C.

69. The method of claim 63 wherein said compound of Formula I-1 comprises Formula I-17 represented by:

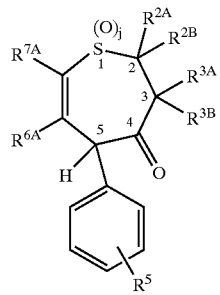

I-17 wherein $R^{2A}$, $R^{2B}$, $R^{3A}$, $R^{3B}$, $R^{5A}$, $R^{5B}$, $R^6$, m and j are as previously defined and $R^5$ is selected from the group consisting of (1)–(69) and (70):

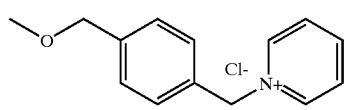
(1)

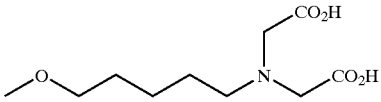
(2)

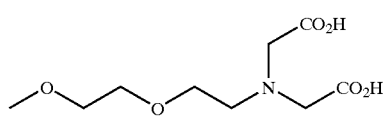
(3)

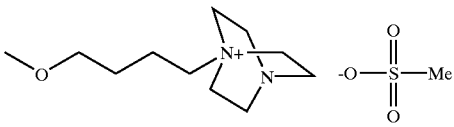
(4)

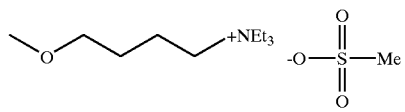
(5)

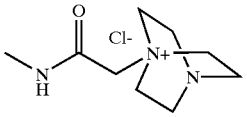
(6)

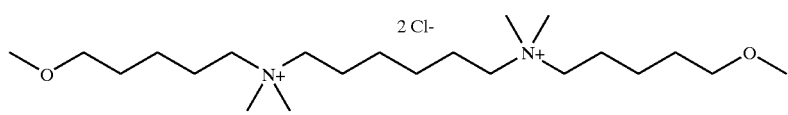
(7)

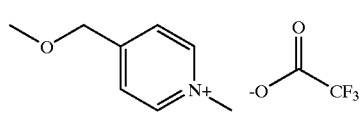
(8)

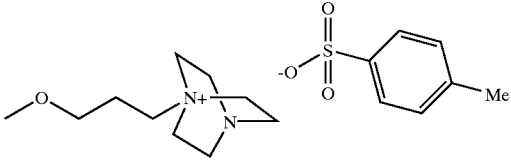
(9)

-continued
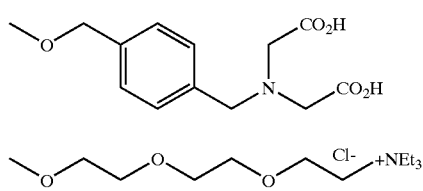
(10)
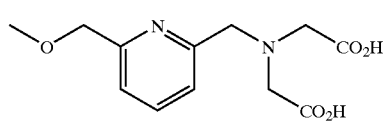
(12)
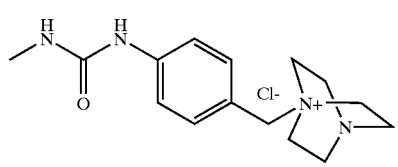
(14)
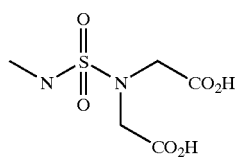
(15a)
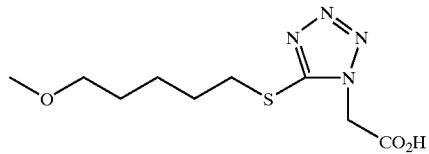
(17)
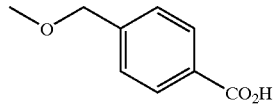
(19)
(21)
(23)
(25)
(11)
(13)
(15)
(16)
(18)
(20)
(22)
(24)
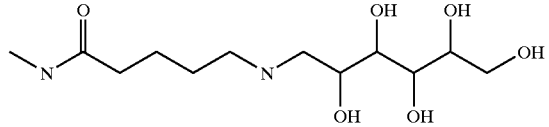
M = Co$^{II, III}$, Mn$^{II, III}$, Fe$^{II, III}$, Ni$^{II, III}$, Cr$^{III}$, Cu$^{II}$, Zn$^{II}$, Cd$^{II}$, Ga$^{III}$, In$^{III}$, V$^{IV}$, Ru$^{II}$, Pr$^{IV}$, Rh$^{III}$ or Ir$^{III}$
(26)

-continued
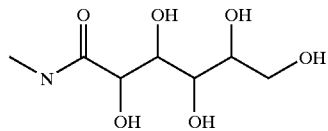 (27)
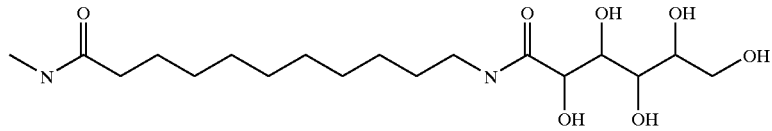 (28)
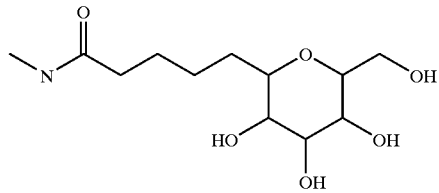 (29)
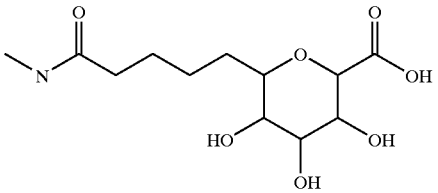 (30)
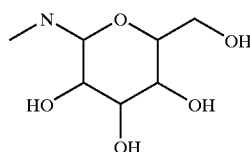 (31)
(32)
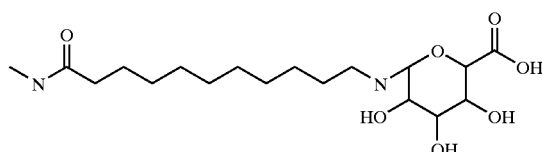 (33)
(34)
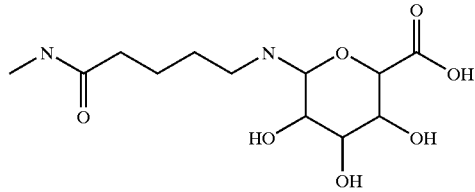 (35)
(36)
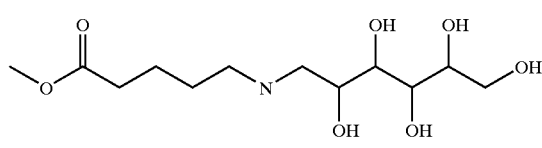 (37)
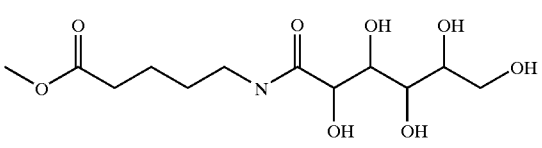 (38)
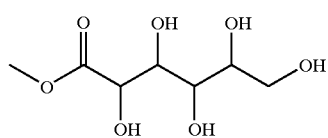 (39)
 (40)

-continued
(41) 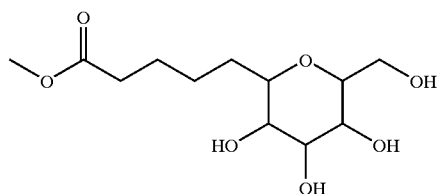
(42) 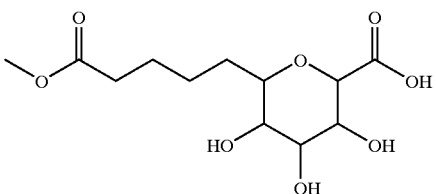
(43) 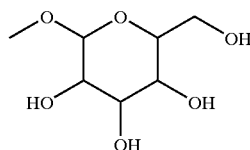
(44) 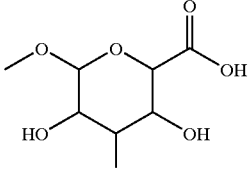
(45) 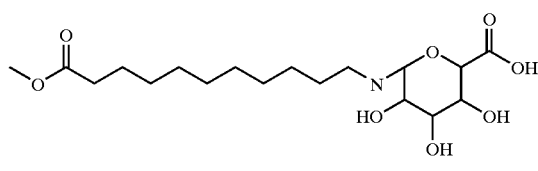
(46) 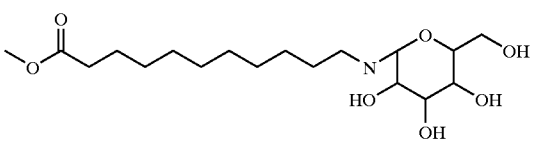
(47) 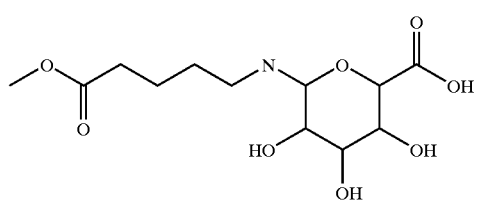
(48)
(49) 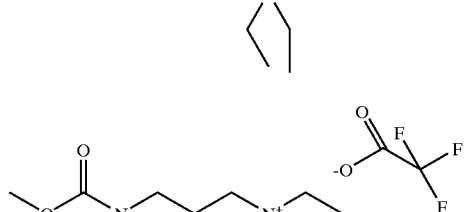
(50) 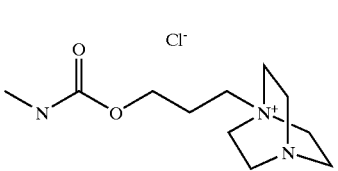
(51) 
(52) 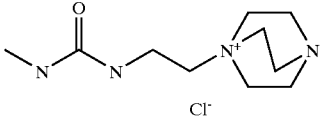
(53) 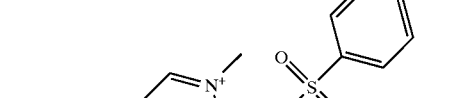
(54) 
(55) 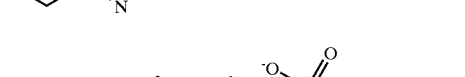
(56) 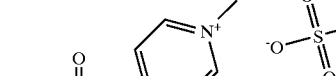

(57)
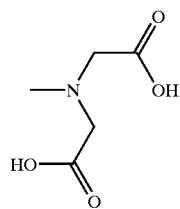
(58)
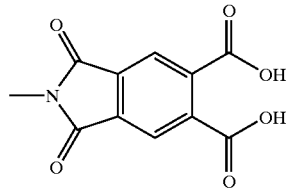
(59)
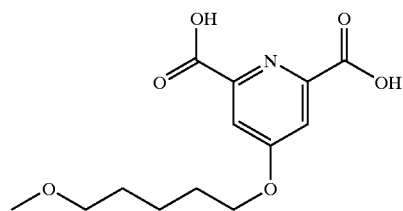
(60)
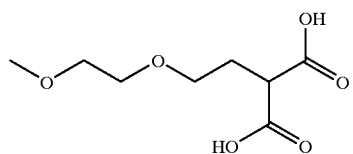
(61)
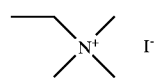
(62)
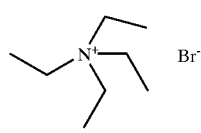
(63)
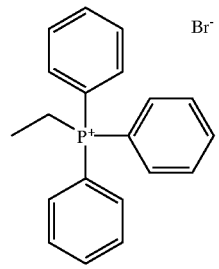
(64)
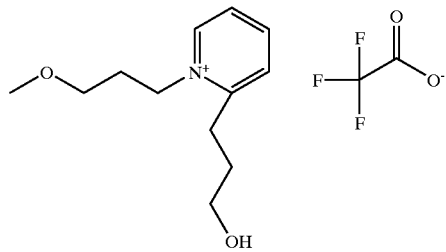
(65)
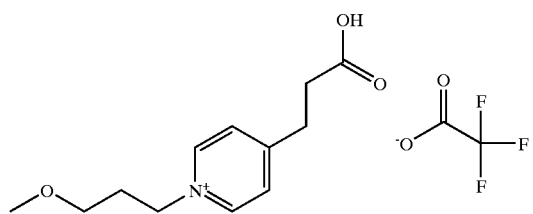
(66)
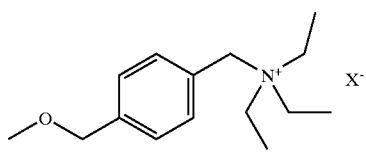
(67)
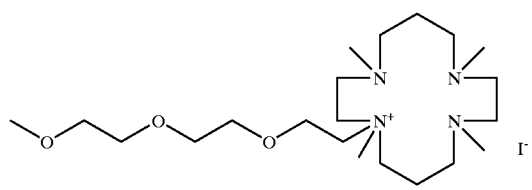
(68)
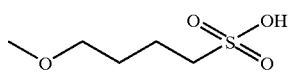
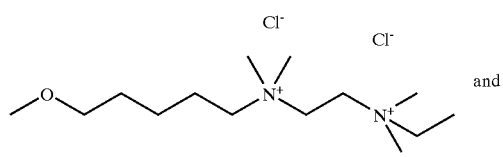 and
(70)
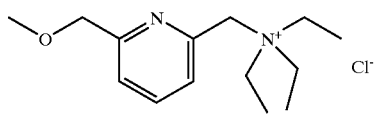

provided that when said $R^5$ is (7), (17) or (24), then said $R^{5A}$ is a left end of said $R^5$ and said $R^{5B}$ is a right end of said $R^5$ or vice versa.

70. The method of claim 69 wherein said Formula I-17 comprises Formulas I-21 or I-22 represented by:

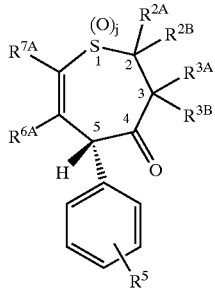

I-21

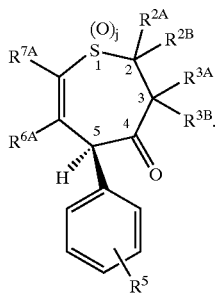

I-22

71. The method of claim 70 wherein said Formulas I-21 and I-22 comprise Formulas I-9 and I-10, respectively, represented by:

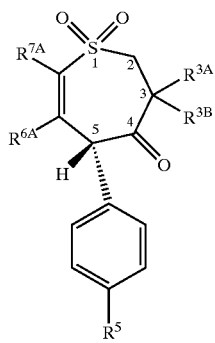

I-9

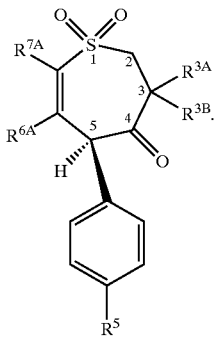

I-10

72. The method of claim 70 wherein said $R^5$ group is attached at least either at a meta position or at a para position of said phenyl ring attached to said 5-carbon position of said benzothiepene of said Formulas I-21 or I-22.

73. The method of claim 66 wherein said compound of Formula I-2 is selected from the group consisting of Formulas I-3 and I-4 represented by:

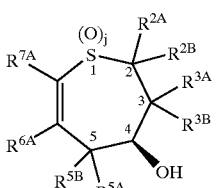

I-3

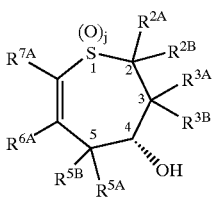

I-4 wherein $R^{2A}, R^{2B}, R^{3A}, R^{3B}, R^{5A}, R^{5B}, R^{6A}, R^{7A}$, m and j are as previously defined and said $R^5$ is selected from the group consisting of (1)–(69) and (70):

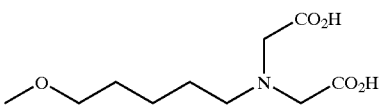

(1)

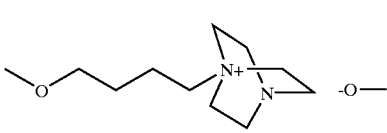

(2)

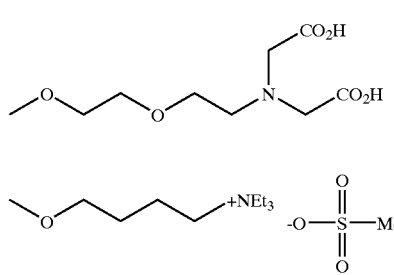

(3)

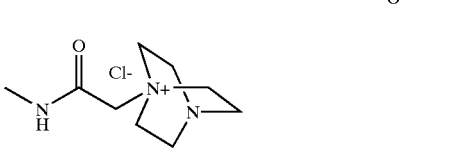

(4)

(5)

(6)

-continued
(7) 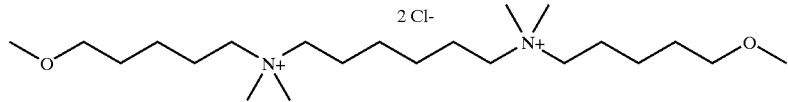
(8) 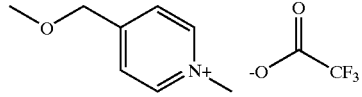
(9) 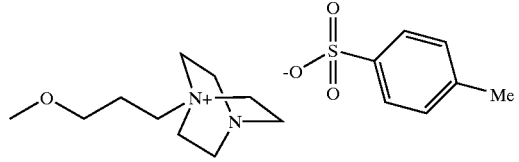
(10) 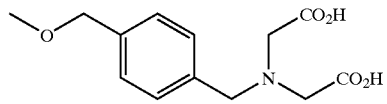
(11) 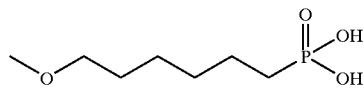
(12) 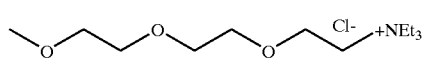
(13) 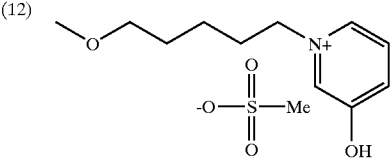
(14) 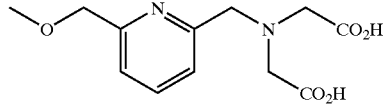
(15) 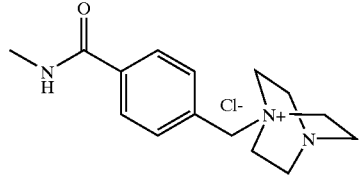
(15a) 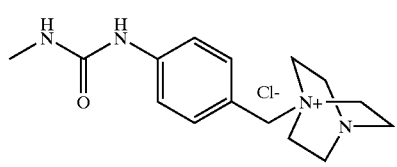
(16) 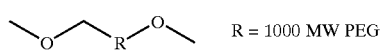
(17) 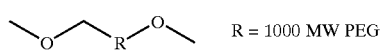
R = 1000 MW PEG
(18) 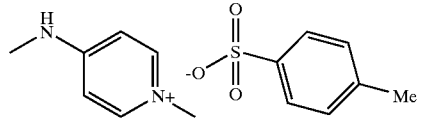
(19) 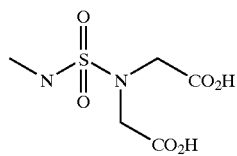
(20) 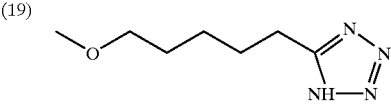
(21) 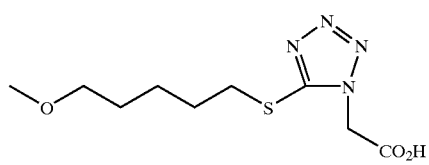
(22) 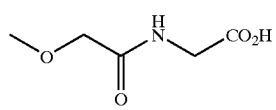

-continued
(23)
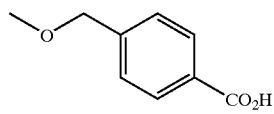
(24)
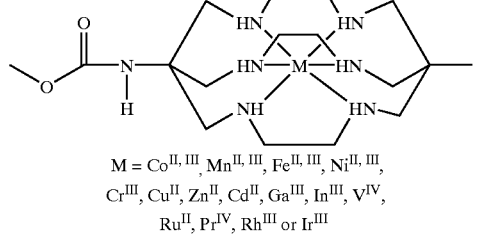
M = $Co^{II, III}$, $Mn^{II, III}$, $Fe^{II, III}$, $Ni^{II, III}$, $Cr^{III}$, $Cu^{II}$, $Zn^{II}$, $Cd^{II}$, $Ga^{III}$, $In^{III}$, $V^{IV}$, $Ru^{II}$, $Pr^{IV}$, $Rh^{III}$ or $Ir^{III}$
(25)
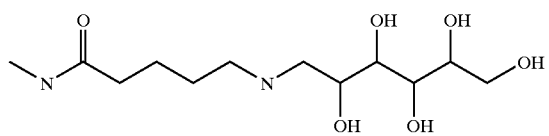
(26)
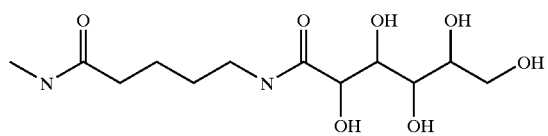
(27)
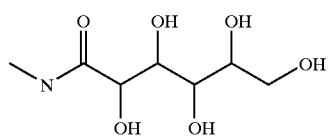
(28)
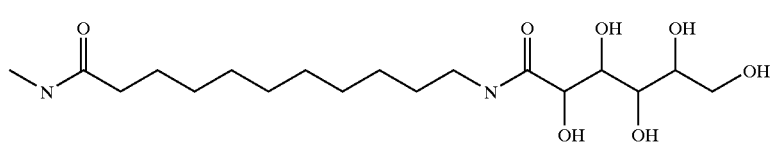
(29)
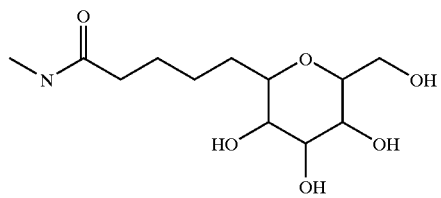
(30)
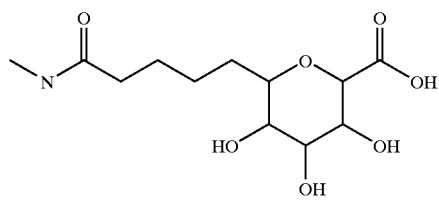
(31)
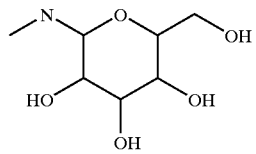
(32)
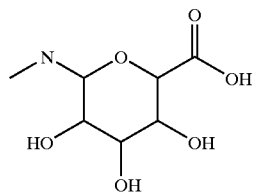
(33)
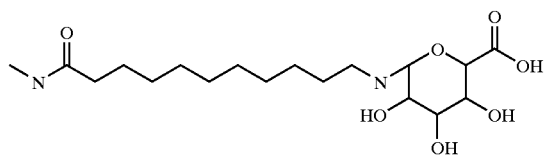
(34)
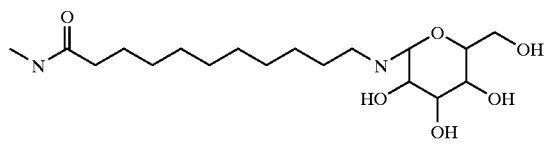
(35)
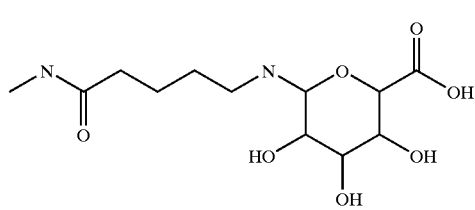
(36)
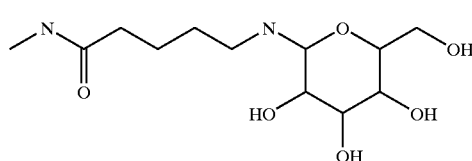

-continued
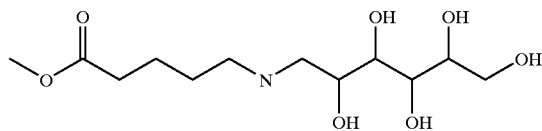 (37)
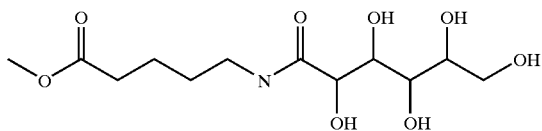 (38)
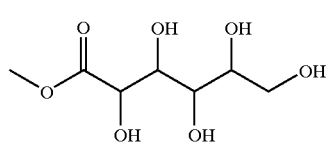 (39)
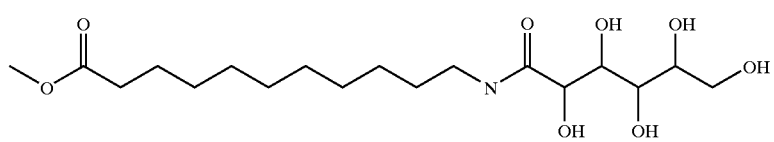 (40)
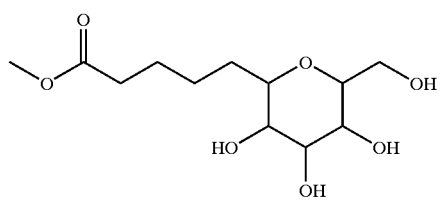 (41)
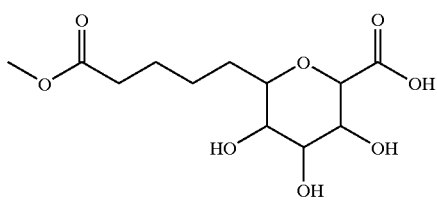 (42)
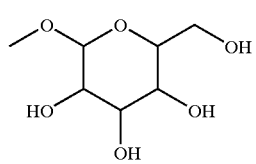 (43)
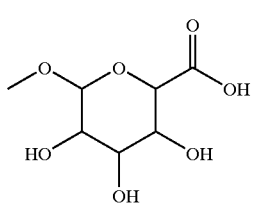 (44)
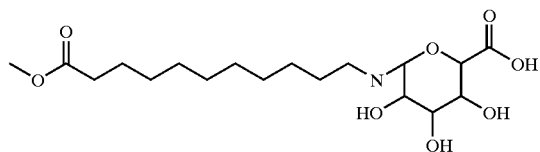 (45)
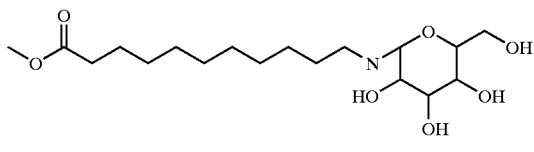 (46)
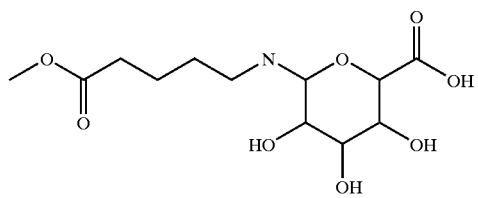 (47)
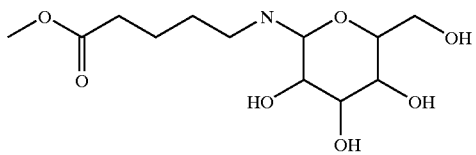 (48)
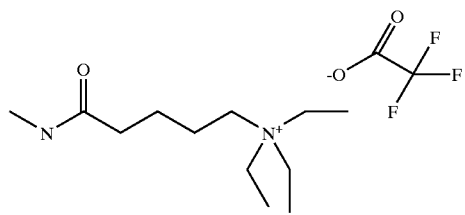 (49)
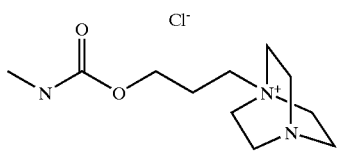 (50)

-continued
(51)
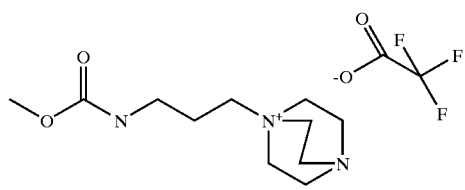
(52)
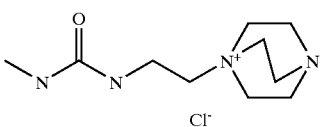
(53)
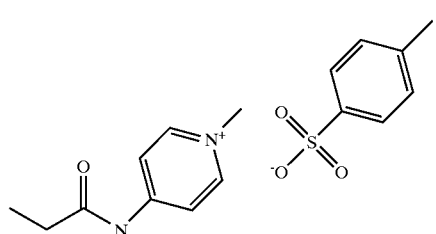
(54)
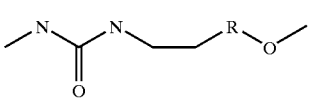
(55)
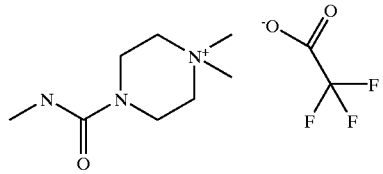
(56)
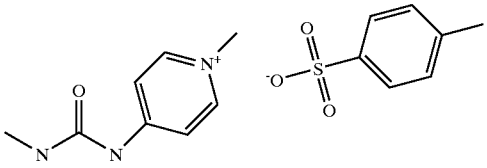
(57)
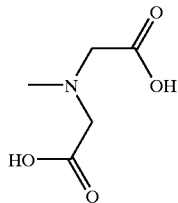
(58)
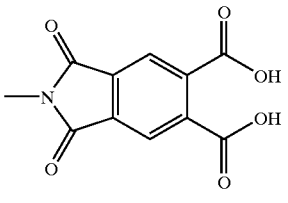
(59)
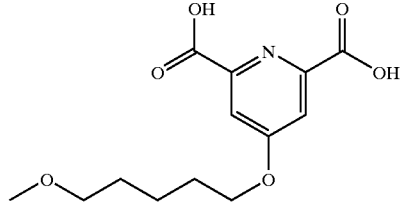
(60)
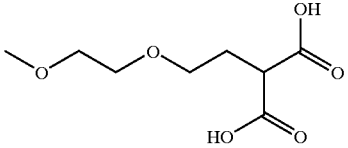
(61)
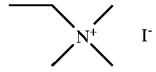
(62)
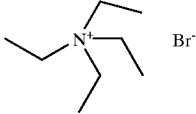
(63)
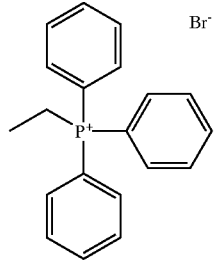
(64)
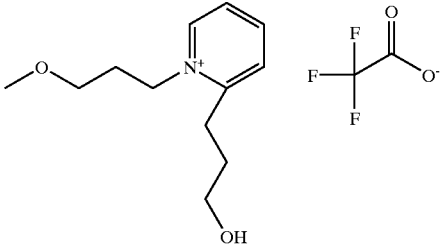

-continued

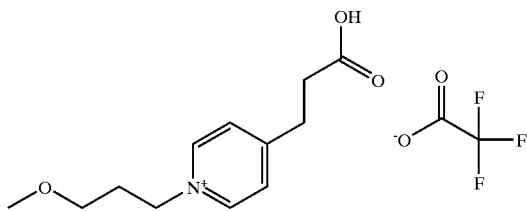
(65)

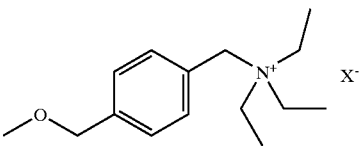
(66)

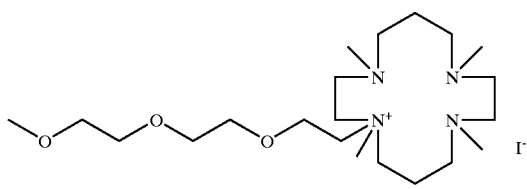
(67)

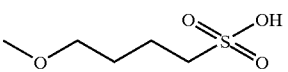
(68)

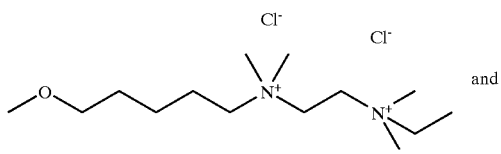
and
(69)

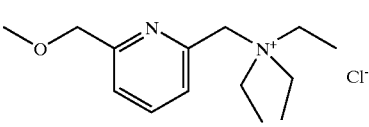
(70)

provided that when said $R^5$ is (7), (17) or (24), then said $R^{5A}$ is a left end of said $R^5$ and said $R^{5B}$ is a right end of said $R^5$ or vice versa.

74. The method of claim 73 wherein said Formula I-3 comprises a member selected from the group consisting of Formulas I-5 and I-6 represented by:

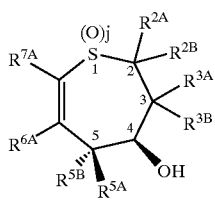
I-5

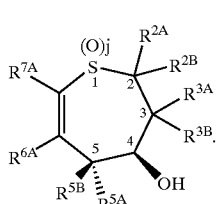
I-6

75. The method of claim 73 wherein said Formula I-4 comprises a member selected from the group consisting of Formulas I-7 and I-8 represented by:

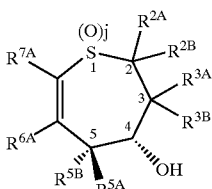
I-7

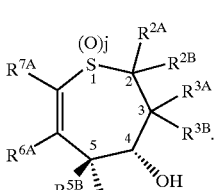
I-8

76. The method of claim 74 wherein said compounds of Formulas I-6 and I-5 comprise Formulas I-13 and I-14, respectively, represented by:

I-13

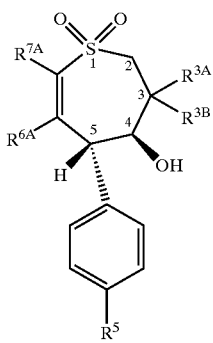

I-14

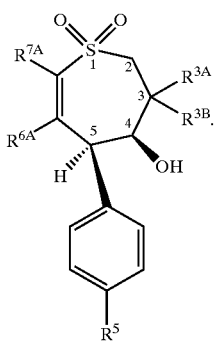

77. The method of claim 75 wherein said Formulas I-7 and I-8 comprise Formulas I-15 and I-16, respectively, represented by:

I-15

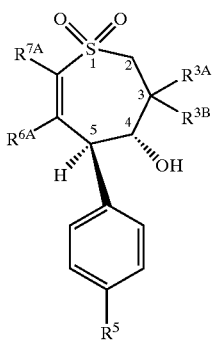

I-16

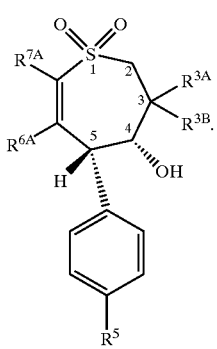

78. The method of claim 66 wherein said compound of Formula I-2 comprises a compound of Formula I-18 represented by:

I-18

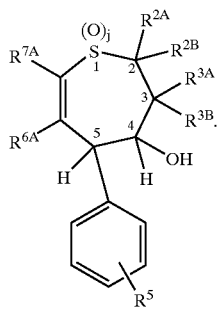

79. The method of claim 78 wherein said compound of Formula I-18 comprises a member selected from the group consisting of Formulas I-23 and I-24 represented by:

I-23

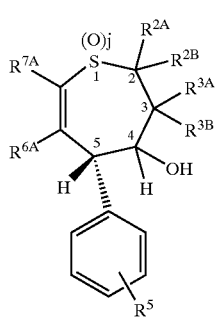

I-24

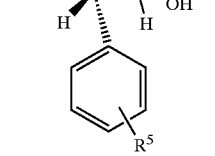

80. The method of claim 79 wherein said compounds of Formulas I-23 and I-24 comprises Formulas I-19 and I-20, respectively, represented by:

I-19

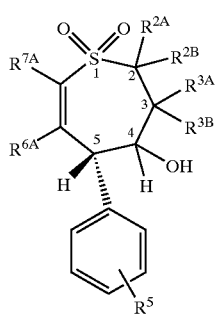

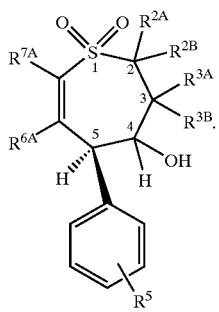

I-20

81. The method of claim 66 wherein said compound of Formula I-2 is selected from the group consisting of Formulas I-11 and I-12, respectively, represented by:

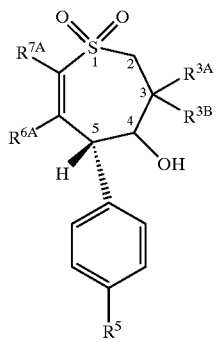

I-11

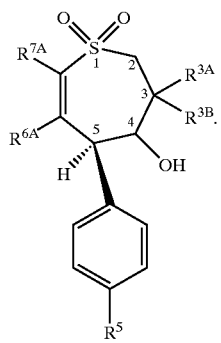

I-12

82. The compound of claim 1 wherein said compound of Formula I-1 comprises Formula I-17 represented by:

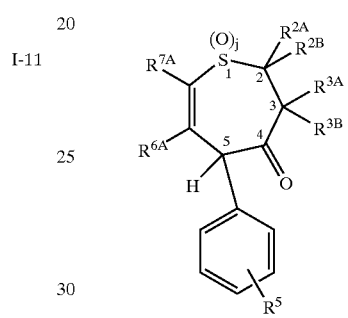

I-17 wherein $R^{2A}$, $R^{2B}$, $R^{3A}$, $R^{3B}$, $R^{5A}$, $R^{5B}$, $R^6$, m and j are as previousoly defined and said $R^5$ is selected from the group consisting of (1)–(69) and (70):

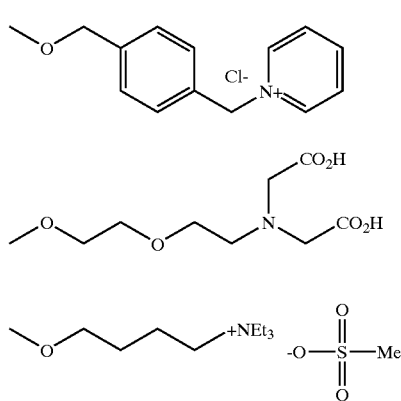

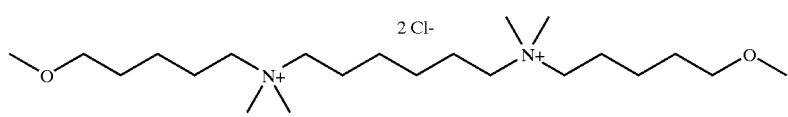

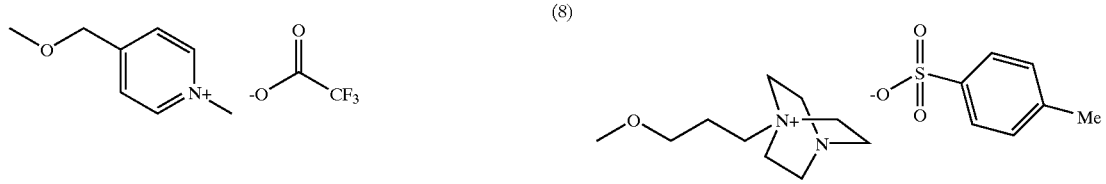

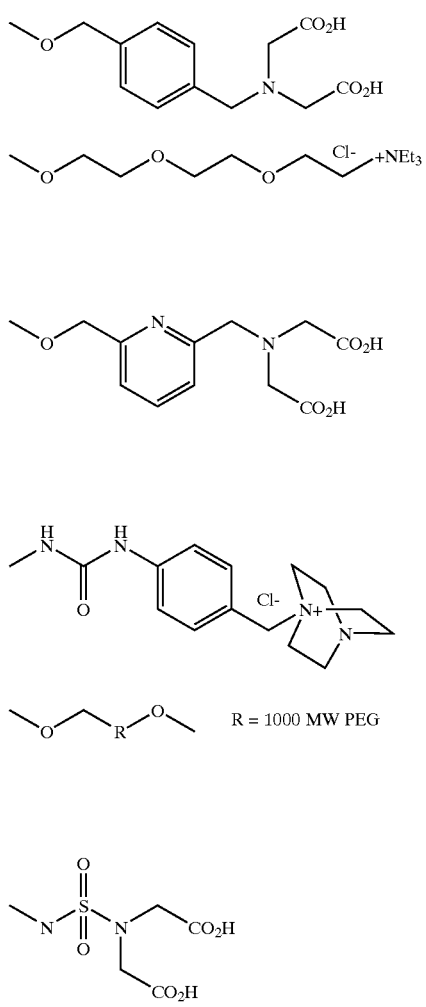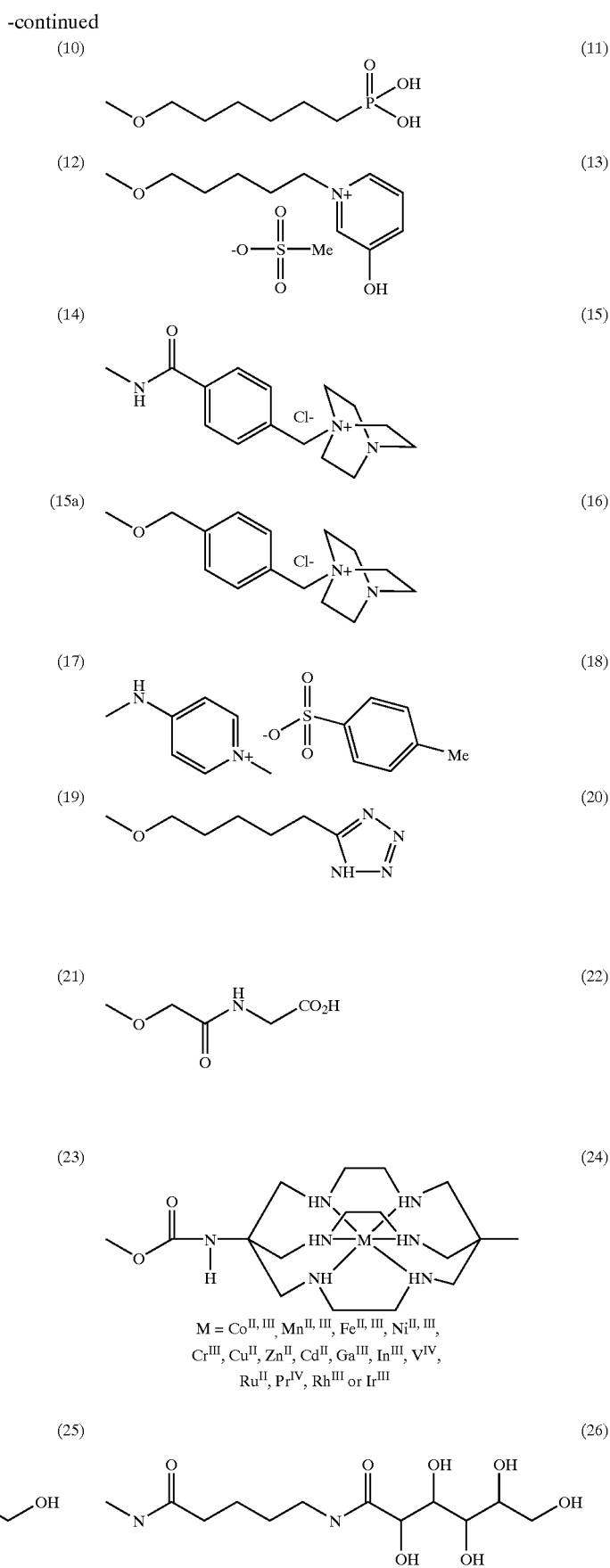

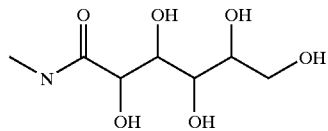
(27)
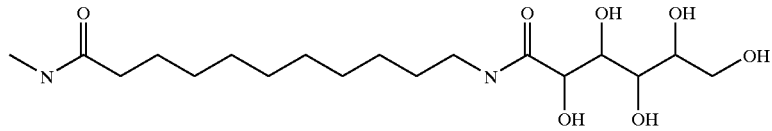
(28)
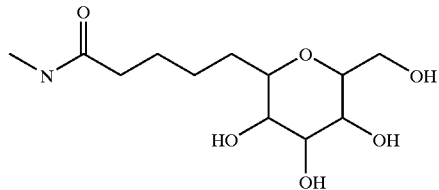
(29)
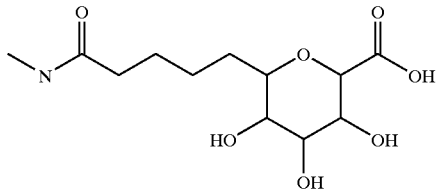
(30)
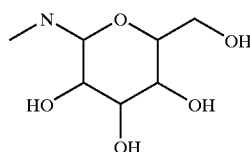
(31)
(32)
(33)
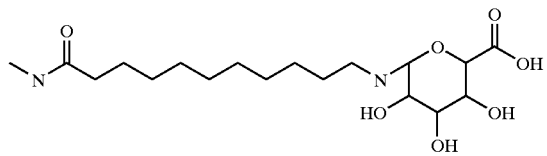
(34)
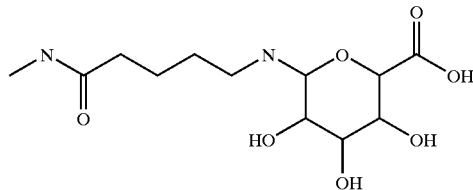
(35)
(36)
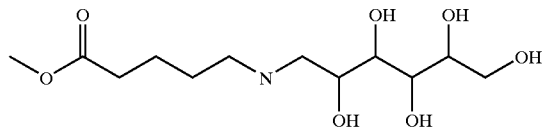
(37)
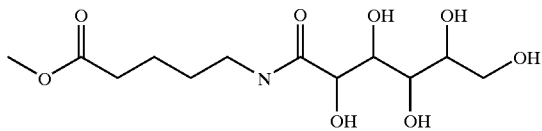
(38)
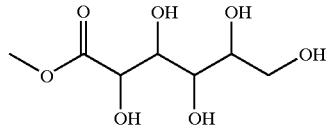
(39)
(40)

-continued
(41)
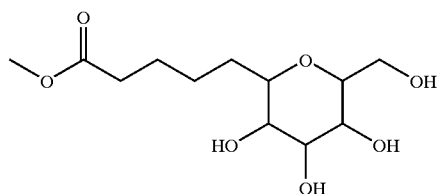
(42)
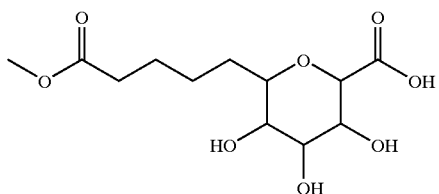
(43)
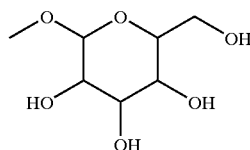
(44)
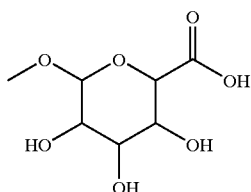
(45)
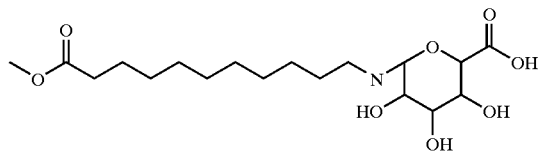
(46)
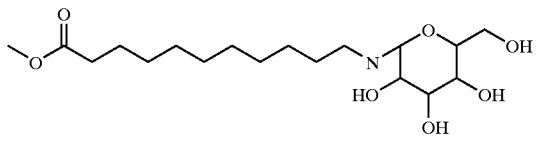
(47)
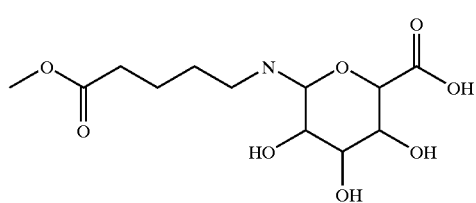
(48)
(49)
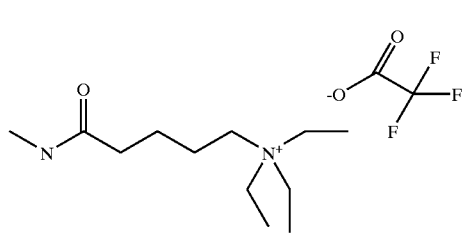
(50)
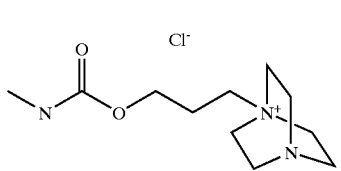
(51)
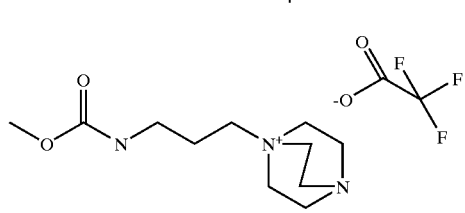
(52)
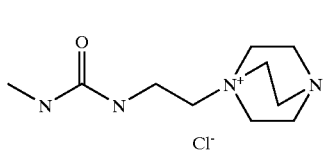
(53)
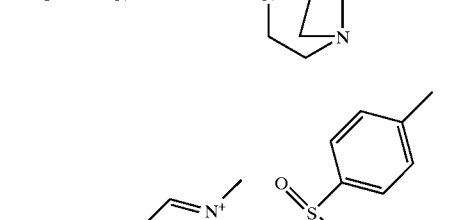
(54)
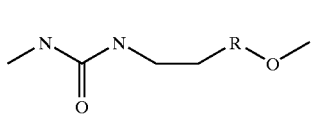
(55)
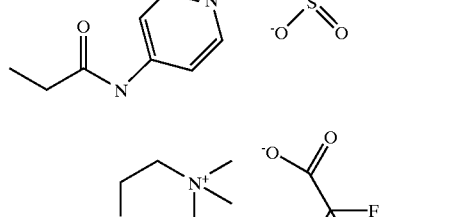
(56)
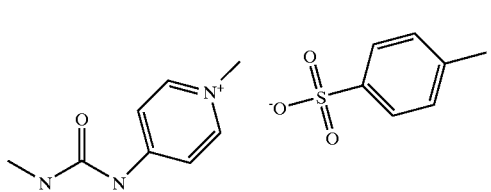

-continued
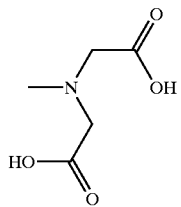 (57)
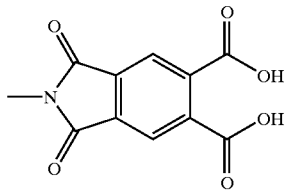 (58)
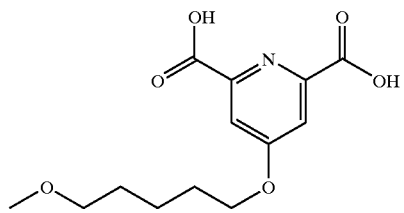 (59)
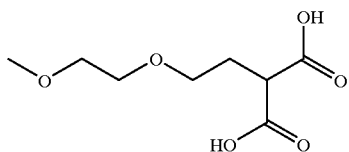 (60)
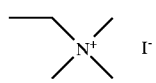 (61)
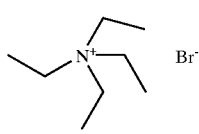 (62)
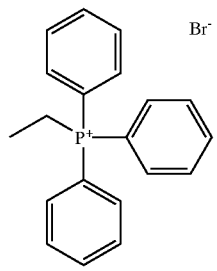 (63)
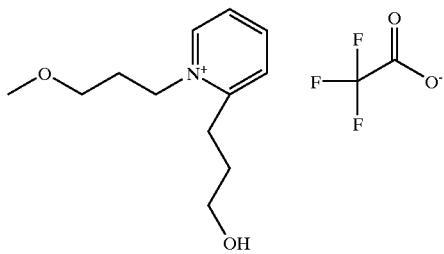 (64)
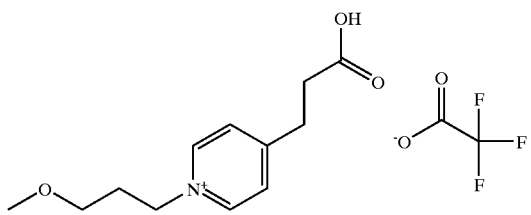 (65)
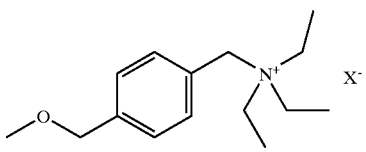 (66)
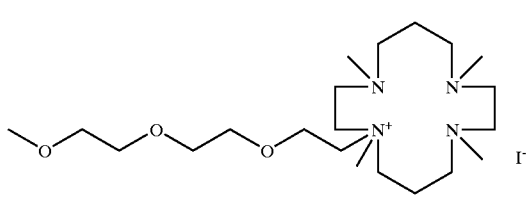 (67)
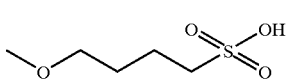 (68)
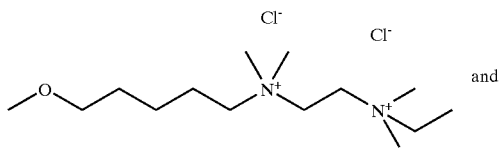 and
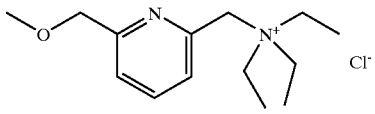 (70)
provided that when said $R^5$ is (7), (17) or (24), then said $R^{5A}$ is a left end of said $R^5$ and said $R^{5B}$ is a right end of said $R^5$ or vice versa.
83. The compound of claim 82 wherein said compound of Formula 17 comprises a member selected from the group consisting of Formulas I-21 and I-22 represented by:

185

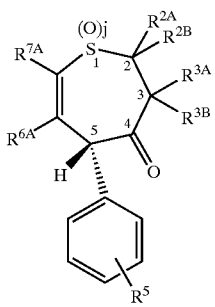

I-21

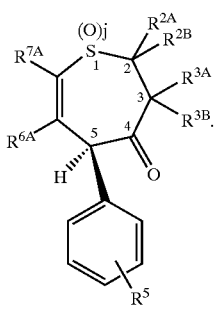

84. The compound of claim 83 wherein said compounds of Formulas I-21 and I-22 comprise Formulas I-9 and I-10, respectively, represented by:

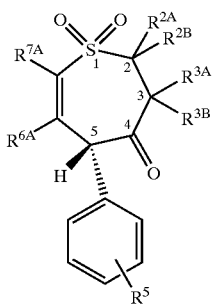

I-9

186

-continued

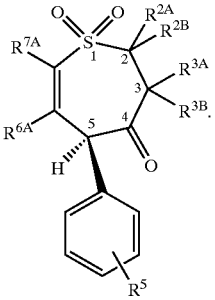

I-10

85. The compound of claim 1 wherein said compound of Formula I-2 is selected from the group consisting of Formulas I-3 and I-4 represented by:

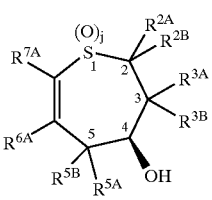

I-3

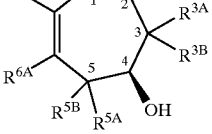

I-4 wherein $R^{2A}$, $R^{2B}$, $R^{3A}$, $R^{3B}$, $R^{5A}$, $R^{5B}$, $R^{6}$, m and j are as previously defined and said $R^5$ is selected from the group consisting of (1)–(69) and (70):

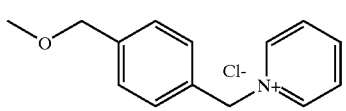

(1)

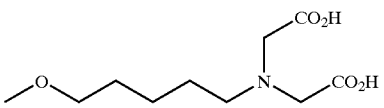

(2)

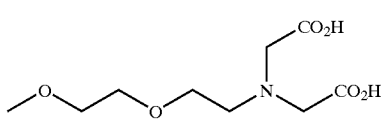

(3)

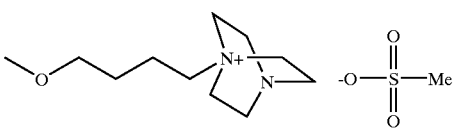

(4)

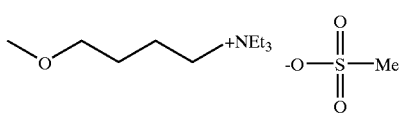

(5)

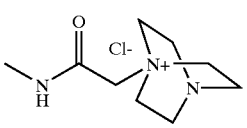

(6)

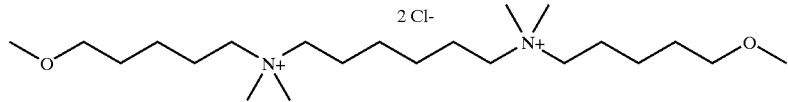
(7)
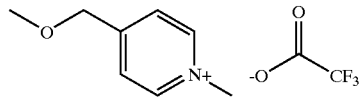
(8)
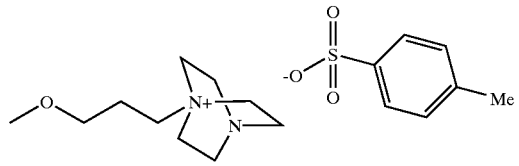
(9)
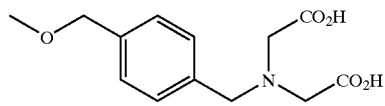
(10)
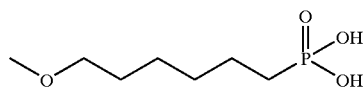
(11)
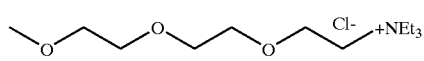
(12)
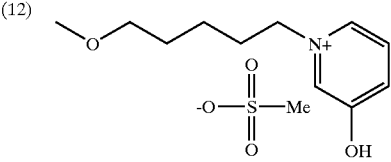
(13)
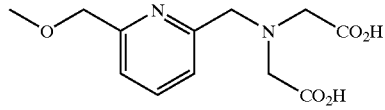
(14)
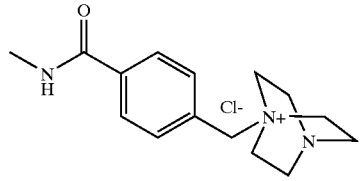
(15)
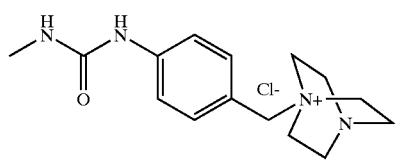
(15a)
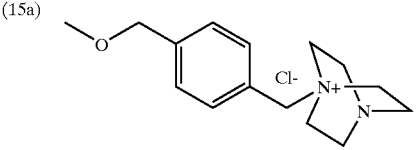
(16)
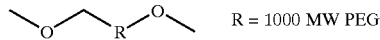
R = 1000 MW PEG
(17)
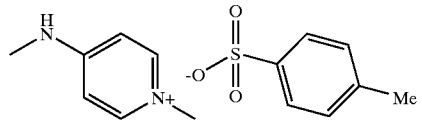
(18)
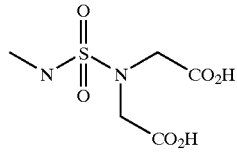
(19)
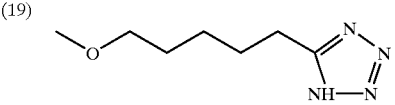
(20)
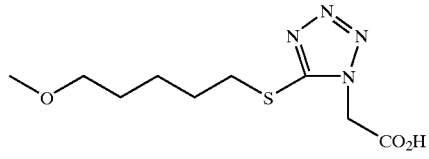
(21)
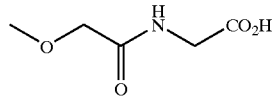
(22)

-continued
(23)
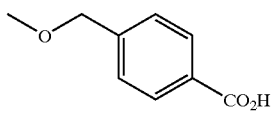
(24)
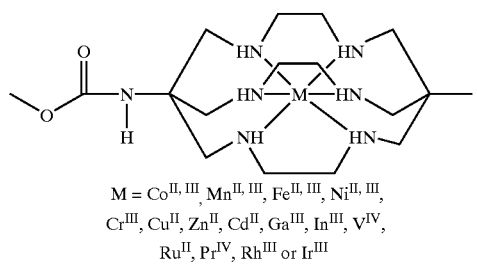
M = $Co^{II, III}$, $Mn^{II, III}$, $Fe^{II, III}$, $Ni^{II, III}$, $Cr^{III}$, $Cu^{II}$, $Zn^{II}$, $Cd^{II}$, $Ga^{III}$, $In^{III}$, $V^{IV}$, $Ru^{II}$, $Pr^{IV}$, $Rh^{III}$ or $Ir^{III}$
(25)
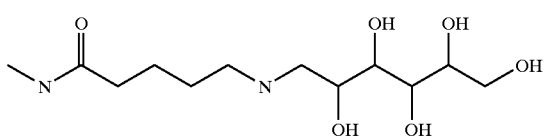
(26)
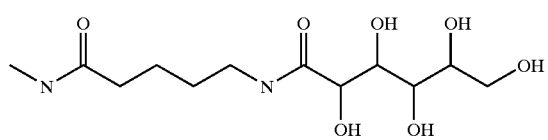
(27)
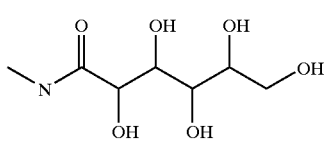
(28)
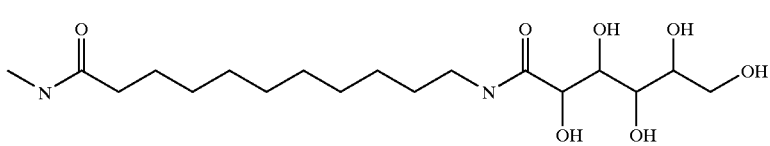
(29)
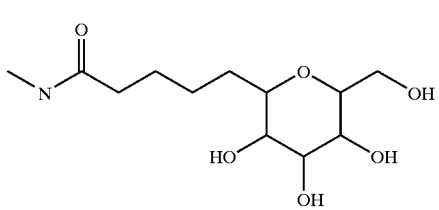
(30)
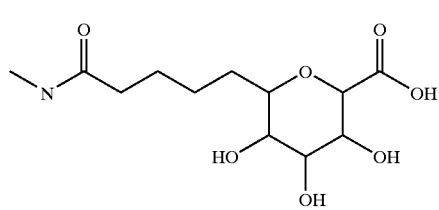
(31)
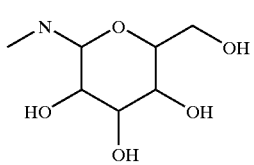
(32)
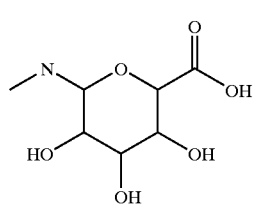
(33)
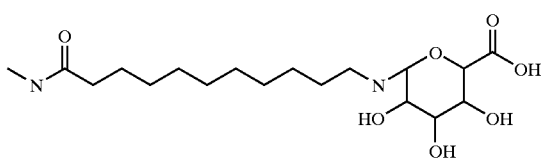
(34)
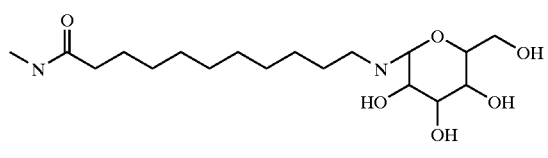
(35)
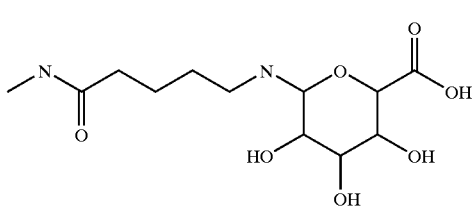
(36)
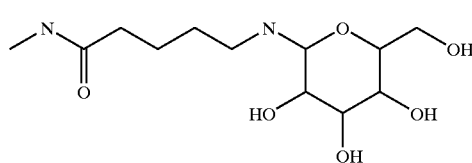

-continued
| (37) | (38) |
|---|---|
| 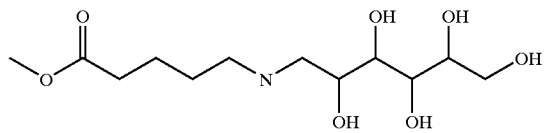 | 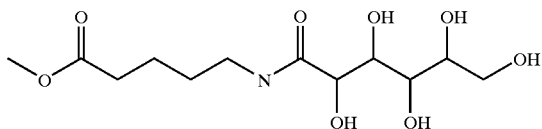 |
(39)
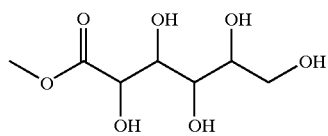
(40)
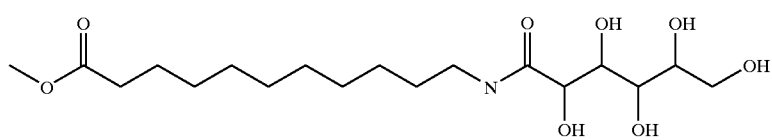
| (41) | (42) |
|---|---|
| 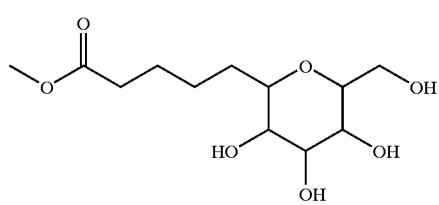 | 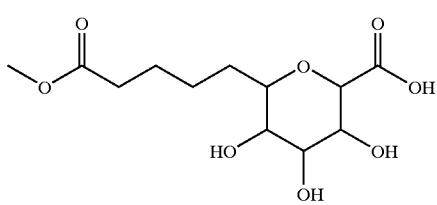 |
| (43) | (44) |
|---|---|
| 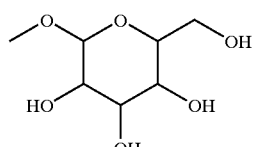 | 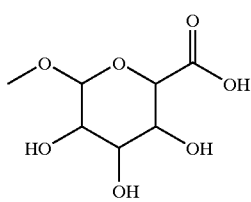 |
| (45) | (46) |
|---|---|
| 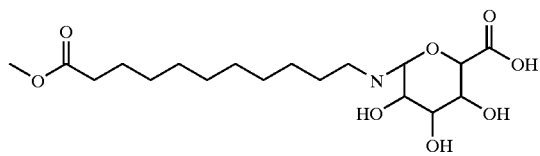 | 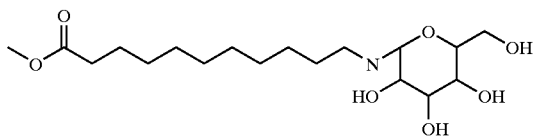 |
| (47) | (48) |
|---|---|
| 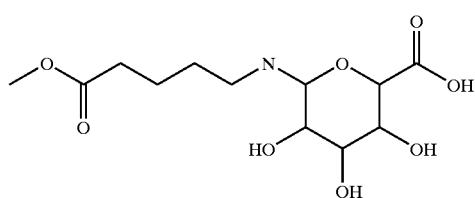 | 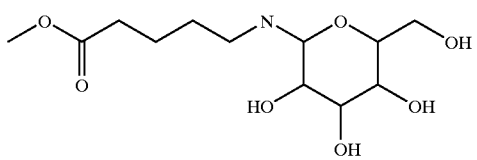 |
| (49) | (50) |
|---|---|
| 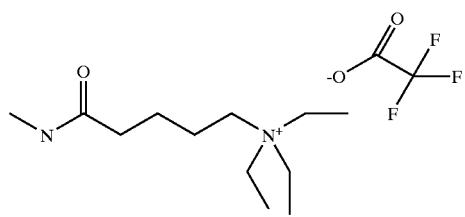 | 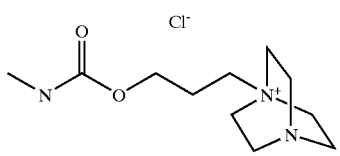 |

-continued
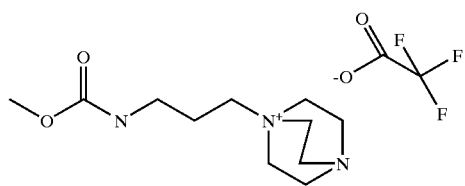
(51)
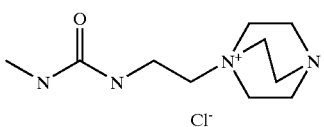
(52)
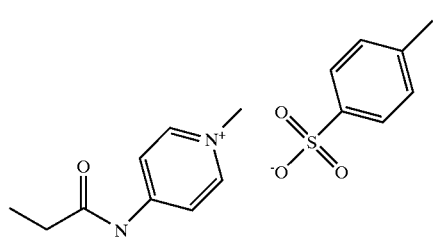
(53)
(54)
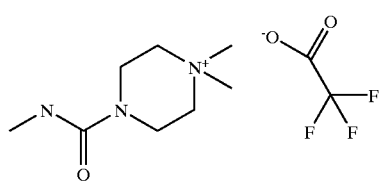
(55)
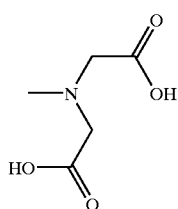
(56)
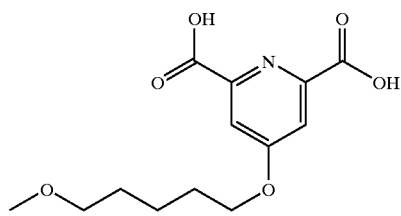
(57)
(58)
(59)
(60)
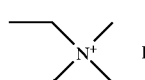
(61)
(62)
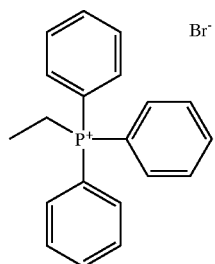
(63)
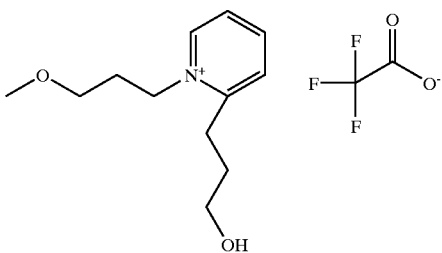
(64)

-continued

(65)
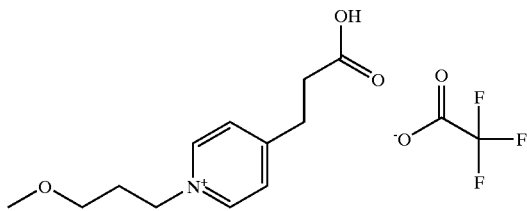

(66)
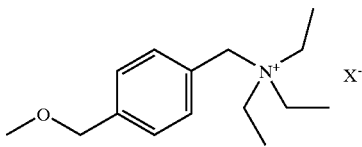

(67)
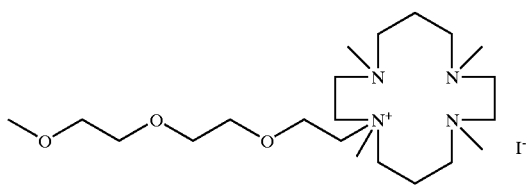

(68)
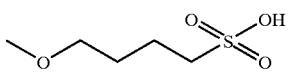

(70)
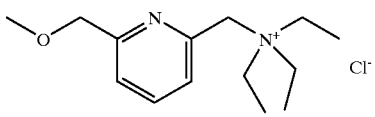

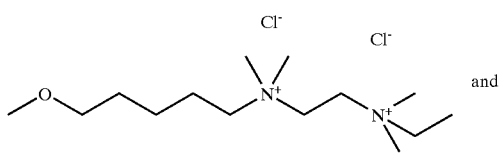 and provided that when said $R^5$ is (7), (17) or (24), then said $R^{5A}$ is a left end of said $R^5$ and said $R^{5B}$ is a right end of said $R^5$ or vice versa.

86. The compound of claim 85 wherein said Formula I-3 comprises a member selected from the group consisting of Formulas I-5 and I-6 represented by:

I-5
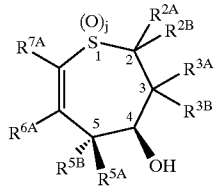

I-6
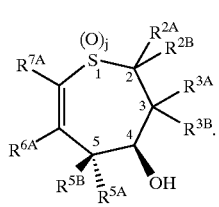

87. The compound of claim 85 wherein said Formula I-4 comprises a member selected from the group consisting of Formulas I-7 and I-8 represented by:

I-7
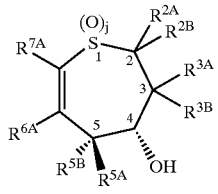

I-8
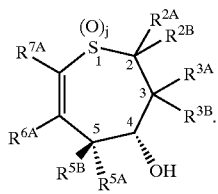

88. The compound of claim 86 wherein said compounds of Formulas I-6 and I-5 comprise Formulas I-13 and I-14, respectively, represented by:

I-13
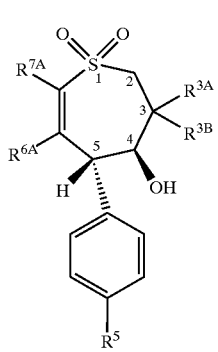

I-14

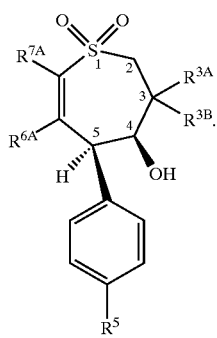

89. The compound of claim 87 wherein said compounds of Formulas I-7 and I-8 comprise Formulas I-15 and I-16, respectively, represented by:

I-15

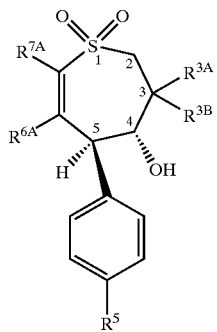

I-16

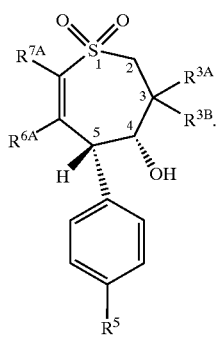

90. The compound of claim 1 wherein said compound of Formula I-2 comprises a compound of Formula I-18 represented by:

I-18

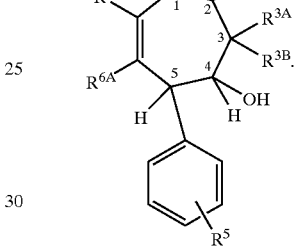

wherein $R^{2A}$, $R^{2B}$, $R^{3A}$, $R^{3B}$, $R^{5A}$, $R^{5B}$, $R^{6A}$, $R^{7A}$, and j are as previously defined and said $R^5$ is selected from the group consisting of (1)–(69) and (70):

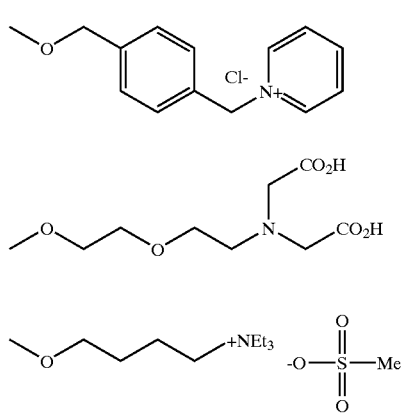

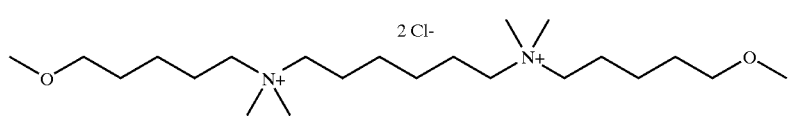

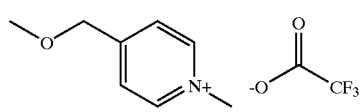

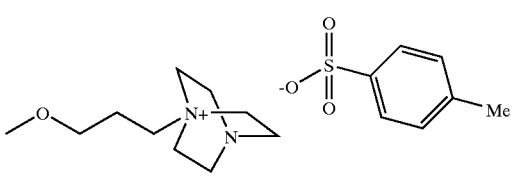

-continued
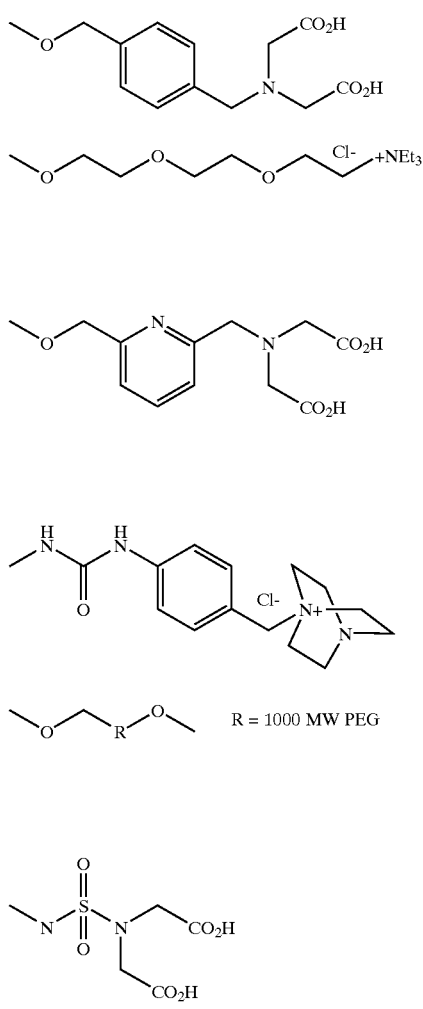
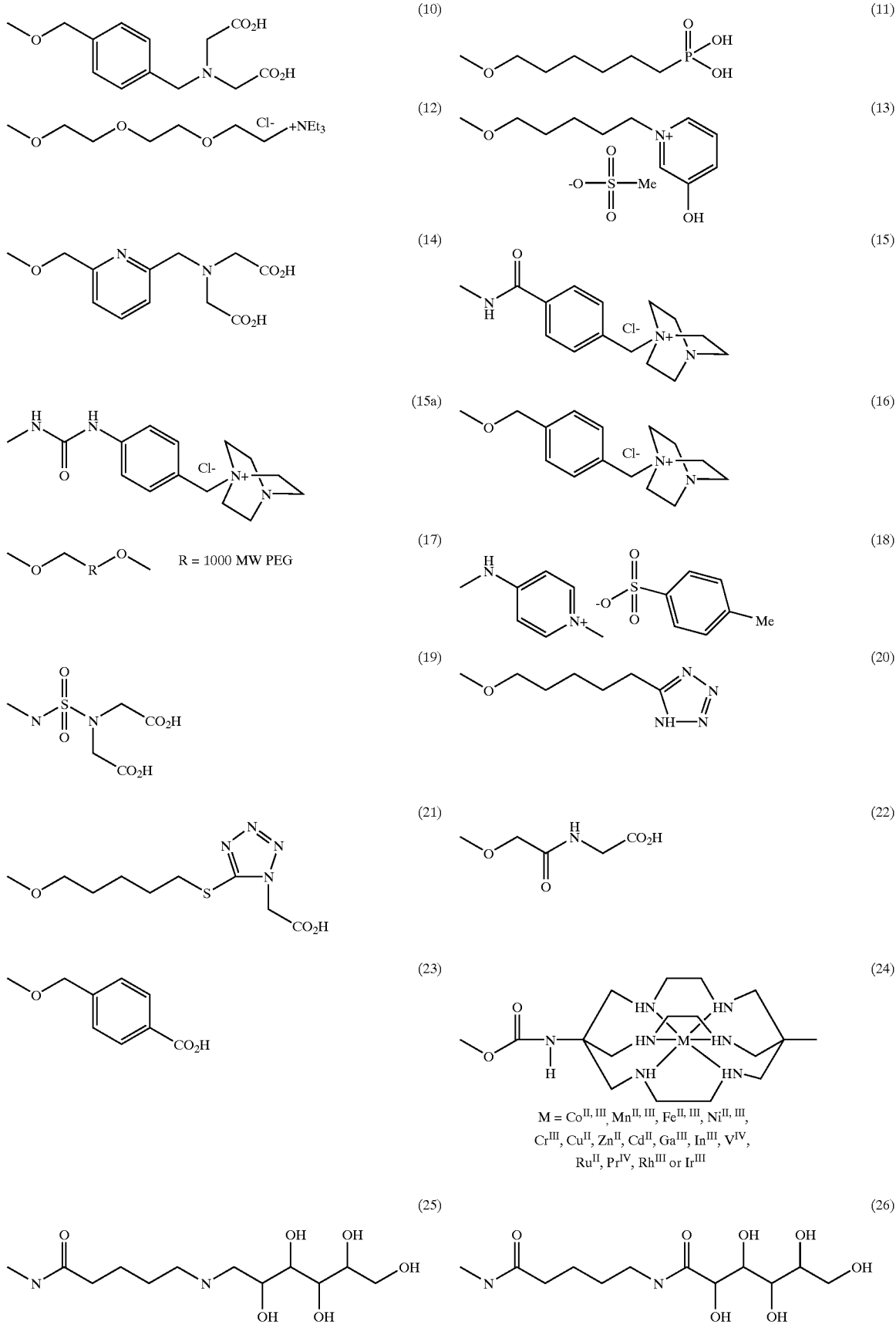

-continued
(27)
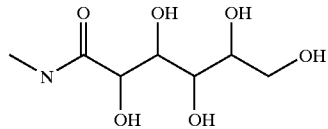
(28)
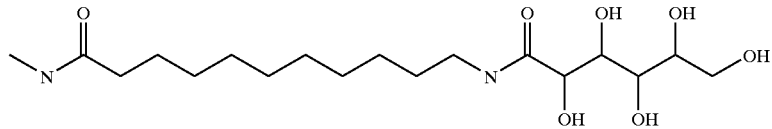
(29)
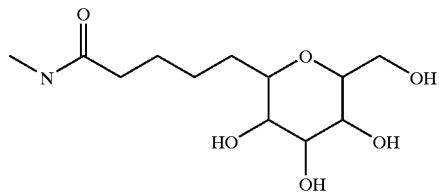
(30)
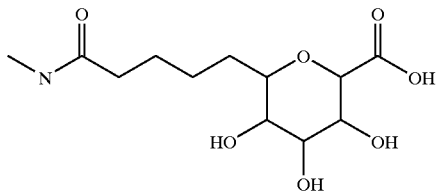
(31)
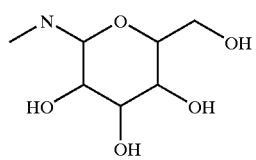
(32)
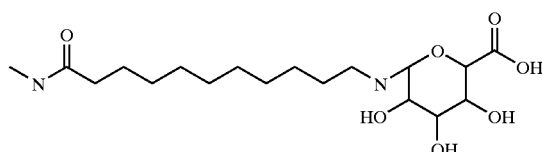
(33)
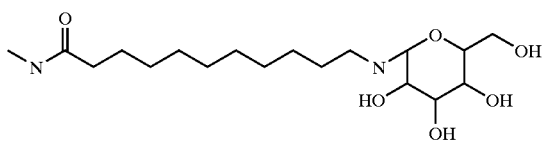
(34)
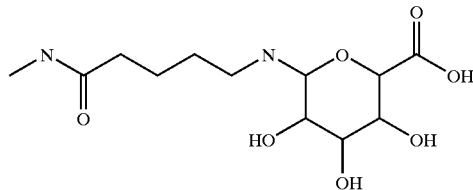
(35)
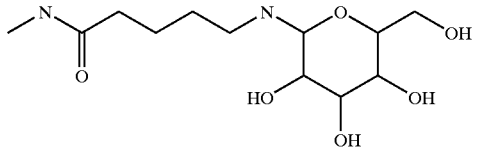
(36)
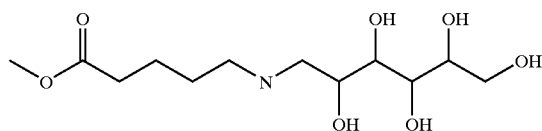
(37)
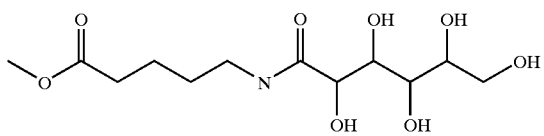
(38)
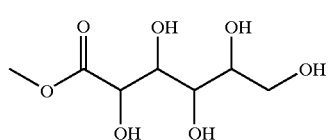
(39)
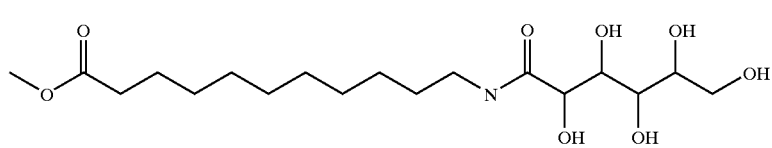
(40)

-continued
(41)
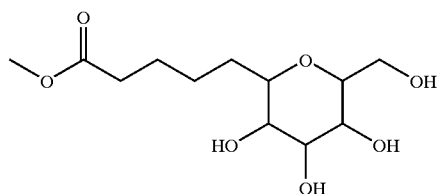
(42)
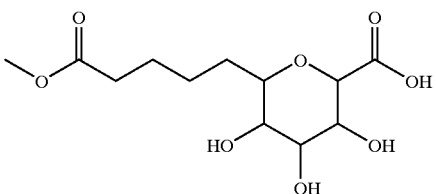
(43)
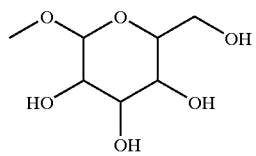
(44)
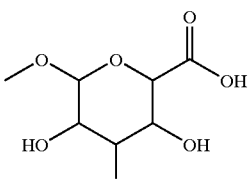
(45)
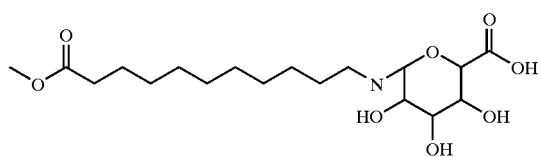
(46)
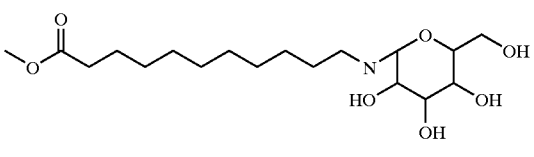
(47)
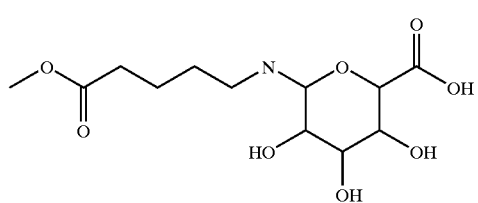
(48)
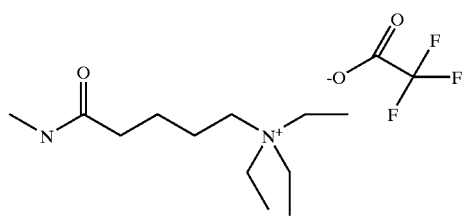
(49)
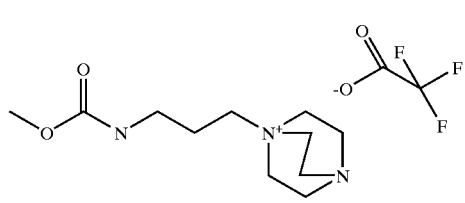
(50)
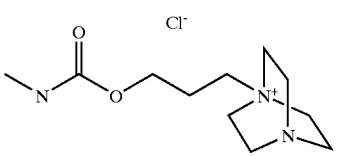
(51)
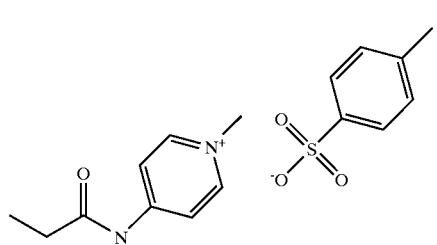
(52)
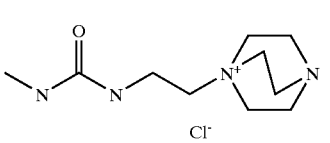
(53)
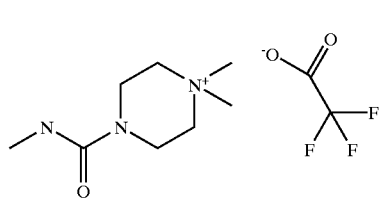
(54)
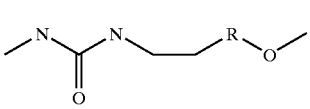
(55)
(56)
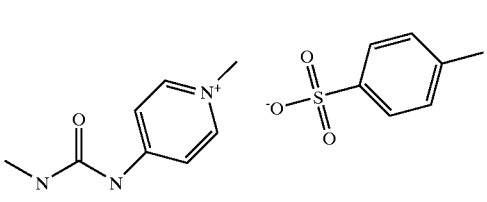

-continued
(57)
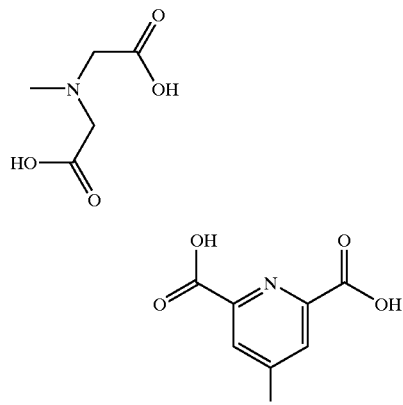
(58)
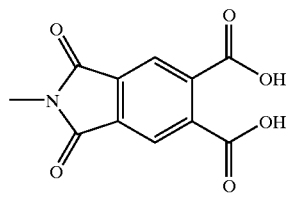
(59)
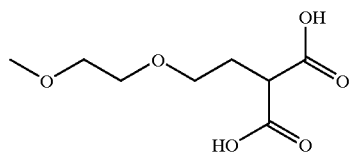
(60)
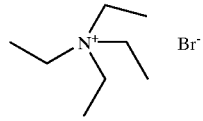
(61)
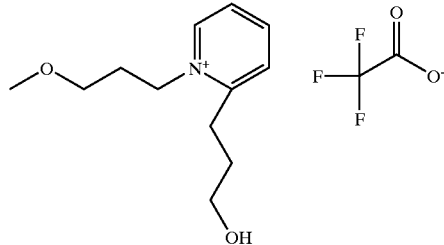 ... I⁻
(62)
(63)
(64)
(65)
(66)
(67)
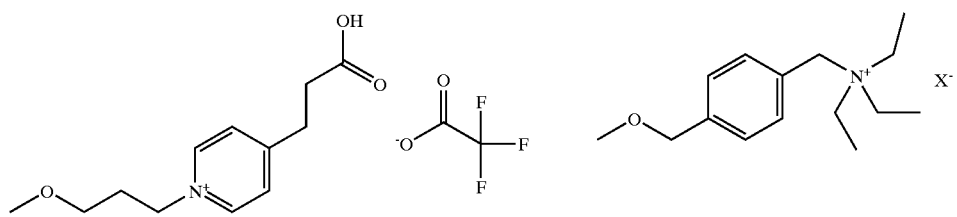
(68)
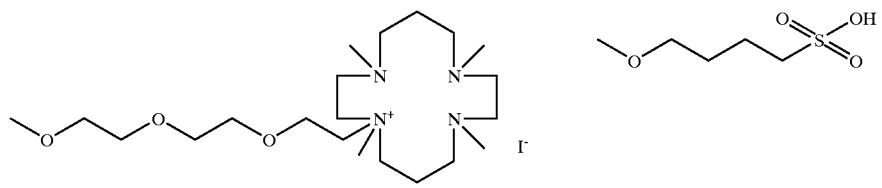 and
(70)
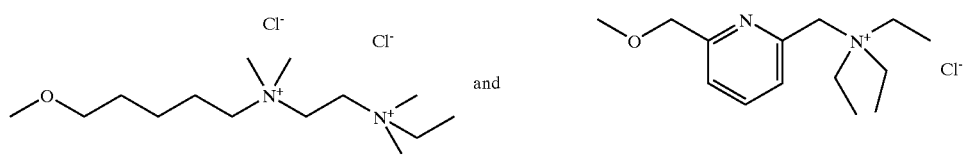
provided that when said R⁵ is (7), (17) or (24), then said R⁵ᴬ is a left end of said R⁵ and said R⁵ᴮ is a right end of said R⁵ or vice versa.
91. The compound of claim 90 wherein said compound of Formula I-18 comprises a member selected from the group consisting of I-23 and I-24 represented by:

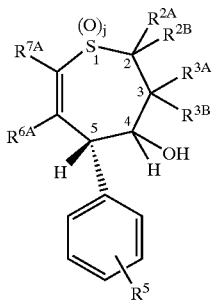
I-23

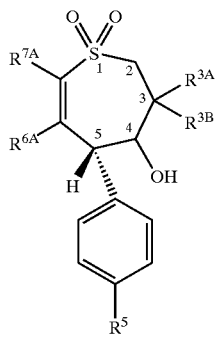
I-11

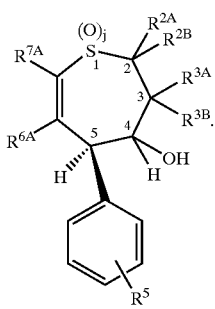
I-24

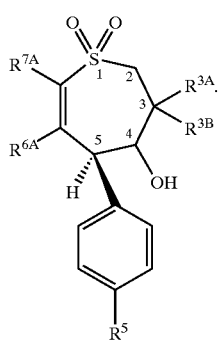
I-12

92. The compound of claim 91 wherein said compounds of Formulas I-23 and I-24 comprise compounds of Formulas I-19 and I-20, respectively, represented by:

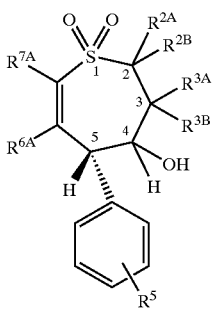
I-19

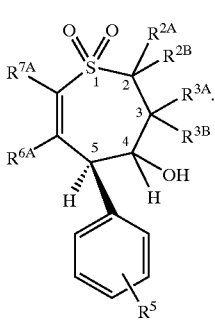
I-20

93. The compound of claim 1 wherein said compound of Formula I-2 is selected from the group consisting of Formulas I-11 and I-12 represented by:

94. The method of claim 39 wherein said hyperlipidemic condition is hypercholesterolemia.

95. The method of claim 94 wherein said therapeutically effective amount is a daily dose from about 0.001 mg to about 10,000 mg.

96. The method of claim 95 wherein said daily dose is from about 0.005 mg to about 1,000 mg.

97. The method of claim 96 wherein said daily dose is from about 0.008 to about 100 mg.

98. The method of claim 97 wherein said daily dose is from about 0.05 mg to about 50 mg.

99. The method of claims 95 to 98 wherein said daily dose is administered as a single dose or in multiple divided doses.

100. The method of claim 40 wherein said therapeutically effective amount is a daily dose from about 0.001 mg to about 10,000 mg.

101. The method of claim 100 wherein said daily dose is from about 0.005 mg to about 1,000 mg.

102. The method of claim 101 wherein said daily dose is from about 0.008 to about 100 mg.

103. The method of claim 102 wherein said daily dose is from about 0.05 mg to about 50 mg.

104. The method of claims 100 to 103 wherein said daily dose is administered as a single dose or in multiple divided doses.

105. The method of claim 95 wherein said daily dose is administered orally.

106. The method of claim 95 wherein said daily dose is administered parenterally.

107. The method of claim 95 wherein said daily dose is administered rectally.

108. The method of claim 107 wherein said daily dose is administered as a rectal dosage form comprising a suppository.

109. The method of claim 94 wherein said therapeutically effective amount is administered as a slow release dosage form.

110. The method of claim 109 wherein said slow release dosage form comprises an implant.

111. The method of claim 105 wherein said daily dose is administered in the form of an oral dosage form selected from the group consisting of a tablet, a capsule, a powder, a solution, a suspension, an emulsion, and a syrup.

112. The method of claim 111 wherein said solution comprises a syrup.

113. The method of claim 111 wherein said oral dosage form comprises a sublingual tablet, an effervescent tablet, or a slow release tablet.

114. The method of claim 106 wherein said parenteral dosage form is selected from the group consisting of an intramuscular injection, an intravenous injection, and a subcutaneous injection.

115. The method of claim 95 wherein said daily dose is administered topically.

116. The method of claim 100 wherein said daily dose is administered parenterally.

117. The method of claim 100 wherein said daily dose is administered rectally or vaginally.

118. The method of claim 117 wherein said daily dose is administered as a rectal dosage form or a vaginal dosage form comprising a suppository.

119. The method of claim 100 wherein said daily dose is administered as a slow release dosage form.

120. The method of claim 119 wherein said slow release dosage form comprises an implant.

121. The method of claim 100 wherein said daily dose is administered in the form of an oral dosage form selected from the group consisting of a tablet, a capsule, a powder, a solution, a suspension, and an emulsion.

122. The method of claim 121 wherein said solution comprises a syrup.

123. The method of claim 121 wherein said tablet comprises a sublingual tablet, an effervescent tablet, or a slow release tablet.

124. The method of claim 116 wherein said parenteral dosage form is selected from the group consisting of an intramuscular injection, an intravenous injection, and a subcutaneous injection.

125. The method of claim 100 wherein said daily dose is administered topically.

126. The method of claim 125 wherein said daily dose is administered in the form of a topical dosage form selected from the group consisting of a lotion, a cream, a suspension, an emulsion, a paste, and a solution.

127. The method of claim 115 wherein said daily dose is administered in the form of a topical dosage form selected from the group consisting of a lotion, a cream, a suspension, an emulsion, a paste, and a solution.

128. A pharmaceutical composition comprising a compound of Formula I-1 or I-2 of claim 1 and a pharmaceutically acceptable carrier.

129. The pharmaceutical composition of claim 128 wherein said compound of Formula I-1 comprises Formula I-17 represented by:

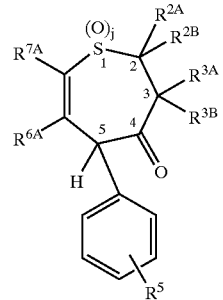

I-17 wherein $R^{2A}$, $R^{2B}$, $R^{3A}$, $R^{3B}$, $R^{5A}$, $R^{5B}$, $R^{6A}$, $R^{7A}$, and j are as previously defined and said $R^5$ is selected from the group consisting of (1)–(69) and (70):

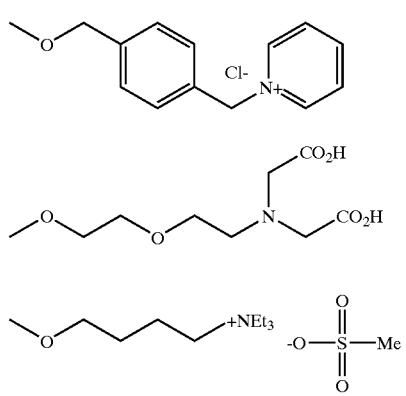

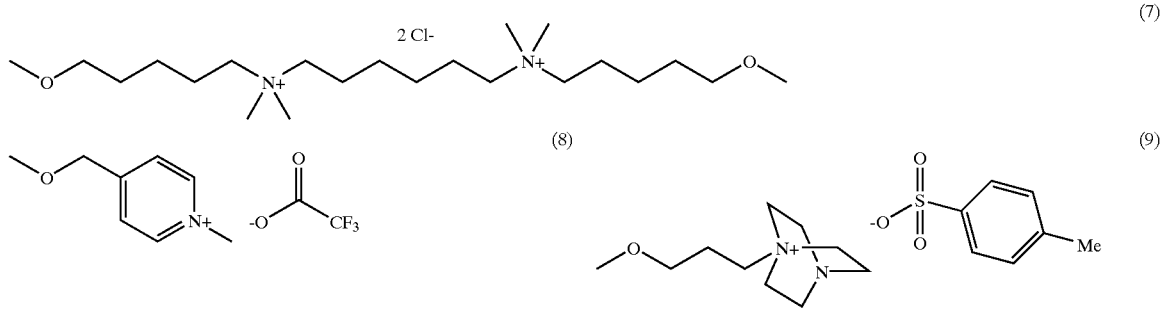

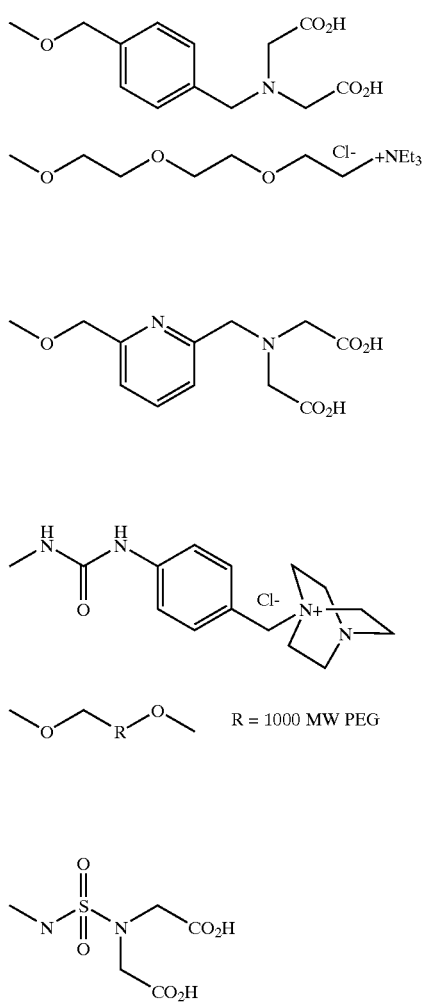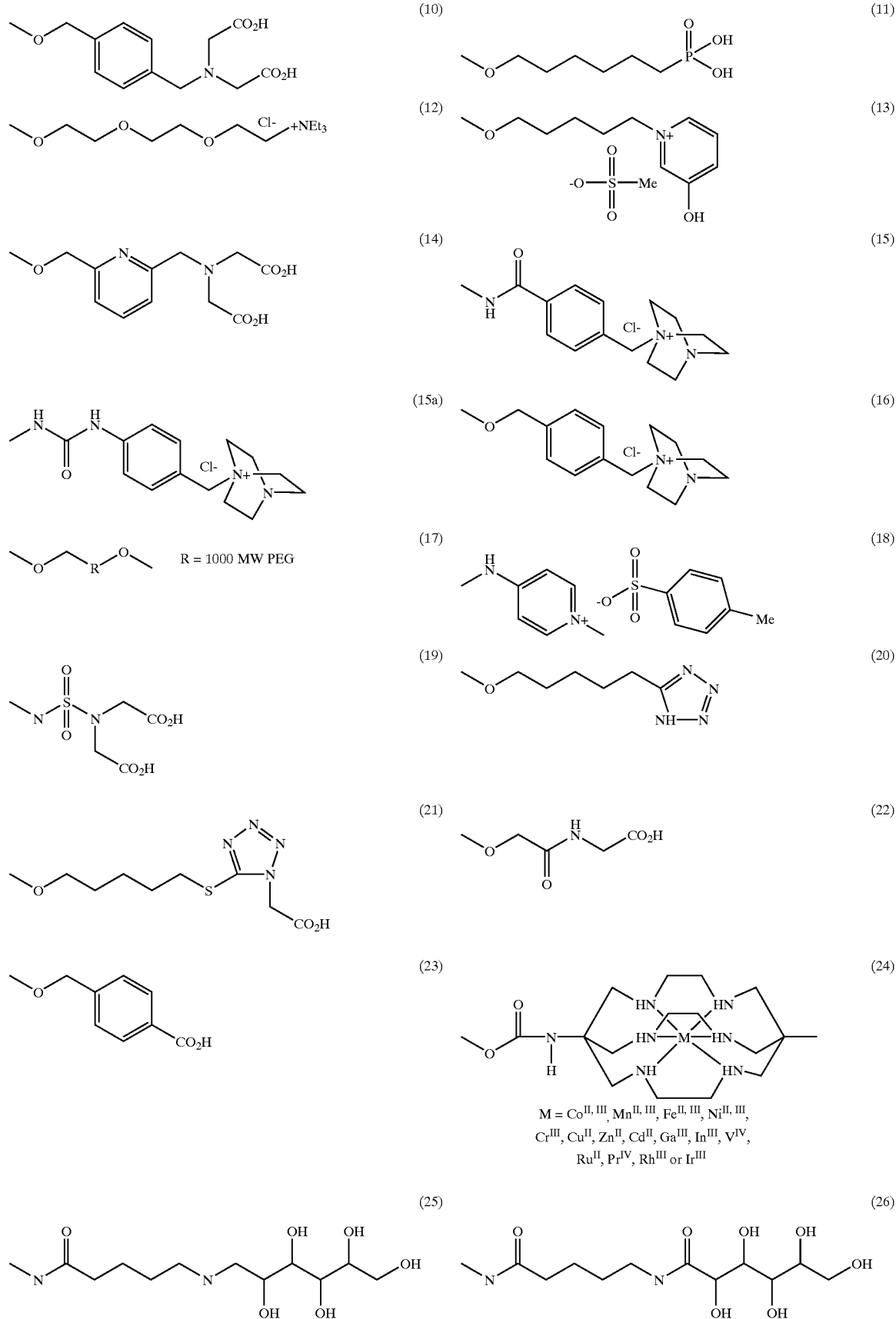

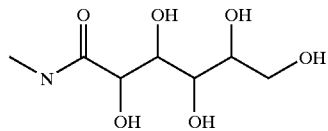
(27)
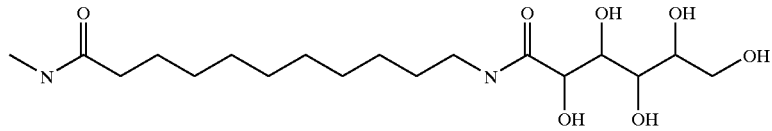
(28)
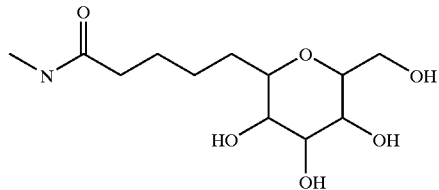
(29)  (30)
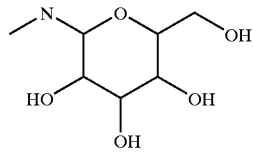
(31)  (32)
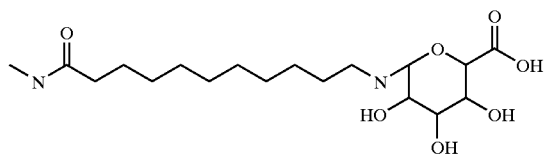
(33)  (34)
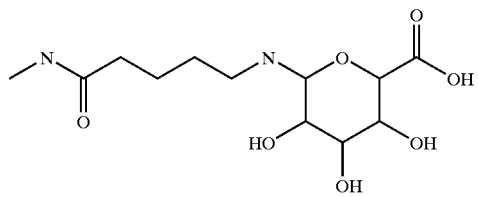
(35)  (36)
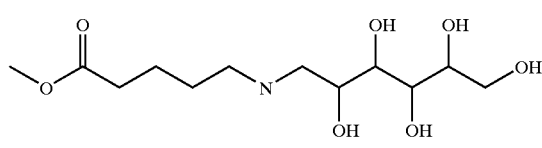
(37)
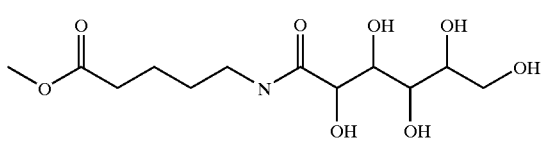
(38)
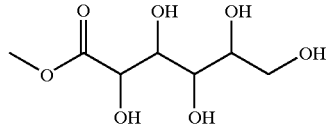
(39)
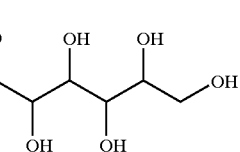
(40)

-continued
(41)
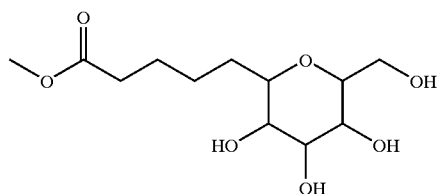
(42)
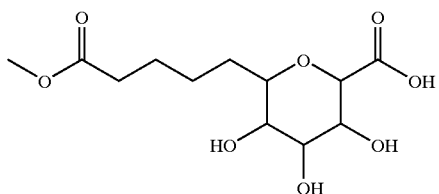
(43)
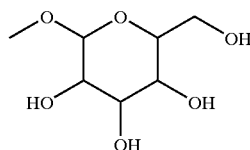
(44)
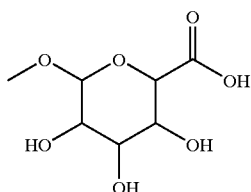
(45)
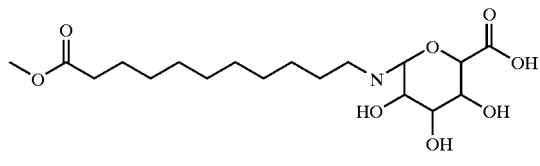
(46)
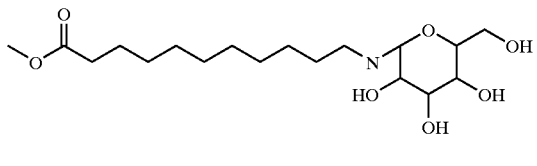
(47)
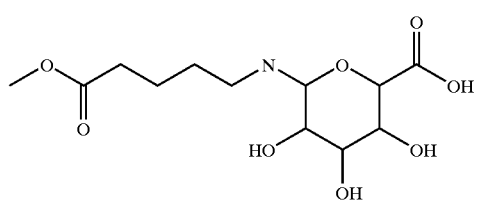
(48)
(49)
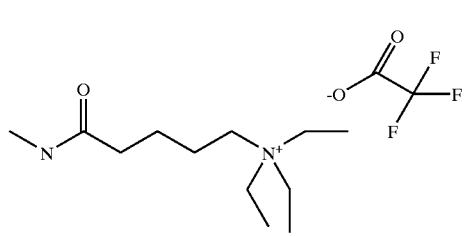
(50)
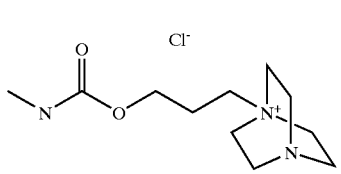
(51)
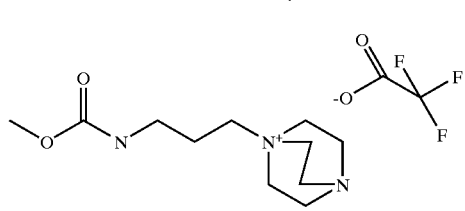
(52)
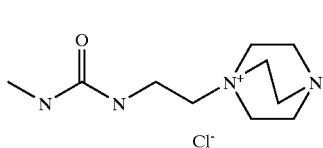
(53)
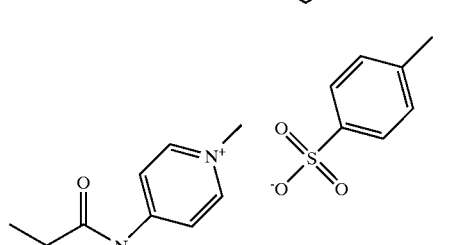
(54)
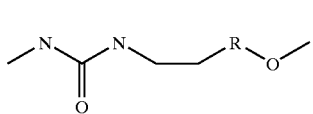
(55)
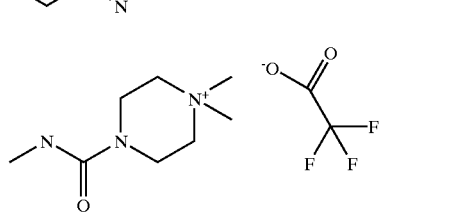
(56)
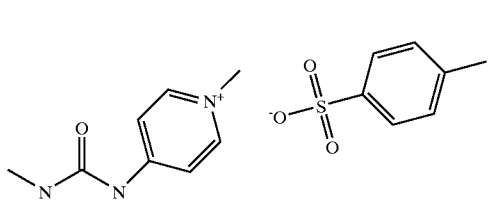

-continued
(57)
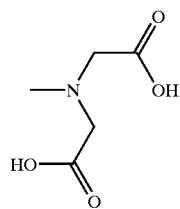
(58)
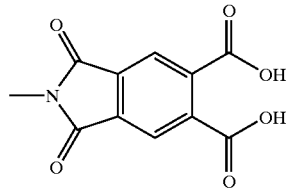
(59)
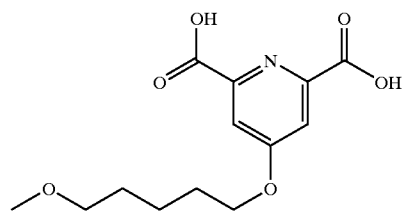
(60)
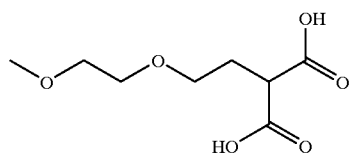
(61)
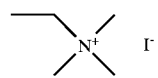
(62)
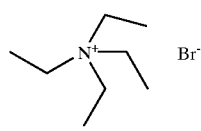
(63)
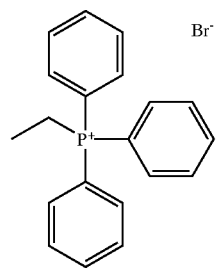
(64)
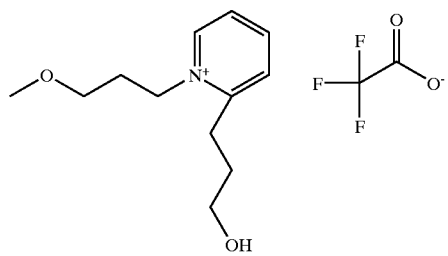
(65)
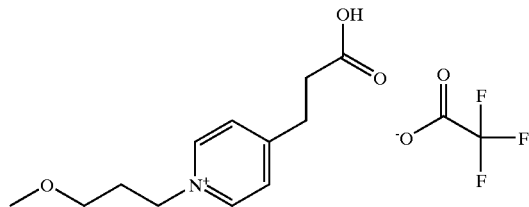
(66)
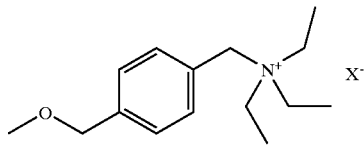
(67)
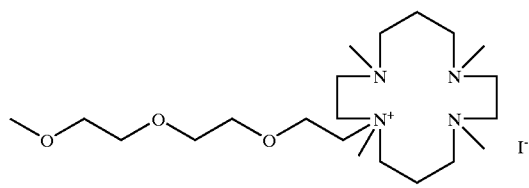
(68)
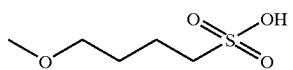
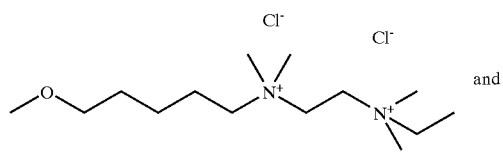 and
(70)
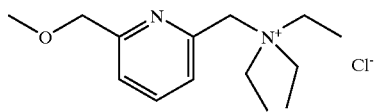

provided that when said $R^5$ is (7), (17) or (24), then said $R^{5A}$ is a left end of said $R^5$ and $R^{5B}$ is a right end of said $R^5$ or vice versa.

130. The pharmaceutical composition of claim 129 wherein said compound of Formula I-17 comprises a member selected from the group consisting of Formulas I-21 and I-22 represented by:

I-21

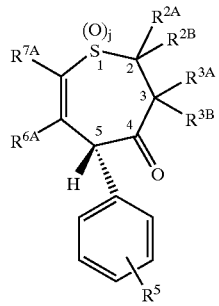

I-22

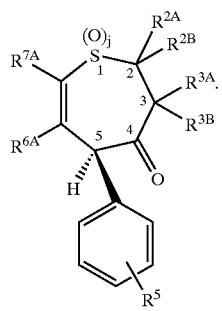

131. The pharmaceutical composition of claim 130 wherein said compounds of Formulas I-21 and I-22 comprise Formulas I-9 and I-10, respectively, represented by:

I-9

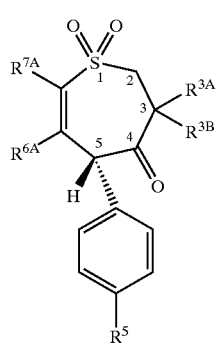

I-10

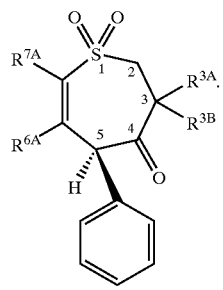

132. The pharmaceutical composition of claim 128 wherein said compound of Formula I-2 is selected from the group consisting of Formulas I-3 and I-4 represented by:

I-3

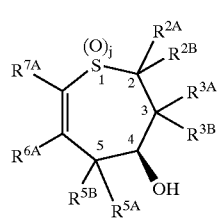

I-4

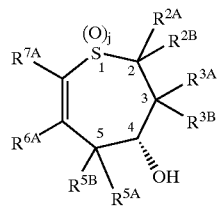

wherein $R^{2A}$, $R^{2B}$, $R^{3A}$, $R^{3B}$, $R^{5A}$, $R^{5B}$, $R^{6A}$, $R^{7A}$, m and j are as previously defined and said $R^5$ is selected from the group consisting of (1)–(69) and (70):

(1)

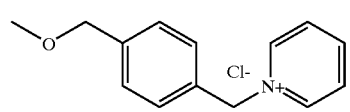

(2)

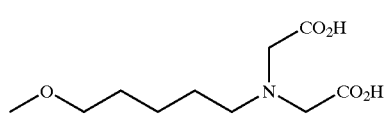

(3)

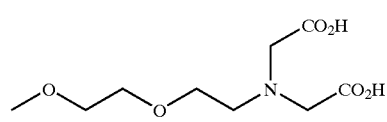

(4)

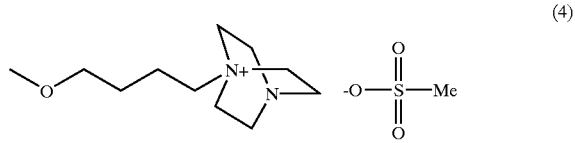

-continued
(5)
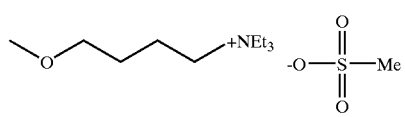
(6)
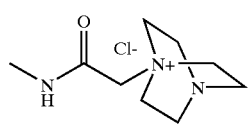
(7)
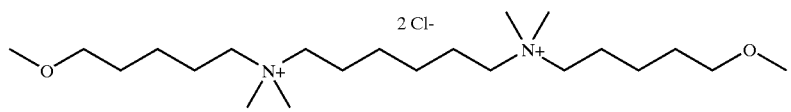
(8)
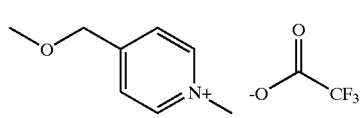
(9)
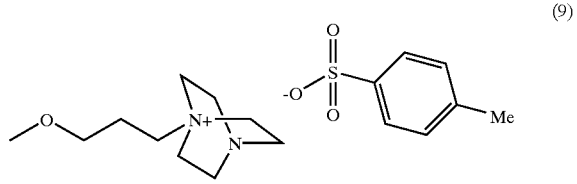
(10)
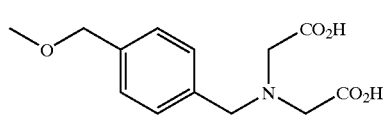
(11)
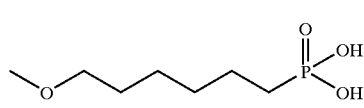
(12)
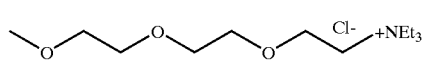
(13)
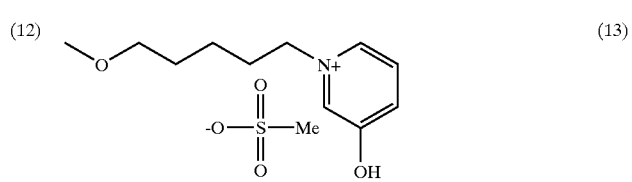
(14)
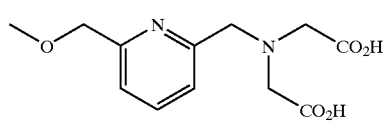
(15)
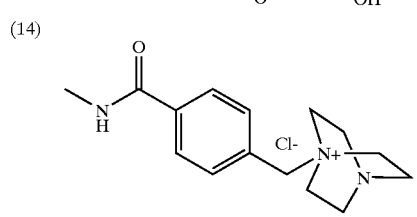
(15a)
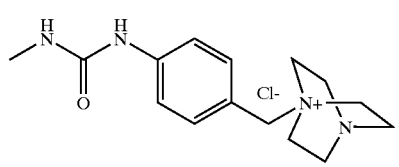
(16)
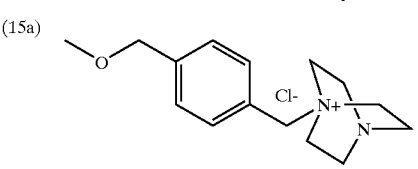
(17)
R = 1000 MW PEG
(18)
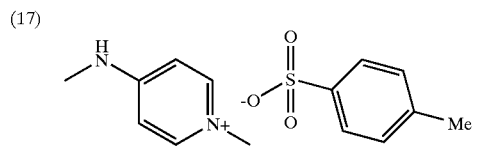
(19)
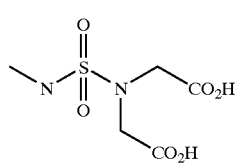
(20)
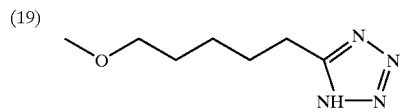
(21)
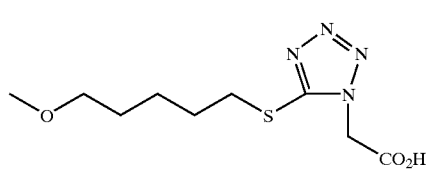
(22)
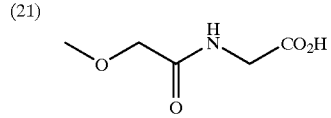

-continued
(23)
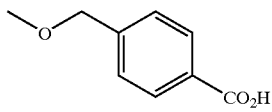
(24)
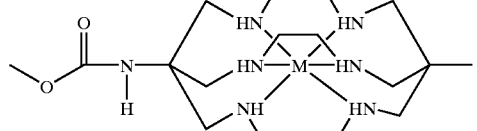
M = Co$^{II, III}$, Mn$^{II, III}$, Fe$^{II, III}$, Ni$^{II, III}$, Cr$^{III}$, Cu$^{II}$, Zn$^{II}$, Cd$^{II}$, Ga$^{III}$, In$^{III}$, V$^{IV}$, Ru$^{II}$, Pr$^{IV}$, Rh$^{III}$ or Ir$^{III}$
(25)
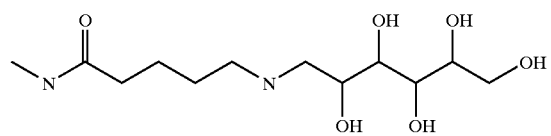
(26)
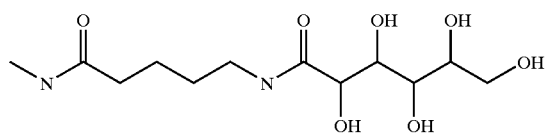
(27)
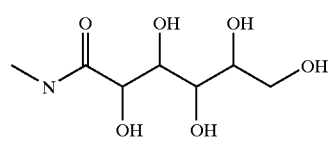
(28)
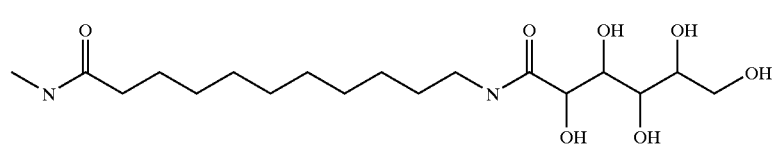
(29)
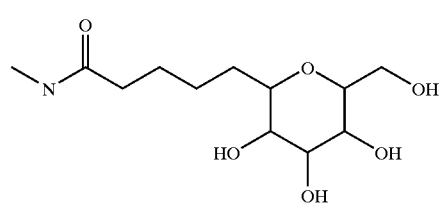
(30)
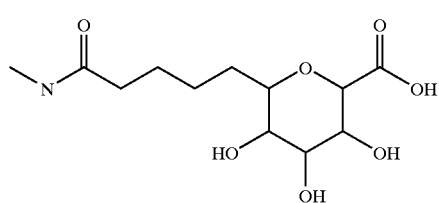
(31)
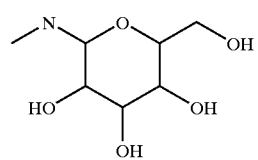
(32)
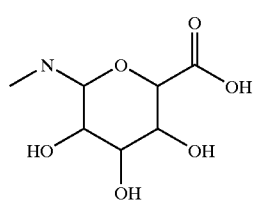
(33)
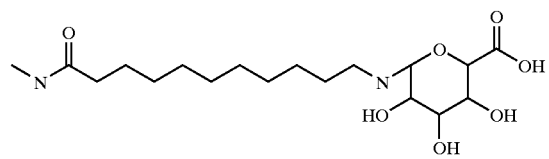
(34)
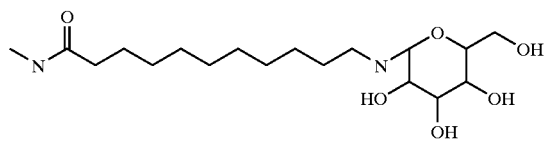
(35)
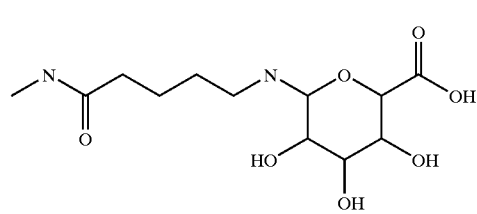
(36)
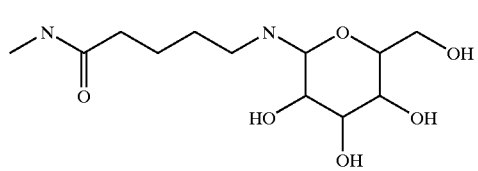

-continued
(37) 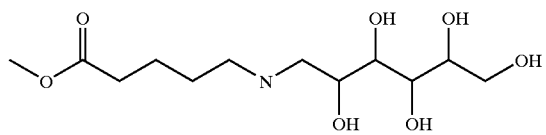
(38) 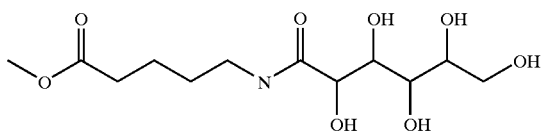
(39) 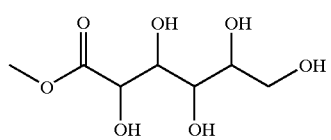
(40) 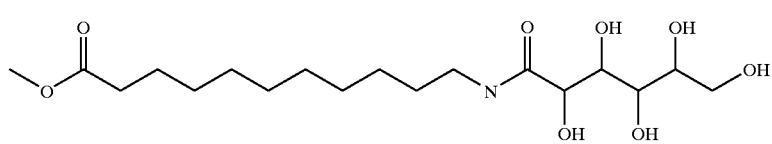
(41) 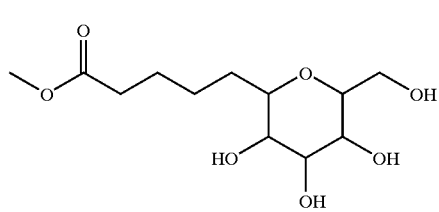
(42) 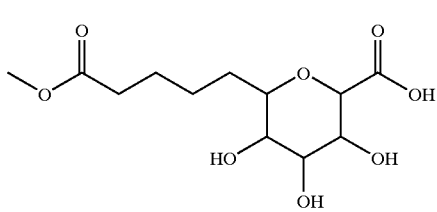
(43) 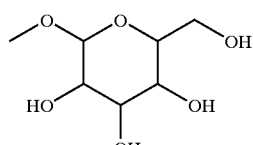
(44) 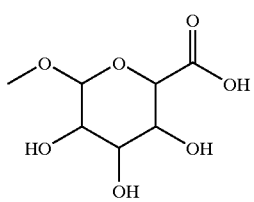
(45) 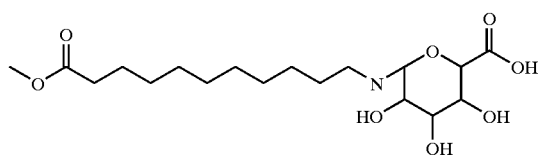
(46) 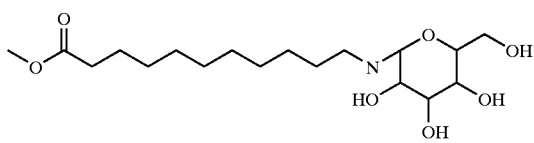
(47) 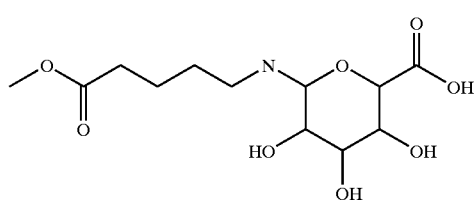
(48) 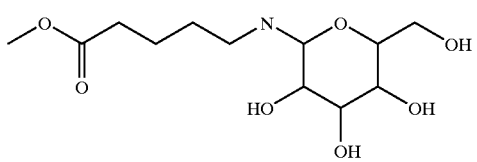
(49) 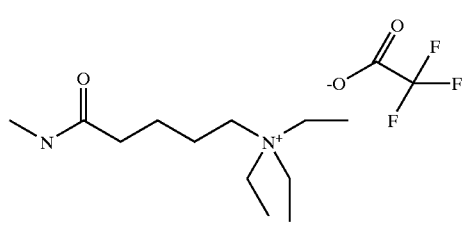
(50) 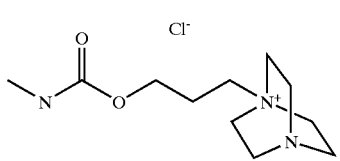

-continued
(51)
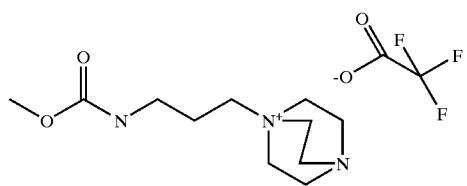
(52)
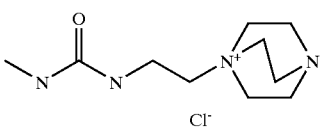
(53)
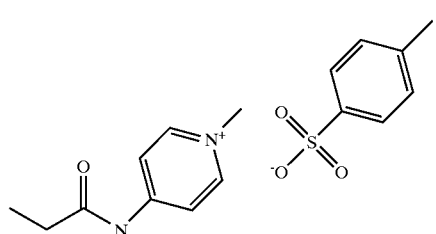
(54)
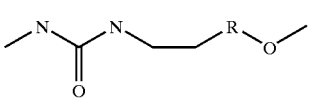
(55)
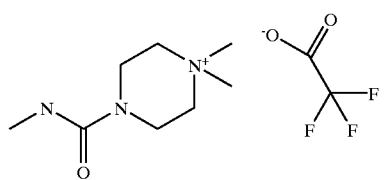
(56)
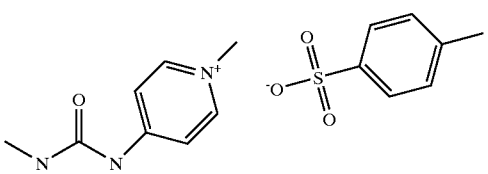
(57)
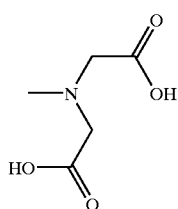
(58)
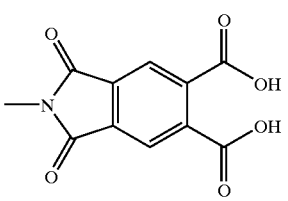
(59)
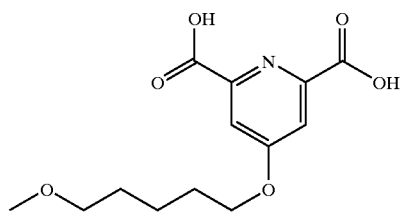
(60)
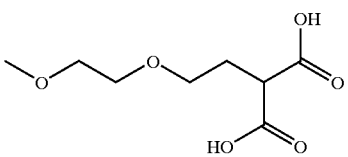
(61)
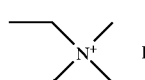
(62)
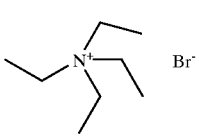
(63)
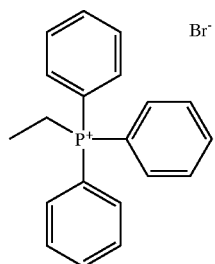
(64)
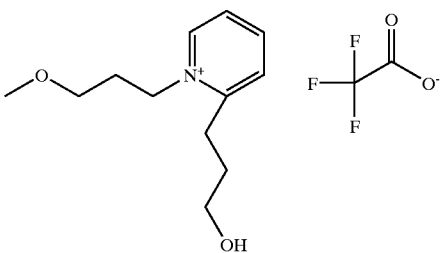

-continued

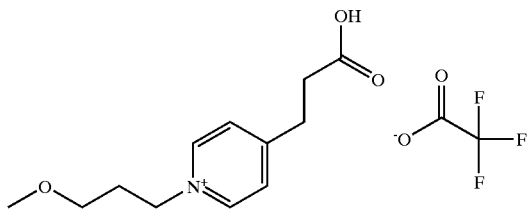 (65)

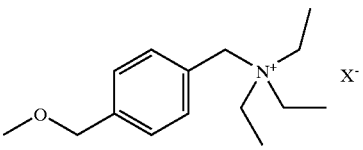 (66)

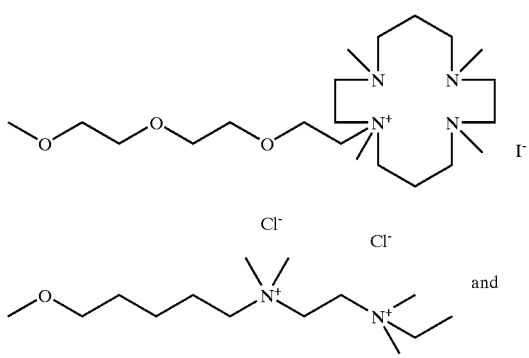 (67)

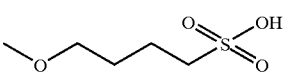 (68)

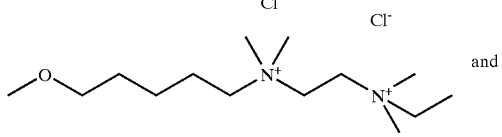 (69)

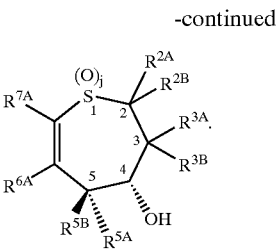 (70)

and provided that when said $R^5$ is (7), (17) or (24), then said $R^{5A}$ is a left end of said $R^5$ and said $R^{5B}$ is a right end of said $R^5$ or vice versa.

133. The pharmaceutical composition of claim 132 wherein said Formula I-3 comprises a member selected from the group consisting of Formulas I-5 and I-6 represented by:

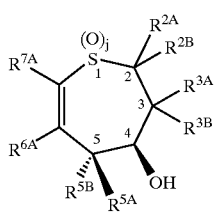 I-5

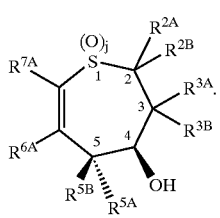 I-6

134. The pharmaceutical composition of claim 132 wherein said Formula I-4 comprises a member selected from the group consisting of Formulas I-7 and I-8 represented by:

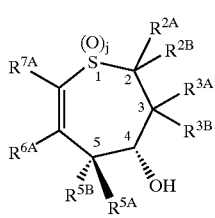 I-7

-continued

I-8

135. The pharmaceutical composition of claim 133 wherein said compounds of Formulas I-6 and I-5 comprise Formulas I-13 and I-14, respectively, represented by:

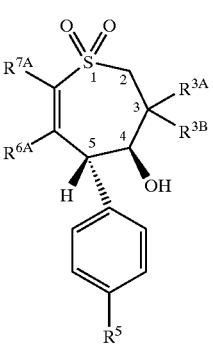 I-13

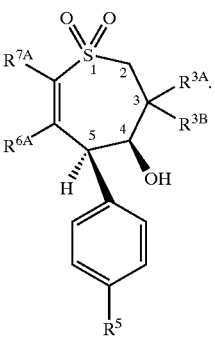 I-14

136. The pharmaceutical composition of claim 134 wherein said compounds of Formulas I-7 and I-8 comprise Formulas I-15 and I-16, respectively, represented by:

I-15

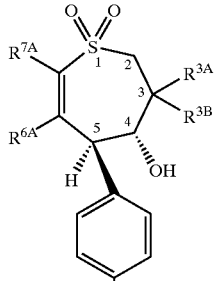

I-16

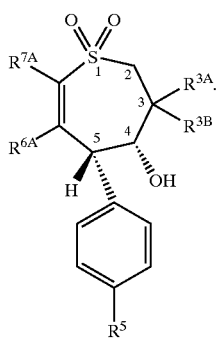

137. The pharmaceutical composition of claim 128 wherein said compound of Formula I-2 comprises a compound of Formula I-18 represented by:

I-18

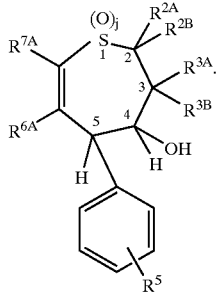

138. The pharmaceutical composition of claim 137 wherein said compound of Formula I-18 comprises a member selected from the group consisting of I-23 and I-24 represented by:

I-23

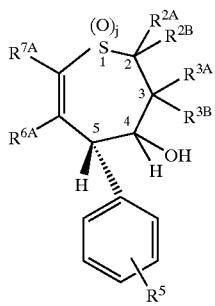

-continued

I-24

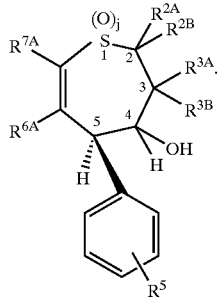

139. The pharmaceutical composition of claim 138 wherein said compounds of Formulas I-23 and I-24 comprise compounds of Formulas I-19 and I-20, respectively, represented by:

I-19

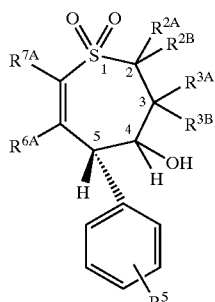

I-20

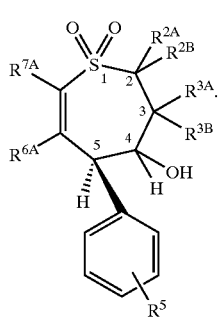

140. The pharmaceutical composition of claim 128 wherein said compound of Formula I-2 is selected from the group consisting of Formulas I-11 and I-12 represented by:

I-11

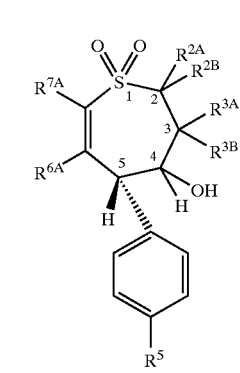

-continued

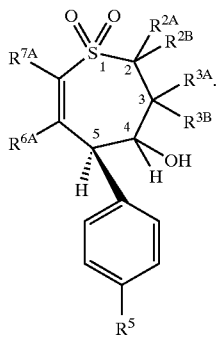

I-12

141. The pharmaceutical composition of claim 128 provided in a coated dosage form, said coated dosage form having a coating of cellulose acetate phthalate, polyvinylacetate pththalate, hydroxypropylmethyl cellulose phthalate, or an anionic polymer of methacrylic acid and methacrylic acid methyl ester.

142. The compound of claim 1 provided in a coated dosage form, said coated dosage form having a coating of cellulose acetate phthalate, polyvinylacetate pththalate, hydroxypropylmethyl cellulose phthalate, or an anionic polymer of methacrylic acid and methacrylic acid methyl ester.

143. The pharmaceutical composition of claim 128 provided in a dosage form selected from the group consisting of a tablet, a capsule, a suspension, an emulsion, a solution, a cream, a paste, a lotion, a suppository, or a powder.

144. The pharmaceutical composition of claim 128 in a dosage form selected from the group consisting of a sublingual tablet, an effervescent tablet, and a coated tablet.

145. The pharmaceutical composition of claim 128 provided in a dosage form comprising a slow release dosage form.

146. The pharmaceutical composition of claim 145 wherein said slow release dosage form is selected from the group consisting of an implant or a coated tablet.

147. The pharmaceutical composition of claim 146 wherein said solution, said suspension or said emulsion are suitable for parenteral administration to said subject.

148. The pharmaceutical composition of claim 143 wherein said solution comprises a syrup.

149. The pharmaceutical composition of claim 128 provided in a dosage form comprising a dispersion.

150. The compound of claim 1 provided in a dosage form selected from the group consisting of a tablet, a capsule, a suspension, an emulsion, a solution, a cream, a paste, a lotion, a suppository, and a powder.

* * * * *